US009181339B2

(12) United States Patent
Rohlff et al.

(10) Patent No.: US 9,181,339 B2
(45) Date of Patent: Nov. 10, 2015

(54) ANTIBODIES SPECIFIC TO CADHERIN-17

(75) Inventors: Christian Rohlff, Oxon (GB); Jonathan Alexander Terrett, San Jose, CA (US)

(73) Assignee: Oxford Bio Therapeutics Ltd., Abingdon (GB)

( * ) Notice: Subject to any disclaimer, the term of this patent is extended or adjusted under 35 U.S.C. 154(b) by 493 days.

(21) Appl. No.: 13/265,517

(22) PCT Filed: Apr. 20, 2010

(86) PCT No.: PCT/US2010/031719
§ 371 (c)(1),
(2), (4) Date: Jan. 9, 2012

(87) PCT Pub. No.: WO2010/123874
PCT Pub. Date: Oct. 28, 2010

(65) Prior Publication Data
US 2012/0114672 A1   May 10, 2012

Related U.S. Application Data

(60) Provisional application No. 61/170,980, filed on Apr. 20, 2009.

(51) Int. Cl.
C07K 16/28 (2006.01)
C07K 16/30 (2006.01)
A61K 39/00 (2006.01)
A61K 47/48 (2006.01)

(52) U.S. Cl.
CPC ............... C07K 16/28 (2013.01); A61K 39/00 (2013.01); A61K 47/48569 (2013.01); C07K 2317/55 (2013.01); C07K 2317/56 (2013.01); C07K 2317/565 (2013.01); C07K 2317/77 (2013.01); C07K 2317/80 (2013.01)

(58) Field of Classification Search
CPC ............ A61K 39/00; A61K 47/48561; A61K 47/48569
USPC ........... 530/350, 387.1, 387.3, 387.7, 388.22, 530/388.8, 391.3, 391.7; 536/23.5; 435/320.1, 325, 69.1; 424/130.1, 424/133.1, 135.1, 136.1, 138.1, 143.1, 424/152.1, 174.1, 181.1, 183.1
See application file for complete search history.

(56) References Cited

U.S. PATENT DOCUMENTS

| | | | |
|---|---|---|---|
| 5,620,855 A | 4/1997 | Dantzig et al. | |
| 5,710,018 A | 1/1998 | Dantzig et al. | |
| 6,699,973 B1 | 3/2004 | O'Mahony et al. | |
| 6,703,362 B1 | 3/2004 | Alvarez et al. | |
| 7,053,177 B1 | 5/2006 | Alvarez et al. | |
| 7,135,457 B1 | 11/2006 | Alvarez et al. | |
| 7,785,801 B2 | 8/2010 | Tureci et al. | |
| 8,535,677 B2 | 9/2013 | Rohlff et al. | |
| 2003/0229208 A1 | 12/2003 | Queen et al. | |
| 2005/0118183 A1 | 6/2005 | Hoffee et al. | |
| 2006/0270594 A1 | 11/2006 | Kong-Beltran et al. | |
| 2006/0280747 A1 | 12/2006 | Fuh et al. | |
| 2008/0025980 A1 | 1/2008 | Hardy et al. | |
| 2010/0092978 A1 | 4/2010 | Luk et al. | |
| 2013/0259878 A1 | 10/2013 | Terrell | |
| 2014/0024048 A1 | 1/2014 | Rohlff | |

FOREIGN PATENT DOCUMENTS

| | | |
|---|---|---|
| WO | 96/40942 A1 | 12/1996 |
| WO | 98/42736 A | 10/1998 |
| WO | 01/49716 A | 7/2001 |
| WO | 02/074156 A | 9/2002 |
| WO | 02/083070 A | 10/2002 |
| WO | 02/101357 A | 12/2002 |
| WO | 03/020934 A | 3/2003 |
| WO | 2004/001072 A | 12/2003 |
| WO | 2004/022778 A | 3/2004 |
| WO | 2004/048529 A | 6/2004 |
| WO | 2005/110338 A | 11/2005 |
| WO | 2006/009805 A | 1/2006 |
| WO | 2006/132971 | 12/2006 |
| WO | 2006/138275 A | 12/2006 |
| WO | 2007/035676 A | 3/2007 |
| WO | 2007/035690 A | 3/2007 |
| WO | 2007/141280 A | 12/2007 |
| WO | 2008/026008 A | 3/2008 |
| WO | 2010/123874 A1 | 10/2010 |

OTHER PUBLICATIONS

Rudikoff et al (Proc. Natl. Acad. Sci. USA. 1982; 79: 1979-1983).*
Mariuzza et al. (Annu. Rev. Biophys. Biophys. Chem. 1987; 16: 139-159).*
Gussow et al. (Methods in Enzymology. 1991; 203: 99-121).*
Winkler et al. (J. Immunol. Oct. 15, 2000; 165 (8): 4505-4514).*
Giusti et al. (Proc. Natl. Acad. Sci. USA. May 1987; 84 (9): 2926-2930).*
Chien et al. (Proc. Natl. Acad. Sci. USA. Jul. 1989; 86 (14): 5532-5536).*

(Continued)

*Primary Examiner* — Stephen Rawlings

(74) *Attorney, Agent, or Firm* — Nelson Mullins Riley & Scarborough LLP; Jane E. Remillard, Esq.; Jill Gorny Sloper, Esq.

(57) ABSTRACT

The present disclosure provides antibodies, including isolated monoclonal antibodies, which specifically bind to Cadherin-17 with high affinity. Nucleic acid molecules encoding Cadherin-17 antibodies, expression vectors, host cells and methods for expressing the Cadherin-17 antibodies are also provided. Bispecific molecules and pharmaceutical compositions comprising the Cadherin-17 antibodies are also provided. Methods for detecting Cadherin-17, as well as methods for treating various cancers, including colorectal cancer, are disclosed.

17 Claims, 33 Drawing Sheets

(56) References Cited

OTHER PUBLICATIONS

Caldas et al. (Mol. Immunol. May 2003; 39 (15): 941-952).*
Vajdos et al. (J. Mol. Biol. Jul. 5, 2002; 320 (2): 415-428).*
De Pascalis et al. (J. Immunol. 2002; 169 (6): 3076-3084).*
Wu et al. (J. Mol. Biol. Nov. 19, 1999; 294 (1): 151-162).*
Casset et al. (Biochem. Biophys. Res. Commun. Jul. 18, 2003; 307 (1): 198-205).*
MacCallum et al. (J. Mol. Biol. Oct. 11, 1996; 262 (5): 732-745).*
Holm et al. (Mol. Immunol. Feb. 2007; 44 (6): 1075-1084).*
Gura (Science. 1997; 278: 1041-1042).*
Dennis (Nature. Aug. 7, 2006; 442: 739-741).*
Saijo et al. (Cancer Sci. Oct. 2004; 95 (10): 772-776).*
Kelland (Eur. J. Cancer. Apr. 2004; 40 (6): 827-836).*
Bergers et al. (Current Opinion in Genetics and Development. 2000; 10: 120-127).*
Lee et al. (Biochim. Biophys. Acta. Dec. 2010; 1806 (2): 138-45).*
Grötzinger et al. (Gut. Jul. 2001; 49 (1): 73-81).*
Liu et al. (Hepatology. Nov. 2009; 50 (5): 1453-63).*
Takamura et al. (Cancer Lett. Aug. 30, 2004; 212 (2): 253-9).*
Wang et al. (Clin. Cancer Res. Jan. 15, 2005; 11 (2 Pt. 1): 483-9).*
Adibi SA, "The oligopeptide transporter (Pept-1) in human intestine: biology and function.", Gastroenterology, 1997, pp. 332-340, vol. 113, No. 1.
Angres B, et al., "LI-cadherin gene expression during mouse intestinal development.", Dev. Dyn., 2001, pp. 182-193, vol. 221, No. 2.
Behrens I, et al., "Do cell culture conditions influence the carrier-mediated transport of peptides in Caco-2 cell monolayers?", Eur. J. Pharm. Sci., 2003, pp. 433-442, vol. 19, No. 5.
Behrens I, et al., "Variation of peptide transporter (PepT1 and HPT1) expression in Caco-2 cells as a function of cell origin.", J. Pharm. Sci., 2004, pp. 1743-1754, vol. 93, No. 7.
Berndorff D, et al., "Liver-intestine cadherin: molecular cloning and characterization of a novel Ca(2+)-dependent cell adhesion molecule expressed in liver and intestine.", J. Cell Biol., 1994, pp. 1353-1369, vol. 125, No. 6.
Chaturvedi P, et al., "MUC4 mucin potentiates pancreatic tumor cell proliferation, survival, and invasive properties and interferes with its interaction to extracellular matrix proteins.", Mol. Cancer Res., 2007, pp. 309-320, vol. 5, No. 4.
Danevad M, "Functional Analysis of the Murine LI-Cadherin Promoter.", Doctoral Thesis, 2004, Germany.
Dong W, et al., "Altered expression of a Li-cadherin in gastric cancer and intestinal metaplasia . . . ", Dig. Dis. Sci., 2007, pp. 536-542, vol. 52, No. 2.
Gendron FP, et al., "The CDX2 transcription factor regulates furin expression during intestinal epithelial cell differentiation.", Am. J. Physiol. Gastrointest. Liver Physiol., 2006, pp. G310-G318, vol. 290, No. 2.
Gessner R, et al., "Intestinal cell adhesion molecules. Liver-intestine cadherin.", Ann. N.Y. Acad. Sci., 2000, pp. 136-143, vol. 915.
Grotzinger C, et al., "LI-cadherin: a marker of gastric metaplasia and neoplasia.", Gut, 2001, pp. 73-81, vol. 49, No. 1.
Heiner S, et al., "Hydrophilic photolabelling of glycopeptides from the murine liver-intestine (LI) cadherin recognition domain.", Bioorg. Med. Chem., 2006, pp. 6149-6164, vol. 14, No. 18.
Herrera-Ruiz D, et al., "Spatial expression patterns of peptide transporters in the human and rat gastrointestinal tracts, Caco-2 in vitro cell culture model, and multiple human tissues.", AAPS PharmSci., 2001, pp. 100-111, vol. 3, No. 1.
Hilgendorf C, et al., "Expression of thirty-six drug transporter genes in human intestine, liver, kidney, and organotypic cell lines.", Drug Metab. Dispos., 2007, pp. 1333-1340, vol. 35, No. 8.
Hinoi T, et al., "CDX2 regulates liver intestine-cadherin expression in normal and malignant colon epithelium and intestinal metaplasia.", Gastroenterology, 2002, pp. 1565-1577, vol. 123, No. 5.
Hippo Y, et al., "Global gene expression analysis of gastric cancer by oligonucleotide microarrays.", Cancer Res., 2002, pp. 233-240, vol. 62, No. 1.

Holmes K, et al., "Genetic Mechanisms and Aberrant Gene Expression during the Development of Gastric Intestinal Metaplasia and Adenocarcinoma.", Curr. Genomics, 2007, pp. 379-397, vol. 8, No. 6.
Horsfield J, et al., "Cadherin-17 is required to maintain pronephric duct integrity during zebrafish development.", Mech. Dev., 2002, pp. 15-26, vol. 115, Nos. 1-2.
Ito R, et al., "Clinicopathological significant and prognostic influence of cadherin-17 expression in gastric cancer.", Virchows Arch., 2005, pp. 717-722, vol. 447, No. 4.
Jung R, et al., "Phylogenetic origin of LI-cadherin revealed by protein and gene structure analysis.", Cell. Mol. Life Sci., 2004, pp. 1157-1166, vol. 61, No. 10.
Kim HR, et al., "Comparative gene expression profiles of intestinal transporters in mice, rats and humans.", Pharmacol. Res., 2007, pp. 224-236, vol. 56, No. 3.
Ko S, et al., "CDX2 co-localizes with liver-intestine cadherin in intestinal metaplasia and adenocarcinoma of the stomach.", J. Pathol., 2005, pp. 615-622, vol. 205, No. 5.
Ko S, et al., "Overexpression of LI-cadherin in gastric cancer is associated with lymph node metastasis.", Biochem. Biophys. Res. Commun., 2004, pp. 562-568, vol. 319, No. 2.
Kreft B, et al., "LI-cadherin-mediated cell-cell adhesion does not require cytoplasmic interactions.", J. Cell Biol., 1997, pp. 1109-1121, vol. 136, No. 5.
Kremmidiotis G, et al., "Localization of human cadherin genes to chromosome regions exhibiting cancer-related loss of heterozygosity.", Genomics, 1998, pp. 467-471, vol. 49, No. 3.
Kuhn A, et al. "Saccharide-induced peptide conformation in glycopeptides of the recognition region of LI-cadherin.", Angew. Chem. Int. Ed. Engl., 2007, pp. 454-458, vol. 46, No. 3.
Kwak JM, et al., "The prognostic significance of E-cadherin and liver intestine-cadherin expression in colorectal cancer.", Diseases of the Colon & Rectum, 2007, pp. 1873-1880, vol. 50, No. 11.
Landowski CP, et al., "Gene expression in the human intestine and correlation with oral valacyclovir pharmacokinetic parameters.", J. Pharmacol. Exp. Ther., 2003, pp. 778-786, vol. 306, No. 2.
Lucka L, et al., "Carcinoembryonic antigen-related cell-cell adhesion molecule C-CAM is greatly increased in serum and urine of rats with liver diseases.", FEBS Lett., 1998, pp. 37-40, vol. 438, Nos. 1-2.
Motoshita J, et al., "Molecular characteristics of differentiated-type gastric carcinoma with distinct mucin phenotype: Ll-cadherin is associated with intestinal phenotype.", Pathol. Int., 2006, pp. 200-205, vol. 56, No. 4.
Ohnishi K, et al., "Lymphocyte-expressed BILL-cadherin/cadherin-17 contributes to the development of B cells at two stages.", Eur. J. Immunol., 2005, pp. 957-963, vol. 35, No. 3.
Oue N, et al., "Gene expression profile of gastric carcinoma: identification of genes and tags potentially involved in invasion, metastasis, and carcinogenesis by serial analysis of gene expression.", Cancer Res., 2004, pp. 2397-2405, vol. 64.
Ouko L, et al., "Wnt11 signaling promotes proliferation, transformation, and migration of IEC6 intestinal epithelial cells.", J. Biol. Chem., 2004, pp. 26707-26715, vol. 279, No. 25.
Park SS, et al., "Expression of liver-intestine cadherin and its correlation with lymph node metastasis in gastric cancer: can it predict N stage preoperatively?", Ann. Surg. Oncol., 2007, pp. 94-99, vol. 14, No. 1.
Reymond MA, et al., "Expression and functional proteomics studies in colorectal cancer.", Pathol. Res. Pract., 2004, pp. 119-127, vol. 200, No. 2.
Rouzier R, et al., "The subtleties of intestinal metaplasia.", Gut, 2001, p. 8, vol. 49, No. 1.
Srebrow A, et al., "The connection between splicing and cancer.", J. Cell Sci., 2006, pp. 2635-2641, vol. 119.
Thomson RB, et al., "cDNA cloning and chromosomal localization of the human and mouse isoforms of Ksp-cadherin.", Genomics, 1998, pp. 445-451, vol. 51, No. 3.
Tian MM, et al., "Phenotypic classification of gastric signet ring cell carcinoma and its relationship with clinicopathologic parameters and prognosis.", World J. Gastroenterol., 2007, pp. 3189-3198, vol. 13, No. 23.
Varghese S, et al., "Site-specific gene expression profiles and novel molecular prognostic factors in patients with lower gastrointestinal

(56) References Cited

OTHER PUBLICATIONS adenocarcinoma diffusely metastatic to liver or peritoneum.", Ann. Surg. Oncol., 2007, pp. 3460-3471, vol. 14, No. 12.

Wagner M, et al., "The (2-phenyl-2-trimethylsilyl)ethyl-(PTMSEL)-linker in the synthesis of glycopeptide partial structures of complex cell surface glycoproteins.", Chemistry, 2003, pp. 6018-6030, vol. 9, No. 24.

Wang XQ, et al., "Alternative mRNA splicing of liver intestine-cadherin in hepatocellular carcinoma.", Clin. Cancer Res., 2005, pp. 483-489, vol. 11.

Wang XQ, et al., "Liver intestine-cadherin (CDH17) haplotype is associated with increased risk of hepatocellular carcinoma.", Clin. Cancer Res., 2006, pp. 5248-5252, vol. 12, No. 17.

Ward DG, et al., "Identification of serum biomarkers for colon cancer by proteomic analysis.", British J. Cancer, 2006, pp. 1898-1905, vol. 94, No. 12.

Wendeler MW, et al., "Intestinal LI-cadherin acts as a Ca2+-dependent adhesion switch.", J. Mol. Biol., 2007, pp. 220-230, vol. 370, No. 2.

Wendeler MW, et al., "Ksp-cadherin is a functional cell-cell adhesion molecule related to LI-cadherin.", Exp. Cell Res., 2004, pp. 345-355, vol. 294, No. 2.

Wendeler MW, et al., "Unique gene structure and paralogy define the 7D-cadherin family.", Cell. Mol. Life Sci., 2006, pp. 1564-1573, vol. 63, No. 13.

Wong BW, et al., "Identification of liver-intestine cadherin in hepatocellular carcinoma-a potential disease marker.", Biochem. Biophys. Res. Commun., 2003, pp. 618-624, vol. 311, No. 3.

Yasui W, et al., "Molecular-pathological prognostic factors of gastric cancer: a review.", Gastric Cancer, 2005, pp. 86-94, vol. 8, No. 2.

Yasui W, et al., "Search for new biomarkers of gastric cancer through serial analysis of gene expression and its clinical implications.", Cancer Sci., 2004, pp. 385-392, vol. 95, No. 5.

Reymond MA, et al., "Standardized characterization of gene expression in human colorectal epithelium by two-dimensional electrophoresis.", Electrophoresis, 1997, pp. 2842-2848, vol. 18, No. 15.

Chen XT, et al., "Effect of monoclonal antibodies against LI-cadherin on the proliferation of human hepatocellular carcinoma cells.", Nan Fang Yi Ke Da Xue Xue Bao, 2009, pp. 880-883, vol. 29, No. 5. Database Medline, accession No. NLM19460698.

Anonymous, "Anti-Human Cadherin-17 Antibody," Internet R&D Systems Catalog, p. 1-1, XP002591715, Sep. 22, 2004, Retrieved form the Internet: URL: http://www.rndsystems.com/pdf/mab1032.pdf [retrieved on Jul. 12, 200] the whole document.

Anonymous, "Datasheet:MCA2998Z, Mouse Anti Human cadherin-17 Antibody," AbD Serotec Catalog, Dec. 1, 2007, p. 1-2, XP002591716, Retrieved from the Internet: URL: http://www.abdserotec.com/catalog/datasheet-MCA2998z.html, [retrieved on Jul. 12, 2010], the whole document.

Databased Medline, U.S. National Library of Medicine, Bethesda, MD, US; May 2009, Chen, Xiao-Ting et al., "Effect of Monoclonal Antibodies Against LI-Cadherin on the Proliferation of Human Hepatocellular Carcinoma Cells," XP002591720, Database Accession No. NLM19460698 Abstract & Chen, Xiao-Ting et al., "Effectof Monoclonal Antibodies Against LI-Cadherin on the Proliferation of Human Hepatocellular Carcinoma Cells," Nan Fang Yi Ke Da Xue Xue Bao = J. of Southern Medical Unviesity, vol. 29, No. 5, p. 880-883, May 2009.

Su, Min-Cheng, et al., "Cadherin-17 is a Useful Diagnostic Marker for Adenocarcinomas of the Digestive System," Modern Pathology: An Offical J. of the U.S. and Canadian Acad. of Pathology, Inc., vol. 21, No. 11, p. 1379-1386, Nov. 2008.

Takamura, Masaaki, et al., "Expression of Liver-Intestine Cadherin and its Possible Interaction with Galectin-3 in Ductal Adenocarcinoma of the Pancreas," Cancer Science, vol. 94, No. 5 p. 425-430, (May 2003).

Takamura, Masaaki, et al., "Reduced Expression of Liver-Intestine Cadherin is Associated with Progression and Lymph Node Metastasis of Human Colorectal Carcinoma," Cancer Letters, vol. 212, No. 2, p. 253-259, Aug. 30, 2004.

Brown, McKay et al., "Tolerance to Single, but Not Multiple, Amino Acid Replacements in Antibody Vh CDR2," J. Immunol., vol. 156(9):3285-3291 (1996).

R&D Systems, "Human Cadherin-17 Antibody," Monoclonal Mouse IgG1 Clone #141713, Catalog No. MAB1032, 1 page (2011).

U.S. Appl. No. 13/880,320, filed Apr. 18, 2013, Jonathan Alexander Terrett.

U.S. Appl. No. 14/549,176, filed Nov. 20, 2014, Jonathan Alexander Terrett.

U.S. Appl. No. 13/963,503, filed Aug. 9, 2013, Christian Rohlff.

U.S. Appl. No. 12/958,373, filed Dec. 1, 2010, Christian Rohlff.

U.S. Appl. No. 13/880,320, Jun. 20, 2014, Sheela Jitendra Huff.

U.S. Appl. No. 13/880,320, Apr. 3, 2014, Sheela Jitendra Huff.

U.S. Appl. No. 12/958,373, May 13, 2013, Laura B. Goddard.

U.S. Appl. No. 12/958,373, Dec. 19, 2012, Laura B. Goddard.

U.S. Appl. No. 12/958,373, Oct. 11, 2012, Laura B. Goddard.

U.S. Appl. No. 13/963,503, May 21, 2014, Laura B. Goddard.

\* cited by examiner

FIG. 1  Anti-Cadherin-17 PTA001_A1 VH

```
1    tgactgggaaaaccctggcgttacccacgctttgtacatggagaaaataaagtgaaacaa    SEQ ID NO: 59
      -  L  G  K  P  W  R  Y  P  R  F  V  H  G  E  N  K  V  K  Q     SEQ ID NO: 35

61   agcactattgcactggcactcttaccgctcttatttaccoctgtggcaaaagccgaagtg
      S  T  I  A  L  A  L  L  P  L  L  F  T  P  V  A  K  A  E  V 121  cagctgttggagactgggggaggcgtagtgaagcccggagggtcccttaaactctcctgt
      Q  L  L  E  T  G  G  G  V  V  K  P  G  G  S  L  K  L  S  C
                                      CDR1
                     ~~~~~~~~~~~~~~~~~~~~~~~~~~~~~~~~~
181  gcagcctctggattcactttcagtaactatggcatgtcttgggttcgccagactccggag   SEQ ID NO: 1
      A  A  S  G  F  T  F  S  N  Y  G  M  S  W  V  R  Q  T  P  E
                                                   CDR2
                     ~~~~~~~~~~~~~~~~~~~~~~~~~~~~~~~~~~~~~~~~~~~~   SEQ ID NO: 5
241  aagaggctggagtgggtcgcagccattaatcgtgatggtggtaccacctactatacagac
      K  R  L  E  W  V  A  A  I  N  R  D  G  G  T  T  Y  Y  T  D ~~~~~~~~~~~
301  aatgtgaagggccgattcaccatctccagagacaatgccaagaacagcctgtacctgcaa
      N  V  K  G  R  F  T  I  S  R  D  N  A  K  N  S  L  Y  L  Q ~~~~~~~~
361  atgagcagtctgaggtctgaggacacagccttgtattactgtgcaagacagttccttctc
      M  S  S  L  R  S  E  D  T  A  L  Y  Y  C  A  R  Q  F  L  L
            CDR3
     ~~~~~~~~~~~~~~~~~~~~~~~~~
421  tgggacggctggtacttcgatgtctggggcgcagggaccacggtcaccgtctcctcagcc   SEQ ID NO: 14
      W  D  G  W  Y  F  D  V  W  G  A  G  T  T  V  T  V  S  S  A 481  aaaacgacaccoccatctgtctatccactggccoctggatctgctgcccaaactaactcc
      K  T  T  P  P  S  V  Y  P  L  A  P  G  S  A  A  Q  T  N  S 541  atggtgaccctgggatgcctggtcaagggctatttccctgagccagtgacagtgacctgg
      M  V  T  L  G  C  L  V  K  G  Y  F  P  E  P  V  T  V  T  W 601  aactctggatccctgtccagcggtgtgcacaccttcccagctgtcctgcagtctgacctc
      N  S  G  S  L  S  S  G  V  H  T  F  P  A  V  L  Q  S  D  L 661  tacactctgagcagctcagtgactgtcccctccagcacctggcccagcgagaccgtcacc
      Y  T  L  S  S  S  V  T  V  P  S  S  T  W  P  S  E  T  V  T 721  tgcaacgttgcccacccggccagcagcaccaaggtggacaagaaaattgtgcccagggat
      C  N  V  A  H  P  A  S  S  T  K  V  D  K  K  I  V  P  R  D 781  tgt
      C
```

FIG. 2  Anti-Cadherin-17 PTA001_A2 VH

```
1    tgactgggaaaaccctggcgttacccacgctttgtacatggagaaaataaagtgaaacaa    SEQ ID NO: 60
      -  L  G  K  P  W  R  Y  P  R  F  V  H  G  E  N  K  V  K  Q
                                                                       SEQ ID NO: 36

61   agcactattgcactggcactcttaccgctcttatttaccoctgtggcaaaagcccaggtt
      S  T  I  A  L  A  L  L  P  L  L  F  T  P  V  A  K  A  Q  V 121  cagctgcaacagtctgacgctgagttggtgaaacctggagcttcagtgaagatatcctgc
      Q  L  Q  Q  S  D  A  E  L  V  K  P  G  A  S  V  K  I  S  C
                                      CDR1
                     ~~~~~~~~~~~~~~~~~~~~~~~~~~~~                     SEQ ID NO: 2
181  aaggtttctggctacaccttcagtgaccatgctattcactggatgagtcagagacctgga
      K  V  S  G  Y  T  F  S  D  H  A  I  H  W  M  S  Q  R  P  G
                                                      CDR2              SEQ ID NO: 6
                                         ~~~~~~~~~~~~~~~~~~~~~~~~~~~~~
241  cagggcctgaaatggattggatatatttatcctagacatggactactaactacaatgag
      Q  G  L  K  W  I  G  Y  I  Y  P  R  H  G  T  T  N  Y  N  E ~~~~~~~~~~~~~
301  aacttcaagggcaaggccacactgactgcagacacatcctccagcacagcctacatgcag
      N  F  K  G  K  A  T  L  T  A  D  T  S  S  S  T  A  Y  M  Q ~~~~~~~~~
361  ctcaacagcctgacatctgaagattctgccgtctatttctgtgcaagaatgagaaactac
      L  N  S  L  T  S  E  D  S  A  V  Y  F  C  A  R  M  R  N  Y CDR3
     ~~~~~~~~~~~~~~~~~~            SEQ ID NO: 15
421  ttctatgttatggactactggggtcaaggaacctcagtcaccgtctcctcagccaaaacg
      F  Y  V  M  D  Y  W  G  Q  G  T  S  V  T  V  S  S  A  K  T 481  acacccccatctgtctatccactggcccctggatctgctgcccaaactaactccatggtg
      T  P  P  S  V  Y  P  L  A  P  G  S  A  A  Q  T  N  S  M  V 541  accctgggatgcctggtcaagggctatttccctgagccagtgacagtgacctggaactct
      T  L  G  C  L  V  K  G  Y  F  P  E  P  V  T  V  T  W  N  S 601  ggatccctgtccagcggtgtgcacaccttcccagctgtcctgcagtctgacctctacact
      G  S  L  S  S  G  V  H  T  F  P  A  V  L  Q  S  D  L  Y  T 661  ctgagcagctcagtgactgtcccctccagcacctggcccagcgagaccgtcacctgcaac
      L  S  S  S  V  T  V  P  S  S  T  W  P  S  E  T  V  T  C  N 721  gttgcccacccggccagcagcaccaaggtggacaagaaaattgtgcccagggattgt
      V  A  H  P  A  S  S  T  K  V  D  K  K  I  V  P  R  D  C
```

FIG. 3  Anti-Cadherin-17 PTA001_A3 VH

```
1    tgactgggaaaaccctggcgttacccacgctttgtacatggagaaaataaagtgaaacaa    SEQ ID NO: 61
       -  L  G  K  P  W  R  Y  P  R  F  V  H  G  E  N  K  V  K  Q     SEQ ID NO: 37

61   agcactattgcactggcactcttaccgctcttatttacccctgtggcaaaagcccaggtt
        S  T  I  A  L  A  L  L  P  L  L  F  T  P  V  A  K  A  Q  V 121  ctgctgcaacagtctgacgctgagttggtgaaacctggggcttcagtgaagatatcctgc
        L  L  Q  Q  S  D  A  E  L  V  K  P  G  A  S  V  K  I  S  C
                                CDR1
                     ~~~~~~~~~~~~~~~~~~~~~~~~~~~~~~~         SEQ ID NO: 3
181  aaggcttctggctacaccttcactgaccatgctattcactgggtgaagcagaggcctgaa
        K  A  S  G  Y  T  F  T  D  H  A  I  H  W  V  K  Q  R  P  E
                                              CDR2     SEQ ID NO: 7
                                      ~~~~~~~~~~~~~~~~~~~~~~~~~~~~~
241  cagggcctggaatggattggatatatttatcctgaacatggaactattaagtataatgag
        Q  G  L  E  W  I  G  Y  I  Y  P  E  H  G  T  I  K  Y  N  E ~~~~~~~~~~~~~~
301  aagttcaaggggcaaggccacattgactgcagataaatcctccagcactgcctatatgcag
        K  F  K  G  K  A  T  L  T  A  D  K  S  S  T  A  Y  M  Q 361  ctcaacagcctgacatctgaggattcagcagtgtatttctgttcaagactcactaactac
        L  N  S  L  T  S  E  D  S  A  V  Y  F  C  S  R  L  T  N  Y
            CDR3
        ~~~~~~~~~~~~~~~~~~~~         SEQ ID NO: 16
421  ttctatgttatggagtattggggtcaaggaacctcagtcaccgtctcctcagccaaaacg
        F  Y  V  M  E  Y  W  G  Q  G  T  S  V  T  V  S  S  A  K  T 481  acacccccatctgtctatccactggcccctggatctgctgcccaaactaactccatggtg
        T  P  P  S  V  Y  P  L  A  P  G  S  A  A  Q  T  N  S  M  V 541  accctgggatgcctggtcaagggctatttccctgagccagtgacagtgacctggaactct
        T  L  G  C  L  V  K  G  Y  F  P  E  P  V  T  V  T  W  N  S 601  ggatccctgtccagcggtgtgcacaccttccagctgtcctgcagtctgacctctacact
        G  S  L  S  S  G  V  H  T  F  P  A  V  L  Q  S  D  L  Y  T 661  ctgagcagctcagtgactgtcccctccagcacctggcccagcgagaccgtcacctgcaac
        L  S  S  S  V  T  V  P  S  S  T  W  P  S  E  T  V  T  C  N 721  gttgcccacccggccagcagcaccaaggtggacaagaaaattgtgcccagggattgt
        V  A  H  P  A  S  S  T  K  V  D  K  K  I  V  P  R  D  C
```

FIG. 4  Anti-Cadherin-17 PTA001_A4 VH

```
1   tgactgggaaaaccctggcgttacccacgctttgtacatggagaaaataaagtgaaacaa     SEQ ID NO: 62
     -  L  G  K  P  W  R  Y  P  R  F  V  H  G  E  N  K  V  K  Q    SEQ ID NO: 38

61  agcactattgcactggcactcttaccgctcttatttaccccctgtggcaaaagccgaggtt
     S  T  I  A  L  A  L  L  P  L  L  F  T  P  V  A  K  A  E  V 121 cagctgcagcagtctgtcgctgagttggtgaaacctggagcttcagtgaagatgtcatgc
     Q  L  Q  Q  S  V  A  E  L  V  K  P  G  A  S  V  K  M  S  C
                                      CDR1
                       ~~~~~~~~~~~~~~~~~~~~~~~~~~~~~~~~~~  SEQ ID NO: 4
181 aaggtttctggctacaccctcactgaccatactattcactggatgaagcagaggcctgaa
     K  V  S  G  Y  T  L  T  D  H  T  I  H  W  M  K  Q  R  P  E
                                                  CDR2
                ~~~~~~~~~~~~~~~~~~~~~~~~~~~~~~~~~~~~~~~~~~~~  SEQ ID NO: 8
241 cagggcctggaatggattggatatatttaccctagagatggaataactgggtacaatgag
     Q  G  L  E  W  I  G  Y  I  Y  P  R  D  G  I  T  G  Y  N  E ~~~~~~~~~~~
301 aagttcaagggcaaggccacactgactgcagacacttcttccagcacagcctacatgcag
     K  F  K  G  K  A  T  L  T  A  D  T  S  S  S  T  A  Y  M  Q ~~~~~~~~~~
361 ctcaacagcctgacatctgaggattctgcagtctatttctgtgccagatggggctatagt
     L  N  S  L  T  S  E  D  S  A  V  Y  F  C  A  R  W  G  Y  S
         CDR3
    ~~~~~~~~~~~~~~~~~~~~~~~~~~~~~~~~~  SEQ ID NO: 17
421 tacaggaattacgcgtactactatgactactggggccaaggcaccactctcacagtctcc
     Y  R  N  Y  A  Y  Y  Y  D  Y  W  G  Q  G  T  T  L  T  V  S 481 tcagccaaaacgacacccccatctgtctatccactggcccctggatctgctgcccaaact
     S  A  K  T  T  P  P  S  V  Y  P  L  A  P  G  S  A  A  Q  T 541 aactccatggtgaccctgggatgcctggtcaagggctatttccctgagccagtgacagtg
     N  S  M  V  T  L  G  C  L  V  K  G  Y  F  P  E  P  V  T  V 601 acctggaactctggatccctgtccagcggtgtgcacaccttcccagctgtcctgcagtct
     T  W  N  S  G  S  L  S  S  G  V  H  T  F  P  A  V  L  Q  S 661 gacctctacactctgagcagctcagtgactgtcccctccagcacctggcccagcgagacc
     D  L  Y  T  L  S  S  S  V  T  V  P  S  S  T  W  P  S  E  T 721 gtcacctgcaacgttgcccacccggccagcagcaccaaggtggacaagaaaattgtgccc
     V  T  C  N  V  A  H  P  A  S  S  T  K  V  D  K  K  I  V  P 781 agggattgt
     R  D  C
```

FIG. 5 Anti-Cadherin-17 PTA001_A5 VH

```
1    tgactgggaaaaccctggcgttacccacgctttgtacatggagaaaataaagtgaaacaa              SEQ ID NO: 63
     -  L  G  K  P  W  R  Y  P  R  F  V  H  G  E  N  K  V  K  Q              SEQ ID NO: 39

61   agcactattgcactggcactcttaccgctcttatttacccctgtggcaaaagcccaggtt
     S  T  I  A  L  A  L  L  P  L  L  F  T  P  V  A  K  A  Q  V 121  cagctgcaacagtctgacgctgacttggtgaaacctggggcttcagtgaagatatcctgc
     Q  L  Q  Q  S  D  A  D  L  V  K  P  G  A  S  V  K  I  S  C
                                 CDR1
                        ~~~~~~~~~~~~~~~~~~~~~~~~~~~  SEQ ID NO: 3
181  aaggcttctggctacaccttcactgaccatgctattcactgggtgaaacagaggcctgaa
     K  A  S  G  Y  T  F  T  D  H  A  I  H  W  V  K  Q  R  P  E
                                                     CDR2
                        ~~~~~~~~~~~~~~~~~~~~~~~~~~~~~~~~~~~  SEQ ID NO: 7
241  cagggcctggaatggattggatatatttatcctgaacatggaactattaagtataatgag
     Q  G  L  E  W  I  G  Y  I  Y  P  E  H  G  T  I  K  Y  N  E ~~~~~~~~~~~
301  aagttcaagggcaaggccacattgactgcagataaatcctccagcactgcctatatgcag
     K  F  K  G  K  A  T  L  T  A  D  K  S  S  S  T  A  Y  M  Q 361  ctcaacagcctgacatctgaggattcagcagtgtatttctgtgcaagactcaggaactat
     L  N  S  L  T  S  E  D  S  A  V  Y  F  C  A  R  L  R  N  Y
        CDR3
     ~~~~~~~~~~~~~~~~~~  SEQ ID NO: 18
421  ttgtatattatggactactggggtcaaggaacctcagtcaccgtctcctcagccaaaacg
     L  Y  I  M  D  Y  W  G  Q  G  T  S  V  T  V  S  S  A  K  T 481  acaccccatctgtctatccactggcccctggatctgctgcccaaactaactccatggtg
     T  P  P  S  V  Y  P  L  A  P  G  S  A  A  Q  T  N  S  M  V 541  accctgggatgcctggtcaagggctatttccctgagccagtgacagtgacctggaactct
     T  L  G  C  L  V  K  G  Y  F  P  E  P  V  T  V  T  W  N  S 601  ggatccctgtccagcggtgtgcacaccttcccagctgtcctgcagtctgacctctacact
     G  S  L  S  S  G  V  H  T  F  P  A  V  L  Q  S  D  L  Y  T 661  ctgagcagctcagtgactgtcccctccagcacctgggccagcgagaccgtcacctgcaac
     L  S  S  S  V  T  V  P  S  S  T  W  P  S  E  T  V  T  C  N 721  gttgcccacccggccagcagcaccaaggtggacaagaaaattgtgcccagggattgt
     V  A  H  P  A  S  S  T  K  V  D  K  K  I  V  P  R  D  C
```

FIG. 6 Anti-Cadherin-17 PTA001_A6, PTA001_A9 and PTA001_A10 VH

```
1   tgactgggaaaaccctggcgttacccacgctttgtacatggagaaaataaagtgaaacaa   SEQ ID NO:64
     -  L  G  K  P  W  R  Y  P  R  F  V  H  G  E  N  K  V  K  Q    SEQ ID NO: 40

61  agcactattgcactggcactcttaccgctcttatttaccoctgtggcaaaagcccaggtt
     S  T  I  A  L  A  L  L  P  L  L  F  T  P  V  A  K  A  Q  V 121 cagctgcaacagtctgacgctgagttggtgaaacctggggcttcagtgaagatatcctgc
     Q  L  Q  Q  S  D  A  E  L  V  K  P  G  A  S  V  K  I  S  C
                                CDR1
                 ~~~~~~~~~~~~~~~~~~~~~~~~~~~~~~~~~  SEQ ID NO: 3
181 aaggcttctggctacaccttcactgaccatgctattcactgggtgaagcagaggcctgaa
     K  A  S  G  Y  T  F  T  D  H  A  I  H  W  V  K  Q  R  P  E
                                                    CDR2
                   ~~~~~~~~~~~~~~~~~~~~~~~~~~~~~~~~~~~~~~~~~~  SEQ ID NO: 7
241 cagggcctggaatggattggatatatttatcctgaacatggaactattaagtataatgag
     Q  G  L  E  W  I  G  Y  I  Y  P  E  H  G  T  I  K  Y  N  E ~~~~~~~~~~~~~~~
301 aagttcaagggcaaggccacattgactgcagataaatcctccagcactgcctatatgcag
     K  F  K  G  K  A  T  L  T  A  D  K  S  S  S  T  A  Y  M  Q 361 ctcaacagcctgacatctgaggattcagcagtgtatttctgttcaagactcactaactac
     L  N  S  L  T  S  E  D  S  A  V  Y  F  C  S  R  L  T  N  Y
          CDR3
     ~~~~~~~~~~~~~~~~~~~~  SEQ ID NO: 16
421 ttctatgttatggagtattggggtcaaggaacctcagtcaccgtctcctcagccaaaacg
     F  Y  V  M  E  Y  W  G  Q  G  T  S  V  T  V  S  S  A  K  T 481 acacccccatctgtctatccactggcccctggatctgctgcccaaactaactccatggtg
     T  P  P  S  V  Y  P  L  A  P  G  S  A  A  Q  T  N  S  M  V 541 accctgggatgcctggtcaagggctatttccctgagccagtgacagtgacctggaactct
     T  L  G  C  L  V  K  G  Y  F  P  E  P  V  T  V  T  W  N  S 601 ggatccctgtccagcggtgtgcacaccttcccagctgtcctgcagtctgacctctacact
     G  S  L  S  S  G  V  H  T  F  P  A  V  L  Q  S  D  L  Y  T 661 ctgagcagctcagtgactgtcccctccagcacctggcccagcgagaccgtcacctgcaac
     L  S  S  S  V  T  V  P  S  S  T  W  P  S  E  T  V  T  C  N 721 gttgcccacccggccagcagcaccaaggtggacaagaaaattgtgcccagggattgt
     V  A  H  P  A  S  S  T  K  V  D  K  K  I  V  P  R  D  C
```

FIG. 7  Anti-Cadherin-17 PTA001_A7 VH

```
1    tgactgggaaaaccctggcgttacccacgctttgtacatggagaaaataaagtgaaacaa    SEQ ID NO: 65
      -  L  G  K  P  W  R  Y  P  R  F  V  H  G  E  N  K  V  K  Q    SEQ ID NO: 41

61   agcactattgcactggcactcttaccgctcttatttaccctgtggcaaaagcccaggtt
      S  T  I  A  L  A  L  L  P  L  L  F  T  P  V  A  K  A  Q  V 121  cagctgcaacagtctgacgctgagttggtgaaacctggagcctcagtgaagatatcctgc
      Q  L  Q  Q  S  D  A  E  L  V  K  P  G  A  S  V  K  I  S  C CDR1                    SEQ ID NO: 3
                      ~~~~~~~~~~~~~~~~~~~~~~~~~~~~~~
181  aaggtttctggctacaccttcactgaccatgctattcactggatgaaacagaggcctgaa
      K  V  S  G  Y  T  F  T  D  H  A  I  H  W  M  K  Q  R  P  E CDR2
                      ~~~~~~~~~~~~~~~~~~~~~~~~~~~~~~~~~~~~~~~~~      SEQ ID NO: 9
241  cagggcctggaatggattggatatatttatcctagagatggttttactaagtacaatgag
      Q  G  L  E  W  I  G  Y  I  Y  P  R  D  G  F  T  K  Y  N  E ~~~~~~~~~~~
301  aagttcaagggcaaggccacactgactgcagacacatcctccagcacagcctacatgcag
      K  F  K  G  K  A  T  L  T  A  D  T  S  S  S  T  A  Y  M  Q ~~~~~~~~~~
361  ctcaacagcctgacatctgaggattctacagtctatttctgtgcaagaatgactaactac
      L  N  S  L  T  S  E  D  S  T  V  Y  F  C  A  R  M  T  N  Y CDR3
      ~~~~~~~~~~~~~~~~~~    SEQ ID NO: 19
421  ttctatactatggactactggggtcaaggaacctcagtcaccgtctcctcagccaaaacg
      F  Y  T  M  D  Y  W  G  Q  G  T  S  V  T  V  S  S  A  K  T 481  acacccccatctgtctatccactggcccctggatctgctgcccaaactaactccatggtg
      T  P  P  S  V  Y  P  L  A  P  G  S  A  A  Q  T  N  S  M  V 541  accctgggatgcctggtcaagggctatttccctgagccagtgacagtgacctggaactct
      T  L  G  C  L  V  K  G  Y  F  P  E  P  V  T  V  T  W  N  S 601  ggatccctgtccagcggtgtgcacaccttccagctgtcctgcagtctgacctctacact
      G  S  L  S  S  G  V  H  T  F  P  A  V  L  Q  S  D  L  Y  T 661  ctgagcagctcagtgactgtcccctccagcacctggcccagcgagaccgtcacctgcaac
      L  S  S  S  V  T  V  P  S  S  T  W  P  S  E  T  V  T  C  N 721  gttgcccacccggccagcagcaccaaggtggacaagaaaattgtgcccagggattgt
      V  A  H  P  A  S  S  T  K  V  D  K  K  I  V  P  R  D  C
```

FIG. 8  Anti-Cadherin-17 PTA001_A8 VH

```
1    tgactgggaaaaccctggcgttacccacgctttgtacatggagaaaataaagtgaaacaa     SEQ ID NO: 66
     -  L  G  K  P  W  R  Y  P  R  F  V  H  G  E  N  K  V  K  Q       SEQ ID NO:42

61   agcactattgcactggcactcttaccgctcttatttaccccgtggcaaaagcccaggtt
     S  T  I  A  L  A  L  L  P  L  L  F  T  P  V  A  K  A  Q  V 121  cagctgcaacagtctgacgctgacttggtgaaacctggggcttcagtgaagatatcctgc
     Q  L  Q  Q  S  D  A  D  L  V  K  P  G  A  S  V  K  I  S  C
                                CDR1
                     ~~~~~~~~~~~~~~~~~~~~~~~~~~~~~~~  SEQ ID NO:3
181  aaggcttctggctacaccttcactgaccatgctattcactgggtgaaacagaggcctgaa
     K  A  S  G  Y  T  F  T  D  H  A  I  H  W  V  K  Q  R  P  E
                                                CDR2
                     ~~~~~~~~~~~~~~~~~~~~~~~~~~~~~~~~~~~~  SEQ ID NO:7
241  cagggcctggaatggattggatatatttatcctgaacatggaactattaagtataatgag
     Q  G  L  E  W  I  G  Y  I  Y  P  E  H  G  T  I  K  Y  N  E 301  aagttcaagggcaaggccacattgactgcagataaatcctccagcactgcctatatgcag
     K  F  K  G  K  A  T  L  T  A  D  K  S  S  S  T  A  Y  M  Q 361  ctcaacagcctgacatctgaggattcagcagtgtatttctgttcaagactcactaactac
     L  N  S  L  T  S  E  D  S  A  V  Y  F  C  S  R  L  T  N  Y
             CDR3
     ~~~~~~~~~~~~~~~~~~~~~ SEQ ID NO:16
421  ttctatgttatggagtattgggggtcaaggaacctcagtcaccgtctcctcagccaaaacg
     F  Y  V  M  E  Y  W  G  Q  G  T  S  V  T  V  S  S  A  K  T 481  acaccccctcatctgtctatccactggcccctggatctgctgcccaaactaactccatggtg
     T  P  P  S  V  Y  P  L  A  P  G  S  A  A  Q  T  N  S  M  V 541  accctgggatgcctggtcaagggctatttccctgagccagtgacagtgacctggaactct
     T  L  G  C  L  V  K  G  Y  F  P  E  P  V  T  V  T  W  N  S 601  ggatccctgtccagcggtgtgcacaccttcccagctgtcctgcagtctgacctctacact
     G  S  L  S  S  G  V  H  T  F  P  A  V  L  Q  S  D  L  Y  T 661  ctgagcagctcagtgactgtcccctccagcacctggcccagcgagaccgtcacctgcaac
     L  S  S  S  V  T  V  P  S  S  T  W  P  S  E  T  V  T  C  N 721  gttgcccacccggccagcagcaccaaggtggacaagaaaattgtgcccagggattgt
     V  A  H  P  A  S  S  T  K  V  D  K  K  I  V  P  R  D  C
```

FIG. 9  Anti-Cadherin-17 PTA001_A11 VH

```
1   tgactgggaaaaccctggcgttacccacgctttgtacatggagaaaataaagtgaaacaa    SEQ ID NO:67
     - L  G  K  P  W  R  Y  P  R  F  V  H  G  E  N  K  V  K  Q
                                                                     SEQ ID NO:43

61  agcactattgcactggcactcttaccgctcttatttacccctgtggcaaaagcccaggtt
     S  T  I  A  L  A  L  L  P  L  L  F  T  P  V  A  K  A  Q  V 121 cagctgcaacagtctgacgctgagttggtgaaacctggggcttcagtgaagatatcctgc
     Q  L  Q  Q  S  D  A  E  L  V  K  P  G  A  S  V  K  I  S  C
                          CDR1
         ~~~~~~~~~~~~~~~~~~~~~~~~~~~~~~  SEQ ID NO:3
181 aaggcttctggctacaccttcactgaccatgctattcactgggtgaagcagaggcctgaa
     K  A  S  G  Y  T  F  T  D  H  A  I  H  W  V  K  Q  R  P  E
                                             CDR2
        ~~~~~~~~~~~~~~~~~~~~~~~~~~~~~~~~~~~~~~~~~~  SEQ ID NO:10
241 cagggcctggaatggattggatatatttatcctgaacatggtagtattacgtataatgag
     Q  G  L  E  W  I  G  Y  I  Y  P  E  H  G  S  I  T  Y  N  E ~~~~~~~~~~~
301 aagttcaagggcaaggccacattgactgcagataaatcctccagtactgtctatatgcac
     K  F  K  G  K  A  T  L  T  A  D  K  S  S  S  T  V  Y  M  H ~~~~~~~~
361 ctcaatagcctgacatctgaggattcagcagtgtatttctgtgcaagactcaggaactac
     L  N  S  L  T  S  E  D  S  A  V  Y  F  C  A  R  L  R  N  Y
        CDR3
     ~~~~~~~~~~~~~~~~~~~  SEQ ID NO:20
421 ttgtatgttatggactactggggtcaaggaacctcagtcaccgtctcctcagccaaaacg
     L  Y  V  M  D  Y  W  G  Q  G  T  S  V  T  V  S  S  A  K  T 481 acacccccatctgtctatccactggcccctggatctgctgcccaaactaactccatggtg
     T  P  P  S  V  Y  P  L  A  P  G  S  A  A  Q  T  N  S  M  V 541 accctgggatgcctggtcaagggctatttccctgagccagtgacagtgacctggaactct
     T  L  G  C  L  V  K  G  Y  F  P  E  P  V  T  V  T  W  N  S 601 ggatccctgtccagcggtgtgcacaccttcccagctgtcctgcagtctgacctctacact
     G  S  L  S  S  G  V  H  T  F  P  A  V  L  Q  S  D  L  Y  T 661 ctgagcagctcagtgactgtcccctccagcacctggcccagcgagaccgtcacctgcaac
     L  S  S  S  V  T  V  P  S  S  T  W  P  S  E  T  V  T  C  N 721 gttgcccacccggccagcagcaccaaggtggacaagaaaattgtgcccagggattgt
     V  A  H  P  A  S  S  T  K  V  D  K  K  I  V  P  R  D  C
```

FIG. 10   Anti-Cadherin-17 PTA001_A12 VH

```
1    tgactgggaaaaccctggcgttacccacgctttgtacatggagaaaataaagtgaaacaa     SEQ ID NO:68
     -  L  G  K  P  W  R  Y  P  R  F  V  H  G  E  N  K  V  K  Q
                                                                     SEQ ID NO:44

61   agcactattgcactggcactcttaccgctcttatttaccccgtgtggcaaaagcccaggtt
     S  T  I  A  L  A  L  L  P  L  L  F  T  P  V  A  K  A  Q  V 121  cagctgcaacagtctgaggctgagcttgtgaagcctggggcttcagtgaagctgtcctgc
     Q  L  Q  Q  S  E  A  E  L  V  K  P  G  A  S  V  K  L  S  C
                          CDR1
                ~~~~~~~~~~~~~~~~~~~~~~~~~~~~~~~~  SEQ ID NO:3
181  aaggcttctggctacaccttcactgaccatgctattcactggatgaaacagaggcctgaa
     K  A  S  G  Y  T  F  T  D  H  A  I  H  W  M  K  Q  R  P  E
                                                         CDR2
                 ~~~~~~~~~~~~~~~~~~~~~~~~~~~~~~~~~~~~~~~~~~~~~~~~ SEQ ID NO:11
241  cagggcctggaatggattggatatatatctaccccagagatgattttgctaaggtgaatgag
     Q  G  L  E  W  I  G  Y  I  Y  P  R  D  D  F  A  K  V  N  E ~~~~~~~~~~
301  aagttcaagggcaaggccacactgacagcagacacatcctccagcacagcctacatgcag
     K  F  K  G  K  A  T  L  T  A  D  T  S  S  S  T  A  Y  M  Q ~~~~~~~~~~
361  ctcaacagcctgacatctgaggattctgcagtctatttctgtgcaagaatgactaactac
     L  N  S  L  T  S  E  D  S  A  V  Y  F  C  A  R  M  T  N  Y
                CDR3
     ~~~~~~~~~~~~~~~~~~~~~~~~~~  SEQ ID NO:21
421  ctctatattatggactactggggtcaaggaacctcagtcaccgtctcctcagccaaaacg
     L  Y  I  M  D  Y  W  G  Q  G  T  S  V  T  V  S  S  A  K  T 481  acacccccatctgtctatccactggcccctggatctgctgcccaaactaactccatggtg
     T  P  P  S  V  Y  P  L  A  P  G  S  A  A  Q  T  N  S  M  V 541  accctgggatgcctggtcaagggctatttccctgagccagtgacagtgacctggaactct
     T  L  G  C  L  V  K  G  Y  F  P  E  P  V  T  V  T  W  N  S 601  ggatccctgtccagcggtgtgcacaccttcccagctgtcctgcagtctgacctctacact
     G  S  L  S  S  G  V  H  T  F  P  A  V  L  Q  S  D  L  Y  T 661  ctgagcagctcagtgactgtcccctccagcacctggcccagcgagaccgtcacctgcaac
     L  S  S  S  V  T  V  P  S  S  T  W  P  S  E  T  V  T  C  N 721  gttgcccacccggccagcagcaccaaggtggacaagaaaattgtgcccagggattgt
     V  A  H  P  A  S  S  T  K  V  D  K  K  I  V  P  R  D  C
```

FIG. 11    Anti-Cadherin-17 PTA001_A13 VH

```
1    tgactgggaaaaccctggcgttacccacgctttgtacatggagaaaataaagtgaaacaa    SEQ ID NO:69
     -  L  G  K  P  W  R  Y  P  R  F  V  H  G  E  N  K  V  K  Q     SEQ ID NO:45

61   agcactattgcactggcactcttaccgctcttatttaccctgtggcaaaagcccaggtt
     S  T  I  A  L  A  L  L  P  L  L  F  T  P  V  A  K  A  Q  V 121  cagctgcaacagtctgacgctgagttggtgaaacctggggcttcagtgaagatatcctgc
     Q  L  Q  Q  S  D  A  E  L  V  K  P  G  A  S  V  K  I  S  C
                                  CDR1
                     ~~~~~~~~~~~~~~~~~~~~~~~~~~~~~  SEQ ID NO:3
181  aaggcttctggctacaccttcactgaccatgctattcactgggtgaagcagaggcctgaa
     K  A  S  G  Y  T  F  T  D  H  A  I  H  W  V  K  Q  R  P  E
                                                  CDR2
                 ~~~~~~~~~~~~~~~~~~~~~~~~~~~~~~~~~~~~~~~  SEQ ID NO:12
241  cagggcctggaatggattggatatatttatcctgaacatggtactattacgtataatgag
     Q  G  L  E  W  I  G  Y  I  Y  P  E  H  G  T  I  T  Y  N  E ~~~~~~~~~~~~
301  aagttcaagggcaaggccacattgactgcagataaatcctccagtactgtctatatgcac
     K  F  K  G  K  A  T  L  T  A  D  K  S  S  S  T  V  Y  M  H ~~~~~~~~~~
361  ctcaatagcctgacatctgaggattcagcagtgtatttctgtgcaagactcaggaactat
     L  N  S  L  T  S  E  D  S  A  V  Y  F  C  A  R  L  R  N  Y
         CDR3
     ~~~~~~~~~~~~~~~~~~~~~  SEQ ID NO:18
421  ttgtatattatggactactggggtcaaggaacctcagtcaccgtctcctcagccaaaacg
     L  Y  I  M  D  Y  W  G  Q  G  T  S  V  T  V  S  S  A  K  T 481  acaccccatctgtctatccactggcccccggatctgctgcccaaactaactccatggtg
     T  P  P  S  V  Y  P  L  A  P  G  S  A  A  Q  T  N  S  M  V 541  accctgggatgcctggtcaagggctatttccctgagccagtgacagtgacctggaactct
     T  L  G  C  L  V  K  G  Y  F  P  E  P  V  T  V  T  W  N  S 601  ggatccctgtccagcggtgtgcacaccttccagctgtcctgcagtctgacctctacact
     G  S  L  S  S  G  V  H  T  F  P  A  V  L  Q  S  D  L  Y  T 661  ctgagcagctcagtgactgtcccctccagcacctggcccagcgagaccgtcacctgcaac
     L  S  S  S  V  T  V  P  S  S  T  W  P  S  E  T  V  T  C  N 721  gttgcccaccggccagcagcaccaaggtggacaagaaaattgtgcccagggattgt
     V  A  H  P  A  S  S  T  K  V  D  K  K  I  V  P  R  D  C
```

FIG. 12  Anti-Cadherin-17 PTA001_A14 VH

```
  1  tgactgggaaaaccctggcgttacccacgctttgtacatggagaaaataaagtgaaacaa    SEQ ID NO:70
        -  L  G  K  P  W  R  Y  P  R  F  V  H  G  E  N  K  V  K  Q
                                                                    SEQ ID NO:46

61  agcactattgcactggcactcttaccgctcttatttaccgctgtggcaaaagcccaggtt
         S  T  I  A  L  A  L  L  P  L  L  F  T  P  V  A  K  A  Q  V 121  cagctgcaacagtctgacgccgcgttggtgaaacctggagcttcagtgaagatatcgtgc
         Q  L  Q  Q  S  D  A  A  L  V  K  P  G  A  S  V  K  I  S  C
                                               CDR1
                                ~~~~~~~~~~~~~~~~~~~~~~~~~~~~~~~    SEQ ID NO:2
181  aaggtttctggctacaccttcagtgaccatgctattcactggatgaagcagaggcctgaa
         K  V  S  G  Y  T  F  S  D  H  A  I  H  W  M  K  Q  R  P  E
                                                                   CDR2
                                                 ~~~~~~~~~~~~~~~~~~~~~~~~~~~~~~  SEQ ID NO:13
241  cagggcctggaatggattggatatatttttcctagagatgcttttagtttgaacaatgag
         Q  G  L  E  W  I  G  Y  I  F  P  R  D  A  F  S  L  N  N  E ~~~~~~~~~~~
301  aagttcaagggcaaggccacactgagtgcagacacatcctccagcacagcctacatggag
         K  F  K  G  K  A  T  L  S  A  D  T  S  S  S  T  A  Y  M  E ~~~~~~~~~~
361  ctcaccagcctgacatttgaggattctgcagtctatttctgtgcaagaatgagaaactac
         L  T  S  L  T  F  E  D  S  A  V  Y  F  C  A  R  M  R  N  Y
            CDR3
         ~~~~~~~~~~~~~~~~~~~~~    SEQ ID NO:15
421  ttctatgttatggactactggggtcaaggaacctcagtcaccgtctcctcagccaaaacg
         F  Y  V  M  D  Y  W  G  Q  G  T  S  V  T  V  S  S  A  K  T 481  acacccccatctgtctatacactggcccctggatctgctgcccaaactaactccatggtg
         T  P  P  S  V  Y  T  L  A  P  G  S  A  A  Q  T  N  S  M  V 541  accctgggatgcctggtcaagggctatttccctgagccagtgacagtgacctggaactct
         T  L  G  C  L  V  K  G  Y  F  P  E  P  V  T  V  T  W  N  S 601  ggatccctgtccagcggtgtgcacaccttcccagctgtcctgcagtctgacctctacact
         G  S  L  S  S  G  V  H  T  F  P  A  V  L  Q  S  D  L  Y  T 661  ctgagcagctcagtgactgtcccctccagcacctggcccagcgagaccgtcacctgcaac
         L  S  S  S  V  T  V  P  S  S  T  W  P  S  E  T  V  T  C  N 721  gttgcccacccggccagcagcaccaaggtggacaagaaaattgtgcccagggattgt
         V  A  H  P  A  S  S  T  K  V  D  K  K  I  V  P  R  D  C
```

FIG. 13 Anti-Cadherin-17 PTA001_A1 VK

```
1    taagattagcggatcctacctgacgcttttttatcgcaactctctactgtttctccatacc    SEQ ID NO:71
         -   -   -  R  I  L  P  D  A  F  Y  R  N  S  L  L  F  L  H  T      SEQ ID NO:47

61   cgttttttggatggagtgaaacgatgaaatacctattgcctacggcagccgctggattg
      R  F  F  G  W  S  E  T  M  K  Y  L  L  P  T  A  A  A  G  L 121  ttattactcgctgcccaaccagccatggccgatgttgtgctgacccagactccactctcc
      L  L  L  A  A  Q  P  A  M  A  D  V  V  L  T  Q  T  P  L  S 181  ctgcctgtcactcttggagatcaagcctccatctcttgcagatctagtcagagccttta
      L  P  V  T  L  G  D  Q  A  S  I  S  C  R  S  S  Q  S  L  L
                                         CDR1
                        ~~~~~~~~~~~~~~~~~~~~~~~~~~  SEQ ID NO:22
241  cacagtaatggaaacacctatttacattggtacctgctgaagccaggccagtctccaaag
      H  S  N  G  N  T  Y  L  H  W  Y  L  L  K  P  G  Q  S  P  K
                              CDR2
                  ~~~~~~~~~~~~~~~~~~~~~~~~  SEQ ID NO:28
301  ctcctgatctacaaagtttccaaccgatttctggggtcccagacaggttcagtggcagt
      L  L  I  Y  K  V  S  N  R  F  S  G  V  P  D  R  F  S  G  S 361  ggatcagggacagatttcacactcaagatcaccagagtggaggctgaggatctgggagtt
      G  S  G  T  D  F  T  L  K  I  T  R  V  E  A  E  D  L  G  V
                              CDR3
                  ~~~~~~~~~~~~~~~~~~~~~~  SEQ ID NO:32
421  tatttctgctctcaaagtacacatgtgctcacgttcggtgctgggaccaagctggagctg
      Y  F  C  S  Q  S  T  H  V  L  T  F  G  A  G  T  K  L  E  L 481  aaacgggctgatgctgcaccaactgtatccatcttcccaccatccagtgagcagttaaca
      K  R  A  D  A  A  P  T  V  S  I  F  P  P  S  S  E  Q  L  T 541  tctggaggtgcctcagtcgtgtgcttcttgaacaacttctacccaaagacatcaatgtc
      S  G  G  A  S  V  V  C  F  L  N  N  F  Y  P  K  D  I  N  V 601  aagtggaagattgatggcagtgaacgacaaaatggcgtcctgaacagttggactgatcag
      K  W  K  I  D  G  S  E  R  Q  N  G  V  L  N  S  W  T  D  Q 661  gacagcaaagacagcacctacagcatgagcagcaccctcacgttgaccaaggacgagtat
      D  S  K  D  S  T  Y  S  M  S  S  T  L  T  L  T  K  D  E  Y 721  gaacgacataacagctatacctgtgaggccactcacaagacatcaacttcacccattgtc
      E  R  H  N  S  Y  T  C  E  A  T  H  K  T  S  T  S  P  I  V 781  aagagcttcaacaggaatgagtcttatccatatgatgtgccagattatgcgagctaa
      K  S  F  N  R  N  E  S  Y  P  Y  D  V  P  D  Y  A  S  -
```

FIG. 14 Anti-Cadherin-17 PTA001_A2 and PTA001_A3 VK

```
1    taagattagcggatcctacctgacgcttttatcgcaactctctactgtttctccatacc   SEQ ID NO:72
              -   -   -   R   I   L   P   D   A   F   Y   R   N   S   L   L   F   L   H   T     SEQ ID NO:48

61   cgttttttggatggagtgaaacgatgaaatacctattgcctacggcagccgctggattg
      R   F   F   G   W   S   E   T   M   K   Y   L   L   P   T   A   A   A   G   L 121  ttattactcgctgcccaaccagccatggccgatattgtgatgacccaggctgcaccctct
      L   L   L   A   A   Q   P   A   M   A   D   I   V   M   T   Q   A   A   P   S 181  gtacctgtcactcctggagagtcagtatccatctcctgcacgtctagtaagagtctcctg
      V   P   V   T   P   G   E   S   V   S   I   S   C   T   S   S   K   S   L   L
              CDR1
     ~~~~~~~~~~~~~~~~~~~~~~~~~~~~~~~  SEQ ID NO:23
241  cgtagtaatggcaacacttacttgtattggttcctgcagaggccaggccagtctcctcag
      R   S   N   G   N   T   Y   L   Y   W   F   L   Q   R   P   G   Q   S   P   Q
                          CDR2
     ~~~~~~~~~~~~~~~~~~~~~~~~  SEQ ID NO:29
301  ctcctgatatatcggatgtccaaccttgcctcgggagtcccagacaggttcagtggcagt
      L   L   I   Y   R   M   S   N   L   A   S   G   V   P   D   R   F   S   G   S 361  gggtcaggaactgctttcacactgagaatcagtagagtggaggctgaggatgtgggtgtt
      G   S   G   T   A   F   T   L   R   I   S   R   V   E   A   E   D   V   G   V
                      CDR3
     ~~~~~~~~~~~~~~~~~~~~~~~~~~~~  SEQ ID NO:33
421  tattactgtatgcaacatctagaatatcctttcacgttcggctcggggacaaagttggaa
      Y   Y   C   M   Q   H   L   E   Y   P   F   T   F   G   S   G   T   K   L   E 481  ataaaacgggctgatgctgcaccaactgtatccatcttcccaccatccagtgagcagtta
      I   K   R   A   D   A   A   P   T   V   S   I   F   P   P   S   S   E   Q   L 541  acatctggaggtgcctcagtcgtgtgcttcttgaacaacttctaccccaaagacatcaat
      T   S   G   G   A   S   V   V   C   F   L   N   N   F   Y   P   K   D   I   N 601  gtcaagtggaagattgatggcagtgaacgacaaaatggcgtcctgaacagttggactgat
      V   K   W   K   I   D   G   S   E   R   Q   N   G   V   L   N   S   W   T   D 661  caggacagcaaagacagcacctacagcatgagcagcaccctcacgttgaccaaggacgag
      Q   D   S   K   D   S   T   Y   S   M   S   S   T   L   T   L   T   K   D   E 721  tatgaacgacataacagctatacctgtgaggccactcacaagacatcaacttcacccatt
      Y   E   R   H   N   S   Y   T   C   E   A   T   H   K   T   S   T   S   P   I 781  gtcaagagcttcaacaggaatgagtcttatccatatgatgtgccagattatgcgagctaa
      V   K   S   F   N   R   N   E   S   Y   P   Y   D   V   P   D   Y   A   S   -
```

FIG. 15  Anti-Cadherin-17 PTA001_A4 VK

```
1    taagattagcggatcctacctgacgcttttatcgcaactctctactgtttctccatacc       SEQ ID NO:73
       -   -   -   R  I  L  P  D  A  F  Y  R  N  S  L  L  F  L  H  T    SEQ ID NO:49

61   cgttttttggatggagtgaaacgatgaaatacctattgcctacggcagccgctggattg
       R  F  F  G  W  S  E  T  M  K  Y  L  L  P  T  A  A  A  G  L 121  ttattactcgctgcccaaccagccatggccgacatcgttatgtctcagtctccatcctcc
       L  L  L  A  A  Q  P  A  M  A  D  I  V  M  S  Q  S  P  S  S 181  ctagctgtgtcagttggagagaaggttactatgagctgcaagtccagccagagccttta
       L  A  V  S  V  G  E  K  V  T  M  S  C  K  S  S  Q  S  L  L
                                            CDR1
                                  ~~~~~~~~~~~~~~~~~~~~~~~~~~~~  SEQ ID NO:24
241  catagtagcaatcaaaagaactacttggcctggtaccagcagaaaccagggcagtctcct
       H  S  S  N  Q  K  N  Y  L  A  W  Y  Q  Q  K  P  G  Q  S  P
                              CDR2
                    ~~~~~~~~~~~~~~~~~~~~~~~~~  SEQ ID NO:30
301  aaagtgctgatttactgggcatccactagagaatctggggtccctgatcgcttcacaggc
       K  V  L  I  Y  W  A  S  T  R  E  S  G  V  P  D  R  F  T  G 361  agtggatctgggacagatttcactctcaccatcaccagtgtgaagtctgaagacctggca
       S  G  S  G  T  D  F  T  L  T  I  T  S  V  K  S  E  D  L  A
                              CDR3
                    ~~~~~~~~~~~~~~~~~~~~~~~~~  SEQ ID NO:34
421  gtttattactgtcagcaatattatagctatccgtggacgttcggtggcggcaccaggctg
       V  Y  Y  C  Q  Q  Y  Y  S  Y  P  W  T  F  G  G  G  T  R  L 481  gaaatcaaacgggctgatgctgcaccaactgtatccatcttcccaccatccagtgagcag
       E  I  K  R  A  D  A  A  P  T  V  S  I  F  P  P  S  S  E  Q 541  ttaacatctggaggtgcctcagtcgtgtgcttcttgaacaacttctaccccaaagacatc
       L  T  S  G  G  A  S  V  V  C  F  L  N  N  F  Y  P  K  D  I 601  aatgtcaagtggaagattgatggcagtgaacgacaaaatggcgtcctgaacagttggact
       N  V  K  W  K  I  D  G  S  E  R  Q  N  G  V  L  N  S  W  T 661  gatcaggacagcaaagacagcacctacagcatgagcagcacctcacgttgaccaaggac
       D  Q  D  S  K  D  S  T  Y  S  M  S  S  T  L  T  L  T  K  D 721  gagtatgaacgacataacagctatacctgtgaggccactcacaagacatcaacttcaccc
       E  Y  E  R  H  N  S  Y  T  C  E  A  T  H  K  T  S  T  S  P 781  attgtcaagagcttcaacaggaatgagtcttatccatatgatgtgccagattatgcgagc
       I  V  K  S  F  N  R  N  E  S  Y  P  Y  D  V  P  D  Y  A  S 841  taa
```

FIG. 16  Anti-Cadherin-17 PTA001_A5 VK

```
1    taagattagcggatcctacctgacgcttttatcgcaactctctactgtttctccatacc    SEQ ID NO:74
         -   -   -   R   I   L   P   D   A   F   Y   R   N   S   L   L   F   L   H   T    SEQ ID NO:50

61   cgttttttggatggagtgaaacgatgaaatacctattgcctacggcagccgctggattg
         R   F   F   G   W   S   E   T   M   K   Y   L   L   P   T   A   A   A   G   L 121  ttattactcgctgcccaaccagccatggccgatattgtgatgacccaggctgcaccctct
         L   L   L   A   A   Q   P   A   M   A   D   I   V   M   T   Q   A   A   P   S 181  gtacctgtcactcctggagagtcagtatccatctcctgcaggtctagtaagagtctcctg
         V   P   V   T   P   G   E   S   V   S   I   S   C   R   S   S   K   S   L   L CDR1
     ~~~~~~~~~~~~~~~~~~~~~~~~    SEQ ID NO:25
241  cgcagtaatggcaacacttacttgtattggttcctgcagaggccaggccagtctcctcag
         R   S   N   G   N   T   Y   L   Y   W   F   L   Q   R   P   G   Q   S   P   Q CDR2
          ~~~~~~~~~~~~~~~~~~~~~    SEQ ID NO:31
301  ctcctgatatatcggctgtccaaccttgcctcaggagtcccagacaggttcagtggcagt
         L   L   I   Y   R   L   S   N   L   A   S   G   V   P   D   R   F   S   G   S 361  gggtctggaactgctttcacactgagaatcagtagagtggaggctgaggatgtgggtgtt
         G   S   G   T   A   F   T   L   R   I   S   R   V   E   A   E   D   V   G   V CDR3
          ~~~~~~~~~~~~~~~~~~~~~~~~~~~    SEQ ID NO:33
421  tattactgtatgcaacatctagaatatcctttcacattcggctcggggacaaagttggaa
         Y   Y   C   M   Q   H   L   E   Y   P   F   T   F   G   S   G   T   K   L   E 481  ataaaacgggctgatgctgcaccaactgtatccatcttccaccatccagtgagcagtta
         I   K   R   A   D   A   A   P   T   V   S   I   F   P   P   S   S   E   Q   L 541  acatctggaggtgcctcagtcgtgtgcttcttgaacaacttctaccccaaagacatcaat
         T   S   G   G   A   S   V   V   C   F   L   N   N   F   Y   P   K   D   I   N 601  gtcaagtggaagattgatggcagtgaacgacaaaatggcgtcctgaacagttggactgat
         V   K   W   K   I   D   G   S   E   R   Q   N   G   V   L   N   S   W   T   D 661  caggacagcaaagacagcacctacagcatgagcagcaccctcacgttgaccaaggacgag
         Q   D   S   K   D   S   T   Y   S   M   S   S   T   L   T   L   T   K   D   E 721  tatgaacgacataacagctatacctgtgaggccactcacaagacatcaacttcacccatt
         Y   E   R   H   N   S   Y   T   C   E   A   T   H   K   T   S   T   S   P   I 781  gtcaagagcttcaacaggaatgagtcttatccatatgatgtgccagattatgcgagctaa
         V   K   S   F   N   R   N   E   S   Y   P   Y   D   V   P   D   Y   A   S   -
```

FIG. 17  Anti-Cadherin-17 PTA001_A6 VK

```
1    taagattagcggatcctacctgacgcttttatcgcaactctctactgtttctccatacc    SEQ ID NO:75
       -  -  -  R  I  L  P  D  A  F  Y  R  N  S  L  L  F  L  H  T
                                                                       SEQ ID NO:51

61   cgttttttggatggagtgaaacgataaaatacctattgcctacggcagccgctggattg
      R  F  F  G  W  S  E  T  I  K  Y  L  L  P  T  A  A  A  G  L 121  ttattactcgctgcccaaccagccatggccgatattgtgatgacccaggctgcaccctct
      L  L  L  A  A  Q  P  A  M  A  D  I  V  M  T  Q  A  A  P  S 181  gtacctgtcactcctggagagtcagtatccatctcctgcacgtctagtaagagtctcctg
      V  P  V  T  P  G  E  S  V  S  I  S  C  T  S  S  K  S  L  L
```
CDR1
~~~~~~~~~~~~~~~~~~~~~~~~~~~~ SEQ ID NO:23
```
241  cgtagtaatggcaacacttacttgtattggttcctgcagaggccaggccagtctcctcag
      R  S  N  G  N  T  Y  L  Y  W  F  L  Q  R  P  G  Q  S  P  Q
```
CDR2
~~~~~~~~~~~~~~~~~~~~~~~~~~ SEQ ID NO:29
```
301  ctcctgatatatcggatgtccaaccttgcctcgggagtcccagacaggttcagtggcagt
      L  L  I  Y  R  M  S  N  L  A  S  G  V  P  D  R  F  S  G  S 361  gggtcaggaactgctttcacactgagaatcagtagagtggaggctgaggatgtgggtgtt
      G  S  G  T  A  F  T  L  R  I  S  R  V  E  A  E  D  V  G  V
```
CDR3
~~~~~~~~~~~~~~~~~~~~~~~~~~~~~ SEQ ID NO:33
```
421  tattactgtatgcaacatctagaatatcctttcacgttcggctcggggacaaagttggaa
      Y  Y  C  M  Q  H  L  E  Y  P  F  T  F  G  S  G  T  K  L  E 481  ataaaacgggctgatgctgcaccaactgtatccatcctcccaccatccagtgagcagtta
      I  K  R  A  D  A  A  P  T  V  S  I  L  P  P  S  S  E  Q  L 541  acatctggaggtgcctcagtcgtgtgcttcttgaacaacttctaccccaaagacatcaat
      T  S  G  G  A  S  V  V  C  F  L  N  N  F  Y  P  K  D  I  N 601  gtcaagtggaagattgatggcagtgaacgacaaaatggcgtcctgaacagttggactgat
      V  K  W  K  I  D  G  S  E  R  Q  N  G  V  L  N  S  W  T  D 661  caggacagcaaagacagcacctacagcatgagcagcaccctcacgttgaccaaggacgag
      Q  D  S  K  D  S  T  Y  S  M  S  S  T  L  T  L  T  K  D  E 721  tatgaacgacataacagctatacctgtgaggccactcacaagacatcaacttcacccatt
      Y  E  R  H  N  S  Y  T  C  E  A  T  H  K  T  S  T  S  P  I 781  gtcaagagcttcaacaggaatgagtcttatccatatgatgtgccagattatgcgagctaa
      V  K  S  F  N  R  N  E  S  Y  P  Y  D  V  P  D  Y  A  -
```

FIG. 18  Anti-Cadherin-17 PTA001_A7 VK

```
1    taagattagcggatcctacctgacgcttttatcgcaactctctactgtttctccatacc    SEQ ID NO:76
         -   -   -   R   I   L   P   D   A   F   Y   R   N   S   L   L   F   L   H   T       SEQ ID NO:52

61   cgttttttggatggagtgaaacgatgaaataccctattgcctacggcagccgctggattg
         R   F   F   G   W   S   E   T   M   K   Y   L   L   P   T   A   A   A   G   L 121  ttattactcgctgcccaaccagccatggccgatattgtgatgacccaggctgcaccctct
         L   L   L   A   A   Q   P   A   M   A   D   I   V   M   T   Q   A   A   P   S 181  gtacctgtcactcctggagagtcagtttccatctcctgcaggtcttctaagagtctcctg
         V   P   V   T   P   G   E   S   V   S   I   S   C   R   S   S   K   S   L   L
                                                         CDR1
                                                                         SEQ ID NO:26
241  cgtactaatggcaacacttacttgcattggttcctgcagaggccaggccagtctcctcag
         R   T   N   G   N   T   Y   L   H   W   F   L   Q   R   P   G   Q   S   P   Q
                                 CDR2
                                                 SEQ ID NO:29
301  ctcctgatatatcggatgtccaaccttgcctcaggagtcccagacaggttcagtggcagt
         L   L   I   Y   R   M   S   N   L   A   S   G   V   P   D   R   F   S   G   S 361  gggtcaggaactgttttcacactgagaatcagtagagtggaggctgaggatgtgggtgtt
         G   S   G   T   V   F   T   L   R   I   S   R   V   E   A   E   D   V   G   V
                                         CDR3
                                                                 SEQ ID NO:33
421  tattactgtatgcaacatctagaatatccattcacgttcggctcggggacaaagttggaa
         Y   Y   C   M   Q   H   L   E   Y   P   F   T   F   G   S   G   T   K   L   E 481  ataaaagggctgatgctgcaccaactgtatccatcttcccaccatccagtgagcagtta
         I   K   R   A   D   A   A   P   T   V   S   I   F   P   P   S   S   E   Q   L 541  acatctggaggtgcctcagtcgtgtgcttcttgaacaacttctaccccaaagacatcaat
         T   S   G   G   A   S   V   V   C   F   L   N   N   F   Y   P   K   D   I   N 601  gtcaagtggaagattgatggcagtgaacgacaaaatggcgtcctgaacagttggactgat
         V   K   W   K   I   D   G   S   E   R   Q   N   G   V   L   N   S   W   T   D 661  caggacagcaaagacagcacctacagcatgagcagcaccctcacgttgaccaaggacgag
         Q   D   S   K   D   S   T   Y   S   M   S   S   T   L   T   L   T   K   D   E 721  tatgaacgacataacagctatacctgtgaggccactcacaagacatcaacttcacccatt
         Y   E   R   H   N   S   Y   T   C   E   A   T   H   K   T   S   T   S   P   I 781  gtcaagagcttcaacaggaatgagtcttatccatatgatgtgccagattatgcgagctaa
         V   K   S   F   N   R   N   E   S   Y   P   Y   D   V   P   D   Y   A   -
```

FIG. 19 Anti-Cadherin-17 PTA001_A8 VK

```
1   taagattagcggatcctaccttacgcttttatcgcaactctctactgtttctccatacc      SEQ ID NO:77
            -  -  -  R  I  L  P  Y  A  F  Y  R  N  S  L  L  F  L  H  T      SEQ ID NO:53

61  cgttttttggatggagtgaaacgatgaaatacctattgcctacggcagccgctggattg
     R  F  F  G  W  S  E  T  M  K  Y  L  L  P  T  A  A  A  G  L 121 ttattactcgctgcccaaccagccatggccgatattgtgatgacccaggctgcaccctct
     L  L  L  A  A  Q  P  A  M  A  D  I  V  M  T  Q  A  A  P  S 181 gtacctgtcactcctggagaatcagtatccatctcctgcaggtctagtaagagtctcctg
     V  P  V  T  P  G  E  S  V  S  I  S  C  R  S  S  K  S  L  L
                                                 CDR1
                                       ~~~~~~~~~~~~~~~~~~~~~~~  SEQ ID NO:25
241 cgtagtaatggcaacacttacttgtattggttcctgcagaggccaggccagtctcctcag
     R  S  N  G  N  T  Y  L  Y  W  F  L  Q  R  P  G  Q  S  P  Q
                                     CDR2
                             ~~~~~~~~~~~~~~~~~~~~~  SEQ ID NO:31
301 ctcctgatatatcggctgtctaaccttgcctcaggagtcccagacaggttcagtggcagt
     L  L  I  Y  R  L  S  N  L  A  S  G  V  P  D  R  F  S  G  S 361 gggtcaggaactgctttcacactgagaatcagtagagtggaggctgaggatgtgggtgtt
     G  S  G  T  A  F  T  L  R  I  S  R  V  E  A  E  D  V  G  V
                           CDR3
                ~~~~~~~~~~~~~~~~~~~~~~~~~~  SEQ ID NO:33
421 tattactgtatgcaacatctagaatatccttttcacattcggctcggggacaaagttggaa
     Y  Y  C  M  Q  H  L  E  Y  P  F  T  F  G  S  G  T  K  L  E 481 ataaaacgggctgatgctgcaccaactgtatccatcttcccaccatccagtgagcagtta
     I  K  R  A  D  A  A  P  T  V  S  I  F  P  P  S  S  E  Q  L 541 acatctggaggtgcctcagtcgtgtgcttcttgaacaacttctaccccaaagacatcaat
     T  S  G  G  A  S  V  V  C  F  L  N  N  F  Y  P  K  D  I  N 601 gtcaagtggaagattgatggcagtgaacgacaaaatggcgtcctgaacagttggactgat
     V  K  W  K  I  D  G  S  E  R  Q  N  G  V  L  N  S  W  T  D 661 caggacagcaaagacagcacctacagcatgagcagcaccctcacgttgaccaaggacgag
     Q  D  S  K  D  S  T  Y  S  M  S  S  T  L  T  L  T  K  D  E 721 tatgaacgacataacagctatacctgtgaggccactcacaagacatcaacttcacccatt
     Y  E  R  H  N  S  Y  T  C  E  A  T  H  K  T  S  T  S  P  I 781 gtcaagagcttcaacaggaatgagtcttatccatatgatgtgccagattatgcgagctaa
     V  K  S  F  N  R  N  E  S  Y  P  Y  D  V  P  D  Y  A  S  -
```

FIG. 20  Anti-Cadherin-17 PTA001_A9 VK

```
1   taagattagcggatcctacctgacgcttttatcgcaactctctactgtttctccatacc      SEQ ID NO:78
         -  -  -  R  I  L  P  D  A  F  Y  R  N  S  L  L  F  L  H  T    SEQ ID NO:54

61  cgtttttttggatggagtgaaacgatgaaatacctattgcctacggcagccgctggattg
      R  F  F  G  W  S  E  T  M  K  Y  L  L  P  T  A  A  A  G  L 121 ttattactcgctgcccaaccagccatggccgatattgtgatgacccaggctgcaccctct
      L  L  A  A  Q  P  A  M  A  D  I  V  M  T  Q  A  A  P  S 181 gtacctgtcactcctggagagtcagtatccatctcctgcacgtctagtaagagtctcctg
      V  P  V  T  P  G  E  S  V  S  I  S  C  T  S  S  K  S  L  L
                                              CDR1
                                    ~~~~~~~~~~~~~~~~~~~~~~~~~~~  SEQ ID NO:23
241 cgtagtaatggcaacacttacttgtattggttcctgcagaggccaggccagtctcctcag
      R  S  N  G  N  T  Y  L  Y  W  F  L  Q  R  P  G  Q  S  P  Q
                          CDR2
                ~~~~~~~~~~~~~~~~~~~~~~~  SEQ ID NO:29
301 ctcctgatatatcggatgtccaaccttgcctcgggagtcccagacaggttcagtggcagt
      L  L  I  Y  R  M  S  N  L  A  S  G  V  P  D  R  F  S  G  S 361 gggtcaggaactgctttcacactgagaatcagtagagtggaggctgaggatgtgggtgtt
      G  S  G  T  A  F  T  L  R  I  S  R  V  E  A  E  D  V  G  V
                    CDR3
          ~~~~~~~~~~~~~~~~~~~~~~~~~~~~~~~  SEQ ID NO:33
421 tattactgtatgcaacatctagaatatcctttcacgttcggctcggggacaaagttggaa
      Y  Y  C  M  Q  H  L  E  Y  P  F  T  F  G  S  G  T  K  L  E 481 ataaaacgggctgatgctgcaccaactgtatccatctccccaccatccagtgagcagtta
      I  K  R  A  D  A  A  P  T  V  S  I  S  P  P  S  S  E  Q  L 541 acatctggaggtgcctcagtcgtgtgcttcttgaacaacttctaccccaaagacatcaat
      T  S  G  G  A  S  V  V  C  F  L  N  N  F  Y  P  K  D  I  N 601 gtcaagtggaagattgatggcagtgaacgacaaaatggcgtcctgaacagttggactgat
      V  K  W  K  I  D  G  S  E  R  Q  N  G  V  L  N  S  W  T  D 661 caggacagcaaagacagcacctacagcatgagcagcaccctcacgttgaccaaggacgag
      Q  D  S  K  D  S  T  Y  S  M  S  S  T  L  T  L  T  K  D  E 721 tatgaacgacataacagctatacctgtgaggccactcacaagacatcaacttcacccatt
      Y  E  R  H  N  S  Y  T  C  E  A  T  H  K  T  S  T  S  P  I 781 gtcaagagcttcaacaggaatgagtcttatccatatgatgtgccagattatgcgagctaa
      V  K  S  F  N  R  N  E  S  Y  P  Y  D  V  P  D  Y  A  S  -
```

FIG. 21 Anti-Cadherin-17 PTA001_A10 and PTA001_A12 VK

```
1   taagattagcggatcctacctgacgcttttatcgcaactctctactgtttctccatacc      SEQ ID NOS:79
        - - - R  I  L  P  D  A  F  Y  R  N  S  L  L  F  L  H  T      and 81
                                                                     SEQ ID NO:55

61  cgttttttggatggagtgaaacgatgaaatacctattgcctacggcagccgctggattg
    R  F  F  G  W  S  E  T  M  K  Y  L  L  P  T  A  A  A  G  L 121 ttattactcgctgcccaaccagccatggccgatattgtgatgacccaggctgcaccctct
    L  L  L  A  A  Q  P  A  M  A  D  I  V  M  T  Q  A  A  P  S t in A12
181 gtacctgtcactcctggagagtcagtatccatctcctgcaggtccagtaagagtctcctg
    V  P  V  T  P  G  E  S  V  S  I  S  C  R  S  S  K  S  L  L CDR1
    ~~~~~~~~~~~~~~~~~~~~~~~~~~~~~    SEQ ID NO:25
241 cgtagtaatggcaacacttacttgtattggttcctgcagaggccaggccagtctcctcag
    R  S  N  G  N  T  Y  L  Y  W  F  L  Q  R  P  G  Q  S  P  Q CDR2
    ~~~~~~~~~~~~~~~~~~~~~~~~    SEQ ID NO:29
301 ctcctcatatatcggatgtccaaccttgcctcaggagtcccagacaggttcagtggcagt
    L  L  I  Y  R  M  S  N  L  A  S  G  V  P  D  R  F  S  G  S 361 gggtcaggaactgccttcacactgagaatcagtagagtggaggctgaggatgtgggtgtt
    G  S  G  T  A  F  T  L  R  I  S  R  V  E  A  E  D  V  G  V CDR3
    ~~~~~~~~~~~~~~~~~~~~~~~~~~~~~    SEQ ID NO:33
421 tattactgtatgcaacatctagaatatcctttcacgttcggaggggggaccaagctggaa
    Y  Y  C  M  Q  H  L  E  Y  P  F  T  F  G  G  G  T  K  L  E 481 ataaaacgggctgatgctgcaccaactgtatccatcttcccaccatccagtgagcagtta
    I  K  R  A  D  A  A  P  T  V  S  I  F  P  P  S  S  E  Q  L 541 acatctggaggtgcctcagtcgtgtgcttcttgaacaacttctaccccaaagacatcaat
    T  S  G  G  A  S  V  V  C  F  L  N  N  F  Y  P  K  D  I  N 601 gtcaagtggaagattgatggcagtgaacgacaaaatggcgtcctgaacagttggactgat
    V  K  W  K  I  D  G  S  E  R  Q  N  G  V  L  N  S  W  T  D 661 caggacagcaaagacagcacctacagcatgagcagcaccctcacgttgaccaaggacgag
    Q  D  S  K  D  S  T  Y  S  M  S  S  T  L  T  L  T  K  D  E 721 tatgaacgacataacagctatacctgtgaggccactcacaagacatcaacttcacccatt
    Y  E  R  H  N  S  Y  T  C  E  A  T  H  K  T  S  T  S  P  I 781 gtcaagagcttcaacaggaatgagtcttatccatatgatgtgccagattatgcgagctaa
    V  K  S  F  N  R  N  E  S  Y  P  Y  D  V  P  D  Y  A  -
```

FIG. 22  Anti-Cadherin-17 PTA001_A11 VK

```
1    taagattagcggatcctacctgacgctttttatcgcaactctcttctgtttctccatacc    SEQ ID NO:80
        -   -   -   R  I  L  P  D  A  F  Y  R  N  S  L  L  F  L  H  T       SEQ ID NO:56

61   cgttttttggatggagtgaaacgatgaaatacctattgcctacggcagccgctggattg
        R  F  F  G  W  S  E  T  M  K  Y  L  L  P  T  A  A  A  G  L 121  ttattactcgctgcccaaccagccatggccgatattgtgatgacccaggctgcaccctct
        L  L  L  A  A  Q  P  A  M  A  D  I  V  M  T  Q  A  A  P  S 181  gtatctgtcactcctggagagtcagtatccatctcctgcaggtctactaagagtctcctg
        V  S  V  T  P  G  E  S  V  S  I  S  C  R  S  T  K  S  L  L
                                                 CDR1
                                       ~~~~~~~~~~~~~~~~~~~~~~~~~~  SEQ ID NO:27
241  cgtagtaatggcaacacttacttgtattggttcctccagaggccaggccagtctcctcag
        R  S  N  G  N  T  Y  L  Y  W  F  L  Q  R  P  G  Q  S  P  Q
                          CDR2
                ~~~~~~~~~~~~~~~~~~~~~~~  SEQ ID NO:29
301  ctcctgatatatcggatgtccaaccttgcctcaggagtcccagacaggttcagtggcagt
        L  L  I  Y  R  M  S  N  L  A  S  G  V  P  D  R  F  S  G  S 361  gggtcaggaactgctttcacactgagaatcagtagagtggaggctgaggatgtgggtgtt
        G  S  G  T  A  F  T  L  R  I  S  R  V  E  A  E  D  V  G  V
                          CDR3
                ~~~~~~~~~~~~~~~~~~~~~~~~~~~~  SEQ ID NO:33
421  tattactgtatgcaacatctagaatatcctttcacgttcggaggggggaccaagctggaa
        Y  Y  C  M  Q  H  L  E  Y  P  F  T  F  G  G  G  T  K  L  E 481  ataaaacgggctgatgctgcaccaactgtatccatcttcccaccatccagtgagcagtta
        I  K  R  A  D  A  A  P  T  V  S  I  F  P  P  S  S  E  Q  L 541  acatctggaggtgcctcagtcgtgtgcttcttgaacaacttctaccccaaagacatcaat
        T  S  G  G  A  S  V  V  C  F  L  N  N  F  Y  P  K  D  I  N 601  gtcaagtggaagattgatggcagtgaacgacaaaatggcgtcctgaacagttggactgat
        V  K  W  K  I  D  G  S  E  R  Q  N  G  V  L  N  S  W  T  D 661  caggacagcaaagacagcacctacagcatgagcagcaccctcacgttgaccaaggacgag
        Q  D  S  K  D  S  T  Y  S  M  S  S  T  L  T  L  T  K  D  E 721  tatgaacgacataacagctatacctgtgaggccactcacaagacatcaacttcacccatt
        Y  E  R  H  N  S  Y  T  C  E  A  T  H  K  T  S  T  S  P  I 781  gtcaagagcttcaacaggaatgagtcttatccatatgatgtgccagattatgcgagctaa
        V  K  S  F  N  R  N  E  S  Y  P  Y  D  V  P  D  Y  A  S  -
```

FIG. 23  Anti-Cadherin-17 PTA001_A13 VK

```
1    taagattagcggatcctacctgacgcttttatcgcaactctctactgtttctccatacc     SEQ ID NO:82
         -  -  -  R  I  L  P  D  A  F  Y  R  N  S  L  L  F  L  H  T  SEQ ID NO:57

61   cgttttttggatggagtgaaacgatgaaataccttattgcctacggcagccgctggattg
      R  F  F  G  W  S  E  T  M  K  Y  L  L  P  T  A  A  A  G  L 121  ttattactcgctgcccaaccagccatggccgatattgtgatgacccaggctgcacctct
      L  L  L  A  A  Q  P  A  M  A  D  I  V  M  T  Q  A  A  P  S 181  gtacctgtcactcctggagagtcagtatccatctcctgcaggtctagtaagagtctcctg
      V  P  V  T  P  G  E  S  V  S  I  S  C  R  S  S  K  S  L  L
                                              CDR1
                                 ~~~~~~~~~~~~~~~~~~~~~~~~~ SEQ ID NO:25
241  cgcagtaatggcaacacttacttgtattggttcctgcagaggccaggccagtctcctcag
      R  S  N  G  N  T  Y  L  Y  W  F  L  Q  R  P  G  Q  S  P  Q
                        CDR2
            ~~~~~~~~~~~~~~~~~~~~~~~ SEQ ID NO:31
301  ctcctgatatatcggctgtccaaccttgcctcaggagtcccagacaggttcagtggcagt
      L  L  I  Y  R  L  S  N  L  A  S  G  V  P  D  R  F  S  G  S 361  gggtcaggaactgctttcacactgagaatcagtagagtggaggctgaggatgtgggtgtt
      G  S  G  T  A  F  T  L  R  I  S  R  V  E  A  E  D  V  G  V
                        CDR3
              ~~~~~~~~~~~~~~~~~~~~~~~~~~~~~ SEQ ID NO:33
421  tattactgtatgcaacatctagaatatcctttcacattcggctcggggacaaagttggaa
      Y  Y  C  M  Q  H  L  E  Y  P  F  T  F  G  S  G  T  K  L  E 481  ataaaacgggctgatgctgcaccaactgtatccatcttcccacaatacagtgagcagtta
      I  K  R  A  D  A  A  P  T  V  S  I  F  P  Q  Y  S  E  Q  L 541  acaactggaggtgcctcagtcgtgtgcttcttgaacaacttctaccccaaagacatcaat
      T  T  G  G  A  S  V  V  C  F  L  N  N  F  Y  P  K  D  I  N 601  gtcaagtggaagattgatggcagtgaacgacaaaatggcgtcctgaacagttggactgat
      V  K  W  K  I  D  G  S  E  R  Q  N  G  V  L  N  S  W  T  D 661  caggacagcaaagacagcacctacagcatgagcagcaccctcacgttgaccaaggacgag
      Q  D  S  K  D  S  T  Y  S  M  S  S  T  L  T  L  T  K  D  E 721  tatgaacgacataacagctatacctgtgaggccactcacaagacatcaacttcacccatt
      Y  E  R  H  N  S  Y  T  C  E  A  T  H  K  T  S  T  S  P  I 781  gtcaagagcttcaacaggaatgagtcttatccatatgatgtgccagattatgcgagctaa
      V  K  S  F  N  R  N  E  S  Y  P  Y  D  V  P  D  Y  A  S  -
```

FIG. 24  Anti-Cadherin-17 PTA001_A14 VK

```
1    cggatcctacctgacgcttttatcgcaactctctactgtttctccatacccgttttttt    SEQ ID NO:83
     R  I  L  P  D  A  F  Y  R  N  S  L  L  F  L  H  T  R  F  F     SEQ ID NO:58

61   ggatggagtgaaacgatgaaatacctattgcctacggcagccgctggattgttattactc
     G  W  S  E  T  M  K  Y  L  L  P  T  A  A  A  G  L  L  L  L 121  gctgcccaaccagccatggccgatattgtgatgacccaggctgcaccctctgtacctgtc
     A  A  Q  P  A  M  A  D  I  V  M  T  Q  A  A  P  S  V  P  V
                                                         CDR1
                                       ~~~~~~~~~~~~~~~~~~~~~~~~~~~~~~    SEQ ID NO:23
181  actcctggagagtcagtatccatctcctgcacgtctagtaagagtctcctgcgtagtaat
     T  P  G  E  S  V  S  I  S  C  T  S  S  K  S  L  L  R  S  N ~~~~~~~~~~~~~~~~~~~
241  ggcaacacttacttgtattggttcctgcagaggccaggccagtctcctcagctcctgata
     G  N  T  Y  L  Y  W  F  L  Q  R  P  G  Q  S  P  Q  L  L  I
          CDR2
     ~~~~~~~~~~~~~~~~~~~~~~~~~~~    SEQ ID NO:29
301  tatcggatgtccaaccttgcctcgggagtcccagacaggttcagtggcagtgggtcagga
     Y  R  M  S  N  L  A  S  G  V  P  D  R  F  S  G  S  G  S  G 361  actgctttcacactgagaatcagtagagtggaggctgaggatgtgggtgtttattactgt
     T  A  F  T  L  R  I  S  R  V  E  A  E  D  V  G  V  Y  Y  C
          CDR3
     ~~~~~~~~~~~~~~~~~~~~~~~~~~~~~~    SEQ ID NO:33
421  atgcaacatctagaatatcctttcacgttcggctcggggacaaatttggaaataaaacgg
     M  Q  H  L  E  Y  P  F  T  F  G  S  G  T  N  L  E  I  K  R 481  gctgatgctgcaccaactgtatccatcttcacaacatccagagagcagttaacatctgga
     A  D  A  A  P  T  V  S  I  F  T  T  S  R  E  Q  L  T  S  G 541  ggtgcctcagtcgtgtgcttcttgaacaacttctacccaaagacatcaatgtcaag
     G  A  S  V  V  C  F  L  N  N  F  Y  P  K  D  I  N  V  K
```

FIG. 25   VH CDR1 Alignments

PTA001_A1
VH CDR1        GGATTCACTTTCAGTAACTATGGCATGTCT    SEQ ID NO:84
VH7-39         GGATTCACTTTCAGTAGCTATGGCATGTCT    SEQ ID NO:125
               **************** ***********

PTA001_A2, PTA001_A14
VH CDR1        GGCTACACCTTCAGTGACCATGCTATTCAC    SEQ ID NO:85
VHII gene H17  GGCTACACCTTCACTGACCATGCTATTCAC    SEQ ID NO:126
               ********** ***************

PTA001_A3, PTA001_A5, PTA001_A6, PTA001_A7, PTA001_A8, PTA001_A9, PTA001_A10, PTA001_A11, PTA001_A12, PTA001_A13
VH CDR1        GGCTACACCTTCACTGACCATGCTATTCAC    SEQ ID NO:86
VHII gene H17  GGCTACACCTTCACTGACCATGCTATTCAC    SEQ ID NO:126
               ******************************

PTA001_A4
VH CDR1        GGCTACACCCTCACTGACCATACTATTCAC    SEQ ID NO:87
VHII gene H17  GGCTACACCTTCACTGACCATACTATTCAC    SEQ ID NO:126
               ******* ******************

FIG. 26  VH CDR2 Alignments

```
PTA001_A2
VH CDR2              TATATTTATCCTAGACATGGGACTACTAACTACAATGAGAACTTCAAGGGC   SEQ ID NO:89
VHII region VH105    TATATTTATCCTAGAGATGGTAGTACTAAGTACAATGAGAAGTTCAAGGGC   SSEQ ID NO:127
                     **************  ****  * ******  **********  *********

PTA001_A3, PTA001_A5, PTA001_A6, PTA001_A8, PTA001_A9, PTA001_A10
VH CDR2              TATATTTATCCTGAACATGGAACTATTAAGTATAATGAGAAGTTCAAGGGC   SEQ ID NO:90
VHII region VH105    TATATTTATCCTAGAGATGGTAGTACTAAGTACAATGAGAAGTTCAAGGGC   SEQ ID NO:127
                     ***********  * **** * ** ****** *******************

PTA001_A4
VH CDR2              TATATTTACCCTAGAGATGGAATAACTGGGTACAATGAGAAGTTCAAGGGC   SEQ ID NO:91
VHII region VH105    TATATTTATCCTAGAGATGGTAGTACTAAGTACAATGAGAAGTTCAAGGGC   SEQ ID NO:127
                     ******** *********** *  ***   *** *****************

PTA001_A7
VH CDR2              TATATTTATCCTAGACATGGGACTACTAACTACAATGAGAACTTCAAGGGC   SEQ ID NO:92
VHII region VH105    TATATTTATCCTAGAGATGGTAGTACTAAGTACAATGAGAAGTTCAAGGGC   SEQ ID NO:127
                     **************  ****  * ******  **********  *********

PTA001_A11
VH CDR2              TATATTTATCCTGAACATGGTAGTATTACGTATAATGAGAAGTTCAAGGGC   SEQ ID NO:93
VHII region VH105    TATATTTATCCTAGAGATGGTAGTACTAAGTACAATGAGAAGTTCAAGGGC   SEQ ID NO:127
                     ***********   * ********  ** *** *******************

PTA001_A12
VH CDR2              TATATCTACCCCAGAGATGATTTTGCTAAGGTGAATGAGAAGTTCAAGGGC   SEQ ID NO:94
VHII region VH105    TATATTTATCCTAGAGATGGTAGTACTAAGTACAATGAGAAGTTCAAGGGC   SEQ ID NO:127
                     ***** ** ** *******   *   *****        *************

PTA001_A13
VH CDR2              TATATTTATCCTGAACATGGTACTATTACGTATAATGAGAAGTTCAAGGGC   SEQ ID NO:95
VHII region VH105    TATATTTATCCTAGAGATGGTAGTACTAAGTACAATGAGAAGTTCAAGGGC   SEQ ID NO:127
                     ***********  * ****** ***  ** *** .*****************

PTA001_A14
VH CDR2              TATATTTTTCCTAGAGATGCTTTTAGTTTGAACAATGAGAAGTTCAAGGGC   SEQ ID NO:96
VHII region VH105    TATATTTATCCTAGAGATGGTAGTACTAAGTACAATGAGAAGTTCAAGGGC   SEQ ID NO:127
                     ****** **********  *   ** *  * *********************
```

FIG. 27  VK CDR1 Alignments

PTA001_A1
VK CDR1      AGATCTAGTCAGAGCCTTTTACACAGTAATGGAAACACCTATTTACAT  SEQ ID NO:105
VK1-110      AGATCTAGTCAGAGCCTTGTACACAGTAATGGAAACACCTATTTACAT  SEQ ID NO:128
             ***************** **************************

PTA001_A4
VK CDR1      AAGTCCAGCCAGAGCCTTTTACATAGTAGCAATCAAAAGAACTACTTGGCC  SEQ ID NO:107
VK8-30       AAGTCCAGTCAGAGCCTTTTATATAGTAGCAATCAAAAGAACTACTTGGCC  SEQ ID NO:130
             ***** ******** ****************************

PTA001_A2, PTA001_A3, PTA001_A6, PTA001_A9, PTA001_A14
VK CDR1      GTCTAGTAAGAGTCTCCTGCGTAGTAATGGCAACACTTACTTGTAT  SEQ ID NO:106
VK24-140     GTCTAGTAAGAGTCTCCTGCATAGTAATGGCAACACTTACTTGTAT  SEQ ID NO:133
             ****************** ***********************

PTA001_A5, PTA001_A13
VK CDR1      AGGTCTAGTAAGAGTCTCCTGCGCAGTAATGGCAACACTTACTTGTAT  SEQ ID NO:108
VK24-140     AGGTCTAGTAAGAGTCTCCTGCATAGTAATGGCAACACTTACTTGTAT  SEQ ID NO:133
             ******************** ***********************

PTA001_A7
VK CDR1      AGGTCTTCTAAGAGTCTCCTGCGTACTAATGGCAACACTTACTTGCAT  SEQ ID NO:109
VK24-140     AGGTCTAGTAAGAGTCTCCTGCATAGTAATGGCAACACTTACTTGTAT  SEQ ID NO:133
             ****  **********  ******************

PTA001_A8
VK CDR1      AGGTCTAGTAAGAGTCTCCTGCGTAGTAATGGCAACACTTACTTGTAT  SEQ ID NO:110
VK24-140     AGGTCTAGTAAGAGTCTCCTGCATAGTAATGGCAACACTTACTTGTAT  SEQ ID NO:133
             ******************** ***********************

PTA001_A10
VK CDR1      AGGTCCAGTAAGAGTCTCCTGCGTAGTAATGGCAACACTTACTTGTAT  SEQ ID NO:111
VK24-140     AGGTCTAGTAAGAGTCTCCTGCATAGTAATGGCAACACTTACTTGTAT  SEQ ID NO:133
             *** ************ ***********************

PTA001_A11
VK CDR1      AGGTCTACTAAGAGTCTCCTGCGTAGTAATGGCAACACTTACTTGTAT  SEQ ID NO:112
VK24-140     AGGTCTAGTAAGAGTCTCCTGCATAGTAATGGCAACACTTACTTGTAT  SEQ ID NO:133
             ****  ********** ***********************

PTA001_A12
VK CDR1      AGGTCTAGTAAGAGTCTCCTACGTAGTAATGGCAACACTTACTTGTAT  SEQ ID NO:113
VK24-140     AGGTCTAGTAAGAGTCTCCTGCATAGTAATGGCAACACTTACTTGTAT  SEQ ID NO:133
             ******************** * *************************

FIG. 28  VK CDR2 Alignments

```
PTA001_A4
VK CDR2        TGGGCATCCACTAGAGAATCT   SEQ ID NO:116
VK8-30         TGGGCATCCACTAGGGAATCT   SEQ ID NO:131
               ***************  ******
```

```
PTA001_A2, PTA001_A3, PTA001_A6, PTA001_A9, PTA001_A14
VK CDR2        CGGATGTCCAACCTTGCCTCG   SEQ ID NO:115
VK24-140       CGGATGTCCAACCTTGCCTCA   SEQ ID NO:134
               ********************
```

```
PTA001_A5, PTA001_A13
VK CDR2        CGGCTGTCCAACCTTGCCTCA   SEQ ID NO:117
VK24-140       CGGATGTCCAACCTTGCCTCA   SEQ ID NO:134
               *** *****************
```

```
PTA001_A7, PTA001_A10, PTA001_A11, PTA001_A12
VK CDR2        CGGATGTCCAACCTTGCCTCA   SEQ ID NO: 118
VK24-140       CGGATGTCCAACCTTGCCTCA   SEQ ID NO:134
               *********************
```

```
PTA001_A8
VK CDR2        CGGCTGTCTAACCTTGCCTCA   SEQ ID NO:119
VK24-140       CGGATGTCCAACCTTGCCTCA   SEQ ID NO:134
               *** **** *************
```

FIG. 29  VK CDR3 Alignments

```
PTA001_A1
VK CDR3        TCTCAAAGTACACATGTGCTCACG   SEQ ID NO:120
VK1-110        TCTCAAAGTACACATGTTCCTCCC   SEQ ID NO:129
               ****************  *   *
```

```
PTA001_A4
VK CDR3        CAGCAATATTATAGCTATCCGTGGACG   SEQ ID NO:122
VK8-30         CAGCAATATTATAGCTATCCTCCCACA   SEQ ID NO:132
               ********************  **
```

```
PTA001_A2, PTA001_A3, PTA001_A6, PTA001_A9, PTA001_A10, PTA001_A11,
PTA001_A12, PTA001_A14
VK CDR3        ATGCAACATCTAGAATATCCTTTCACG   SEQ ID NO:121
VK24-140       ATGCAACATCTAGAATATCCTTTCACA   SEQ ID NO: 135
               **************************
```

```
PTA001_A5, PTA001_A8, PTA001_A13
VK CDR3        ATGCAACATCTAGAATATCCTTTCACA   SEQ ID NO:123
VK24-140       ATGCAACATCTAGAATATCCTTTCACA   SEQ ID NO:135
               ***************************
```

```
PTA001_A7
VK CDR3        ATGCAACATCTAGAATATCCATTCACG   SEQ ID NO:124
VK24-140       ATGCAACATCTAGAATATCCTTTCACA   SEQ ID NO:135
               ********************  *****
```

Anti-Cadherin-17 PTA001_A4 Western Blot
Error! Objects cannot be created from editing field codes.
FIG. 30
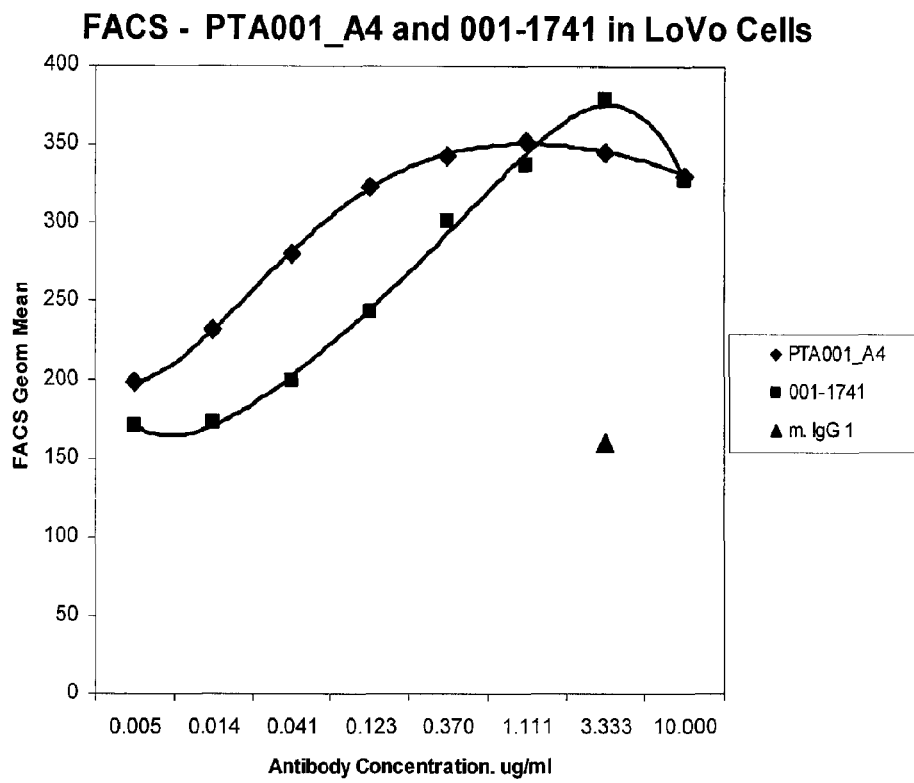
FIG. 31
FACS: PTA001_A4 vs LoVo, LS 174T
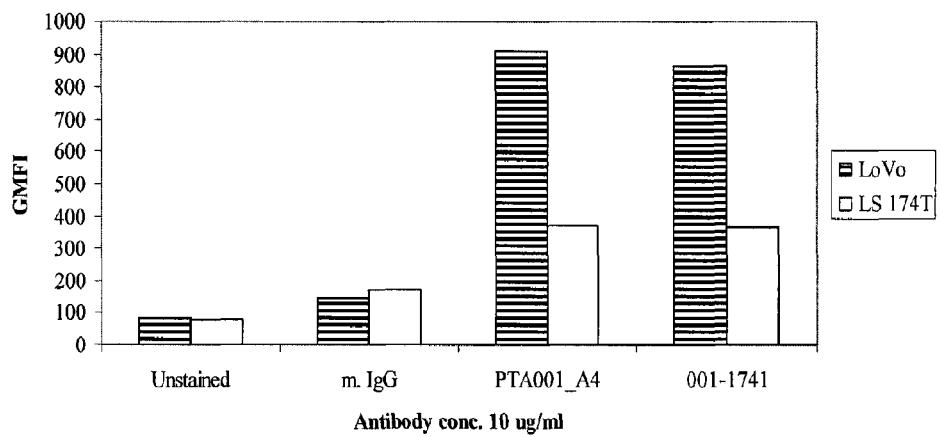
FIG. 32

ANTIBODIES SPECIFIC TO CADHERIN-17

SEQUENCE LISTING

The instant application contains a Sequence Listing which has been submitted via EFS-Web and is hereby incorporated by reference in its entirety. Said ASCII copy, created on Dec. 23, 2014, is named OTJ_012US_SL.txt, and is 107, 865 bytes in size.

FIELD OF THE INVENTION

The present invention relates generally to the fields of immunology and molecular biology. More specifically, provided herein are antibodies and other therapeutic proteins directed against cell adhesion molecule Cadherin-17, nucleic acids encoding such antibodies and therapeutic proteins, methods for preparing inventive monoclonal antibodies and other therapeutic proteins, and methods for the treatment of diseases, such as cancers mediated by Cadherin-17 expression/activity and/or associated with abnormal expression/activity of ligands therefore.

BACKGROUND OF THE INVENTION

Cadherins are calcium dependent cell adhesion molecules. They preferentially interact with themselves in a homophilic manner in connecting cells; cadherins may thus contribute to the sorting of heterogeneous cell types. The cadherin molecule Cadherin-17 is also known as liver-intestine cadherin or intestinal peptide-associated transporter HPT-1. Cadherin-17 may have a role in the morphological organization of liver and intestine. It is also involved in intestinal peptide transport. The Cadherin-17 structure is characterized as having an extracellular domain with 7 cadherin domains, a single hydrophobic transmembrane domain and a short C-terminal cytoplasmic tail. Only one human Cadherin-17 isoform is known, Genbank® Accession No. NM_004063. Cadherin-17 has the accession number Q12864 in the SWISS-PROT and trEMBL databases (held by the Swiss Institute of Bioinformatics (SIB) and the European Bioinformatics Institute (EBI) which are available at www.expasy.com). The mouse Cadherin-17 orthologue (Q9R100) shows 76% identity to the human Cadherin-17.

According to SWISS-PROT, Cadherin-17 is expressed in the gastrointestinal tract and pancreatic duct. It is not detected in kidney, lung, liver, brain, adrenal gland or skin. Cadherin-17 expression has been reported in gastric cancer (see, for example, Ito et al., *Virchows Arch.* 2005 October; 447(4):717-22; Su et al., *Mod Pathol.* 2008 November; 21(11):1379-86; Ko et al., *Biochem Biophys Res Commun.* 2004 Jun. 25; 319(2):562-8; and Dong et al., *Dig Dis Sci.* 2007 February; 52(2):536-42), pancreatic cancer and colorectal cancer (Su et al., *Mod Pathol.* 2008 November; 21(11):1379-86) and hepatocellular carcinoma (Wong et al., *Biochem Biophys Res Commun.* 2003 Nov. 21; 311(3):618-24). International Patent Application WO2008/026008 discloses Cadherin-17 as a marker for colorectal cancer and as a biological target for therapeutic antibodies and other pharmaceutical agents.

SUMMARY OF THE INVENTION

The present invention provides antibodies directed against Cadherin-17, nucleic acids encoding such antibodies and therapeutic proteins, methods for preparing anti-Cadherin-17 monoclonal antibodies and other therapeutic proteins, and methods for the treatment of diseases, such as Cadherin-17 mediated disorders, e.g., human cancers, including colorectal cancer.

Thus, the present invention provides isolated monoclonal antibodies, in particular murine, chimeric, humanized, and fully-human monoclonal antibodies, that bind to Cadherin-17 and that exhibit one or more desirable functional property. Such properties include, for example, high affinity specific binding to human Cadherin-17. Also provided are methods for treating a variety of Cadherin-17-mediated diseases using the antibodies, proteins, and compositions of the present invention.

The present invention provides an isolated monoclonal antibody, or an antigen-binding portion thereof, an antibody fragment, or an antibody mimetic which binds an epitope on human Cadherin-17 recognized by an antibody comprising a heavy chain variable region comprising an amino acid sequence set forth in a SEQ ID NO: selected from the group consisting of 38, 35, 36, 37, 39, 40, 41, 42, 43, 44, 45 and 46 and a light chain variable region comprising an amino acid sequence set forth in a SEQ ID NO: selected from the group consisting of 49, 47, 48, 50, 51, 52, 53, 54, 55, 56, 57 and 58. In some embodiments the isolated antibody is a full-length antibody of an IgG1, IgG2, IgG3, or IgG4 isotype.

In some embodiments, the antibody of the present invention is selected from the group consisting of: a whole antibody, an antibody fragment, a humanized antibody, a single chain antibody, an immunoconjugate, a defucosylated antibody, and a bispecific antibody. The antibody fragment may be selected from the group consisting of: a UniBody®, a domain antibody, and a Nanobody®. In some embodiments, the immunoconjugates of the invention comprise a therapeutic agent. In another aspect of the invention, the therapeutic agent is a cytotoxin or a radioactive isotope.

In some embodiments, the antibody of the present invention is selected from the group consisting of: an Affibody®, a DARPin®, an Anticalin®, an Avimer, a Versabody, and a Duocalin.

In alternative embodiments, compositions of the present invention comprise an isolated antibody or antigen-binding portion and a pharmaceutically acceptable carrier.

In other aspects, the antibody of the present invention is a composition comprising the isolated antibody or antigen-binding portion according to the invention and a pharmaceutically acceptable carrier.

In some embodiments, the invention comprises an isolated nucleic acid molecule encoding the heavy or light chain of the isolated antibody or antigen-binding portion which binds an epitope on human Cadherin-17. Other aspects of the invention comprise expression vectors comprising such nucleic acid molecules, and host cells comprising such expression vectors.

In some embodiments, the present invention provides a method for preparing an anti-Cadherin-17 antibody, said method comprising the steps of: obtaining a host cell that contains one or more nucleic acid molecules encoding the antibody of the invention; growing the host cell in a host cell culture; providing host cell culture conditions wherein the one or more nucleic acid molecules are expressed; and recovering the antibody from the host cell or from the host cell culture.

In other embodiments, the invention is directed to methods for treating or preventing a disease associated with target cells expressing Cadherin-17, said method comprising the step of administering to a subject an anti-Cadherin-17 antibody, or antigen-binding portion thereof, in an amount effective to treat or prevent the disease. In some aspects, the disease treated or prevented by the antibodies or antigen-binding portion thereof of the invention, is human cancer. In some embodiments, the disease treated or prevented by the antibodies of the present invention is colorectal cancer.

In other embodiments, the invention is directed to an anti-Cadherin-17 antibody, or antigen-binding portion thereof, for use in treating or preventing a disease associated with target cells expressing Cadherin-17. In some aspects, the disease treated or prevented by the antibodies or antigen-binding portion thereof of the invention, is human cancer. In some embodiments, the disease treated or prevented by the antibodies of the present invention is colorectal cancer.

In other embodiments, the invention is directed to the use of an anti-Cadherin-17 antibody, or antigen-binding portion thereof, for the manufacture of a medicament for use in treating or preventing a disease associated with target cells expressing Cadherin-17. In some aspects, the disease treated or prevented by the medicament of the invention, is human cancer. In some embodiments, the disease treated or prevented by the medicament of the present invention is colorectal cancer.

In other embodiments, the present invention is an isolated monoclonal antibody or an antigen binding portion thereof, an antibody fragment, or an antibody mimetic which binds an epitope on human Cadherin-17 recognized by an antibody comprising a heavy chain variable region and a light chain variable region selected from the group consisting of the heavy chain variable region amino acid sequence set forth in SEQ ID NO:35 and the light chain variable region amino acid sequence set forth in SEQ ID NO:47; the heavy chain variable region amino acid sequence set forth in SEQ ID NO:36 and the light chain variable region amino acid sequence set forth in SEQ ID NO:48; the heavy chain variable region amino acid sequence set forth in SEQ ID NO:37 and the light chain variable region amino acid sequence set forth in SEQ ID NO:48; the heavy chain variable region amino acid sequence set forth in SEQ ID NO:38 and the light chain variable region amino acid sequence set forth in SEQ ID NO:49; the heavy chain variable region amino acid sequence set forth in SEQ ID NO:39 and the light chain variable region amino acid sequence set forth in SEQ ID NO:50; the heavy chain variable region amino acid sequence set forth in SEQ ID NO:40 and the light chain variable region amino acid sequence set forth in SEQ ID NO:51; the heavy chain variable region amino acid sequence set forth in SEQ ID NO:40 and the light chain variable region amino acid sequence set forth in SEQ ID NO:54; the heavy chain variable region amino acid sequence set forth in SEQ ID NO:40 and the light chain variable region amino acid sequence set forth in SEQ ID NO:55; the heavy chain variable region amino acid sequence set forth in SEQ ID NO:41 and the light chain variable region amino acid sequence set forth in SEQ ID NO:52; the heavy chain variable region amino acid sequence set forth in SEQ ID NO:42 and the light chain variable region amino acid sequence set forth in SEQ ID NO:53; the heavy chain variable region amino acid sequence set forth in SEQ ID NO:43 and the light chain variable region amino acid sequence set forth in SEQ ID NO:56; the heavy chain variable region amino acid sequence set forth in SEQ ID NO:44 and the light chain variable region amino acid sequence set forth in SEQ ID NO:55; the heavy chain variable region amino acid sequence set forth in SEQ ID NO:45 and the light chain variable region amino acid sequence set forth in SEQ ID NO:57; and the heavy chain variable region amino acid sequence set forth in SEQ ID NO:46 and the light chain variable region amino acid sequence set forth in SEQ ID NO:58. In further aspects, the antibody is selected from the group consisting of: a whole antibody, an antibody fragment, a humanized antibody, a single chain antibody, an immunoconjugate, a defucosylated antibody, and a bispecific antibody. In further aspects of the invention, the antibody fragment is selected from the group consisting of: a UniBody®, a domain antibody, and a Nanobody®. In some embodiments, the antibody mimetic is selected from the group consisting of: an Affibody®, a DARPin®, an Anticalin®, an Avimer, a Versabody, and a Duocalin. In further embodiments, the composition comprises the isolated antibody or antigen binding portion thereof and a pharmaceutically acceptable carrier.

In some embodiments, the present invention is an isolated nucleic acid molecule encoding the heavy or light chain of the isolated antibody or antigen binding portion thereof of antibody of the invention, and in further aspects may include an expression vector comprising such nucleic acids, and host cells comprising such expression vectors.

Another embodiment of the present invention is a hybridoma expressing the antibody or antigen binding portion thereof of any one of antibodies of the invention.

Other aspects of the invention are directed to methods of making the antibodies of the invention, comprising the steps of:
  immunizing an animal with a Cadherin-17 peptide;
  recovering mRNA from the B cells of said animal;
  converting said mRNA to cDNA;
  expressing said cDNA in phages such that anti-Cadherin-17 antibodies encoded by said cDNA are presented on the surface of said phages;
  selecting phages that present anti-Cadherin-17 antibodies;
  recovering nucleic acid molecules from said selected phages that encode said anti-Cadherin-17 immunoglobulins;
  expressing said recovered nucleic acid molecules in a host cell; and
  recovering antibodies from said host cell that bind Cadherin-17.

In some aspects of the invention, the isolated monoclonal antibody, or an antigen binding portion thereof, binds an epitope on the Cadherin-17 polypeptide having an amino acid sequence of SEQ ID NOS: 136 or 137 recognized by an antibody comprising a heavy chain variable region comprising an amino acid sequence set forth in a SEQ ID NO: selected from the group consisting of 38, 35, 36, 37, 39, 40, 41, 42, 43, 44, 45, or 46 and a light chain variable region comprising an amino acid sequence set forth in a SEQ ID NO: selected from the group consisiting of 49, 47, 48, 50, 51, 52, 53, 54, 55, 56, 57, or 58.

Other features and advantages of the instant invention will be apparent from the following detailed description and examples which should not be construed as limiting. The contents of all references, Genbank® entries, patents and published patent applications cited throughout this application are expressly incorporated herein by reference.

BRIEF DESCRIPTION OF THE DRAWINGS

FIG. 1 shows the nucleotide sequence (SEQ ID NO:59) and amino acid sequence (SEQ ID NO:35) of the heavy chain variable region of the PTA001_A1 monoclonal antibody. The CDR1 (SEQ ID NO:1), CDR2 (SEQ ID NO:5) and CDR3 (SEQ ID NO:14) regions are delineated.

FIG. 2 shows the nucleotide sequence (SEQ ID NO:60) and amino acid sequence (SEQ ID NO:36) of the heavy chain variable region of the PTA001_A2 monoclonal antibody. The CDR1 (SEQ ID NO:2), CDR2 (SEQ ID NO:6) and CDR3 (SEQ ID NO:15) regions are delineated.

FIG. 3 shows the nucleotide sequence (SEQ ID NO:61) and amino acid sequence (SEQ ID NO:37) of the heavy chain variable region of the PTA001_A3 monoclonal antibody. The CDR1 (SEQ ID NO:3), CDR2 (SEQ ID NO:7) and CDR3 (SEQ ID NO:16) regions are delineated.

FIG. 4 shows the nucleotide sequence (SEQ ID NO:62) and amino acid sequence (SEQ ID NO:38) of the heavy chain variable region of the PTA001_A4 monoclonal antibody. The CDR1 (SEQ ID NO:4), CDR2 (SEQ ID NO:8) and CDR3 (SEQ ID NO:17) regions are delineated.

FIG. 5 shows the nucleotide sequence (SEQ ID NO:63) and amino acid sequence (SEQ ID NO:39) of the heavy chain variable region of the PTA001_A5 monoclonal antibody. The CDR1 (SEQ ID NO:3), CDR2 (SEQ ID NO:7) and CDR3 (SEQ ID NO:18) regions are delineated.

FIG. 6 shows the nucleotide sequence (SEQ ID NO:64) and amino acid sequence (SEQ ID NO:40) of the heavy chain variable region of the PTA001_A6, PTA001_A9 and PTA001_A10 monoclonal antibodies. The CDR1 (SEQ ID NO:3), CDR2 (SEQ ID NO:7) and CDR3 (SEQ ID NO:16) regions are delineated.

FIG. 7 shows the nucleotide sequence (SEQ ID NO:65) and amino acid sequence (SEQ ID NO:41) of the heavy chain variable region of the PTA001_A7 monoclonal antibody. The CDR1 (SEQ ID NO:3), CDR2 (SEQ ID NO:9) and CDR3 (SEQ ID NO:19) regions are delineated.

FIG. 8 shows the nucleotide sequence (SEQ ID NO:66) and amino acid sequence (SEQ ID NO:42) of the heavy chain variable region of the PTA001_A8 monoclonal antibody. The CDR1 (SEQ ID NO:3), CDR2 (SEQ ID NO:7) and CDR3 (SEQ ID NO:16) regions are delineated.

FIG. 9 shows the nucleotide sequence (SEQ ID NO:67) and amino acid sequence (SEQ ID NO:43) of the heavy chain variable region of the PTA001_A11 monoclonal antibody. The CDR1 (SEQ ID NO:3), CDR2 (SEQ ID NO:10) and CDR3 (SEQ ID NO:20) regions are delineated.

FIG. 10 shows the nucleotide sequence (SEQ ID NO:68) and amino acid sequence (SEQ ID NO:44) of the heavy chain variable region of the PTA001_A12 monoclonal antibody. The CDR1 (SEQ ID NO:3), CDR2 (SEQ ID NO:11) and CDR3 (SEQ ID NO:21) regions are delineated.

FIG. 11 shows the nucleotide sequence (SEQ ID NO:69) and amino acid sequence (SEQ ID NO:45) of the heavy chain variable region of the PTA001_A13 monoclonal antibody. The CDR1 (SEQ ID NO:3), CDR2 (SEQ ID NO:12) and CDR3 (SEQ ID NO:18) regions are delineated.

FIG. 12 shows the nucleotide sequence (SEQ ID NO:70) and amino acid sequence (SEQ ID NO:46) of the heavy chain variable region of the PTA001_A14 monoclonal antibody. The CDR1 (SEQ ID NO:2), CDR2 (SEQ ID NO:13) and CDR3 (SEQ ID NO:15) regions are delineated.

FIG. 13 shows the nucleotide sequence (SEQ ID NO:71) and amino acid sequence (SEQ ID NO:47) of the light chain variable region of the PTA001_A1 monoclonal antibody. The CDR1 (SEQ ID NO:22), CDR2 (SEQ ID NO:28) and CDR3 (SEQ ID NO:32) regions are delineated.

FIG. 14 shows the nucleotide sequence (SEQ ID NO:72) and amino acid sequence (SEQ ID NO:48) of the light chain variable region of the PTA001_A2 and PTA001_A3 monoclonal antibodies. The CDR1 (SEQ ID NO:23), CDR2 (SEQ ID NO:29) and CDR3 (SEQ ID NO:33) regions are delineated.

FIG. 15 shows the nucleotide sequence (SEQ ID NO:73) and amino acid sequence (SEQ ID NO:49) of the light chain variable region of the PTA001_A4 monoclonal antibody. The CDR1 (SEQ ID NO:24), CDR2 (SEQ ID NO:30) and CDR3 (SEQ ID NO:34) regions are delineated.

FIG. 16 shows the nucleotide sequence (SEQ ID NO:74) and amino acid sequence (SEQ ID NO:50) of the light chain variable region of the PTA001_A5 monoclonal antibody. The CDR1 (SEQ ID NO:25), CDR2 (SEQ ID NO:31) and CDR3 (SEQ ID NO:33) regions are delineated.

FIG. 17 shows the nucleotide sequence (SEQ ID NO:75) and amino acid sequence (SEQ ID NO:51) of the light chain variable region of the PTA001_A6 monoclonal antibody. The CDR1 (SEQ ID NO:23), CDR2 (SEQ ID NO:29) and CDR3 (SEQ ID NO:33) regions are delineated.

FIG. 18 shows the nucleotide sequence (SEQ ID NO:76) and amino acid sequence (SEQ ID NO:52) of the light chain variable region of the PTA001_A7 monoclonal antibody. The CDR1 (SEQ ID NO:26), CDR2 (SEQ ID NO:29) and CDR3 (SEQ ID NO:33) regions are delineated.

FIG. 19 shows the nucleotide sequence (SEQ ID NO:77) and amino acid sequence (SEQ ID NO:53) of the light chain variable region of the PTA001_A8 monoclonal antibody. The CDR1 (SEQ ID NO:25), CDR2 (SEQ ID NO:31) and CDR3 (SEQ ID NO:33) regions are delineated.

FIG. 20 shows the nucleotide sequence (SEQ ID NO:78) and amino acid sequence (SEQ ID NO:54) of the light chain variable region of the PTA001_A9 monoclonal antibody. The CDR1 (SEQ ID NO:23), CDR2 (SEQ ID NO:29) and CDR3 (SEQ ID NO:33) regions are delineated.

FIG. 21 shows the nucleotide sequence (SEQ ID NOs:79 and 81) and amino acid sequence (SEQ ID NO:55) of the light chain variable region of the PTA001_A10 and PTA001_A12 monoclonal antibodies. The CDR1 (SEQ ID NO:25), CDR2 (SEQ ID NO:29) and CDR3 (SEQ ID NO:33) regions are delineated.

FIG. 22 shows the nucleotide sequence (SEQ ID NO:80) and amino acid sequence (SEQ ID NO:56) of the light chain variable region of the PTA001_A11 monoclonal antibody. The CDR1 (SEQ ID NO:27), CDR2 (SEQ ID NO:29) and CDR3 (SEQ ID NO:33) regions are delineated.

FIG. 23 shows the nucleotide sequence (SEQ ID NO:82) and amino acid sequence (SEQ ID NO:57) of the light chain variable region of the PTA001_A13 monoclonal antibody. The CDR1 (SEQ ID NO:25), CDR2 (SEQ ID NO:31) and CDR3 (SEQ ID NO:33) regions are delineated.

FIG. 24 shows the nucleotide sequence (SEQ ID NO:83) and amino acid sequence (SEQ ID NO:58) of the light chain variable region of the PTA001_A14 monoclonal antibody. The CDR1 (SEQ ID NO:23), CDR2 (SEQ ID NO:29) and CDR3 (SEQ ID NO:33) regions are delineated.

FIG. 25 shows the alignment of the nucleotide sequences of the heavy chain CDR1 region of PTA001_A1 (SEQ ID NO:84) with nucleotides 240-269 of the mouse germline $V_H$ 7-39 nucleotide sequence (SEQ ID NO:125) and the alignments of the nucleotide sequences of the heavy chain CDR1 regions of PTA001_A2 and PTA001_A14 (SEQ ID NO:85); PTA001_A3, PTA001_A5, PTA001_A6, PTA001_A7, PTA001_A8, PTA001_A9, PTA001_A10, PTA001_A11, PTA001_A12 and PTA001_A13 (SEQ ID NO:86); and PTA001_A4 (SEQ ID NO:87) with nucleotides 67-96 of the mouse germline $V_H$ II gene H17 nucleotide sequence (SEQ ID NO:126).

FIG. 26 shows the alignments of the nucleotide sequences of the heavy chain CDR2 regions of PTA001_A2 (SEQ ID NO:89); PTA001_A3, PTA001_A5, PTA001_A6, PTA001_A8, PTA001_A9 and PTA001_A10 (SEQ ID NO:90); PTA001_A4 (SEQ ID NO:91); PTA001_A7 (SEQ ID NO:92); PTA001_A11 (SEQ ID NO:93); PTA001_A12 (SEQ ID NO:94); PTA001_A13 (SEQ ID NO:95); and PTA001_A14 (SEQ ID NO:96) with nucleotides 1096-1146 of the mouse germline $V_H$ II region VH105 nucleotide sequence (SEQ ID NO:127).

FIG. 27 shows the alignment of the nucleotide sequence of the light chain CDR1 region of PTA001_A1 (SEQ ID NO:105) with nucleotides 1738-1785 of the mouse germline $V_K$ 1-110 nucleotide sequence (SEQ ID NO:128), the alignment of the nucleotide sequence of the light chain CDR1 region of PTA001_A4 (SEQ ID NO:107) with nucleotides 510-560 of the mouse germline $V_K$ 8-30 nucleotide sequence (SEQ ID NO: 130) and the alignments of the nucleotide sequences of the light chain CDR1 regions of PTA001_A2, PTA001_A3, PTA001_A6, PTA001_A9 and PTA001_A14 (SEQ ID NO:106); PTA001_A5 and PTA001_A13 (SEQ ID NO:108); PTA001_A7 (SEQ ID NO:109); PTA001_A8 (SEQ ID NO:110); PTA001_A10 (SEQ ID NO:111); PTA001_A11 (SEQ ID NO:112); and PTA001_A12 (SEQ ID NO:113) with nucleotides 1807-1854 of the mouse germline $V_K$ 24-140 nucleotide sequence (SEQ ID NO:133).

FIG. 28 shows the alignment of the nucleotide sequence of the light chain CDR2 region of PTA001_A4 (SEQ ID NO:116) with nucleotides 606-626 of the mouse germline $V_K$ 8-30 nucleotide sequence (SEQ ID NO:131) and the alignments of the nucleotide sequences of the light chain CDR2 regions of PTA001_A2, PTA001_A3, PTA001_A6, PTA001_A9 and PTA001_A14 (SEQ ID NO:115); PTA001_A5 and PTA001_A13 (SEQ ID NO:117); PTA001_A7, PTA001_A10, PTA001_A11 and PTA001_A12 (SEQ ID NO:118); and PTA001_A8 (SEQ ID NO:119) with nucleotides 1900-1920 of the mouse germline $V_K$ 24-140 nucleotide sequence (SEQ ID NO:134).

FIG. 29 shows the alignment of the nucleotide sequence of the light chain CDR3 region of PTA001_A1 (SEQ ID NO:120) with nucleotides 1948-1971 of the mouse germline $V_K$ 1-110 nucleotide sequence (SEQ ID NO:129), the alignment of the nucleotide sequence of the light chain CDR3 region of PTA001_A4 (SEQ ID NO:122) with nucleotides 723-749 of the mouse germline $V_K$ 8-30 nucleotide sequence (SEQ ID NO:132) and the alignments of the nucleotide sequences of the light chain CDR3 regions of PTA001_A2, PTA001_A3, PTA001_A6, PTA001_A9, PTA001_A10, PTA001_A11, PTA001_A12 and PTA001_A14 (SEQ ID NO:121); PTA001_A5, PTA001_A8 and PTA001_A13 (SEQ ID NO:123); and PTA001_A7 (SEQ ID NO:124) with nucleotides 2017-2043 of the mouse germline $V_K$ 24-140 nucleotide sequence (SEQ ID NO:135).

FIG. 30 shows the Western Blotting analysis of Cadherin-17 using the PTA001_A4 monoclonal antibody.

FIG. 31 shows results of FACS analysis on PTA001_A4 in LoVo cells.

FIG. 32 shows results of FACS analysis on PTA001_A4 in LoVo and LS174T cells.

DETAILED DESCRIPTION OF THE INVENTION

Figure 33A:
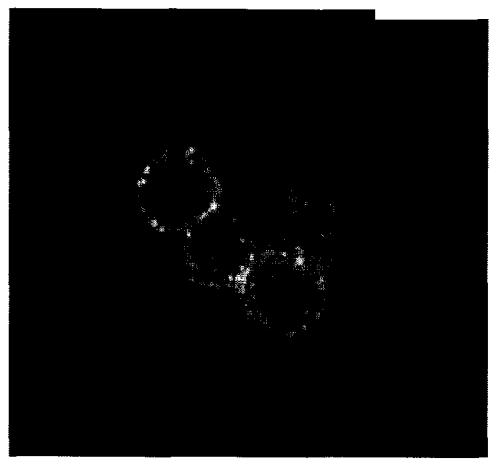
FIG. 33A shows surface binding of PTA001_A4/secondary antibody FITC conjugate complex to LoVo cells after 60 minutes of incubation.
Figure 33B:
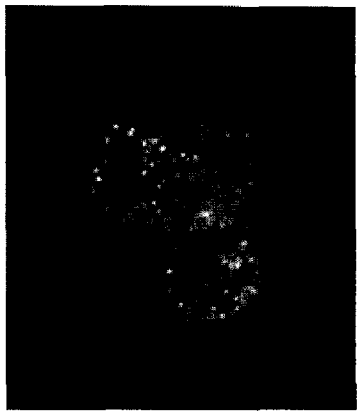
FIG. 33B shows internalization of PTA001_A4/secondary antibody FITC conjugate complex after 120 minutes of incubation with LoVo cells.
Figure 34A:
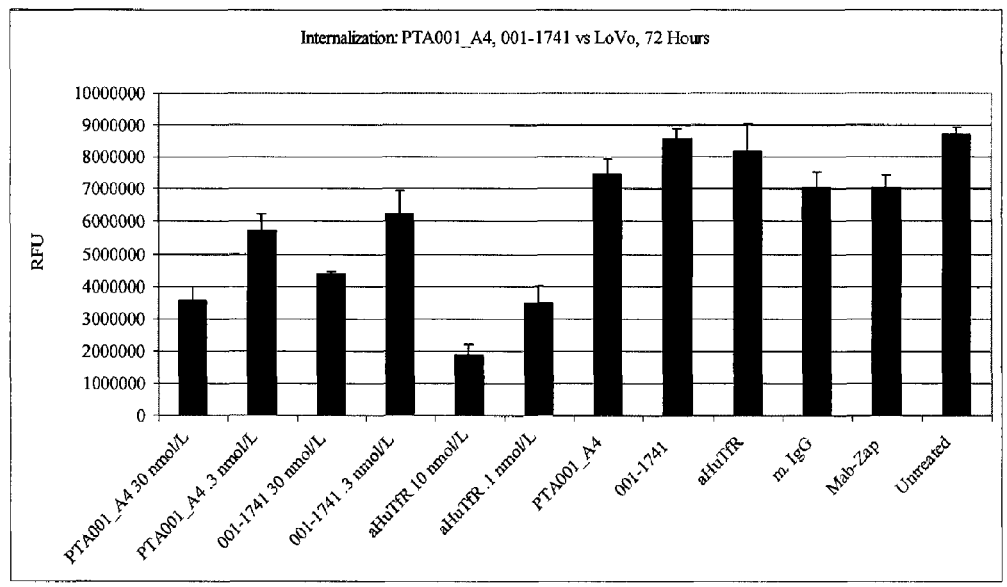
FIG. 34A shows results of internalisation of PTA001_A4 by MabZAP assay in LoVo colon cancer cells.
Figure 34B:
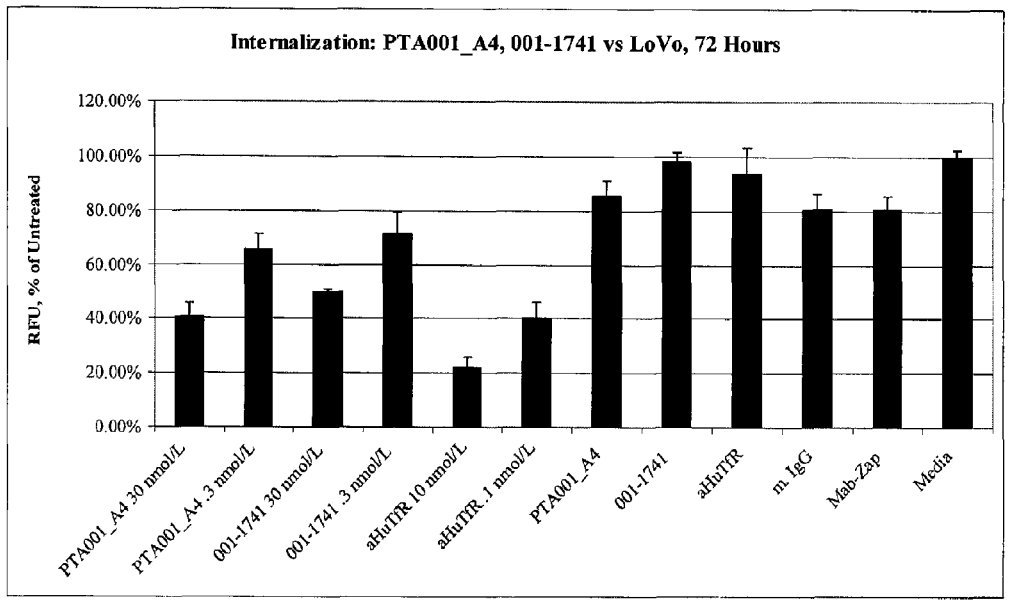
FIG. 34B shows results of internalisation of PTA001_A4 by MabZAP assay in LoVo colon cancer cells.
Figure 34C:
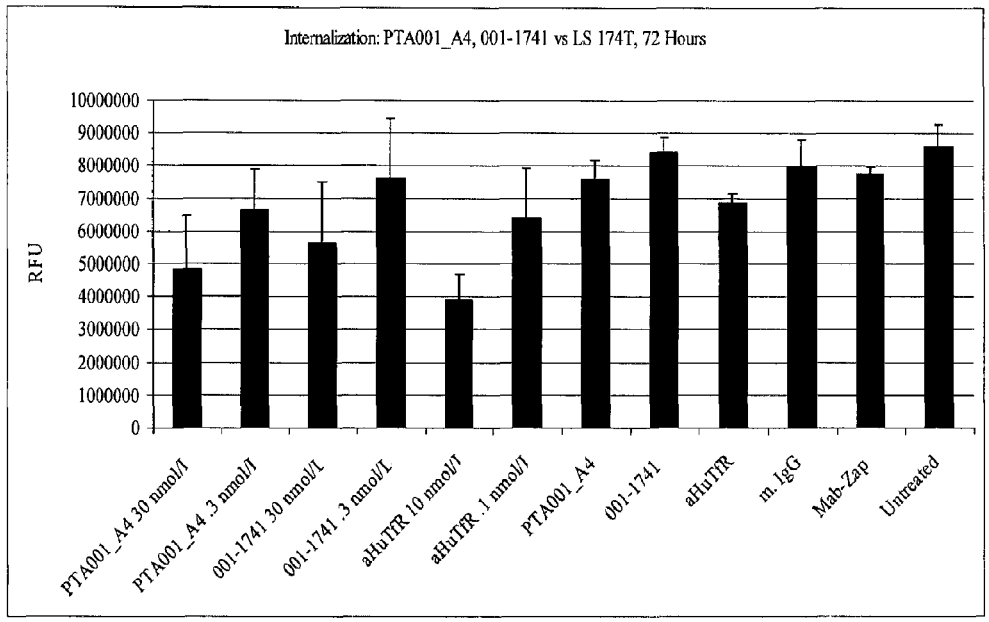
FIG. 34C shows results of internalisation of PTA001_A4 by MabZAP assay in LS174T colon cancer cells.
Figure 34D:
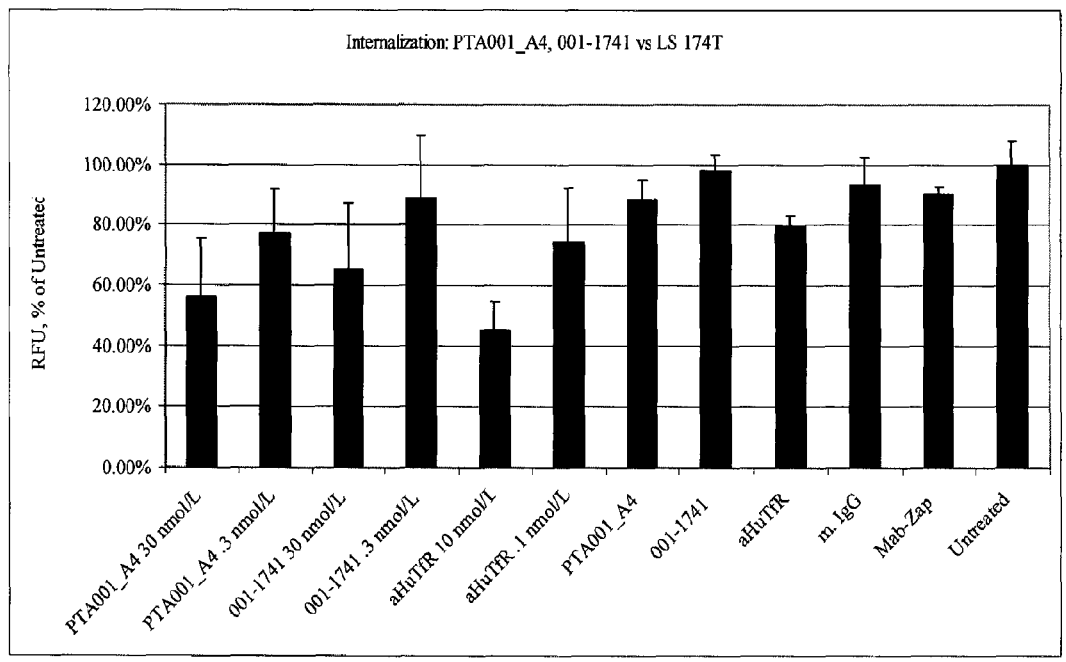
FIG. 34D shows results of internalisation of PTA001_A4 by MabZAP assay in LS174T colon cancer cells.

The present invention relates to isolated antibodies, including, but not limited to monoclonal antibodies, for example, which bind specifically to Cadherin-17 with high affinity. In certain embodiments, the antibodies of the invention comprise particular structural features such as CDR regions comprising particular amino acid sequences. The invention provides isolated antibodies, defucosylated antibodies, immunoconjugates, bispecific molecules, affibodies, domain antibodies, Nanobodies®, and Unibodies®, methods of making said molecules, and pharmaceutical compositions comprising said molecules and a pharmaceutical carrier. The invention also relates to methods of using the molecules, such as to detect Cadherin-17, as well as to treat diseases associated with expression of Cadherin-17, such as Cadherin-17 expressed on tumors, including those tumors of colorectal cancer.

In order that the present invention may be more readily understood, certain terms are first defined. Additional definitions are set forth throughout the detailed description.

The terms "Cadherin-17", "Liver-intestine cadherin", "LI-cadherin", "Intestinal peptide-associated transported HPT-1" and "CDH17" are used interchangeably. Cadherin-17 has also been identified as OGTA001 in International Patent Application WO2008/026008, which is incorporated herein by reference in its entirety. Human antibodies of this disclosure may, in certain cases, cross-react with Cadherin-17 from species other than human. In certain embodiments, the antibodies may be completely specific for one or more human Cadherin-17 and may not exhibit species or other types of non-human cross-reactivity. The complete amino acid sequence of an exemplary human Cadherin-17 has Genbank® accession number NM_004063.

The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

A "signal transduction pathway" refers to the biochemical relationship between various of signal transduction molecules that play a role in the transmission of a signal from one portion of a cell to another portion of a cell. As used herein, the phrase "cell surface receptor" includes, for example, molecules and complexes of molecules capable of receiving a signal and the transmission of such a signal across the plasma membrane of a cell. An example of a "cell surface receptor" of the present invention is the Cadherin-17 receptor.

The term "antibody" as referred to herein includes whole antibodies and any antigen binding fragment (i.e., "antigen-binding portion") or single chains thereof. An "antibody" refers to a glycoprotein which may comprise at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, $C_H1$, $C_H2$ and $C_H3$. Each light chain is comprised of a light chain variable region (abbreviated herein as $V_L$ or $V_K$) and a light chain constant region. The light chain constant region is comprised of one domain, $C_L$. The $V_H$ and $V_L/V_K$ regions can be further subdivided into regions of hypervariability, termed complementarity determining regions (CDR), interspersed with regions that are more conserved, termed framework regions (FR). Each $V_H$ and $V_L/V_K$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The definition of "antibody" includes, but is not limited to, full length antibodies, antibody fragments, single chain antibodies, bispecific antibodies, minibodies, domain antibodies, synthetic antibodies (sometimes referred to herein as "antibody mimetics"), chimeric antibodies, humanized antibodies, antibody fusions (sometimes referred to as "antibody conjugates"), and fragments of each, respectively.

In one embodiment, the antibody is an antibody fragment. Specific antibody fragments include, but are not limited to, (i) the Fab fragment consisting of VL, VH, CL and CH1 domains, (ii) the Fd fragment consisting of the VH and CH1 domains, (iii) the Fv fragment consisting of the VL and VH domains of a single antibody, (iv) the dAb fragment, which consists of a single variable domain, (v) isolated CDR regions, (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site, (viii) bispecific single chain Fv dimers, and (ix) "diabodies" or "triabodies", multivalent or multispecific fragments constructed by gene fusion. The antibody fragments may be modified. For example, the molecules may be stabilized by the incorporation of disulfide bridges linking the VH and VL domains. Examples of antibody formats and architectures are described in Holliger & Hudson, 2006, Nature Biotechnology 23(9):1126-1136, and Carter 2006, Nature Reviews Immunology 6:343-357 and references cited therein, all expressly incorporated by reference. In one embodiment, an antibody disclosed herein may be a multispecific antibody, and notably a bispecific antibody, also sometimes referred to as "diabodies". These are antibodies that bind to two (or more) different antigens. Diabodies can be manufactured in a variety of ways known in the art, e.g., prepared chemically or from hybrid hybridomas. In one embodiment, the antibody is a minibody. Minibodies are minimized antibody-like proteins comprising a scFv joined to a CH3 domain. In some cases, the scFv can be joined to the Fc region, and may include some or all of the hinge region. For a description of multispecific antibodies see Holliger & Hudson, 2006, Nature Biotechnology 23(9):1126-1136 and references cited therein, all expressly incorporated by reference.

By "CDR" as used herein is meant a Complementarity Determining Region of an antibody variable domain. Systematic identification of residues included in the CDRs have been developed by Kabat (Kabat et al., 1991, Sequences of Proteins of Immunological Interest, 5th Ed., United States Public Health Service, National Institutes of Health, Bethesda) and alternately by Chothia (Chothia & Lesk, 1987, J. Mol. Biol. 196: 901-917; Chothia et al., 1989, Nature 342: 877-883; Al-Lazikani et al., 1997, J. Mol. Biol. 273: 927-948). For the purposes of the present invention, CDRs are defined as a slightly smaller set of residues than the CDRs defined by Chothia. VL CDRs are herein defined to include residues at positions 27-32 (CDR1), 50-56 (CDR2), and 91-97 (CDR3), wherein the numbering is according to Chothia. Because the VL CDRs as defined by Chothia and Kabat are identical, the numbering of these VL CDR positions is also according to Kabat. VH CDRs are herein defined to include residues at positions 27-33 (CDR1), 52-56 (CDR2), and 95-102 (CDR3), wherein the numbering is according to Chothia. These VH CDR positions correspond to Kabat positions 27-35 (CDR1), 52-56 (CDR2), and 95-102 (CDR3).

As will be appreciated by those in the art, the CDRs disclosed herein may also include variants. for example when backmutating the CDRs disclosed herein into different framework regions. Generally, the amino acid identity between individual variant CDRs are at least 80% to the sequences depicted herein, and more typically with preferably increasing identities of at least 85%, 90%, 91%, 92%, 93%, 94%, 95%, 96%, 97%, 98%, 99%, and almost 100%. In a similar manner, "percent (%) nucleic acid sequence identity" with respect to the nucleic acid sequence of the binding proteins identified herein is defined as the percentage of nucleotide residues in a candidate sequence that are identical with the nucleotide residues in the coding sequence of the antigen binding protein. A specific method utilizes the BLASTN module of WU-BLAST-2 set to the default parameters, with overlap span and overlap fraction set to 1 and 0.125, respectively.

Generally, the nucleic acid sequence identity between the nucleotide sequences encoding individual variant CDRs and the nucleotide sequences depicted herein are at least 80%, and more typically with preferably increasing identities of at least 80%, 81%, 82%, 83%, 84%, 85%, 86%, 87%, 88%, 89%, 90%, 91%, 92%, 93%, 94%, 95%, 96%, 97%, 98%, or 99%, and almost 100%.

Thus, a "variant CDR" is one with the specified homology, similarity, or identity to the parent CDR of the invention, and shares biological function, including, but not limited to, at least 80%, 81%, 82%, 83%, 84%, 85%, 86%, 87%, 88%, 89%, 90%, 91%, 92%, 93%, 94%, 95%, 96%, 97%, 98%, or 99% of the specificity and/or activity of the parent CDR.

While the site or region for introducing an amino acid sequence variation is predetermined, the mutation per se need not be predetermined. For example, in order to optimize the performance of a mutation at a given site, random mutagenesis may be conducted at the target codon or region and the expressed antigen binding protein CDR variants screened for the optimal combination of desired activity. Techniques for making substitution mutations at predetermined sites in DNA having a known sequence are well known, for example, M13 primer mutagenesis and PCR mutagenesis. Screening of the mutants is done using assays of antigen binding protein activities as described herein.

Amino acid substitutions are typically of single residues; insertions usually will be on the order of from about one (1) to about twenty (20) amino acid residues, although considerably larger insertions may be tolerated. Deletions range from about one (1) to about twenty (20) amino acid residues, although in some cases deletions may be much larger.

Substitutions, deletions, insertions or any combination thereof may be used to arrive at a final derivative or variant. Generally these changes are done on a few amino acids to minimize the alteration of the molecule, particularly the immunogenicity and specificity of the antigen binding protein. However, larger changes may be tolerated in certain circumstances.

By "Fab" or "Fab region" as used herein is meant the polypeptide that comprises the VH, CH1, VL, and CL immunoglobulin domains. Fab may refer to this region in isolation, or this region in the context of a full length antibody, antibody fragment or Fab fusion protein, or any other antibody embodiments as outlined herein.

By "Fv" or "Fv fragment" or "Fv region" as used herein is meant a polypeptide that comprises the VL and VH domains of a single antibody.

By "framework" as used herein is meant the region of an antibody variable domain exclusive of those regions defined as CDRs. Each antibody variable domain framework can be further subdivided into the contiguous regions separated by the CDRs (FR1, FR2, FR3 and FR4).

The term "antigen-binding portion" of an antibody (or simply "antibody portion"), as used herein, refers to one or more fragments of an antibody that retain the ability to specifically bind to an antigen (e.g., Cadherin-17). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L/V_K$, $V_H$, $C_L$ and $C_H1$ domains; (ii) a F(ab')$_2$ fragment, a bivalent fragment comprising two Fab fragments linked by a disulfide bridge at the hinge region; (iii) a Fab' fragment, which is essentially an Fab with part of the hinge region (see, FUNDAMENTAL IMMUNOLOGY (Paul ed., 3.sup.rd ed. 1993); (iv) a Fd fragment consisting of the $V_H$ and $C_H1$ domains; (v) a Fv fragment consisting of the $V_L$ and $V_H$ domains of a single arm of an antibody; (vi) a dAb fragment (Ward et al., (1989) Nature 341:544-546), which consists of a $V_H$ domain; (vii) an isolated complementarity determining region (CDR); and (viii) a Nanobody®, a heavy chain variable region containing a single variable domain and two constant domains. Furthermore, although the two domains of the Fv fragment, $V_L/V_K$ and $V_H$, are coded for by separate genes, they can be joined, using recombinant methods, by a synthetic linker that enables them to be made as a single protein chain in which the $V_L/V_K$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

An "isolated antibody" as used herein, is intended to refer to an antibody that is substantially free of other antibodies having different antigenic specificities (e.g., an isolated antibody that specifically binds Cadherin-17 is substantially free of antibodies that specifically bind antigens other than Cadherin-17). An isolated antibody that specifically binds Cadherin-17 may, however, have cross-reactivity to other antigens, such as Cadherin-17 molecules from other species. Moreover, and/or alternatively an isolated antibody may be substantially free of other cellular material and/or chemicals in a form not normally found in nature.

In some embodiments, the antibodies of the invention are recombinant proteins, isolated proteins or substantially pure proteins. An "isolated" protein is unaccompanied by at least some of the material with which it is normally associated in its natural state, for example constituting at least about 5%, or at least about 50% by weight of the total protein in a given sample. It is understood that the isolated protein may constitute from 5 to 99.9% by weight of the total protein content depending on the circumstances. For example, the protein may be made at a significantly higher concentration through the use of an inducible promoter or high expression promoter, such that the protein is made at increased concentration levels. In the case of recombinant proteins, the definition includes the production of an antibody in a wide variety of organisms and/or host cells that are known in the art in which it is not naturally produced.

The terms "monoclonal antibody" or "monoclonal antibody composition" as used herein refer to a preparation of antibody molecules of single molecular composition. A monoclonal antibody composition displays a single binding specificity and affinity for a particular epitope.

As used herein, "isotype" refers to the antibody class (e.g., IgM or IgG1) that is encoded by the heavy chain constant region genes.

The phrases "an antibody recognizing an antigen" and "an antibody specific for an antigen" are used interchangeably herein with the term "an antibody which binds specifically to an antigen".

The term "antibody derivatives" refers to any modified form of the antibody, e.g., a conjugate of the antibody and another agent or antibody. For example, antibodies of the present invention may be conjugated to a toxin, a label, etc. The antibodies of the present invention may be nonhuman, chimeric, humanized, or fully human. For a description of the concepts of chimeric and humanized antibodies see Clark et al., 2000 and references cited therein (Clark, 2000, *Immunol Today* 21:397-402). Chimeric antibodies comprise the variable region of a nonhuman antibody, for example VH and VL domains of mouse or rat origin, operably linked to the constant region of a human antibody (see for example U.S. Pat. No. 4,816,567). In a preferred embodiment, the antibodies of the present invention are humanized. By "humanized" antibody as used herein is meant an antibody comprising a human framework region (FR) and one or more complementarity determining regions (CDR's) from a non-human (usually mouse or rat) antibody. The non-human antibody providing the CDR's is called the "donor" and the human immunoglobulin providing the framework is called the "acceptor". Humanization relies principally on the grafting of donor CDRs onto acceptor (human) VL and VH frameworks (U.S. Pat. No. 5,225,539). This strategy is referred to as "CDR grafting". "Backmutation" of selected acceptor framework residues to the corresponding donor residues is often required to regain affinity that is lost in the initial grafted construct (U.S. Pat. No. 5,530,101; U.S. Pat. No. 5,585,089; U.S. Pat. No. 5,693,761; U.S. Pat. No. 5,693,762; U.S. Pat. No. 6,180,370; U.S. Pat. No. 5,859,205; U.S. Pat. No. 5,821,337; U.S. Pat. No. 6,054,297; U.S. Pat. No. 6,407,213). The humanized antibody optimally also will comprise at least a portion of an immunoglobulin constant region, typically that of a human immunoglobulin, and thus will typically comprise a human Fc region. Methods for humanizing non-human antibodies are well known in the art, and can be essentially performed following the method of Winter and co-workers (Jones et al., 1986, *Nature* 321:522-525; Riechmann et al., 1988, *Nature* 332:323-329; Verhoeyen et al., 1988, *Science*, 239:1534-1536). Additional examples of humanized murine monoclonal antibodies are also known in the art, for example antibodies binding human protein C (O'Connor et al., 1998, *Protein Eng* 11:321-8), interleukin 2 receptor (Queen et al., 1989, *Proc Natl Acad Sci, USA* 86:10029-33), and human epidermal growth factor receptor 2 (Carter et al., 1992, *Proc Natl Acad Sci USA* 89:4285-9). In an alternate embodiment, the antibodies of the present invention may be fully human, that is the sequences of the antibodies are completely or substantially human. A number of methods are known in the art for generating fully human antibodies, including the use of transgenic mice (Bruggemann et al., 1997, *Curr Opin Biotechnol* 8:455-458) or human antibody libraries coupled with selection methods (Griffiths et al., 1998, *Curr Opin Biotechnol* 9:102-108).

The term "humanized antibody" is intended to refer to antibodies in which CDR sequences derived from the germline of another mammalian species, such as a mouse, have been grafted onto human framework sequences. Additional framework region modifications may be made within the human framework sequences.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

The term "specifically binds" (or "immunospecifically binds") is not intended to indicate that an antibody binds exclusively to its intended target. Rather, an antibody "specifically binds" if its affinity for its intended target is about 5-fold greater when compared to its affinity for a non-target molecule. Suitably there is no significant cross-reaction or cross-binding with undesired substances, especially naturally occurring proteins or tissues of a healthy person or animal. The affinity of the antibody will, for example, be at least about 5 fold, such as 10 fold, such as 25-fold, especially 50-fold, and particularly 100-fold or more, greater for a target molecule than its affinity for a non-target molecule. In some embodiments, specific binding between an antibody or other binding agent and an antigen means a binding affinity of at least $10^6$ $M^{-1}$. Antibodies may, for example, bind with affinities of at least about $10^7$ $M^{-1}$, such as between about $10^8$ $M^{-1}$ to about $10^9$ $M^{-1}$, about $10^9$ $M^{-1}$ to about $10^{10}$ $M^{-1}$, or about $10^{10}$ $M^{-1}$ to about $10^{11}$ $M^{-1}$. Antibodies may, for example, bind with an $EC_{50}$ of 50 nM or less, 10 nM or less, 1 nM or less, 100 pM or less, or more preferably 10 pM or less.

The term "does not substantially bind" to a protein or cells, as used herein, means does not bind or does not bind with a high affinity to the protein or cells, i.e. binds to the protein or cells with a $K_D$ of $1\times10^{-6}$ M or more, more preferably $1\times10^{-5}$ M or more, more preferably $1\times10^{-4}$ M or more, more preferably $1\times10^{-3}$ M or more, even more preferably $1\times10^{-2}$ M or more.

The term "$EC_{50}$" as used herein, is intended to refer to the potency of a compound by quantifying the concentration that leads to 50% maximal response/effect. $EC_{50}$ may be determined by Scratchard or FACS.

The term "$K_{assoc}$" or "$K_a$," as used herein, is intended to refer to the association rate of a particular antibody-antigen interaction, whereas the term "$K_{dis}$" or "$K_d$," as used herein, is intended to refer to the dissociation rate of a particular antibody-antigen interaction. The term "$K_D$," as used herein, is intended to refer to the dissociation constant, which is obtained from the ratio of $K_d$ to $K_a$ (i.e., $K_d/K_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a Biacore® system.

As used herein, the term "high affinity" for an IgG antibody refers to an antibody having a $K_D$ of $1\times10^{-7}$ M or less, more preferably $5\times10^{-8}$ M or less, even more preferably $1\times10^{-8}$ M or less, even more preferably $5\times10^{-9}$ M or less and even more preferably $1\times10^{-9}$ M or less for a target antigen. However, "high affinity" binding can vary for other antibody isotypes. For example, "high affinity" binding for an IgM isotype refers to an antibody having a $K_D$ of $10^{-6}$ M or less, more preferably $10^{-7}$ M or less, even more preferably $10^{-8}$ M or less.

The term "epitope" or "antigenic determinant" refers to a site on an antigen to which an immunoglobulin or antibody specifically binds. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods of determining spatial conformation of epitopes include techniques in the art and those described herein, for example, x-ray crystallography and 2-dimensional nuclear magnetic resonance (see, e.g., *Epitope Mapping Protocols in Methods in Molecular Biology*, Vol. 66, G. E. Morris, Ed. (1996)).

Accordingly, also encompassed by the present invention are antibodies that bind to (i.e., recognize) the same epitope as the antibodies described herein (i.e., PTA001_A1, PTA001_A2, PTA001_A3, PTA001_A4, PTA001_A5, PTA001_A6, PTA001_A7, PTA001_A8, PTA001_A9, PTA001_A10, PTA001_A11, PTA001_A12, PTA001_A13 and PTA001_A14). Antibodies that bind to the same epitope can be identified by their ability to cross-compete with (i.e., competitively inhibit binding of) a reference antibody to a target antigen in a statistically significant manner. Competitive inhibition can occur, for example, if the antibodies bind to identical or structurally similar epitopes (e.g., overlapping epitopes), or spatially proximal epitopes which, when bound, causes steric hindrance between the antibodies.

Competitive inhibition can be determined using routine assays in which the immunoglobulin under test inhibits specific binding of a reference antibody to a common antigen. Numerous types of competitive binding assays are known, for example: solid phase direct or indirect radioimmunoassay (RIA), solid phase direct or indirect enzyme immunoassay (EIA), sandwich competition assay (see Stahli et al., *Methods in Enzymology* 9:242 (1983)); solid phase direct biotin-avidin EIA (see Kirkland et al., *J. Immunol.* 137:3614 (1986)); solid phase direct labeled assay, solid phase direct labeled sandwich assay (see Harlow and Lane, *Antibodies: A Laboratory Manual*, Cold Spring Harbor Press (1988)); solid phase direct label RIA using I-125 label (see Morel et al., *Mol. Immunol.* 25(1):7 (1988)); solid phase direct biotin-avidin EIA (Cheung et al., *Virology* 176:546 (1990)); and direct labeled RIA. (Moldenhauer et al., *Scand. J. Immunol.* 32:77 (1990)). Typically, such an assay involves the use of purified antigen bound to a solid surface or cells bearing either of these, an unlabeled test immunoglobulin and a labeled reference immunoglobulin. Competitive inhibition is measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70% 70-75% or more.

Other techniques include, for example, epitope mapping methods, such as x-ray analyses of crystals of antigen:antibody complexes which provides atomic resolution of the epitope. Other methods monitor the binding of the antibody to antigen fragments or mutated variations of the antigen where loss of binding due to a modification of an amino acid residue within the antigen sequence is often considered an indication of an epitope component. In addition, computational combinatorial methods for epitope mapping can also be used. These methods rely on the ability of the antibody of interest to affinity isolate specific short peptides from combinatorial phage display peptide libraries. The peptides are then regarded as leads for the definition of the epitope corresponding to the antibody used to screen the peptide library. For epitope mapping, computational algorithms have also been developed which have been shown to map conformational discontinuous epitopes.

As used herein, the term "subject" includes any human or nonhuman animal. The term "nonhuman animal" includes all vertebrates, e.g., mammals and non-mammals, such as non-human primates, sheep, dogs, cats, horses, cows, chickens, amphibians, reptiles, etc.

Various aspects of the invention are described in further detail in the following subsections.

Anti-Cadherin-17 Antibodies

The antibodies of the invention are characterized by particular functional features or properties of the antibodies. For example, the antibodies bind specifically to human Cadherin-17. Preferably, an antibody of the invention binds to Cadherin-17 with high affinity, for example with a $K_D$ of $8 \times 10^{-7}$ M or less, even more typically $1 \times 10^{-8}$ M or less. The anti-Cadherin-17 antibodies of the invention preferably exhibit one or more of the following characteristics:

binds to human Cadherin-17 with a $EC_{50}$ of 50 nM or less, 10 nM or less, 1 nM or less, 100 pM or less, or more preferably 10 pM or less;
  binds to human cells expressing Cadherin-17.

In one embodiment, the antibodies preferably bind to an antigenic epitope present in Cadherin-17, which epitope is not present in other proteins. The antibodies typically bind Cadherin-17 but does not bind to other proteins, or binds to proteins with a low affinity, such as a $K_D$ of $1 \times 10^{-6}$ M or more, more preferably $1 \times 10^{-5}$ M or more, more preferably $1 \times 10^{-4}$ M or more, more preferably $1 \times 10^{-3}$ M or more, even more preferably $1 \times 10^{-2}$ M or more. Preferably, the antibodies do not bind to related proteins, for example, the antibodies do not substantially bind to other cell adhesion molecules. In one embodiment, the antibody may be internalized into a cell expressing Cadherin-17. Standard assays to evaluate antibody internalization are known in the art, including, for example, a HumZap internalization assay.

Standard assays to evaluate the binding ability of the antibodies toward Cadherin-17 are known in the art, including for example, ELISAs, Western blots, RIAs, and flow cytometry analysis. Suitable assays are described in detail in the Examples. The binding kinetics (e.g., binding affinity) of the antibodies also can be assessed by standard assays known in the art, such as by Biacore® system analysis. To assess binding to Raji or Daudi B cell tumor cells, Raji (ATCC Deposit No. CCL-86) or Daudi (ATCC Deposit No. CCL-213) cells can be obtained from publicly available sources, such as the American Type Culture Collection, and used in standard assays, such as flow cytometric analysis.

Monoclonal Antibodies of the Invention

Preferred antibodies of the invention are the monoclonal antibodies PTA001_A1, PTA001_A2, PTA001_A3, PTA001_A4, PTA001_A5, PTA001_A6, PTA001_A7, PTA001_A8, PTA001_A9, PTA001_A10, PTA001_A11, PTA001_A12, PTA001_A13 and PTA001_A14, isolated and structurally characterized as described in Examples 1-6. The $V_H$ amino acid sequences of PTA001_A1, PTA001_A2, PTA001_A3, PTA001_A4, PTA001_A5, PTA001_A6, PTA001_A7, PTA001_A8, PTA001_A9, PTA001_A10, PTA001_A11, PTA001_A12, PTA001_A13 and PTA001_A14 are shown in SEQ ID NOs:35-46. The $V_K$ amino acid sequences of PTA001_A1, PTA001_A2, PTA001_A3, PTA001_A4, PTA001_A5, PTA001_A6, PTA001_A7, PTA001_A8, PTA001_A9, PTA001_A10, PTA001_A11, PTA001_A12, PTA001_A13 and PTA001_A14 are shown in SEQ ID NOs:47-58.

Given that each of these antibodies can bind to Cadherin-17, the $V_H$ and $V_K$ sequences can be "mixed and matched" to create other anti-Cadherin-17 binding molecules of the invention. Cadherin-17 binding of such "mixed and matched" antibodies can be tested using the binding assays described above and in the Examples (e.g., ELISAs). Preferably, when $V_H$ and $V_K$ chains are mixed and matched, a $V_H$ sequence from a particular $V_H/V_K$ pairing is replaced with a structurally similar $V_H$ sequence. Likewise, preferably a $V_K$ sequence from a particular $V_H/V_K$ pairing is replaced with a structurally similar $V_K$ sequence.

Accordingly, in one aspect, the invention provides an antibody, comprising: a heavy chain variable region comprising an amino acid sequence set forth in a SEQ ID NO: selected from the group consisting of 38, 35, 36, 37, 39, 40, 41, 42, 43, 44, 45 and 46 and a light chain variable region comprising an amino acid sequence set forth in a SEQ ID NO: selected from the group consisting of 49, 47, 48, 50, 51, 52, 53, 54, 55, 56, 57 and 58; wherein the antibody specifically binds Cadherin-17, preferably human Cadherin-17.

Preferred heavy and light chain combinations include:
a heavy chain variable region comprising the amino acid sequence of SEQ ID NO:35 and a light chain variable region comprising the amino acid sequence of SEQ ID NO:47; or a heavy chain variable region comprising the amino acid sequence of SEQ ID NO:36; and a light chain variable region comprising the amino acid sequence of SEQ ID NO:48, or a heavy chain variable region comprising the amino acid sequence of SEQ ID NO:37; and a light chain variable region comprising the amino acid sequence of SEQ ID NO:48, or a heavy chain variable region comprising the amino acid sequence of SEQ ID NO:38; and a light chain variable region comprising the amino acid sequence of SEQ ID NO:49, or a heavy chain variable region comprising the amino acid sequence of SEQ ID NO:39; and a light chain variable region comprising the amino acid sequence of SEQ ID NO:50, or a heavy chain variable region comprising the amino acid sequence of SEQ ID NO:40; and a light chain variable region comprising the amino acid sequence of SEQ ID NO:51, or a heavy chain variable region comprising the amino acid sequence of SEQ ID NO:41; and a light chain variable region comprising the amino acid sequence of SEQ ID NO:52, or a heavy chain variable region comprising the amino acid sequence of SEQ ID NO:42; and a light chain variable region comprising the amino acid sequence of SEQ ID NO:53, or a heavy chain variable region comprising the amino acid sequence of SEQ ID NO:40; and a light chain variable region comprising the amino acid sequence of SEQ ID NO:54, or a heavy chain variable region comprising the amino acid sequence of SEQ ID NO:40; and a light chain variable region comprising the amino acid sequence of SEQ ID NO:55, or a heavy chain variable region comprising the amino acid sequence of SEQ ID NO:43; and a light chain variable region comprising the amino acid sequence of SEQ ID NO:56, or a heavy chain variable region comprising the amino acid sequence of SEQ ID NO:44; and a light chain variable region comprising the amino acid sequence of SEQ ID NO:55, or a heavy chain variable region comprising the amino acid sequence of SEQ ID NO:45; and a light chain variable region comprising the amino acid sequence of SEQ ID NO:57, or a heavy chain variable region comprising the amino acid sequence of SEQ ID NO:46; and a light chain variable region comprising the amino acid sequence of SEQ ID NO:58.

In another aspect, the invention provides antibodies that comprise the heavy chain and light chain CDR1s, CDR2s and CDR3s of PTA001_A1, PTA001_A2, PTA001_A3, PTA001_A4, PTA001_A5, PTA001_A6, PTA001_A7, PTA001_A8, PTA001_A9, PTA001_A10, PTA001_A11, PTA001_A12, PTA001_A13 and PTA001_A14, or combinations thereof. The amino acid sequences of the $V_H$ CDR1s of PTA001_A1, PTA001_A2, PTA001_A3, PTA001_A4, PTA001_A5, PTA001_A6, PTA001_A7, PTA001_A8, PTA001_A9, PTA001_A10, PTA001_A11, PTA001_A12, PTA001_A13 and PTA001_A14 are shown in SEQ ID NOs: 1-4. The amino acid sequences of the $V_H$ CDR2s of PTA001_A1, PTA001_A2, PTA001_A3, PTA001_A4, PTA001_A5, PTA001_A6, PTA001_A7, PTA001_A8, PTA001_A9, PTA001_A10, PTA001_A11, PTA001_A12, PTA001_A13 and PTA001_A14 are shown in SEQ ID NOs: 5-13. The amino acid sequences of the $V_H$ CDR3s of PTA001_A1, PTA001_A2, PTA001_A3, PTA001_A4, PTA001_A5, PTA001_A6, PTA001_A7, PTA001_A8, PTA001_A9, PTA001_A10, PTA001_A11, PTA001_A12, PTA001_A13 and PTA001_A14 are shown in SEQ ID NOs: 14-21. The amino acid sequences of the $V_K$ CDR1s of PTA001_A1, PTA001_A2, PTA001_A3, PTA001_A4, PTA001_A5, PTA001_A6, PTA001_A7, PTA001_A8, PTA001_A9, PTA001_A10, PTA001_A11, PTA001_A12, PTA001_A13 and PTA001_A14 are shown in SEQ ID NOs: 22-27. The amino acid sequences of the $V_K$ CDR2s of PTA001_A1, PTA001_A2, PTA001_A3, PTA001_A4, PTA001_A5, PTA001_A6, PTA001_A7, PTA001_A8, PTA001_A9, PTA001_A10, PTA001_A11, PTA001_A12, PTA001_A13 and PTA001_A14 are shown in SEQ ID NOs: 28-31. The amino acid sequences of the $V_K$ CDR3s of PTA001_A1, PTA001_A2, PTA001_A3, PTA001_A4, PTA001_A5, PTA001_A6, PTA001_A7, PTA001_A8, PTA001_A9, PTA001_A10, PTA001_A11, PTA001_A12, PTA001_A13 and PTA001_A14 are shown in SEQ ID NOs: 32-34. The CDR regions are delineated using the Kabat system (Kabat, E. A., et al. (1991) Sequences of Proteins of Immunological Interest, Fifth Edition, U.S. Department of Health and Human Services, NIH Publication No. 91-3242).

Given that each of these antibodies can bind to Cadherin-17 and that antigen-binding specificity is provided primarily by the CDR1, CDR2, and CDR3 regions, the $V_H$ CDR1, CDR2, and CDR3 sequences and $V_K$ CDR1, CDR2, and CDR3 sequences can be "mixed and matched" (i.e., CDRs from different antibodies can be mixed and matched, although each antibody generally contains a $V_H$ CDR1, CDR2, and CDR3 and a $V_K$ CDR1, CDR2, and CDR3) to create other anti-Cadherin-17 binding molecules of the invention. Accordingly, the invention specifically includes every possible combination of CDRs of the heavy and light chains.

Cadherin-17 binding of such "mixed and matched" antibodies can be tested using the binding assays described above and in the Examples (e.g., ELISAs, Biacore® analysis). Preferably, when $V_H$ CDR sequences are mixed and matched, the CDR1, CDR2 and/or CDR3 sequence from a particular $V_H$ sequence is replaced with a structurally similar CDR sequence(s). Likewise, when $V_K$ CDR sequences are mixed and matched, the CDR1, CDR2 and/or CDR3 sequence from a particular $V_K$ sequence preferably is replaced with a structurally similar CDR sequence(s). It will be readily apparent to the ordinarily skilled artisan that novel $V_H$ and $V_K$ sequences can be created by substituting one or more $V_H$ and/or $V_L/V_K$ CDR region sequences with structurally similar sequences from the CDR sequences disclosed herein for monoclonal antibodies PTA001_A1, PTA001_A2, PTA001_A3, PTA001_A4, PTA001_A5, PTA001_A6, PTA001_A7, PTA001_A8, PTA001_A9, PTA001_A10, PTA001_A11, PTA001_A12, PTA001_A13 and PTA001_A14.

Accordingly, in another aspect, the invention provides an isolated monoclonal antibody, or antigen binding portion thereof comprising:

a heavy chain variable region CDR1 comprising an amino acid sequence selected from the group consisting of SEQ ID NOs:1-4;

a heavy chain variable region CDR2 comprising an amino acid sequence selected from the group consisting of SEQ ID NOs:5-13;

a heavy chain variable region CDR3 comprising an amino acid sequence selected from the group consisting of SEQ ID NOs:14-21;

a light chain variable region CDR1 comprising an amino acid sequence selected from the group consisting of SEQ ID NOs: 22-27;

a light chain variable region CDR2 comprising an amino acid sequence selected from the group consisting of SEQ ID NOs: 28-31; and a light chain variable region CDR3 comprising an amino acid sequence selected from the group consisting of SEQ ID NOs: 32-34;

with all possible combinations being possible, wherein the antibody specifically binds Cadherin-17, preferably human Cadherin-17

In a preferred embodiment, the antibody comprises:
a heavy chain variable region CDR1 comprising SEQ ID NO:1;
a heavy chain variable region CDR2 comprising SEQ ID NO:5;
a heavy chain variable region CDR3 comprising SEQ ID NO:14;
a light chain variable region CDR1 comprising SEQ ID NO:22;
a light chain variable region CDR2 comprising SEQ ID NO:28; and
a light chain variable region CDR3 comprising SEQ ID NO:32.

In another preferred embodiment, the antibody comprises:
a heavy chain variable region CDR1 comprising SEQ ID NO:2;
a heavy chain variable region CDR2 comprising SEQ ID NO:6;
a heavy chain variable region CDR3 comprising SEQ ID NO:15;
a light chain variable region CDR1 comprising SEQ ID NO:23;
a light chain variable region CDR2 comprising SEQ ID NO:29; and
a light chain variable region CDR3 comprising SEQ ID NO:33.

In another preferred embodiment, the antibody comprises:
a heavy chain variable region CDR1 comprising SEQ ID NO:3;
a heavy chain variable region CDR2 comprising SEQ ID NO:7;
a heavy chain variable region CDR3 comprising SEQ ID NO:16;
a light chain variable region CDR1 comprising SEQ ID NO:23;
a light chain variable region CDR2 comprising SEQ ID NO:29; and a light chain variable region CDR3 comprising SEQ ID NO:33.

In another preferred embodiment, the antibody comprises:
a heavy chain variable region CDR1 comprising SEQ ID NO:4;
a heavy chain variable region CDR2 comprising SEQ ID NO:8;
a heavy chain variable region CDR3 comprising SEQ ID NO:17;
a light chain variable region CDR1 comprising SEQ ID NO:24;
a light chain variable region CDR2 comprising SEQ ID NO:30; and
a light chain variable region CDR3 comprising SEQ ID NO:34.

In another preferred embodiment, the antibody comprises:
a heavy chain variable region CDR1 comprising SEQ ID NO:3;
a heavy chain variable region CDR2 comprising SEQ ID NO:7;
a heavy chain variable region CDR3 comprising SEQ ID NO:18;
a light chain variable region CDR1 comprising SEQ ID NO:25;
a light chain variable region CDR2 comprising SEQ ID NO:31; and
a light chain variable region CDR3 comprising SEQ ID NO:33.

In another preferred embodiment, the antibody comprises:
a heavy chain variable region CDR1 comprising SEQ ID NO:3;
a heavy chain variable region CDR2 comprising SEQ ID NO:9;
a heavy chain variable region CDR3 comprising SEQ ID NO:19;
a light chain variable region CDR1 comprising SEQ ID NO:26;
a light chain variable region CDR2 comprising SEQ ID NO:29; and
a light chain variable region CDR3 comprising SEQ ID NO:33.

In another preferred embodiment, the antibody comprises:
a heavy chain variable region CDR1 comprising SEQ ID NO:3;
a heavy chain variable region CDR2 comprising SEQ ID NO:7;
a heavy chain variable region CDR3 comprising SEQ ID NO:16;
a light chain variable region CDR1 comprising SEQ ID NO:25;
a light chain variable region CDR2 comprising SEQ ID NO:31; and
a light chain variable region CDR3 comprising SEQ ID NO:33.

In another preferred embodiment, the antibody comprises:
a heavy chain variable region CDR1 comprising SEQ ID NO:3;
a heavy chain variable region CDR2 comprising SEQ ID NO:7;
a heavy chain variable region CDR3 comprising SEQ ID NO:16;
a light chain variable region CDR1 comprising SEQ ID NO:25;
a light chain variable region CDR2 comprising SEQ ID NO:29; and
a light chain variable region CDR3 comprising SEQ ID NO:33.

In another preferred embodiment, the antibody comprises:
a heavy chain variable region CDR1 comprising SEQ ID NO:3;
a heavy chain variable region CDR2 comprising SEQ ID NO:10;
a heavy chain variable region CDR3 comprising SEQ ID NO:20;
a light chain variable region CDR1 comprising SEQ ID NO:27;
a light chain variable region CDR2 comprising SEQ ID NO:29; and
a light chain variable region CDR3 comprising SEQ ID NO:33.

In another preferred embodiment, the antibody comprises:
a heavy chain variable region CDR1 comprising SEQ ID NO:3;
a heavy chain variable region CDR2 comprising SEQ ID NO:11;
a heavy chain variable region CDR3 comprising SEQ ID NO:21;
a light chain variable region CDR1 comprising SEQ ID NO:25;
a light chain variable region CDR2 comprising SEQ ID NO:29; and
a light chain variable region CDR3 comprising SEQ ID NO:33.

In another preferred embodiment, the antibody comprises:
a heavy chain variable region CDR1 comprising SEQ ID NO:3;
a heavy chain variable region CDR2 comprising SEQ ID NO:12;
a heavy chain variable region CDR3 comprising SEQ ID NO:18;
a light chain variable region CDR1 comprising SEQ ID NO:25;
a light chain variable region CDR2 comprising SEQ ID NO:31; and
a light chain variable region CDR3 comprising SEQ ID NO:33.

In another preferred embodiment, the antibody comprises:
a heavy chain variable region CDR1 comprising SEQ ID NO:2;
a heavy chain variable region CDR2 comprising SEQ ID NO:13;
a heavy chain variable region CDR3 comprising SEQ ID NO:15;
a light chain variable region CDR1 comprising SEQ ID NO:23;
a light chain variable region CDR2 comprising SEQ ID NO:29; and
a light chain variable region CDR3 comprising SEQ ID NO:33.

It is well known in the art that the CDR3 domain, independently from the CDR1 and/or CDR2 domain(s), alone can determine the binding specificity of an antibody for a cognate antigen and that multiple antibodies can predictably be generated having the same binding specificity based on a common CDR3 sequence. See, for example, Klimka et al., *British J. of Cancer* 83(2):252-260 (2000) (describing the production of a humanized anti-CD30 antibody using only the heavy chain variable domain CDR3 of murine anti-CD30 antibody Ki-4); Beiboer et al., *J. Mol. Biol.* 296:833-849 (2000) (describing recombinant epithelial glycoprotein-2 (EGP-2) antibodies using only the heavy chain CDR3 sequence of the parental murine MOC-31 anti-EGP-2 antibody); Rader et al., *Proc. Natl. Acad. Sci. U.S.A.* 95:8910-8915 (1998) (describing a panel of humanized anti-integrin $\alpha_v\beta_3$ antibodies using a heavy and light chain variable CDR3 domain of a murine anti-integrin $\alpha_v\beta_3$ antibody LM609 wherein each member antibody comprises a distinct sequence outside the CDR3 domain and capable of binding the same epitope as the parent murine antibody with affinities as high or higher than the parent murine antibody); Barbas et al., *J. Am. Chem. Soc.* 116:2161-2162 (1994) (disclosing that the CDR3 domain provides the most significant contribution to antigen binding); Barbas et al., *Proc. Natl. Acad. Sci. U.S.A.* 92:2529-2533 (1995) (describing the grafting of heavy chain CDR3 sequences of three Fabs (SI-1, SI-40, and SI-32) against human placental DNA onto the heavy chain of an anti-tetanus toxoid Fab thereby replacing the existing heavy chain CDR3 and demonstrating that the CDR3 domain alone conferred binding specificity); and Ditzel et al., *J. Immunol.* 157:739-749 (1996) (describing grafting studies wherein transfer of only the heavy chain CDR3 of a parent polyspecific Fab LNA3 to a heavy chain of a monospecific IgG tetanus toxoid-binding Fab p313 antibody was sufficient to retain binding specificity of the parent Fab). Each of these references is hereby incorporated by reference in its entirety.

Accordingly, the present invention provides monoclonal antibodies comprising one or more heavy and/or light chain CDR3 domains from an antibody derived from a human or non-human animal, wherein the monoclonal antibody is capable of specifically binding to Cadherin-17. Within certain aspects, the present invention provides monoclonal antibodies comprising one or more heavy and/or light chain CDR3 domain from a non-human antibody, such as a mouse or rat antibody, wherein the monoclonal antibody is capable of specifically binding to Cadherin-17. Within some embodiments, such inventive antibodies comprising one or more heavy and/or light chain CDR3 domain from a non-human antibody (a) are capable of competing for binding with; (b) retain the functional characteristics; (c) bind to the same epitope; and/or (d) have a similar binding affinity as the corresponding parental non-human antibody.

Within other aspects, the present invention provides monoclonal antibodies comprising one or more heavy and/or light chain CDR3 domains from a human antibody, such as, for example, a human antibody obtained from a non-human animal, wherein the human antibody is capable of specifically binding to Cadherin-17. Within other aspects, the present invention provides monoclonal antibodies comprising one or more heavy and/or light chain CDR3 domain from a first human antibody, such as, for example, a human antibody obtained from a non-human animal, wherein the first human antibody is capable of specifically binding to Cadherin-17 and wherein the CDR3 domain from the first human antibody replaces a CDR3 domain in a human antibody that is lacking binding specificity for Cadherin-17 to generate a second human antibody that is capable of specifically binding to Cadherin-17. Within some embodiments, such inventive antibodies comprising one or more heavy and/or light chain CDR3 domain from the first human antibody (a) are capable of competing for binding with; (b) retain the functional characteristics; (c) bind to the same epitope; and/or (d) have a similar binding affinity as the corresponding parental first human antibody.

Antibodies Having Particular Germline Sequences

In certain embodiments, an antibody of the invention comprises a heavy chain variable region from a particular germline heavy chain immunoglobulin gene and/or a light chain variable region from a particular germline light chain immunoglobulin gene.

For example, in a preferred embodiment, the invention provides an isolated monoclonal antibody, or an antigen-binding portion thereof, comprising a heavy chain variable region that is the product of or derived from a murine $V_H$ 7-39 gene, a murine $V_H$ II region VH105 gene or a murine $V_H$ II gene H17, wherein the antibody specifically binds Cadherin-17. In yet another preferred embodiment, the invention provides an isolated monoclonal antibody, or an antigen-binding portion thereof, comprising a light chain variable region that is the product of or derived from a murine $V_K$ 1-110 gene, a murine $V_K$ 8-30 gene or a murine $V_K$ 24-140 gene, wherein the antibody specifically binds Cadherin-17.

In yet another preferred embodiment, the invention provides an isolated monoclonal antibody, or antigen-binding portion thereof, wherein the antibody:
comprises a heavy chain variable region that is the product of or derived from a murine $V_H$ 7-39 gene (which gene includes the nucleotide sequence set forth in SEQ ID NO: 125);
comprises a light chain variable region that is the product of or derived from a murine $V_K$ 1-110 gene (which gene includes the nucleotide sequences set forth in SEQ ID NOs: 128 and 129); andspecifically binds to Cadherin-17, preferably human Cadherin-17. Examples of an antibody having $V_H$ and $V_K$ of $V_H$ 7-39 and $V_K$ 1-110, respectively, is PTA001_A1.

In yet another preferred embodiment, the invention provides an isolated monoclonal antibody, or antigen-binding portion thereof, wherein the antibody:
comprises a heavy chain variable region that is the product of or derived from a murine $V_H$ II gene H17 or a murine $V_H$ II region VH105 gene (which genes include the nucleotide sequences set forth in SEQ ID NO: 126 and 127 respectively);
comprises a light chain variable region that is the product of or derived from a murine $V_K$ 8-30 gene (which gene includes the nucleotide sequences set forth in SEQ ID NOs: 130, 131 and 132); and
specifically binds to Cadherin-17, preferably human Cadherin-17.

Examples of an antibody having $V_H$ of $V_H$ II gene H17 or $V_H$ II region VH105 and $V_K$ of $V_K$ 8-30 is PTA001_A4.

In yet another preferred embodiment, the invention provides an isolated monoclonal antibody, or antigen-binding portion thereof, wherein the antibody:
comprises a heavy chain variable region that is the product of or derived from a murine $V_H$ II gene H17 or a murine $V_H$ II region VH105 gene (which genes include the nucleotide sequences set forth in SEQ ID NO: 126 and 127 respectively);
comprises a light chain variable region that is the product of or derived from a murine $V_K$ 24-140 gene (which gene includes the nucleotide sequences set forth in SEQ ID NOs: 133, 134 and 135); and
specifically binds to Cadherin-17, preferably human Cadherin-17. Examples of antibodies having $V_H$ of $V_H$ II gene H17 or $V_H$ II region VH105 and $V_K$ of $V_K$ 24-140 are PTA001_A2, PTA001_A3, PTA001_A5, PTA001_A6, PTA001_A7, PTA001_A8, PTA001_A9, PTA001_A10, PTA001_A11, PTA001_A12, PTA001_A13 and PTA001_A14.

As used herein, an antibody comprises heavy or light chain variable regions that is "the product of" or "derived from" a particular germline sequence if the variable regions of the antibody are obtained from a system that uses murine germline immunoglobulin genes. Such systems include screening a murine immunoglobulin gene library displayed on phage with the antigen of interest. An antibody that is "the product of" or "derived from" a murine germline immunoglobulin sequence can be identified as such by comparing the nucleotide or amino acid sequence of the antibody to the nucleotide or amino acid sequences of murine germline immunoglobulins and selecting the murine germline immunoglobulin sequence that is closest in sequence (i.e., greatest % identity) to the sequence of the antibody. An antibody that is "the product of" or "derived from" a particular murine germline immunoglobulin sequence may contain amino acid differences as compared to the germline sequence, due to, for example, naturally-occurring somatic mutations or intentional introduction of site-directed mutation. However, a selected antibody typically is at least 90% identical in amino acids sequence to an amino acid sequence encoded by a murine germline immunoglobulin gene and contains amino acid residues that identify the antibody as being murine when compared to the germline immunoglobulin amino acid sequences of other species (e.g., human germline sequences). In certain cases, an antibody may be at least 95%, or even at least 96%, 97%, 98%, or 99% identical in amino acid sequence to the amino acid sequence encoded by the germline immunoglobulin gene. Typically, an antibody derived from a particular murine germline sequence will display no more than 10 amino acid differences from the amino acid sequence encoded by the murine germline immunoglobulin gene. In certain cases, the antibody may display no more than 5, or even no more than 4, 3, 2, or 1 amino acid difference from the amino acid sequence encoded by the germline immunoglobulin gene.

Homologous Antibodies

In yet another embodiment, an antibody of the invention comprises heavy and light chain variable regions comprising amino acid sequences that are homologous to the amino acid sequences of the preferred antibodies described herein, and wherein the antibodies retain the desired functional properties of the anti-Cadherin-17 antibodies of the invention.

For example, the invention provides an isolated monoclonal antibody, or antigen binding portion thereof, comprising a heavy chain variable region and a light chain variable region, wherein:

the heavy chain variable region comprises an amino acid sequence that is at least 80% identical to an amino acid sequence selected from the group consisting of SEQ ID NOs: 35-46;

the light chain variable region comprises an amino acid sequence that is at least 80% identical to an amino acid sequence selected from the group consisting of SEQ ID NOs: 47-58; and the antibody binds to human Cadherin-17. Such antibodies may bind to human Cadherin-17 with an $EC_{50}$ of 50 nM or less, 10 nM or less, 1 nM or less, 100 pM or less, or more preferably 10 pM or less.

The antibody may also bind to CHO cells transfected with human Cadherin-17.

In various embodiments, the antibody can be, for example, a human antibody, a humanized antibody or a chimeric antibody.

In other embodiments, the $V_H$ and/or $V_K$ amino acid sequences may be 85%, 90%, 95%, 96%, 97%, 98% or 99% homologous to the sequences set forth above. An antibody having $V_H$ and $V_K$ regions having high (i.e., 80% or greater) identical to the $V_H$ and $V_K$ regions of the sequences set forth above, can be obtained by mutagenesis (e.g., site-directed or PCR-mediated mutagenesis) of nucleic acid molecules encoding SEQ ID NOs:59-83 followed by testing of the encoded altered antibody for retained function using the functional assays described herein.

The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two amino acid sequences can be determined using the algorithm of E. Meyers and W. Miller (*Comput. Appl. Biosci.*, 4:11-17 (1988)) which has been incorporated into the ALIGN program (version 2.0), using a PAM 120 weight residue table, a gap length penalty of 12 and a gap penalty of 4. In addition, the percent identity between two amino acid sequences can be determined using the Needleman and Wunsch (*J. Mol. Biol.* 48:444-453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

Additionally or alternatively, the protein sequences of the present invention can further be used as a "query sequence" to perform a search against public databases to, for example, identify related sequences. Such searches can be performed using the XBLAST program (version 2.0) of Altschul, et al. (1990) *J. Mol. Biol.* 215:403-10. BLAST protein searches can be performed with the XBLAST program, score=50, wordlength=3 to obtain amino acid sequences homologous to the antibody molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See www.ncbi.nlm.nih.gov.

Antibodies with Conservative Modifications

In certain embodiments, an antibody of the invention comprises a heavy chain variable region comprising CDR1, CDR2 and CDR3 sequences and a light chain variable region comprising CDR1, CDR2 and CDR3 sequences, wherein one or more of these CDR sequences comprise specified amino acid sequences based on the preferred antibodies described herein (e.g., PTA001_A1, PTA001_A2, PTA001_A3, PTA001_A4, PTA001_A5, PTA001_A6, PTA001_A7, PTA001_A8, PTA001_A9, PTA001_A10, PTA001_A11, PTA001_A12, PTA001_A13 or PTA001_A14), or conservative modifications thereof, and wherein the antibodies retain the desired functional properties of the anti-Cadherin-17 antibodies of the invention. Accordingly, the invention provides an isolated monoclonal antibody, or antigen binding portion thereof, comprising a heavy chain variable region comprising CDR1, CDR2, and CDR3 sequences and a light chain variable region comprising CDR1, CDR2, and CDR3 sequences, wherein:

the heavy chain variable region CDR3 sequence comprises an amino acid sequence selected from the group consisting of amino acid sequences of SEQ ID NOs:14-21, and conservative modifications thereof;

the light chain variable region CDR3 sequence comprises an amino acid sequence selected from the group consisting of amino acid sequence of SEQ ID NOs:32-34, and conservative modifications thereof; and the antibody binds to human Cadherin-17. Such antibodies may bind to human Cadherin-17 with an $EC_{50}$ of 50 nM or less, 10 nM or less, 1 nM or less, 100 pM or less, or more preferably 10 pM or less.

The antibody may also bind to CHO cells transfected with human Cadherin-17.

In a preferred embodiment, the heavy chain variable region CDR2 sequence comprises an amino acid sequence selected from the group consisting of amino acid sequences of SEQ ID NOs:5-13, and conservative modifications thereof; and the light chain variable region CDR2 sequence comprises an amino acid sequence selected from the group consisting of amino acid sequences of SEQ ID NOs:28-31, and conservative modifications thereof. In another preferred embodiment, the heavy chain variable region CDR1 sequence comprises an amino acid sequence selected from the group consisting of amino acid sequences of SEQ ID NOs:1-4, and conservative modifications thereof; and the light chain variable region CDR1 sequence comprises an amino acid sequence selected from the group consisting of amino acid sequences of SEQ ID NOs:22-27, and conservative modifications thereof.

In various embodiments, the antibody can be, for example, human antibodies, humanized antibodies or chimeric antibodies.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for retained function using the functional assays described herein.

The heavy chain CDR1 sequence of SEQ ID NO:1-4 may comprise one or more conservative sequence modification, such as one, two, three, four, five or more amino acid substitutions, additions or deletions; the light chain CDR1 sequence of SEQ ID NO:22-27 may comprise one or more conservative sequence modification, such as one, two, three, four, five or more amino acid substitutions, additions or deletions; the heavy chain CDR2 sequence shown in SEQ ID NO:5-13 may comprise one or more conservative sequence modification, such as one, two, three, four, five or more amino acid substitutions, additions or deletions; the light chain CDR2 sequence shown in SEQ ID NO:28-31 may comprise one or more conservative sequence modification, such as one, two, three, four, five or more amino acid substitutions, additions or deletions; the heavy chain CDR3 sequence shown in SEQ ID NO:14-21 may comprise one or more conservative sequence modification, such as one, two, three, four, five or more amino acid substitutions, additions or deletions; and/or the light chain CDR3 sequence shown in SEQ ID NO:32-34 may comprise one or more conservative sequence modification, such as one, two, three, four, five or more amino acid substitutions, additions or deletions.

Antibodies that Bind to the Same Epitope as Anti-Cadherin-17 Antibodies of the Invention In another embodiment, the invention provides antibodies that bind to the same epitope on human Cadherin-17 as any of the Cadherin-17 monoclonal antibodies of the invention (i.e., antibodies that have the ability to cross-compete for binding to Cadherin-17 with any of the monoclonal antibodies of the invention). In preferred embodiments, the reference antibody for cross-competition studies can be the monoclonal antibody PTA001_A1 (having $V_H$ and $V_K$ sequences as shown in SEQ ID NOs:35 and 47, respectively), the monoclonal antibody PTA001_A2 (having $V_H$ and $V_K$ sequences as shown in SEQ ID NOs:36 and 48 respectively), the monoclonal antibody PTA001_A3 (having $V_H$ and $V_K$ sequences as shown in SEQ ID NOs:37 and 48 respectively), the monoclonal antibody PTA001_A4 (having $V_H$ and $V_K$ sequences as shown in SEQ ID NOs:38 and 49 respectively), the monoclonal antibody PTA001_A5 (having $V_H$ and $V_K$ sequences as shown in SEQ ID NOs:39 and 50 respectively), the monoclonal antibody PTA001_A6 (having $V_H$ and $V_K$ sequences as shown in SEQ ID NOs:40 and 51 respectively), the monoclonal antibody PTA001_A7 (having $V_H$ and $V_K$ sequences as shown in SEQ ID NOs:41 and 52 respectively), the monoclonal antibody PTA001_A8 (having $V_H$ and $V_K$ sequences as shown in SEQ ID NOs:42 and 53 respectively), the monoclonal antibody PTA001_A9 (having $V_H$ and $V_K$ sequences as shown in SEQ ID NOs:40 and 54 respectively), the monoclonal antibody PTA001_A10 (having $V_H$ and $V_K$ sequences as shown in SEQ ID NOs:40 and 55 respectively), the monoclonal antibody PTA001_A11 (having $V_H$ and $V_K$ sequences as shown in SEQ ID NOs:43 and 56 respectively), the monoclonal antibody PTA001_A12 (having $V_H$ and $V_K$ sequences as shown in SEQ ID NOs:44 and 55 respectively), the monoclonal antibody PTA001_A13 (having $V_H$ and $V_K$ sequences as shown in SEQ ID NOs:45 and 57 respectively) or the monoclonal antibody PTA001_A14 (having $V_H$ and $V_K$ sequences as shown in SEQ ID NOs:46 and 58 respectively). Such cross-competing antibodies can be identified based on their ability to cross-compete with PTA001_A1, PTA001_A2, PTA001_A3, PTA001_A4, PTA001_A5, PTA001_A6, PTA001_A7, PTA001_A8, PTA001_A9, PTA001_A10, PTA001_A11, PTA001_A12, PTA001_A13 or PTA001_A14 in standard Cadherin-17 binding assays. For example, BIAcore® analysis, ELISA assays or flow cytometry may be used to demonstrate cross-competition with the antibodies of the current invention. The ability of a test antibody to inhibit the binding of, for example, PTA001_A1, PTA001_A2, PTA001_A3, PTA001_A4, PTA001_A5, PTA001_A6, PTA001_A7, PTA001_A8, PTA001_A9, PTA001_A10, PTA001_A11, PTA001_A12, PTA001_A13 or PTA001_A14, to human Cadherin-17 demonstrates that the test antibody can compete with PTA001_A1, PTA001_A2, PTA001_A3, PTA001_A4, PTA001_A5, PTA001_A6, PTA001_A7, PTA001_A8, PTA001_A9, PTA001_A10, PTA001_A11, PTA001_A12, PTA001_A13 or PTA001_A14 for binding to human Cadherin-17 and thus binds to the same epitope on human Cadherin-17 as PTA001_A1, PTA001_A2, PTA001_A3, PTA001_A4, PTA001_A5, PTA001_A6, PTA001_A7, PTA001_A8, PTA001_A9, PTA001_A10, PTA001_A11, PTA001_A12, PTA001_A13 or PTA001_A14.

Engineered and Modified Antibodies

An antibody of the invention further can be prepared using an antibody having one or more of the $V_H$ and/or $V_L$ sequences disclosed herein which can be used as starting material to engineer a modified antibody, which modified antibody may have altered properties as compared to the starting antibody. An antibody can be engineered by modifying one or more amino acids within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

In certain embodiments, CDR grafting can be used to engineer variable regions of antibodies. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) Nature 332:323-327; Jones, P. et al. (1986) Nature 321:522-525; Queen, C. et al. (1989) Proc. Natl. Acad. See. U.S.A. 86:10029-10033; U.S. Pat. No. 5,225,539 to Winter, and U.S. Pat. Nos. 5,530,101; 5,585,089; 5,693,762 and 6,180,370 to Queen et al.)

Accordingly, another embodiment of the invention pertains to an isolated monoclonal antibody, or antigen binding portion thereof, comprising a heavy chain variable region comprising CDR1, CDR2, and CDR3 sequences comprising an amino acid sequence selected from the group consisting of SEQ ID NOs:1-4, SEQ ID NOs:5-13, and SEQ ID NOs:14-21, respectively, and a light chain variable region comprising CDR1, CDR2, and CDR3 sequences comprising an amino acid sequence selected from the group consisting of SEQ ID NOs:22-27, SEQ ID NOs:28-31, and SEQ ID NOs:32-34, respectively. Thus, such antibodies contain the $V_H$ and $V_K$ CDR sequences of monoclonal antibodies PTA001_A1, PTA001_A2, PTA001_A3, PTA001_A4, PTA001_A5, PTA001_A6, PTA001_A7, PTA001_A8, PTA001_A9, PTA001_A10, PTA001_A11, PTA001_A12, PTA001_A13 or PTA001_A14 yet may contain different framework sequences from these antibodies.

Such framework sequences can be obtained from public DNA databases or published references that include germline antibody gene sequences. For example, germline DNA sequences for murine heavy and light chain variable region genes can be found in the IMGT (international ImMunoGeneTics) murine germline sequence database (available on the Internet at imgt.cines.fr/), as well as in Kabat, E. A., et al. (1991) Sequences of Proteins of Immunological Interest, Fifth Edition, U.S. Department of Health and Human Services, NIH Publication No. 91-3242; the contents of each of which are expressly incorporated herein by reference. As another example, the germline DNA sequences for murine heavy and light chain variable region genes can be found in the Genbank® database.

Antibody protein sequences are compared against a compiled protein sequence database using one of the sequence similarity searching methods called the Gapped BLAST (Altschul et al. (1997) Nucleic Acids Research 25:3389-3402), which is well known to those skilled in the art. BLAST is a heuristic algorithm in that a statistically significant alignment between the antibody sequence and the database sequence is likely to contain high-scoring segment pairs (HSP) of aligned words. Segment pairs whose scores cannot be improved by extension or trimming is called a hit. Briefly, the nucleotide sequences in the database are translated and the region between and including FR1 through FR3 framework region is retained. The database sequences have an average length of 98 residues. Duplicate sequences which are exact matches over the entire length of the protein are removed. A BLAST search for proteins using the program blastp with default, standard parameters except the low complexity filter, which is turned off, and the substitution matrix of BLOSUM62, filters for top 5 hits yielding sequence matches. The nucleotide sequences are translated in all six frames and the frame with no stop codons in the matching segment of the database sequence is considered the potential hit. This is in turn confirmed using the BLAST program tblastx, which translates the antibody sequence in all six frames and compares those translations to the nucleotide sequences in the database dynamically translated in all six frames.

The identities are exact amino acid matches between the antibody sequence and the protein database over the entire length of the sequence. The positives (identities+substitution match) are not identical but amino acid substitutions guided by the BLOSUM62 substitution matrix. If the antibody sequence matches two of the database sequences with same identity, the hit with most positives would be decided to be the matching sequence hit.

Preferred framework sequences for use in the antibodies of the invention are those that are structurally similar to the framework sequences used by selected antibodies of the invention, e.g., similar to the $V_H$ 7-39 framework sequence, the $V_H$ II gene H17 framework sequence, the $V_H$ II region VH105 framework sequence, the $V_K$ 1-110 framework sequence, the $V_K$ 8-30 framework sequence and/or the $V_K$ 24-140 framework sequences used by preferred monoclonal antibodies of the invention. The $V_H$ CDR1, CDR2, and CDR3 sequences, and the $V_K$ CDR1, CDR2, and CDR3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al.).

Another type of variable region modification is to mutate amino acid residues within the $V_H$ and/or $V_K$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. In some embodiments, conservative modifications (as discussed above) are introduced. Alternatively, non-conservative modifications can be made. The mutations may be amino acid substitutions, additions or deletions, but are preferably substitutions. Moreover, typically no more than one, two, three, four or five residues within a CDR region are altered, although as will be appreciated by those in the art, variants in other areas (framework regions for example) can be greater.

Accordingly, in another embodiment, the instant disclosure provides isolated anti-Cadherin-17 monoclonal antibodies, or antigen binding portions thereof, comprising a heavy chain variable region comprising: (a) a $V_H$ CDR1 region comprising an amino acid sequence selected from the group consisting of SEQ ID NOs:1-4, or an amino acid sequence having one, two, three, four or five amino acid substitutions, deletions or additions as compared to SEQ ID NOs:1-4; (b) a $V_H$ CDR2 region comprising an amino acid sequence selected from the group consisting of SEQ ID NOs:5-13, or an amino acid sequence having one, two, three, four or five amino acid substitutions, deletions or additions as compared to SEQ ID NOs:5-13; (c) a $V_H$ CDR3 region comprising an amino acid sequence selected from the group consisting of SEQ ID NOs:14-21, or an amino acid sequence having one, two, three, four or five amino acid substitutions, deletions or additions as compared to SEQ ID NOs:14-21; (d) a $V_K$ CDR1 region comprising an amino acid sequence selected from the group consisting of SEQ ID NOs:22-27, or an amino acid sequence having one, two, three, four or five amino acid substitutions, deletions or additions as compared to SEQ ID NOs:22-27; (e) a $V_K$ CDR2 region comprising an amino acid sequence selected from the group consisting of SEQ ID NOs: 28-31, or an amino acid sequence having one, two, three, four or five amino acid substitutions, deletions or additions as compared to SEQ ID NOs:28-31; and (f) a $V_K$ CDR3 region comprising an amino acid sequence selected from the group consisting of SEQ ID NOs:32-34, or an amino acid sequence having one, two, three, four or five amino acid substitutions, deletions or additions as compared to SEQ ID NOs:32-34.

Engineered antibodies of the invention include those in which modifications have been made to framework residues within $V_H$ and/or $V_K$, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 2003/0153043 by Carr et al.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half life of the antibody. More specifically, one or more amino acid mutations are introduced into the CH2-CH3 domain interface region of the Fc-hinge fragment such that the antibody has impaired Staphylococcal protein A (SpA) binding relative to native Fc-hinge domain SpA binding. This approach is described in further detail in U.S. Pat. No. 6,165,745 by Ward et al.

In another embodiment, the antibody is modified to increase its biological half life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the CH1 or $C_L$ region to contain a salvage receptor binding epitope taken from two loops of a CH2 domain of an Fc region of an IgG, as described in U.S. Pat. Nos. 5,869,046 and 6,121,022 by Presta et al.

In another embodiment, the antibody is produced as a UniBody® as described in WO2007/059782 which is incorporated herein by reference in its entirety.

In yet other embodiments, the Fc region is altered by replacing at least one amino acid residue with a different amino acid residue to alter the effector function(s) of the antibody. For example, one or more amino acids selected from amino acid residues 234, 235, 236, 237, 297, 318, 320 and 322 can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another example, one or more amino acids selected from amino acid residues 329, 331 and 322 can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another example, one or more amino acid residues within amino acid positions 231 and 239 are altered to thereby alter the ability of the antibody to fix complement. This approach is described further in PCT Publication WO 94/29351 by Bodmer et al.

In yet another example, the Fc region is modified to increase the ability of the antibody to mediate antibody dependent cellular cytotoxicity (ADCC) and/or to increase the affinity of the antibody for an Fcγ receptor by modifying one or more amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072 by Presta. Moreover, the binding sites on human IgG1 for FcγR1, FcγRII, FcγRIII and FcRn have been mapped and variants with improved binding have been described (see Shields, R. L. et al. (2001) *J. Biol. Chem.* 276:6591-6604). Specific mutations at positions 256, 290, 298, 333, 334 and 339 were shown to improve binding to FcγRIII Additionally, the following combination mutants were shown to improve FcγRIII binding: T256A/S298A, S298A/E333A, S298A/K224A and S298A/E333A/K334A. Further ADCC variants are described for example in WO2006/019447.

In yet another example, the Fc region is modified to increase the half-life of the antibody, generally by increasing binding to the FcRn receptor, as described for example in PCT/US2008/088053, U.S. Pat. No. 7,371,826, U.S. Pat. No. 7,670,600 and WO 97/34631.

In still another embodiment, the glycosylation of an antibody is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al., and can be accomplished by removing the asparagine at position 297.

Additionally or alternatively, an antibody can be made that has an altered type of glycosylation, such as a hypofucosylated antibody having reduced amounts of fucosyl residues or an antibody having increased bisecting GlcNac structures. This is sometimes referred to in the art as a "engineered glycoform". Such altered glycosylation patterns have been demonstrated to increase the ADCC ability of antibodies. Such carbohydrate modifications can generally be accomplished in two ways; for example, in some embodiments, the antibody is expressed in a host cell with altered glycosylation machinery. Cells with altered glycosylation machinery have been described in the art and can be used as host cells in which to express recombinant antibodies of the invention to thereby produce an antibody with altered glycosylation. Reference is made to the POTELLIGENT® technology. For example, the cell lines Ms704, Ms705, and Ms709 lack the fucosyltransferase gene, FUT8 (alpha (1,6) fucosyltransferase), such that antibodies expressed in the Ms704, Ms705, and Ms709 cell lines lack fucose on their carbohydrates. The Ms704, Ms705, and Ms709 FUT8$^{-/-}$ cell lines were created by the targeted disruption of the FUT8 gene in CHO/DG44 cells using two replacement vectors (see U.S. Patent Publication No. 2004/0110704 by Yamane et al., U.S. Pat. No. 7,517,670 and Yamane-Ohnuki et al. (2004) *Biotechnol Bioeng* 87:614-22). As another example, EP 1,176,195 by Hanai et al. describes a cell line with a functionally disrupted FUT8 gene, which encodes a fucosyl transferase, such that antibodies expressed in such a cell line exhibit hypofucosylation by reducing or eliminating the alpha 1,6 bond-related enzyme. Hanai et al. also describe cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al. (2002) *J. Biol. Chem.* 277:26733-26740). PCT Publication WO 99/54342 by Umana et al. describes cell lines engineered to express glycoprotein-modifying glycosyl transferases (e.g., beta(1,4)-N-acetylglucosaminyltransferase III (GnTIII)) such that antibodies expressed in the engineered cell lines exhibit increased bisecting GlcNac structures which results in increased ADCC activity of the antibodies (see also Umana et al. (1999) *Nat. Biotech.* 17:176-180). Alternatively, the fucose residues of the antibody may be cleaved off using a fucosidase enzyme. For example, the fucosidase alpha-L-fucosidase removes fucosyl residues from antibodies (Tarentino, A. L. et al. (1975) *Biochem.* 14:5516-23).

Alternatively, engineered glycoforms, particularly afucosylation, can be done using small molecule inhibitors of glycosylation pathway enzymes. See for example Rothman et al., Mol. Immunol. 26(12):113-1123 (1989); Elbein, FASEB J. 5:3055 (1991); PCT/US2009/042610 and U.S. Pat. No. 7,700,321.

Another modification of the antibodies herein that is contemplated by the invention is pegylation. An antibody can be pegylated to, for example, increase the biological (e.g., serum) half life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention. See for example, EP 0 154 316 by Nishimura et al. and EP 0 401 384 by Ishikawa et al.

In additional embodiments, for example in the use of the antibodies of the invention for diagnostic or detection purposes, the antibodies may comprise a label. By "labeled" herein is meant that a compound has at least one element, isotope or chemical compound attached to enable the detection of the compound. In general, labels fall into three classes: a) isotopic labels, which may be radioactive or heavy isotopes; b) magnetic, electrical, thermal; and c) colored or luminescent dyes; although labels include enzymes and particles such as magnetic particles as well. Preferred labels include, but are not limited to, fluorescent lanthanide complexes (including those of Europium and Terbium), and fluorescent labels including, but not limited to, quantum dots, fluorescein, rhodamine, tetramethylrhodamine, eosin, erythrosin, coumarin, methyl-coumarins, pyrene, Malacite green, stilbene, Lucifer Yellow, Cascade Blue, Texas Red, the Alexa dyes, the Cy dyes, and others described in the 6th Edition of the Molecular Probes Handbook by Richard P. Haugland, hereby expressly incorporated by reference.

Antibody Physical Properties

The antibodies of the present invention may be further characterized by the various physical properties of the anti-Cadherin-17 antibodies. Various assays may be used to detect and/or differentiate different classes of antibodies based on these physical properties.

In some embodiments, antibodies of the present invention may contain one or more glycosylation sites in either the light or heavy chain variable region. The presence of one or more glycosylation sites in the variable region may result in increased immunogenicity of the antibody or an alteration of the pK of the antibody due to altered antigen binding (Marshall et al (1972) *Annu Rev Biochem* 41:673-702; Gala F A and Morrison S L (2004) *J Immunol* 172:5489-94; Wallick et al (1988) *J Exp Med* 168:1099-109; Spiro RG (2002) *Glycobiology* 12:43R-56R; Parekh et al (1985) *Nature* 316:452-7; Mimura et al. (2000) *Mol Immunol* 37:697-706). Glycosylation has been known to occur at motifs containing an N-X-S/T sequence. Variable region glycosylation may be tested using a Glycoblot assay, which cleaves the antibody to produce a Fab, and then tests for glycosylation using an assay that measures periodate oxidation and Schiff base formation. Alternatively, variable region glycosylation may be tested using Dionex® light chromatography (Dionex-LC), which cleaves saccharides from a Fab into monosaccharides and analyzes the individual saccharide content. In some instances, it is preferred to have an anti-Cadherin-17 antibody that does not contain variable region glycosylation. This can be achieved either by selecting antibodies that do not contain the glycosylation motif in the variable region or by mutating residues within the glycosylation motif using standard techniques well known in the art.

In a preferred embodiment, the antibodies of the present invention do not contain asparagine isomerism sites. A deamidation or isoaspartic acid effect may occur on N-G or D-G sequences, respectively. The deamidation or isoaspartic acid effect results in the creation of isoaspartic acid which decreases the stability of an antibody by creating a kinked structure off a side chain carboxy terminus rather than the main chain. The creation of isoaspartic acid can be measured using an iso-quant assay, which uses a reverse-phase HPLC to test for isoaspartic acid.

Each antibody will have a unique isoelectric point (pI), but generally antibodies will fall in the pH range of between 6 and 9.5. The pI for an IgG1 antibody typically falls within the pH range of 7-9.5 and the pI for an IgG4 antibody typically falls within the pH range of 6-8. Antibodies may have a pI that is outside this range. Although the effects are generally unknown, there is speculation that antibodies with a pI outside the normal range may have some unfolding and instability under in vivo conditions. The isoelectric point may be tested using a capillary isoelectric focusing assay, which creates a pH gradient and may utilize laser focusing for increased accuracy (Janini et al (2002) *Electrophoresis* 23:1605-11; Ma et al. (2001) Chromatographia 53:S75-89; Hunt et al (1998) *J Chromatogr A* 800:355-67). In some instances, it is preferred to have an anti-Cadherin-17 antibody that contains a pI value that falls in the normal range. This can be achieved either by selecting antibodies with a pI in the normal range, or by mutating charged surface residues using standard techniques well known in the art.

Each antibody will have a melting temperature that is indicative of thermal stability (Krishnamurthy R and Manning M C (2002) *Curr Pharm Biotechnol* 3:361-71). A higher thermal stability indicates greater overall antibody stability in vivo. The melting point of an antibody may be measured using techniques such as differential scanning calorimetry (Chen et al (2003) *Pharm Res* 20:1952-60; Ghirlando et al (1999) *Immunol Lett* 68:47-52). $T_{M1}$ indicates the temperature of the initial unfolding of the antibody. $T_{M2}$ indicates the temperature of complete unfolding of the antibody. Generally, it is preferred that the $T_{M1}$ of an antibody of the present invention is greater than 60° C., preferably greater than 65° C., even more preferably greater than 70° C. Alternatively, the thermal stability of an antibody may be measure using circular dichroism (Murray et al. (2002) *J. Chromatogr Sci* 40:343-9).

In a preferred embodiment, antibodies are selected that do not rapidly degrade. Fragmentation of an anti-Cadherin-17 antibody may be measured using capillary electrophoresis (CE) and MALDI-MS, as is well understood in the art (Alexander A J and Hughes D E (1995) *Anal Chem* 67:3626-32).

In another preferred embodiment, antibodies are selected that have minimal aggregation effects. Aggregation may lead to triggering of an unwanted immune response and/or altered or unfavorable pharmacokinetic properties. Generally, antibodies are acceptable with aggregation of 25% or less, preferably 20% or less, even more preferably 15% or less, even more preferably 10% or less and even more preferably 5% or less. Aggregation may be measured by several techniques well known in the art, including size-exclusion column (SEC) high performance liquid chromatography (HPLC), and light scattering to identify monomers, dimers, trimers or multimers.

Methods of Engineering Antibodies

As discussed above, the anti-Cadherin-17 antibodies having $V_H$ and $V_K$ sequences disclosed herein can be used to create new anti-Cadherin-17 antibodies by modifying the $V_H$ and/or $V_K$ sequences, or the constant region(s) attached thereto. Thus, in another aspect of the invention, the structural features of an anti-Cadherin-17 antibody of the invention, e.g. PTA001_A1, PTA001_A2, PTA001_A3, PTA001_A4, PTA001_A5, PTA001_A6, PTA001_A7, PTA001_A8, PTA001_A9, PTA001_A10, PTA001_A11, PTA001_A12, PTA001_A13 or PTA001_A14, are used to create structurally related anti-Cadherin-17 antibodies that retain at least one functional property of the antibodies of the invention, such as binding to human Cadherin-17. For example, one or more CDR regions of PTA001_A1, PTA001_A2, PTA001_A3, PTA001_A4, PTA001_A5, PTA001_A6, PTA001_A7, PTA001_A8, PTA001_A9, PTA001_A10, PTA001_A11, PTA001_A12, PTA001_A13 or PTA001_A14, or mutations thereof, can be combined recombinantly with known framework regions and/or other CDRs to create additional, recombinantly-engineered, anti-Cadherin-17 antibodies of the invention, as discussed above. Other types of modifications include those described in the previous section. The starting material for the engineering method is one or more of the $V_H$ and/or $V_K$ sequences provided herein, or one or more CDR regions thereof. To create the engineered antibody, it is not necessary to actually prepare (i.e., express as a protein) an antibody having one or more of the $V_H$ and/or $V_K$ sequences provided herein, or one or more CDR regions thereof. Rather, the information contained in the sequence(s) is used as the starting material to create a "second generation" sequence(s) derived from the original sequence(s) and then the "second generation" sequence(s) is prepared and expressed as a protein.

Accordingly, in another embodiment, the invention provides a method for preparing an anti-Cadherin-17 antibody comprising:

providing: (i) a heavy chain variable region antibody sequence comprising a CDR1 sequence selected from the group consisting of SEQ ID NOs:1-4, a CDR2 sequence selected from the group consisting of SEQ ID NOs:5-13, and/or a CDR3 sequence selected from the group consisting of SEQ ID NOs:14-21; and/or (ii) a light chain variable region antibody sequence comprising a CDR1 sequence selected from the group consisting of SEQ ID NOs:22-27, a CDR2 sequence selected from the group consisting of SEQ ID NOs: 28-31, and/or a CDR3 sequence selected from the group consisting of SEQ ID NOs:32-34;

altering at least one amino acid residue within the heavy chain variable region antibody sequence and/or the light chain variable region antibody sequence to create at least one altered antibody sequence; and expressing the altered antibody sequence as a protein.

Standard molecular biology techniques can be used to prepare and express the altered antibody sequence.

Preferably, the antibody encoded by the altered antibody sequence(s) is one that retains one, some or all of the functional properties of the anti-Cadherin-17 antibodies described herein, which functional properties include, but are not limited to:

binds to human Cadherin-17 with a $K_D$ of $1 \times 10^{-7}$ M or less; binds to human CHO cells transfected with Cadherin-17.

The functional properties of the altered antibodies can be assessed using standard assays available in the art and/or described herein, such as those set forth in the Examples (e.g., flow cytometry, binding assays).

In certain embodiments of the methods of engineering antibodies of the invention, mutations can be introduced randomly or selectively along all or part of an anti-Cadherin-17 antibody coding sequence and the resulting modified anti-Cadherin-17 antibodies can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

Nucleic Acid Molecules Encoding Antibodies of the Invention

Another aspect of the invention pertains to nucleic acid molecules that encode the antibodies of the invention. The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. (1987) Current Protocols in Molecular Biology, Greene Publishing and Wiley Interscience, New York. A nucleic acid of the invention can be, for example, DNA or RNA and may or may not contain intronic sequences. In a preferred embodiment, the nucleic acid is a cDNA molecule.

Nucleic acids of the invention can be obtained using standard molecular biology techniques. For antibodies expressed by hybridomas, cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acids encoding the antibody can be recovered from the library.

Preferred nucleic acids molecules of the invention are those encoding the $V_H$ and $V_K$ sequences of the PTA001_A1, PTA001_A2, PTA001_A3, PTA001_A4, PTA001_A5, PTA001_A6, PTA001_A7, PTA001_A8, PTA001_A9, PTA001_A10, PTA001_A11, PTA001_A12, PTA001_A13 or PTA001_A14 monoclonal antibodies. DNA sequences encoding the $V_H$ sequences of PTA001_A1, PTA001_A2, PTA001_A3, PTA001_A4, PTA001_A5, PTA001_A6, PTA001_A7, PTA001_A8, PTA001_A9, PTA001_A10, PTA001_A11, PTA001_A12, PTA001_A13 and PTA001_A14 are shown in SEQ ID NOs: 59-70. DNA sequences encoding the $V_K$ sequences of PTA001_A1, PTA001_A2, PTA001_A3, PTA001_A4, PTA001_A5, PTA001_A6, PTA001_A7, PTA001_A8, PTA001_A9, PTA001_A10, PTA001_A11, PTA001_A12, PTA001_A13 and PTA001_A14 are shown in SEQ ID NOs: 71-83.

Other preferred nucleic acids of the invention are nucleic acids having at least 80% sequence identity, such as at least 85%, at least 90%, at least 95%, at least 98% or at least 99% sequence identity, with one of the sequences shown in SEQ ID NOs: 59-83, which nucleic acids encode an antibody of the invention, or an antigen-binding portion thereof.

The percent identity between two nucleic acid sequences is the number of positions in the sequence in which the nucleotide is identical, taking into account the number of gaps and the length of each gap, which need to be introduced for optimal alignment of the two sequences. The comparison of sequences and determination of percent identity between two sequences can be accomplished using a mathematical algorithm, such as the algorithm of Meyers and Miller or the XBLAST program of Altschul described above.

Still further, preferred nucleic acids of the invention comprise one or more CDR-encoding portions of the nucleic acid sequences shown in SEQ ID NOs:59-83. In this embodiment, the nucleic acid may encode the heavy chain CDR1, CDR2 and/or CDR3 sequence of PTA001_A1, PTA001_A2, PTA001_A3, PTA001_A4, PTA001_A5, PTA001_A6, PTA001_A7, PTA001_A8, PTA001_A9, PTA001_A10, PTA001_A11, PTA001_A12, PTA001_A13 or PTA001_A14 or the light chain CDR1, CDR2 and/or CDR3 sequence of PTA001_A1, PTA001_A2, PTA001_A3, PTA001_A4, PTA001_A5, PTA001_A6, PTA001_A7, PTA001_A8, PTA001_A9, PTA001_A10, PTA001_A11, PTA001_A12, PTA001_A13 or PTA001_A14.

Nucleic acids which have at least 80%, such as at least 85%, at least 90%, at least 95%, at least 98% or at least 99% sequence identity, with such a CDR-encoding portion of SEQ ID NO:59-83 ($V_H$ and $V_K$ segs) are also preferred nucleic acids of the invention. Such nucleic acids may differ from the corresponding portion of SEQ ID NO:59-83 in a non-CDR coding region and/or in a CDR-coding region. Where the difference is in a CDR-coding region, the nucleic acid CDR region encoded by the nucleic acid typically comprises one or more conservative sequence modifications as defined herein compared to the corresponding CDR sequence of PTA001_A1, PTA001_A2, PTA001_A3, PTA001_A4, PTA001_A5, PTA001_A6, PTA001_A7, PTA001_A8, PTA001_A9, PTA001_A10, PTA001_A11, PTA001_A12, PTA001_A13 or PTA001_A14.

Once DNA fragments encoding $V_H$ and $V_K$ segments are obtained, these DNA fragments can be further manipulated by standard recombinant DNA techniques, for example to convert the variable region genes to full-length antibody chain genes, to Fab fragment genes or to a scFv gene. In these manipulations, a $V_K$- or $V_H$-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the $V_H$-encoding DNA to another DNA molecule encoding heavy chain constant regions (CH1, CH2 and CH3). The sequences of murine heavy chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the $V_H$-encoding DNA can be operatively linked to another DNA molecule encoding only the heavy chain CH1 constant region.

The isolated DNA encoding the $V_L/V_K$ region can be converted to a full-length light chain gene (as well as a Fab light chain gene) by operatively linking the $V_L$-encoding DNA to another DNA molecule encoding the light chain constant region, CL. The sequences of murine light chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. In preferred embodiments, the light chain constant region can be a kappa or lambda constant region.

To create a scFv gene, the $V_H$- and $V_L/V_K$-encoding DNA fragments are operatively linked to another fragment encoding a flexible linker, e.g., encoding the amino acid sequence $(Gly_4\text{-Ser})_3$, such that the $V_H$ and $V_L/V_K$ sequences can be expressed as a contiguous single-chain protein, with the $V_L/V_K$ and $V_H$ regions joined by the flexible linker (see e.g., Bird et al. (1988) *Science* 242:423-426; Huston et al. (1988) *Proc. Natl. Acad. Sci. USA* 85:5879-5883; McCafferty et al., (1990) *Nature* 348:552-554).

Production of Monoclonal Antibodies

According to the invention Cadherin-17 or a fragment or derivative thereof may be used as an immunogen to generate antibodies which immunospecifically bind such an immunogen. Such immunogens can be isolated by any convenient means. One skilled in the art will recognize that many procedures are available for the production of antibodies, for example, as described in Antibodies, A Laboratory Manual, Ed Harlow and David Lane, Cold Spring Harbor Laboratory (1988), Cold Spring Harbor, N.Y. One skilled in the art will also appreciate that binding fragments or Fab fragments which mimic antibodies can also be prepared from genetic information by various procedures (Antibody Engineering: A Practical Approach (Borrebaeck, C., ed.), 1995, Oxford University Press, Oxford; J. Immunol. 149, 3914-3920 (1992)).

In one embodiment of the invention, antibodies to a specific domain of Cadherin-17 are produced. In a specific embodiment, hydrophilic fragments of Cadherin-17 are used as immunogens for antibody production.

In the production of antibodies, screening for the desired antibody can be accomplished by techniques known in the art, e.g. ELISA (enzyme-linked immunosorbent assay). For example, to select antibodies which recognize a specific domain of Cadherin-17, one may assay generated hybridomas for a product which binds to a Cadherin-17 fragment containing such domain. For selection of an antibody that specifically binds a first Cadherin-17 homolog but which does not specifically bind to (or binds less avidly to) a second Cadherin-17 homolog, one can select on the basis of positive binding to the first Cadherin-17 homolog and a lack of binding to (or reduced binding to) the second Cadherin-17 homolog. Similarly, for selection of an antibody that specifically binds Cadherin-17 but which does not specifically bind to (or binds less avidly to) a different isoform of the same protein (such as a different glycoform having the same core peptide as Cadherin-17), one can select on the basis of positive binding to Cadherin-17 and a lack of binding to (or reduced binding to) the different isoform (e.g. a different glycoform). Thus, the present invention provides an antibody (such as a monoclonal antibody) that binds with greater affinity (for example at least 2-fold, such as at least 5-fold, particularly at least 10-fold greater affinity) to Cadherin-17 than to a different isoform or isoforms (e.g. glycoforms) of Cadherin-17.

Polyclonal antibodies which may be used in the methods of the invention are heterogeneous populations of antibody molecules derived from the sera of immunized animals. Unfractionated immune serum can also be used. Various procedures known in the art may be used for the production of polyclonal antibodies to Cadherin-17, a fragment of Cadherin-17, a Cadherin-17-related polypeptide, or a fragment of a Cadherin-17-related polypeptide. For example, one way is to purify polypeptides of interest or to synthesize the polypeptides of interest using, e.g. solid phase peptide synthesis methods well known in the art. See, e.g. *Guide to Protein Purification*, Murray P. Deutcher, ed., Meth. Enzymol. Vol 182 (1990); *Solid Phase Peptide Synthesis*, Greg B. Fields ed., *Meth. Enzymol.* Vol 289 (1997); Kiso et al., *Chem. Pharm. Bull.* (Tokyo) 38: 1192-99, 1990; Mostafavi et al., *Biomed. Pept. Proteins Nucleic Acids* 1: 255-60, 1995; Fujiwara et al., *Chem. Pharm. Bull.* (Tokyo) 44: 1326-31, 1996. The selected polypeptides may then be used to immunize by injection various host animals, including but not limited to rabbits, mice, rats, etc., to generate polyclonal or monoclonal antibodies. Various adjuvants (i.e. immunostimulants) may be used to enhance the immunological response, depending on the host species, including, but not limited to, complete or incomplete Freund's adjuvant, a mineral gel such as aluminum hydroxide, surface active substance such as lysolecithin, pluronic polyol, a polyanion, a peptide, an oil emulsion, keyhole limpet hemocyanin, dinitrophenol, and an adjuvant such as BCG (bacille Calmette-Guerin) or corynebacterium parvum. Additional adjuvants are also well known in the art.

For preparation of monoclonal antibodies (mAbs) directed toward Cadherin-17, any technique which provides for the production of antibody molecules by continuous cell lines in culture may be used. For example, the hybridoma technique originally developed by Kohler and Milstein (1975, Nature 256:495-497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77-96). Such antibodies may be of any immunoglobulin class including IgG, IgM, IgE, IgA, IgD and any subclass thereof. The hybridoma producing the monoclonal antibodies may be cultivated in vitro or in vivo. In an additional embodiment of the invention, monoclonal antibodies can be produced in germ-free animals utilizing known technology (PCT/US90/02545, incorporated herein by reference).

The preferred animal system for preparing hybridomas is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known.

The monoclonal antibodies include but are not limited to human monoclonal antibodies and chimeric monoclonal antibodies (e.g. human-mouse chimeras).

Chimeric or humanized antibodies of the present invention can be prepared based on the sequence of a non-human monoclonal antibody prepared as described above. DNA encoding the heavy and light chain immunoglobulins can be obtained from the non-human hybridoma of interest and engineered to contain non-murine (e.g., human) immunoglobulin sequences using standard molecular biology techniques. For example, to create a chimeric antibody, murine variable regions can be linked to human constant regions using methods known in the art (see e.g., U.S. Pat. No. 4,816,567 to Cabilly et al.). To create a humanized antibody, murine CDR regions can be inserted into a human framework using methods known in the art (see e.g., U.S. Pat. No. 5,225,539 to Winter, and U.S. Pat. Nos. 5,530,101; 5,585,089; 5,693,762 and 6,180,370 to Queen et al.).

Completely human antibodies can be produced using transgenic or transchromosomic mice which are incapable of expressing endogenous immunoglobulin heavy and light chain genes, but which can express human heavy and light chain genes. The transgenic mice are immunized in the normal fashion with a selected antigen, e.g. all or a portion of Cadherin-17. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. These transgenic and transchromosomic mice include mice of the HuMAb Mouse® (Medarex®, Inc.) and KM Mouse® strains. The HuMAb Mouse® strain (Medarex®, Inc.) is described in Lonberg and Huszar (1995, Int. Rev. Immunol. 13:65-93). For a detailed discussion of this technology for producing human antibodies and human monoclonal antibodies and protocols for producing such antibodies, see, e.g. U.S. Pat. No. 5,625,126; U.S. Pat. No. 5,633,425; U.S. Pat. No. 5,569,825; U.S. Pat. No. 5,661,016; and U.S. Pat. No. 5,545,806. The KM Mouse® strain refers to a mouse that carries a human heavy chain transgene and a human light chain transchromosome and is described in detail in PCT Publication WO 02/43478 to Ishida et al.

Still further, alternative transgenic animal systems expressing human immunoglobulin genes are available in the art and can be used to raise anti-Cadherin-17 antibodies of the invention. For example, an alternative transgenic system referred to as the Xenomouse (Amgen, Inc.) can be used; such mice are described in, for example, U.S. Pat. Nos. 5,939,598; 6,075,181; 6,114,598; 6,150,584 and 6,162,963 to Kucherlapati et al.

Completely human antibodies which recognize a selected epitope can be generated using a technique referred to as "guided selection". In this approach a selected non-human monoclonal antibody, e.g. a mouse antibody, is used to guide the selection of a completely human antibody recognizing the same epitope. (Jespers et al. (1994) Bio/technology 12:899-903).

Moreover, alternative transchromosomic animal systems expressing human immunoglobulin genes are available in the art and can be used to raise anti-Cadherin-17 antibodies. For example, mice carrying both a human heavy chain transchromosome and a human light chain tranchromosome, referred to as "TC mice" can be used; such mice are described in Tomizuka et al. (2000) *Proc. Natl. Acad. Sci. USA* 97:722-727. Furthermore, cows carrying human heavy and light chain transchromosomes have been described in the art (Kuroiwa et al. (2002) *Nature Biotechnology* 20:889-894) and PCT application No. WO2002/092812 and can be used to raise anti-Cadherin-17 antibodies.

Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

The antibodies of the present invention can be generated by the use of phage display technology to produce and screen libraries of polypeptides for binding to a selected target. See, e.g. Cwirla et al., *Proc. Natl. Acad. Sci. USA* 87, 6378-82, 1990; Devlin et al., *Science* 249, 404-6, 1990, Scott and Smith, *Science* 249, 386-88, 1990; and Ladner et al., U.S. Pat. No. 5,571,698. A basic concept of phage display methods is the establishment of a physical association between DNA encoding a polypeptide to be screened and the polypeptide. This physical association is provided by the phage particle, which displays a polypeptide as part of a capsid enclosing the phage genome which encodes the polypeptide. The establishment of a physical association between polypeptides and their genetic material allows simultaneous mass screening of very large numbers of phage bearing different polypeptides. Phage displaying a polypeptide with affinity to a target bind to the target and these phage are enriched by affinity screening to the target. The identity of polypeptides displayed from these phage can be determined from their respective genomes. Using these methods a polypeptide identified as having a binding affinity for a desired target can then be synthesized in bulk by conventional means. See, e.g. U.S. Pat. No. 6,057,098, which is hereby incorporated in its entirety, including all tables, figures, and claims. In particular, such phage can be utilized to display antigen binding domains expressed from a repertoire or combinatorial antibody library (e.g. human or murine). Phage expressing an antigen binding domain that binds the antigen of interest can be selected or identified with antigen, e.g. using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Phage display methods that can be used to make the antibodies of the present invention include those disclosed in Brinkman et al., J. Immunol. Methods 182:41-50 (1995); Ames et al., J. Immunol. Methods 184:177-186 (1995); Kettleborough et al., Eur. J. Immunol. 24:952-958 (1994); Persic et al., Gene 187 9-18 (1997); Burton et al., Advances in Immunology 57:191-280 (1994); PCT Application No. PCT/GB91/01134; PCT Publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g. as described in detail below. For example, techniques to recombinantly produce Fab, Fab' and F(ab')$_2$ fragments can also be employed using methods known in the art such as those disclosed in PCT publication WO 92/22324; Mullinax et al., BioTechniques 12(6):864-869 (1992); and Sawai et al., AJRI 34:26-34 (1995); and Better et al., Science 240:1041-1043 (1988) (said references incorporated by reference in their entireties).

Examples of techniques which can be used to produce single-chain Fvs and antibodies include those described in U.S. Pat. Nos. 4,946,778 and 5,258,498; Huston et al., *Methods in Enzymology* 203:46-88 (1991); Shu et al., *PNAS* 90:7995-7999 (1993); and Skerra et al., *Science* 240:1038-1040 (1988).

The invention provides functionally active fragments, derivatives or analogs of the anti-Cadherin-17 immunoglobulin molecules. Functionally active means that the fragment, derivative or analog is able to elicit anti-anti-idiotype antibodies (i.e., tertiary antibodies) that recognize the same antigen that is recognized by the antibody from which the fragment, derivative or analog is derived. Specifically, in a particular embodiment the antigenicity of the idiotype of the immunoglobulin molecule may be enhanced by deletion of framework and CDR sequences that are C-terminal to the CDR sequence that specifically recognizes the antigen. To determine which CDR sequences bind the antigen, synthetic peptides containing the CDR sequences can be used in binding assays with the antigen by any binding assay method known in the art.

The present invention provides antibody fragments such as, but not limited to, F(ab')$_2$ fragments and Fab fragments. Antibody fragments which recognize specific epitopes may be generated by known techniques. F(ab')$_2$ fragments consist of the variable region, the light chain constant region and the CH1 domain of the heavy chain and are generated by pepsin digestion of the antibody molecule. Fab fragments are generated by reducing the disulfide bridges of the F(ab')$_2$ fragments. The invention also provides heavy chain and light chain dimers of the antibodies of the invention, or any minimal fragment thereof such as Fvs or single chain antibodies (SCAs) (e.g. as described in U.S. Pat. No. 4,946,778; Bird, 1988, Science 242:423-42; Huston et al., 1988, Proc. Natl. Acad. Sci. USA 85:5879-5883; and Ward et al., 1989, Nature 334:544-54), or any other molecule with the same specificity as the antibody of the invention. Single chain antibodies are formed by linking the heavy and light chain fragments of the Fv region via an amino acid bridge, resulting in a single chain polypeptide. Techniques for the assembly of functional Fv fragments in *E. coli* may be used (Skerra et al., 1988, Science 242:1038-1041).

In other embodiments, the invention provides fusion proteins of the immunoglobulins of the invention (or functionally active fragments thereof), for example in which the immunoglobulin is fused via a covalent bond (e.g. a peptide bond), at either the N-terminus or the C-terminus to an amino acid sequence of another protein (or portion thereof, preferably at least 10, 20 or 50 amino acid portion of the protein) that is not the immunoglobulin. Preferably the immunoglobulin, or fragment thereof, is covalently linked to the other protein at the N-terminus of the constant domain. As stated above, such fusion proteins may facilitate purification, increase half-life in vivo, and enhance the delivery of an antigen across an epithelial barrier to the immune system.

The immunoglobulins of the invention include analogs and derivatives that are modified, i.e., by the covalent attachment of any type of molecule as long as such covalent attachment does not impair immunospecific binding. For example, but not by way of limitation, the derivatives and analogs of the immunoglobulins include those that have been further modified, e.g. by glycosylation, acetylation, pegylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, etc. Additionally, the analog or derivative may contain one or more non-classical amino acids.

Immunization of Mice

Mice can be immunized with a purified or enriched preparation of Cadherin-17 antigen and/or recombinant Cadherin-17, or cells expressing Cadherin-17. Preferably, the mice will be 6-16 weeks of age upon the first infusion. For example, a purified or recombinant preparation (100 µg) of Cadherin-17 antigen can be used to immunize the mice intraperitoneally.

Cumulative experience with various antigens has shown that the mice respond when immunized intraperitoneally (IP) with antigen in complete Freund's adjuvant. However, adjuvants other than Freund's are also found to be effective. In addition, whole cells in the absence of adjuvant are found to be highly immunogenic. The immune response can be monitored over the course of the immunization protocol with plasma samples being obtained by retroorbital bleeds. The plasma can be screened by ELISA (as described below) to test for satisfactory titres. Mice can be boosted intravenously with antigen on 3 consecutive days with sacrifice and removal of the spleen taking place 5 days later. In one embodiment, A/J mouse strains (Jackson Laboratories, Bar Harbor, Me.) may be used.

Generation of Transfectomas Producing Monoclonal Antibodies

Antibodies of the invention can be produced in a host cell transfectoma using, for example, a combination of recombinant DNA techniques and gene transfection methods as is well known in the art (e.g., Morrison, S. (1985) *Science* 229:1202).

For example, to express the antibodies, or antibody fragments thereof, DNAs encoding partial or full-length light and heavy chains, can be obtained by standard molecular biology techniques (e.g., PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used.

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain should be placed before the heavy chain to avoid an excess of toxic free heavy chain (Proudfoot, 1986, Nature 322:52; Kohler, 1980, Proc. Natl. Acad. Sci. USA 77:2197). The coding sequences for the heavy and light chains may comprise cDNA or genomic DNA.

The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_K$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. Methods in Enzymology 185, Academic Press, San Diego, Calif. (1990)). It will be appreciated by those skilled in the art that the design of the expression vector, including the selection of regulatory sequences, may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences may be used, such as the ubiquitin promoter or β-globin promoter. Still further, regulatory elements composed of sequences from different sources, such as the SRα promoter system, which contains sequences from the SV40 early promoter and the long terminal repeat of human T cell leukemia virus type 1 (Takebe, Y. et al. (1988) Mol. Cell. Biol. 8:466-472).

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr- host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R. (1985) Immunology Today 6:12-13).

Preferred mammalian host cells for expressing the recombinant antibodies of the invention include Chinese hamster ovary cells (CHO), in conjunction with a vector such as the major intermediate early gene promoter element from human cytomegalovirus (Foecking et al., 1986, Gene 45:101; Cockett et al., 1990, Bio/Technology 8:2), dhfr-CHO cells, described in Urlaub and Chasin, (1980) Proc. Natl. Acad. Sci. USA 77:4216-4220, used with a DHFR selectable marker, e.g., as described in R. J. Kaufman and P. A. Sharp (1982) J. Mol. Biol. 159:601-621), NSO myeloma cells, COS cells and SP2 cells. In particular, for use with NSO myeloma cells, another preferred expression system is the GS gene expression system disclosed in WO 87/04462 (to Wilson), WO 89/01036 (to Bebbington) and EP 338,841 (to Bebbington).

A variety of host-expression vector systems may be utilized to express an antibody molecule of the invention. Such host-expression systems represent vehicles by which the coding sequences of interest may be produced and subsequently purified, but also represent cells which may, when transformed or transfected with the appropriate nucleotide coding sequences, express the antibody molecule of the invention in situ. These include but are not limited to microorganisms such as bacteria (e.g. E. coli, B. subtilis) transformed with recombinant bacteriophage DNA, plasmid DNA or cosmid DNA expression vectors containing antibody coding sequences; yeast (e.g. Saccharomyces, Pichia) transformed with recombinant yeast expression vectors containing antibody coding sequences; insect cell systems infected with recombinant virus expression vectors (e.g. baculovirus) containing the antibody coding sequences; plant cell systems infected with recombinant virus expression vectors (e.g. cauliflower mosaic virus, CaMV; tobacco mosaic virus, TMV) or transformed with recombinant plasmid expression vectors (e.g. Ti plasmid) containing antibody coding sequences; or mammalian cell systems (e.g. COS, CHO, BHK, 293, 3T3 cells) harboring recombinant expression constructs containing promoters derived from the genome of mammalian cells (e.g. metallothionein promoter) or from mammalian viruses (e.g. the adenovirus late promoter; the vaccinia virus 7.5K promoter).

In bacterial systems, a number of expression vectors may be advantageously selected depending upon the use intended for the antibody molecule being expressed. For example, when a large quantity of such a protein is to be produced, for the generation of pharmaceutical compositions comprising an antibody molecule, vectors which direct the expression of high levels of fusion protein products that are readily purified may be desirable. Such vectors include, but are not limited, to the E. coli expression vector pUR278 (Ruther et al., 1983, EMBO J. 2:1791), in which the antibody coding sequence may be ligated individually into the vector in frame with the lac Z coding region so that a fusion protein is produced; pIN vectors (Inouye & Inouye, 1985, Nucleic Acids Res. 13:3101-3109; Van Heeke & Schuster, 1989, J. Biol. Chem. 24:5503-5509); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In an insect system, Autographa californica nuclear polyhedrosis virus (AcNPV) is used as a vector to express foreign genes. The virus grows in Spodoptera frugiperda cells. The antibody coding sequence may be cloned individually into non-essential regions (for example the polyhedrin gene) of the virus and placed under control of an AcNPV promoter (for example the polyhedrin promoter). In mammalian host cells, a number of viral-based expression systems (e.g. an adenovirus expression system) may be utilized.

As discussed above, a host cell strain may be chosen which modulates the expression of the inserted sequences, or modifies and processes the gene product in the specific fashion desired. Such modifications (e.g. glycosylation) and processing (e.g. cleavage) of protein products may be important for the function of the protein.

For long-term, high-yield production of recombinant antibodies, stable expression is preferred. For example, cell lines that stably express an antibody of interest can be produced by transfecting the cells with an expression vector comprising the nucleotide sequence of the antibody and the nucleotide sequence of a selectable (e.g. neomycin or hygromycin), and selecting for expression of the selectable marker. Such engineered cell lines may be particularly useful in screening and evaluation of compounds that interact directly or indirectly with the antibody molecule.

The expression levels of the antibody molecule can be increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., 1983, Mol. Cell. Biol. 3:257).

When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Once the antibody molecule of the invention has been recombinantly expressed, it may be purified by any method known in the art for purification of an antibody molecule, for example, by chromatography (e.g. ion exchange chromatography, affinity chromatography such as with protein A or specific antigen, and sizing column chromatography), centrifugation, differential solubility, or by any other standard technique for the purification of proteins.

Alternatively, any fusion protein may be readily purified by utilizing an antibody specific for the fusion protein being expressed. For example, a system described by Janknecht et al. allows for the ready purification of non-denatured fusion proteins expressed in human cell lines (Janknecht et al., 1991, Proc. Natl. Acad. Sci. USA 88:8972-897). In this system, the gene of interest is subcloned into a vaccinia recombination plasmid such that the open reading frame of the gene is translationally fused to an amino-terminal tag consisting of six histidine residues. The tag serves as a matrix binding domain for the fusion protein. Extracts from cells infected with recombinant vaccinia virus are loaded onto $Ni^{2+}$ nitrilo-acetic acid-agarose columns and histidine-tagged proteins are selectively eluted with imidazole-containing buffers.

Characterization of Antibody Binding to Antigen

The antibodies that are generated by these methods may then be selected by first screening for affinity and specificity with the purified polypeptide of interest and, if required, comparing the results to the affinity and specificity of the antibodies with polypeptides that are desired to be excluded from binding. The antibodies can be tested for binding to Cadherin-17 by, for example, standard ELISA. The screening procedure can involve immobilization of the purified polypeptides in separate wells of microtiter plates. The solution containing a potential antibody or groups of antibodies is then placed into the respective microtiter wells and incubated for about 30 min to 2 h. The microtiter wells are then washed and a labeled secondary antibody (for example, an anti-mouse antibody conjugated to alkaline phosphatase if the raised antibodies are mouse antibodies) is added to the wells and incubated for about 30 min and then washed. Substrate is added to the wells and a color reaction will appear where antibody to the immobilized polypeptide(s) is present.

The antibodies so identified may then be further analyzed for affinity and specificity in the assay design selected. In the development of immunoassays for a target protein, the purified target protein acts as a standard with which to judge the sensitivity and specificity of the immunoassay using the antibodies that have been selected. Because the binding affinity of various antibodies may differ; certain antibody pairs (e.g. in sandwich assays) may interfere with one another sterically, etc., assay performance of an antibody may be a more important measure than absolute affinity and specificity of an antibody.

Those skilled in the art will recognize that many approaches can be taken in producing antibodies or binding fragments and screening and selecting for affinity and specificity for the various polypeptides, but these approaches do not change the scope of the invention.

To determine if the selected anti-Cadherin-17 monoclonal antibodies bind to unique epitopes, each antibody can be biotinylated using commercially available reagents (Pierce, Rockford, Ill.). Competition studies using unlabeled monoclonal antibodies and biotinylated monoclonal antibodies can be performed using Cadherin-17 coated-ELISA plates. Biotinylated mAb binding can be detected with a strep-avidin-alkaline phosphatase probe.

To determine the isotype of purified antibodies, isotype ELISAs can be performed using reagents specific for antibodies of a particular isotype.

Anti-Cadherin-17 antibodies can be further tested for reactivity with Cadherin-17 antigen by Western blotting. Briefly, Cadherin-17 can be prepared and subjected to sodium dodecyl sulfate polyacrylamide gel electrophoresis. After electrophoresis, the separated antigens are transferred to nitrocellulose membranes, blocked with 10% fetal calf serum, and probed with the monoclonal antibodies to be tested.

The binding specificity of an antibody of the invention may also be determined by monitoring binding of the antibody to cells expressing Cadherin-17, for example by flow cytometry. Typically, a cell line, such as a CHO cell line, may be transfected with an expression vector encoding Cadherin-17. The transfected protein may comprise a tag, such as a myc-tag, preferably at the N-terminus, for detection using an antibody to the tag. Binding of an antibody of the invention to Cadherin-17 may be determined by incubating the transfected cells with the antibody, and detecting bound antibody. Binding of an antibody to the tag on the transfected protein may be used as a positive control.

The specificity of an antibody of the invention for Cadherin-17 may be further studied by determining whether or not the antibody binds to other proteins, such as another member of the Cadherin family using the same methods by which binding to Cadherin-17 is determined.

Immunoconjugates

In another aspect, the present invention features an anti-Cadherin-17 antibody, or a fragment thereof, conjugated to a therapeutic moiety, such as a cytotoxin, a drug (e.g., an immunosuppressant) or a radiotoxin. Such conjugates are referred to herein as "immunoconjugates". Immunoconjugates that include one or more cytotoxins are referred to as "immunotoxins." A cytotoxin or cytotoxic agent includes any agent that is detrimental to (e.g., kills) cells. Examples include Taxol®, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Other preferred examples of therapeutic cytotoxins that can be conjugated to an antibody of the invention include duocarmycins, calicheamicins, maytansines and auristatins, and derivatives thereof. An example of a calicheamicin antibody conjugate is commercially available (Mylotarg®; American Home Products).

Cytotoxins can be conjugated to antibodies of the invention using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D).

Examples of cytotoxins are described, for example, in U.S. Pat. Nos. 6,989,452, 7,087,600, and 7,129,261, and in PCT Application Nos. PCT/US2002/17210, PCT/US2005/017804, PCT/US2006/37793, PCT/US2006/060050, PCT/US2006/060711, WO2006/110476, and in U.S. Patent Application No. 60/891,028, all of which are incorporated herein by reference in their entirety. For further discussion of types of cytotoxins, linkers and methods for conjugating therapeutic agents to antibodies, see also Saito, G. et al. (2003) Adv. Drug Deliv. Rev. 55:199-215; Trail, P. A. et al. (2003) Cancer Immunol. Immunother. 52:328-337; Payne, G. (2003) Cancer Cell 3:207-212; Allen, T. M. (2002) Nat. Rev. Cancer 2:750-763; Pastan, I. and Kreitman, R. J. (2002) Curr. Opin. Investig. Drugs 3:1089-1091; Senter, P. D. and Springer, C. J. (2001) Adv. Drug Deliv. Rev. 53:247-264.

Antibodies of the present invention also can be conjugated to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, iodine131, indium111, yttrium90 and lutetium177. Method for preparing radioimmunoconjugates are established in the art. Examples of radioimmunoconjugates are commercially available, including Zevalin® (IDEC Pharmaceuticals) and Bexxar® (Corixa Pharmaceuticals), and similar methods can be used to prepare radioimmunoconjugates using the antibodies of the invention.

The antibody conjugates of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Amon et al., "Monoclonal Antibodies For Immunotargeting Of Drugs In Cancer Therapy," in Monoclonal Antibodies And Cancer Therapy, Reisfeld et al. (eds.), pp. 243-56 (Alan R. Liss, Inc. 1985); Hellstrom et al., "Antibodies For Drug Delivery," in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review," in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy," in Monoclonal Antibodies For Cancer Detection And Therapy, Baldwin et al. (eds.), pp. 303-16 (Academic Press 1985), and Thorpe et al., Immunol. Rev., 62:119-58 (1982).

Bispecific Molecules

In another aspect, the present invention features bispecific molecules comprising an anti-Cadherin-17 antibody, or a fragment thereof, of the invention. An antibody of the invention, or antigen-binding portions thereof, can be derivatized or linked to another functional molecule, e.g., another peptide or protein (e.g., another antibody or ligand for a receptor) to generate a bispecific molecule that binds to at least two different binding sites or target molecules. The antibody of the invention may in fact be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule of the invention, an antibody of the invention can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, the present invention includes bispecific molecules comprising at least one first binding specificity for Cadherin-17 and a second binding specificity for a second target epitope. In a particular embodiment of the invention, the second target epitope is an Fc receptor, e.g., human FcγRI (CD64) or a human Fcα receptor (CD89). Therefore, the invention includes bispecific molecules capable of binding both to FcγR or FcαR expressing effector cells (e.g., monocytes, macrophages or polymorphonuclear cells (PMNs)), and to target cells expressing Cadherin-17. These bispecific molecules target Cadherin-17 expressing cells to effector cell and trigger Fc receptor-mediated effector cell activities, such as phagocytosis of Cadherin-17 expressing cells, antibody dependent cell-mediated cytotoxicity (ADCC), cytokine release, or generation of superoxide anion.

In an embodiment of the invention in which the bispecific molecule is multispecific, the molecule can further include a third binding specificity, in addition to an anti-Fc binding specificity and an anti-Cadherin-17 binding specificity. In one embodiment, the third binding specificity is an anti-enhancement factor (EF) portion, e.g., a molecule which binds to a surface protein involved in cytotoxic activity and thereby increases the immune response against the target cell. The "anti-enhancement factor portion" can be an antibody, functional antibody fragment or a ligand that binds to a given molecule, e.g., an antigen or a receptor, and thereby results in an enhancement of the effect of the binding determinants for the Fc receptor or target cell antigen. The "anti-enhancement factor portion" can bind an Fc receptor or a target cell antigen. Alternatively, the anti-enhancement factor portion can bind to an entity that is different from the entity to which the first and second binding specificities bind. For example, the anti-enhancement factor portion can bind a cytotoxic T-cell (e.g. via CD2, CD3, CD8, CD28, CD4, CD40, ICAM-1 or other immune cell that results in an increased immune response against the target cell).

In one embodiment, the bispecific molecules of the invention comprise as a binding specificity at least one antibody, or an antibody fragment thereof, including, e.g., an Fab, Fab', $F(ab')_2$, Fv, Fd, dAb or a single chain Fv. The antibody may also be a light chain or heavy chain dimer, or any minimal fragment thereof such as a Fv or a single chain construct as described in U.S. Pat. No. 4,946,778 to Ladner et al., the contents of which is expressly incorporated by reference.

In one embodiment, the binding specificity for an Fcγ receptor is provided by a monoclonal antibody, the binding of which is not blocked by human immunoglobulin G (IgG). As used herein, the term "IgG receptor" refers to any of the eight γ-chain genes located on chromosome 1. These genes encode a total of twelve transmembrane or soluble receptor isoforms which are grouped into three Fcγ receptor classes: FcγRI (CD64), Fcγ RII(CD32), and FcγRIII (CD16). In one preferred embodiment, the Fcγ receptor is a human high affinity FcγRI. The human FcγRI is a 72 kDa molecule, which shows high affinity for monomeric IgG ($10^8$-$10^9$ $M^{-1}$).

The production and characterization of certain preferred anti-Fcγ monoclonal antibodies are described in PCT Publication WO 88/00052 and in U.S. Pat. No. 4,954,617 to Fanger et al., the teachings of which are fully incorporated by reference herein. These antibodies bind to an epitope of FcγRI, FcγRII or FcγRIII at a site which is distinct from the Fcγ binding site of the receptor and, thus, their binding is not blocked substantially by physiological levels of IgG. Specific anti-FcγRI antibodies useful in this invention are mAb 22, mAb 32, mAb 44, mAb 62 and mAb 197. The hybridoma producing mAb 32 is available from the American Type Culture Collection, ATCC Accession No. HB9469. In other embodiments, the anti-Fcγ receptor antibody is a humanized form of monoclonal antibody 22 (H22). The production and characterization of the H22 antibody is described in Graziano, R. F. et al. (1995) *J. Immunol* 155 (10): 4996-5002 and PCT Publication WO 94/10332 to Tempest et al. The H22 antibody producing cell line was deposited at the American Type Culture Collection under the designation HA022CL1 and has the accession no. CRL 11177.

In still other preferred embodiments, the binding specificity for an Fc receptor is provided by an antibody that binds to a human IgA receptor, e.g., an Fc-alpha receptor (FcαRI (CD89)), the binding of which is preferably not blocked by human immunoglobulin A (IgA). The term "IgA receptor" is intended to include the gene product of one α-gene (FcαRI) located on chromosome 19. This gene is known to encode several alternatively spliced transmembrane isoforms of 55 to 110 kDa. FcαRI (CD89) is constitutively expressed on monocytes/macrophages, eosinophilic and neutrophilic granulocytes, but not on non-effector cell populations. FcαRI has medium affinity ($\approx 5 \times 10^7$ $M^{-1}$) for both IgA1 and IgA2, which is increased upon exposure to cytokines such as G-CSF or GM-CSF (Morton, H. C. et al. (1996) *Critical Reviews in Immunology* 16:423-440). Four FcαRI-specific monoclonal antibodies, identified as A3, A59, A62 and A77, which bind FcαRI outside the IgA ligand binding domain, have been described (Monteiro, R. C. et al. (1992) *J. Immunol.* 148: 1764).

FcαRI and FcγRI are preferred trigger receptors for use in the bispecific molecules of the invention because they are (1) expressed primarily on immune effector cells, e.g., monocytes, PMNs, macrophages and dendritic cells; (2) expressed at high levels (e.g., 5,000-100,000 per cell); (3) mediators of cytotoxic activities (e.g., ADCC, phagocytosis); and (4) mediate enhanced antigen presentation of antigens, including self-antigens, targeted to them.

Antibodies which can be employed in the bispecific molecules of the invention are murine, human, chimeric and humanized monoclonal antibodies.

The bispecific molecules of the present invention can be prepared by conjugating the constituent binding specificities, e.g., the anti-FcR and anti-Cadherin-17 binding specificities, using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio) propionate (SPDP), and sulfosuccinimidyl 4-(N-maleimidomethyl) cyclohaxane-1-carboxylate (sulfo-SMCC) (see e.g., Karpovsky et al. (1984) *J. Exp. Med.* 160: 1686; Liu, M A et al. (1985) *Proc. Natl. Acad. Sci. USA* 82:8648). Other methods include those described in Paulus (1985) Behring Ins. Mitt. No. 78, 118-132; Brennan et al. (1985) *Science* 229:81-83, and Glennie et al. (1987) *J. Immunol.* 139: 2367-2375). Preferred conjugating agents are SATA and sulfo-SMCC, both available from Pierce Chemical Co. (Rockford, Ill.).

When the binding specificities are antibodies, they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific molecule is a mAb×mAb, mAb×Fab, Fab×F(ab')$_2$ or ligand x Fab fusion protein. A bispecific molecule of the invention can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. Nos. 5,260,203; 5,455,030; 4,881,175; 5,132,405; 5,091,513; 5,476,786; 5,013,653; 5,258,498; and 5,482,858, all of which are expressly incorporated herein by reference.

Binding of the bispecific molecules to their specific targets can be confirmed by, for example, enzyme-linked immunosorbent assay (ELISA), radioimmunoassay (RIA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest. For example, the FcR-antibody complexes can be detected using e.g., an enzyme-linked antibody or antibody fragment which recognizes and specifically binds to the antibody-FcR complexes. Alternatively, the complexes can be detected using any of a variety of other immunoassays. For example, the antibody can be radioactively labeled and used in a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a γ counter or a scintillation counter or by autoradiography.

Antibody Fragments and Antibody Mimetics

The instant invention is not limited to traditional antibodies and may be practiced through the use of antibody fragments and antibody mimetics. As detailed below, a wide variety of antibody fragment and antibody mimetic technologies have now been developed and are widely known in the art. While a number of these technologies, such as domain antibodies, Nanobodies®, and UniBodies® make use of fragments of, or other modifications to, traditional antibody structures, there are also alternative technologies, such as Affibodies®, DARPins®, Anticalins®, Avimers, and Versabodies that employ binding structures that, while they mimic traditional antibody binding, are generated from and function via distinct mechanisms.

Domain Antibodies (dAbs) are the smallest functional binding units of antibodies, corresponding to the variable regions of either the heavy ($V_H$) or light ($V_L$) chains of human antibodies. Domain Antibodies have a molecular weight of approximately 13 kDa. Domantis has developed a series of large and highly functional libraries of fully human $V_H$ and $V_L$ dAbs (more than ten billion different sequences in each library), and uses these libraries to select dAbs that are specific to therapeutic targets. In contrast to many conventional antibodies, Domain Antibodies are well expressed in bacterial, yeast, and mammalian cell systems. Further details of domain antibodies and methods of production thereof may be obtained by reference to U.S. Pat. Nos. 6,291,158; 6,582,915; 6,593,081; 6,172,197; 6,696,245; US Serial No. 2004/0110941; European patent application No. 1433846 and European Patents 0368684 & 0616640; WO05/035572, WO04/101790, WO04/081026, WO04/058821, WO04/003019 and WO03/002609, each of which is herein incorporated by reference in its entirety.

Nanobodies® are antibody-derived therapeutic proteins that contain the unique structural and functional properties of naturally-occurring heavy-chain antibodies. These heavy-chain antibodies contain a single variable domain (VHH) and two constant domains (CH2 and CH3). Importantly, the cloned and isolated VHH domain is a perfectly stable polypeptide harboring the full antigen-binding capacity of the original heavy-chain antibody. Nanobodies® have a high homology with the VH domains of human antibodies and can be further humanized without any loss of activity. Importantly, Nanobodies® have a low immunogenic potential, which has been confirmed in primate studies with Nanobody® lead compounds.

Nanobodies® combine the advantages of conventional antibodies with important features of small molecule drugs Like conventional antibodies, Nanobodies® show high target specificity, high affinity for their target and low inherent toxicity. However, like small molecule drugs they can inhibit enzymes and readily access receptor clefts. Furthermore, Nanobodies® are extremely stable, can be administered by means other than injection (see e.g. WO 04/041867, which is herein incorporated by reference in its entirety) and are easy to manufacture. Other advantages of Nanobodies® include recognizing uncommon or hidden epitopes as a result of their small size, binding into cavities or active sites of protein targets with high affinity and selectivity due to their unique 3-dimensional, drug format flexibility, tailoring of half-life and ease and speed of drug discovery.

Nanobodies® are encoded by single genes and are efficiently produced in almost all prokaryotic and eukaryotic hosts e.g. *E. coli* (see e.g. U.S. Pat. No. 6,765,087, which is herein incorporated by reference in its entirety), molds (for example *Aspergillus* or *Trichoderma*) and yeast (for example *Saccharomyces, Kluyveromyces, Hansenula* or *Pichia*) (see e.g. U.S. Pat. No. 6,838,254, which is herein incorporated by reference in its entirety). The production process is scalable and multi-kilogram quantities of Nanobodies® have been produced. Because Nanobodies® exhibit a superior stability compared with conventional antibodies, they can be formulated as a long shelf-life, ready-to-use solution.

The Nanoclone method (see e.g. WO 06/079372, which is herein incorporated by reference in its entirety) is a proprietary method for generating Nanobodies® against a desired target, based on automated high-throughput selection of B-cells and could be used in the context of the instant invention.

UniBodies® are another antibody fragment technology; however this one is based upon the removal of the hinge region of IgG4 antibodies. The deletion of the hinge region results in a molecule that is essentially half the size of traditional IgG4 antibodies and has a univalent binding region rather than the bivalent binding region of IgG4 antibodies. It is also well known that IgG4 antibodies are inert and thus do not interact with the immune system, which may be advantageous for the treatment of diseases where an immune response is not desired, and this advantage is passed onto UniBodies®. For example, UniBodies® may function to inhibit or silence, but not kill, the cells to which they are bound. Additionally, UniBody® binding to cancer cells do not stimulate them to proliferate. Furthermore, because UniBodies® are about half the size of traditional IgG4 antibodies, they may show better distribution over larger solid tumors with potentially advantageous efficacy. UniBodies® are cleared from the body at a similar rate to whole IgG4 antibodies and are able to bind with a similar affinity for their antigens as whole antibodies. Further details of UniBodies® may be obtained by reference to patent application WO2007/059782, which is herein incorporated by reference in its entirety.

Affibody® molecules represent a new class of affinity proteins based on a 58-amino acid residue protein domain, derived from one of the IgG-binding domains of staphylococcal protein A. This three helix bundle domain has been used as a scaffold for the construction of combinatorial phagemid libraries, from which Affibody® variants that target the desired molecules can be selected using phage display technology (Nord K, Gunneriusson E, Ringdahl J, Stahl S, Uhlen M, Nygren P A, Binding proteins selected from combinatorial libraries of an a-helical bacterial receptor domain, Nat Biotechnol 1997; 15:772-7. Ronmark J, Gronlund H, Uhlen M, Nygren P A, Human immunoglobulin A (IgA)-specific ligands from combinatorial engineering of protein A, Eur J Biochem 2002; 269:2647-55.). The simple, robust structure of Affibody® molecules in combination with their low molecular weight (6 kDa), make them suitable for a wide variety of applications, for instance, as detection reagents (Ronmark J, Hansson M, Nguyen T, et al, Construction and characterization of affibody-Fc chimeras produced in *Escherichia coli*, J Immunol Methods 2002; 261:199-211) and to inhibit receptor interactions (Sandstorm K, Xu Z, Forsberg G, Nygren P A, Inhibition of the CD28-CD80 co-stimulation signal by a CD28-binding Affibody® ligand developed by combinatorial protein engineering, Protein Eng 2003; 16:691-7). Further details of Affibodies and methods of production thereof may be obtained by reference to U.S. Pat. No. 5,831,012 which is herein incorporated by reference in its entirety.

Labelled Affibodies may also be useful in imaging applications for determining abundance of Isoforms.

DARPins (Designed Ankyrin Repeat Proteins) are one example of an antibody mimetic DRP (Designed Repeat Protein) technology that has been developed to exploit the binding abilities of non-antibody polypeptides. Repeat proteins such as ankyrin or leucine-rich repeat proteins, are ubiquitous binding molecules, which occur, unlike antibodies, intra- and extracellularly. Their unique modular architecture features repeating structural units (repeats), which stack together to form elongated repeat domains displaying variable and modular target-binding surfaces. Based on this modularity, combinatorial libraries of polypeptides with highly diversified binding specificities can be generated. This strategy includes the consensus design of self-compatible repeats displaying variable surface residues and their random assembly into repeat domains.

DARPins can be produced in bacterial expression systems at very high yields and they belong to the most stable proteins known. Highly specific, high-affinity DARPins to a broad range of target proteins, including human receptors, cytokines, kinases, human proteases, viruses and membrane proteins, have been selected. DARPins having affinities in the single-digit nanomolar to picomolar range can be obtained.

DARPins have been used in a wide range of applications, including ELISA, sandwich ELISA, flow cytometric analysis (FACS), immunohistochemistry (IHC), chip applications, affinity purification or Western blotting. DARPins also proved to be highly active in the intracellular compartment for example as intracellular marker proteins fused to green fluorescent protein (GFP). DARPins were further used to inhibit viral entry with IC50 in the pM range. DARPins are not only ideal to block protein-protein interactions, but also to inhibit enzymes. Proteases, kinases and transporters have been successfully inhibited, most often an allosteric inhibition mode. Very fast and specific enrichments on the tumor and very favorable tumor to blood ratios make DARPins well suited for in vivo diagnostics or therapeutic approaches.

Additional information regarding DARPins and other DRP technologies can be found in US Patent Application Publication No. 2004/0132028, and International Patent Application Publication No. WO 02/20565, both of which are hereby incorporated by reference in their entirety.

Anticalins® are an additional antibody mimetic technology, however in this case the binding specificity is derived from lipocalins, a family of low molecular weight proteins that are naturally and abundantly expressed in human tissues and body fluids. Lipocalins have evolved to perform a range of functions in vivo associated with the physiological transport and storage of chemically sensitive or insoluble compounds. Lipocalins have a robust intrinsic structure comprising a highly conserved B-barrel which supports four loops at one terminus of the protein. These loops form the entrance to a binding pocket and conformational differences in this part of the molecule account for the variation in binding specificity between individual lipocalins.

While the overall structure of hypervariable loops supported by a conserved B-sheet framework is reminiscent of immunoglobulins, lipocalins differ considerably from antibodies in terms of size, being composed of a single polypeptide chain of 160-180 amino acids which is marginally larger than a single immunoglobulin domain.

Lipocalins are cloned and their loops are subjected to engineering in order to create Anticalins®. Libraries of structurally diverse Anticalins® have been generated and Anticalin® display allows the selection and screening of binding function, followed by the expression and production of soluble protein for further analysis in prokaryotic or eukaryotic systems. Studies have successfully demonstrated that Anticalins® can be developed that are specific for virtually any human target protein can be isolated and binding affinities in the nanomolar or higher range can be obtained.

Anticalins® can also be formatted as dual targeting proteins, so-called Duocalins. A Duocalin binds two separate therapeutic targets in one easily produced monomeric protein using standard manufacturing processes while retaining target specificity and affinity regardless of the structural orientation of its two binding domains.

Modulation of multiple targets through a single molecule is particularly advantageous in diseases known to involve more than a single causative factor. Moreover, bi- or multivalent binding formats such as Duocalins have significant potential in targeting cell surface molecules in disease, mediating agonistic effects on signal transduction pathways or inducing enhanced internalization effects via binding and clustering of cell surface receptors. Furthermore, the high intrinsic stability of Duocalins is comparable to monomeric Anticalins®, offering flexible formulation and delivery potential for Duocalins.

Additional information regarding Anticalins® can be found in U.S. Pat. No. 7,250,297 and International Patent Application Publication No. WO 99/16873, both of which are hereby incorporated by reference in their entirety.

Another antibody mimetic technology useful in the context of the instant invention are Avimers. Avimers are evolved from a large family of human extracellular receptor domains by in vitro exon shuffling and phage display, generating multidomain proteins with binding and inhibitory properties. Linking multiple independent binding domains has been shown to create avidity and results in improved affinity and specificity compared with conventional single-epitope binding proteins. Other potential advantages include simple and efficient production of multitarget-specific molecules in *Escherichia coli*, improved thermostability and resistance to proteases. Avimers with sub-nanomolar affinities have been obtained against a variety of targets.

Additional information regarding Avimers can be found in US Patent Application Publication Nos. 2006/0286603, 2006/0234299, 2006/0223114, 2006/0177831, 2006/0008844, 2005/0221384, 2005/0164301, 2005/0089932, 2005/0053973, 2005/0048512, 2004/0175756, all of which are hereby incorporated by reference in their entirety.

Versabodies are another antibody mimetic technology that could be used in the context of the instant invention. Versabodies are small proteins of 3-5 kDa with >15% cysteines, which form a high disulfide density scaffold, replacing the hydrophobic core that typical proteins have. The replacement of a large number of hydrophobic amino acids, comprising the hydrophobic core, with a small number of disulfides results in a protein that is smaller, more hydrophilic (less aggregation and non-specific binding), more resistant to proteases and heat, and has a lower density of T-cell epitopes, because the residues that contribute most to MHC presentation are hydrophobic. All four of these properties are well-known to affect immunogenicity, and together they are expected to cause a large decrease in immunogenicity.

The inspiration for Versabodies comes from the natural injectable biopharmaceuticals produced by leeches, snakes, spiders, scorpions, snails, and anemones, which are known to exhibit unexpectedly low immunogenicity. Starting with selected natural protein families, by design and by screening the size, hydrophobicity, proteolytic antigen processing, and epitope density are minimized to levels far below the average for natural injectable proteins.

Given the structure of Versabodies, these antibody mimetics offer a versatile format that includes multi-valency, multi-specificity, a diversity of half-life mechanisms, tissue targeting modules and the absence of the antibody Fc region. Furthermore, Versabodies are manufactured in *E. coli* at high yields, and because of their hydrophilicity and small size, Versabodies are highly soluble and can be formulated to high concentrations. Versabodies are exceptionally heat stable (they can be boiled) and offer extended shelf-life.

Additional information regarding Versabodies can be found in US Patent Application Publication No. 2007/0191272 which is hereby incorporated by reference in its entirety.

The detailed description of antibody fragment and antibody mimetic technologies provided above is not intended to be a comprehensive list of all technologies that could be used in the context of the instant specification. For example, and also not by way of limitation, a variety of additional technologies including alternative polypeptide-based technologies, such as fusions of complimentary determining regions as outlined in Qui et al., Nature Biotechnology, 25(8) 921-929 (2007), which is hereby incorporated by reference in its entirety, as well as nucleic acid-based technologies, such as the RNA aptamer technologies described in U.S. Pat. Nos. 5,789,157, 5,864,026, 5,712,375, 5,763,566, 6,013,443, 6,376,474, 6,613,526, 6,114,120, 6,261,774, and 6,387,620, all of which are hereby incorporated by reference, could be used in the context of the instant invention.

Pharmaceutical Compositions

In another aspect, the present invention provides a composition, e.g., a pharmaceutical composition, containing one or a combination of monoclonal antibodies, or antigen-binding portion(s) thereof, of the present invention, formulated together with a pharmaceutically acceptable carrier. Such compositions may include one or a combination of (e.g., two or more different) antibodies, or immunoconjugates or bispecific molecules of the invention. For example, a pharmaceutical composition of the invention can comprise a combination of antibodies (or immunoconjugates or bispecifics) that bind to different epitopes on the target antigen or that have complementary activities.

Pharmaceutical compositions of the invention also can be administered in combination therapy, i.e., combined with other agents. For example, the combination therapy can include an anti-Cadherin-17 antibody of the present invention combined with at least one other anti-tumor agent, or an anti-inflammatory or immunosuppressant agent. Examples of therapeutic agents that can be used in combination therapy are described in greater detail below in the section on uses of the antibodies of the invention.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, immunoconjugate, or bispecific molecule, may be coated in a material to protect the compound from the action of acids and other natural conditions that may inactivate the compound.

The pharmaceutical compounds of the invention may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the invention also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred per cent, this amount will range from about 0.01 per cent to about ninety-nine percent of active ingredient, preferably from about 0.1 per cent to about 70 per cent, most preferably from about 1 per cent to about 30 per cent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for an anti-Cadherin-17 antibody of the invention include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks.

In some methods, two or more monoclonal antibodies with different binding specificities are administered simultaneously, in which case the dosage of each antibody administered falls within the ranges indicated. Antibody is usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 µg/ml and in some methods about 25-300 µg/ml.

Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an anti-Cadherin-17 antibody of the invention preferably results in a decrease in severity of disease symptoms, an increase in frequency and duration of disease symptom-free periods, or a prevention of impairment or disability due to the disease affliction. For example, for the treatment of Cadherin-17$^+$ tumors, a "therapeutically effective dosage" preferably inhibits cell growth or tumor growth by at least about 20%, more preferably by at least about 40%, even more preferably by at least about 60%, and still more preferably by at least about 80% relative to untreated subjects. The ability of a compound to inhibit tumor growth can be evaluated in an animal model system predictive of efficacy in human tumors. Alternatively, this property of a composition can be evaluated by examining the ability of the compound to inhibit cell growth, such inhibition can be measured in vitro by assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

A composition of the present invention can be administered via one or more routes of administration using one or more of a variety of methods known in the art. As will be appreciated by the skilled artisan, the route and/or mode of administration will vary depending upon the desired results. Preferred routes of administration for antibodies of the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an antibody of the invention can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the monoclonal antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J. Physiol.* 1233:134); p120 (Schreier et al. (1994) *J. Biol. Chem.* 269:9090); see also K. Keinanen; M. L. Laukkanen (1994) *FEBS Lett.* 346:123; J. J. Killion; I. J. Fidler (1994) *Immunomethods* 4:273.

Uses and Methods

The antibodies, antibody compositions and methods of the present invention have numerous in vitro and in vivo diagnostic and therapeutic utilities involving the diagnosis and treatment of Cadherin-17 mediated disorders.

In some embodiments, these molecules can be administered to cells in culture, in vitro or ex vivo, or to human subjects, e.g., in vivo, to treat, prevent and to diagnose a variety of disorders. As used herein, the term "subject" is intended to include human and non-human animals. Non-human animals include all vertebrates, e.g., mammals and non-mammals, such as non-human primates, sheep, dogs, cats, cows, horses, chickens, amphibians, and reptiles. Preferred subjects include human patients having disorders mediated by Cadherin-17 activity. The methods are particularly suitable for treating human patients having a disorder associated with aberrant Cadherin-17 expression. When antibodies to Cadherin-17 are administered together with another agent, the two can be administered in either order or simultaneously.

Given the specific binding of the antibodies of the invention for Cadherin-17, the antibodies of the invention can be used to specifically detect Cadherin-17 expression on the surface of cells and, moreover, can be used to purify Cadherin-17 via immunoaffinity purification.

Furthermore, given the expression of Cadherin-17 on tumor cells, the antibodies, antibody compositions and methods of the present invention can be used to treat a subject with a tumorigenic disorder, e.g., a disorder characterized by the presence of tumor cells expressing Cadherin-17 including, for example, colorectal cancer. Cadherin-17 has been demonstrated to be internalised on antibody binding as illustrated in Example 10 below, thus enabling the antibodies of the invention to be used in any payload mechanism of action e.g. an ADC approach, radio immuno conjugate, or ADEPT approach.

In one embodiment, the antibodies (e.g., monoclonal antibodies, multispecific and bispecific molecules and compositions) of the invention can be used to detect levels of Cadherin-17, or levels of cells which contain Cadherin-17 on their membrane surface, which levels can then be linked to certain disease symptoms. Alternatively, the antibodies can be used to inhibit or block Cadherin-17 function which, in turn, can be linked to the prevention or amelioration of certain disease symptoms, thereby implicating Cadherin-17 as a mediator of the disease. This can be achieved by contacting a sample and a control sample with the anti-Cadherin-17 antibody under conditions that allow for the formation of a complex between the antibody and Cadherin-17. Any complexes formed between the antibody and Cadherin-17 are detected and compared in the sample and the control.

In another embodiment, the antibodies (e.g., monoclonal antibodies, multispecific and bispecific molecules and compositions) of the invention can be initially tested for binding activity associated with therapeutic or diagnostic use in vitro. For example, compositions of the invention can be tested using the flow cytometric assays described in the Examples below.

The antibodies (e.g., monoclonal antibodies, multispecific and bispecific molecules, immunoconjugates and compositions) of the invention have additional utility in therapy and diagnosis of Cadherin-17 related diseases. For example, the monoclonal antibodies, the multispecific or bispecific molecules and the immunoconjugates can be used to elicit in vivo or in vitro one or more of the following biological activities: to inhibit the growth of and/or kill a cell expressing Cadherin-17; to mediate phagocytosis or ADCC of a cell expressing Cadherin-17 in the presence of human effector cells, or to block Cadherin-17 ligand binding to Cadherin-17.

In a particular embodiment, the antibodies (e.g., monoclonal antibodies, multispecific and bispecific molecules and compositions) are used in vivo to treat, prevent or diagnose a variety of Cadherin-17-related diseases. Examples of Cadherin-17-related diseases include, among others, human cancer tissues representing colorectal cancer.

Suitable routes of administering the antibody compositions (e.g., monoclonal antibodies, multispecific and bispecific molecules and immunoconjugates) of the invention in vivo and in vitro are well known in the art and can be selected by those of ordinary skill. For example, the antibody compositions can be administered by injection (e.g., intravenous or subcutaneous). Suitable dosages of the molecules used will depend on the age and weight of the subject and the concentration and/or formulation of the antibody composition.

As previously described, anti-Cadherin-17 antibodies of the invention can be co-administered with one or other more therapeutic agents, e.g., a cytotoxic agent, a radiotoxic agent or an immunosuppressive agent. The antibody can be linked to the agent (as an immunocomplex) or can be administered separate from the agent. In the latter case (separate administration), the antibody can be administered before, after or concurrently with the agent or can be co-administered with other known therapies, e.g., an anti-cancer therapy, e.g., radiation. Such therapeutic agents include, among others, anti-neoplastic agents such as doxorubicin (adriamycin), cis-platin bleomycin sulfate, carmustine, chlorambucil, and cyclophosphamide hydroxyurea which, by themselves, are only effective at levels which are toxic or subtoxic to a patient. Cisplatin is intravenously administered as a 100 mg/kg dose once every four weeks and adriamycin is intravenously administered as a 60-75 mg/ml dose once every 21 days. Other agents suitable for co-administration with the antibodies of the invention include other agents used for the treatment of cancers, e.g. pancreatic or colorectal cancer, such as Avastin®, 5FU and gemcitabine. Co-administration of the anti-Cadherin-17 antibodies, or antigen binding fragments thereof, of the present invention with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells which would render them unreactive with the antibody.

Target-specific effector cells, e.g., effector cells linked to compositions (e.g., monoclonal antibodies, multispecific and bispecific molecules) of the invention can also be used as therapeutic agents. Effector cells for targeting can be human leukocytes such as macrophages, neutrophils or monocytes. Other cells include eosinophils, natural killer cells and other IgG- or IgA-receptor bearing cells. If desired, effector cells can be obtained from the subject to be treated. The target-specific effector cells can be administered as a suspension of cells in a physiologically acceptable solution. The number of cells administered can be in the order of $10^8$-$10^9$ but will vary depending on the therapeutic purpose. In general, the amount will be sufficient to obtain localization at the target cell, e.g., a tumor cell expressing Cadherin-17, and to affect cell killing by, e.g., phagocytosis. Routes of administration can also vary.

Therapy with target-specific effector cells can be performed in conjunction with other techniques for removal of targeted cells. For example, anti-tumor therapy using the compositions (e.g., monoclonal antibodies, multispecific and bispecific molecules) of the invention and/or effector cells armed with these compositions can be used in conjunction with chemotherapy. Additionally, combination immunotherapy may be used to direct two distinct cytotoxic effector populations toward tumor cell rejection. For example, anti-Cadherin-17 antibodies linked to anti-Fc-gamma RI or anti-CD3 may be used in conjunction with IgG- or IgA-receptor specific binding agents.

Bispecific and multispecific molecules of the invention can also be used to modulate FcγR or FcγR levels on effector cells, such as by capping and elimination of receptors on the cell surface. Mixtures of anti-Fc receptors can also be used for this purpose.

The compositions (e.g., monoclonal antibodies, multispecific and bispecific molecules and immunoconjugates) of the invention which have complement binding sites, such as portions from IgG1, -2, or -3 or IgM which bind complement, can also be used in the presence of complement. In one embodiment, ex vivo treatment of a population of cells comprising target cells with a binding agent of the invention and appropriate effector cells can be supplemented by the addition of complement or serum containing complement. Phagocytosis of target cells coated with a binding agent of the invention can be improved by binding of complement proteins. In another embodiment target cells coated with the compositions (e.g., monoclonal antibodies, multispecific and bispecific molecules) of the invention can also be lysed by complement. In yet another embodiment, the compositions of the invention do not activate complement.

The compositions (e.g., monoclonal antibodies, multispecific and bispecific molecules and immunoconjugates) of the invention can also be administered together with complement. In certain embodiments, the instant disclosure provides compositions comprising antibodies, multispecific or bispecific molecules and serum or complement. These compositions can be advantageous when the complement is located in close proximity to the antibodies, multispecific or bispecific molecules. Alternatively, the antibodies, multispecific or bispecific molecules of the invention and the complement or serum can be administered separately.

Also within the scope of the present invention are kits comprising the antibody compositions of the invention (e.g., monoclonal antibodies, bispecific or multispecific molecules, or immunoconjugates) and instructions for use. The kit can further contain one more more additional reagents, such as an immunosuppressive reagent, a cytotoxic agent or a radiotoxic agent, or one or more additional antibodies of the invention (e.g., an antibody having a complementary activity which binds to an epitope in the Cadherin-17 antigen distinct from the first antibody).

Accordingly, patients treated with antibody compositions of the invention can be additionally administered (prior to, simultaneously with, or following administration of an antibody of the invention) with another therapeutic agent, such as a cytotoxic or radiotoxic agent, which enhances or augments the therapeutic effect of the antibodies.

In other embodiments, the subject can be additionally treated with an agent that modulates, e.g., enhances or inhibits, the expression or activity of Fcγ or Fcγ receptors by, for example, treating the subject with a cytokine. Preferred cytokines for administration during treatment with the multispecific molecule include of granulocyte colony-stimulating factor (G-CSF), granulocyte-macrophage colony-stimulating factor (GM-CSF), interferon-γ (IFN-γ), and tumor necrosis factor (TNF).

The compositions (e.g., antibodies, multispecific and bispecific molecules) of the invention can also be used to target cells expressing FcγR or Cadherin-17, for example for labeling such cells. For such use, the binding agent can be linked to a molecule that can be detected. Thus, the invention provides methods for localizing ex vivo or in vitro cells expressing Fc receptors, such as FcγR, or Cadherin-17. The detectable label can be, e.g., a radioisotope, a fluorescent compound, an enzyme, or an enzyme co-factor.

In a particular embodiment, the invention provides methods for detecting the presence of Cadherin-17 antigen in a sample, or measuring the amount of Cadherin-17 antigen, comprising contacting the sample, and a control sample, with a monoclonal antibody, or an antigen binding portion thereof, which specifically binds to Cadherin-17, under conditions that allow for formation of a complex between the antibody or portion thereof and Cadherin-17. The formation of a complex is then detected, wherein a difference complex formation between the sample compared to the control sample is indicative the presence of Cadherin-17 antigen in the sample.

In other embodiments, the invention provides methods for treating a Cadherin-17 mediated disorder in a subject, e.g., human cancers, including colorectal cancer.

In yet another embodiment, immunoconjugates of the invention can be used to target compounds (e.g., therapeutic agents, labels, cytotoxins, radiotoxins immunosuppressants, etc.) to cells which have Cadherin-17 cell surface receptors by linking such compounds to the antibody. For example, an anti-Cadherin-17 antibody can be conjugated to any of the toxin compounds described in U.S. Pat. Nos. 6,281,354 and 6,548,530, US patent publication Nos. 2003/0050331, 2003/0064984, 2003/0073852, and 2004/0087497, or published in WO 03/022806. Thus, the invention also provides methods for localizing ex vivo or in vivo cells expressing Cadherin-17 (e.g., with a detectable label, such as a radioisotope, a fluorescent compound, an enzyme, or an enzyme co-factor). Alternatively, the immunoconjugates can be used to kill cells which have Cadherin-17 cell surface receptors by targeting cytotoxins or radiotoxins to Cadherin-17.

The present invention is further illustrated by the following examples which should not be construed as further limiting.

All references cited in this specification, including without limitation all papers, publications, patents, patent applications, presentations, texts, reports, manuscripts, brochures, books, internet postings, journal articles, periodicals, product fact sheets, and the like, one hereby incorporated by reference into this specification in their entireties. The discussion of the references herein is intended to merely summarize the assertions made by their authors and no admission is made that any reference constitutes prior art and Applicants' reserve the right to challenge the accuracy and pertinence of the cited references.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the dependant claims.

EXAMPLES

Example 1

Construction of a Phage-Display Library

A recombinant protein composed of domains 1-2 of the extracellular domain of Cadherin-17 (SEQ ID NO:136) was generated in bacteria by standard recombinant methods and used as antigen for immunization (see below). A recombinant protein composed of the full length extracellular domain of Cadherin-17 (SEQ ID NO:137) was also eurkaryotically synthesized by standard recombinant methods and used for screening.

Immunization and mRNA Isolation

A phage display library for identification of Cadherin-17-binding molecules was constructed as follows. A/J mice (Jackson Laboratories, Bar Harbor, Me.) were immunized intraperitoneally with recombinant Cadherin-17 antigen (domains 1-2 of the extracellular domain), using 100 µg protein in Freund's complete adjuvant, on day 0, and with 100 µg antigen on day 28. Test bleeds of mice were obtained through puncture of the retro-orbital sinus. If, by testing the titers, they were deemed high by ELISA using biotinylated Cadherin-17 antigen immobilized via neutravidin (Reacti-Bind™ NeutrAvidin®-Coated Polystyrene Plates, Pierce, Rockford, Ill.), the mice were boosted with 100 µg of protein on day 70, 71 and 72, with subsequent sacrifice and splenectomy on day 77. If titers of antibody were not deemed satisfactory, mice were boosted with 100 µg antigen on day 56 and a test bleed taken on day 63. If satisfactory titers were obtained, the animals were boosted with 100 µg of antigen on day 98, 99, and 100 and the spleens harvested on day 105.

The spleens were harvested in a laminar flow hood and transferred to a petri dish, trimming off and discarding fat and connective tissue. The spleens were macerated quickly with the plunger from a sterile 5 cc syringe in the presence of 1.0 ml of solution D (25.0 g guanidine thiocyanate (Boehringer Mannheim, Indianapolis, Ind.), 29.3 ml sterile water, 1.76 ml 0.75 M sodium citrate pH 7.0, 2.64 ml 10% sarkosyl (Fisher Scientific, Pittsburgh, Pa.), 0.36 ml 2-mercaptoethanol (Fisher Scientific, Pittsburgh, Pa.)). This spleen suspension was pulled through an 18 gauge needle until all cells were lysed and the viscous solution was transferred to a microcentrifuge tube. The petri dish was washed with 100 µl of solution D to recover any remaining spleen. This suspension was then pulled through a 22 gauge needle an additional 5-10 times.

The sample was divided evenly between two microcentrifuge tubes and the following added, in order, with mixing by inversion after each addition: 50 µl 2 M sodium acetate pH 4.0, 0.5 ml water-saturated phenol (Fisher Scientific, Pittsburgh, Pa.), 100 µl chloroform/isoamyl alcohol 49:1 (Fisher Scientific, Pittsburgh, Pa.). The solution was vortexed for 10 seconds and incubated on ice for 15 min. Following centrifugation at 14 krpm for 20 min at 2-8° C., the aqueous phase was transferred to a fresh tube. An equal volume of water saturated phenol:chloroform:isoamyl alcohol (50:49:1) was added, and the tube vortexed for ten seconds. After a 15 min incubation on ice, the sample was centrifuged for 20 min at 2-8° C., and the aqueous phase transferred to a fresh tube and precipitated with an equal volume of isopropanol at −20° C. for a minimum of 30 min. Following centrifugation at 14 krpm for 20 min at 4° C., the supernatant was aspirated away, the tubes briefly spun and all traces of liquid removed from the RNA pellet.

The RNA pellets were each dissolved in 300 µl of solution D, combined, and precipitated with an equal volume of isopropanol at −20° C. for a minimum of 30 min. The sample was centrifuged 14 krpm for 20 min at 4° C., the supernatant aspirated as before, and the sample rinsed with 100 µl of ice-cold 70% ethanol. The sample was again centrifuged 14 krpm for 20 min at 4° C., the 70% ethanol solution aspirated, and the RNA pellet dried in vacuo. The pellet was resuspended in 100 µl of sterile diethyl pyrocarbonate-treated water. The concentration was determined by A260 using an absorbance of 1.0 for a concentration of 40 µg/ml. The RNAs were stored at −80° C.

Preparation of Complementary DNA (cDNA)

The total RNA purified from mouse spleens as described above was used directly as template for cDNA preparation. RNA (50 µg) was diluted to 100 µL with sterile water, and 10 µL of 130 ng/µL oligo dT12 (synthesized on Applied Biosystems Model 392 DNA synthesizer) was added. The sample was heated for 10 min at 70° C., then cooled on ice. Forty µL 5* first strand buffer was added (Gibco/BRL, Gaithersburg, Md.), along with 20 µL 0.1 M dithiothreitol (Gibco/BRL, Gaithersburg, Md.), 10 µL 20 mM deoxynucleoside triphosphates (dNTP's, Boehringer Mannheim, Indianapolis, Ind.), and 10 µL water on ice. The sample was then incubated at 37° C. for 2 min. Ten µL reverse transcriptase (Superscript™ II, Gibco/BRL, Gaithersburg, Md.) was added and incubation was continued at 37° C. for 1 hr. The cDNA products were used directly for polymerase chain reaction (PCR).

Amplification of Antibody Genes by PCR

To amplify substantially all of the H and L chain genes using PCR, primers were chosen that corresponded to substantially all published sequences. Because the nucleotide sequences of the amino termini of H and L contain considerable diversity, 33 oligonucleotides were synthesized to serve as 5' primers for the H chains, and 29 oligonucleotides were synthesized to serve as 5' primers for the kappa L chains as described in U.S. patent application Ser. No. 08/835,159, filed Apr. 4, 1997. The constant region nucleotide sequences for each chain required only one 3' primer for the H chains and one 3' primer for the kappa L chains.

A 50 µL reaction was performed for each primer pair with 50 µmol of 5' primer, 50 µmol of 3' primer, 0.25 µL Taq DNA Polymerase (5 units/µL, Boehringer Mannheim, Indianapolis, Ind.), 3 µL cDNA (prepared as described), 5 µL 2 mM dNTP's, 5 µL 10*Taq DNA polymerase buffer with MgCl2 (Boehringer Mannheim, Indianapolis, Ind.), and H2O to 50 µL. Amplification was done using a GeneAmp® 9600 thermal cycler (Perkin Elmer, Foster City, Calif.) with the following thermocycle program: 94° C. for 1 min; 30 cycles of 94° C. for 20 sec, 55° C. for 30 sec, and 72° C. for 30 sec; 72° C. for 6 min; 4° C.

The dsDNA products of the PCR process were then subjected to asymmetric PCR using only a 3' primer to generate substantially only the anti-sense strand of the target genes. A 100 µL reaction was done for each dsDNA product with 200 µmol of 3' primer, 2 µL of ds-DNA product, 0.5 µL Taq DNA Polymerase, 10 µL 2 mM dNTP's, 10 µL 10*Taq DNA polymerase buffer with MgCl2 (Boehringer Mannheim, Indianapolis, Ind.), and H2O to 100 µL. The same PCR program as that described above was used to amplify the single-stranded (ss)-DNA.

Purification of Single-Stranded DNA by High Performance Liquid Chromatography and Kinasing Single-Stranded DNA The H chain ss-PCR products and the L chain single-stranded PCR products were ethanol precipitated by adding 2.5 volumes ethanol and 0.2 volumes 7.5 M ammonium acetate and incubating at −20° C. for at least 30 min. The DNA was pelleted by centrifuging in an Eppendorf centrifuge at 14 krpm for 10 min at 2-8° C. The supernatant was carefully aspirated, and the tubes were briefly spun a 2nd time. The last drop of supernatant was removed with a pipette. The DNA was dried in vacuo for 10 min on medium heat. The H chain products were pooled in 210 µL water and the L chain products were pooled separately in 210 µL water. The single-stranded DNA was purified by high performance liquid chromatography (HPLC) using a Hewlett Packard 1090 HPLC and a GenPak® FAX anion exchange column (Millipore Corp., Milford, Mass.). The gradient used to purify the single-stranded DNA is shown in Table 1, and the oven temperature was 60° C. Absorbance was monitored at 260 nm. The single-stranded DNA eluted from the HPLC was collected in 0.5 min fractions. Fractions containing single-stranded DNA were ethanol precipitated, pelleted and dried as described above. The dried DNA pellets were pooled in 200 µL sterile water.

TABLE 1

| HPLC gradient for purification of ss-DNA | | | | |
|---|---|---|---|---|
| Time (min) | % A | % B | % C | Flow (ml/min) |
| 0 | 70 | 30 | 0 | 0.75 |
| 2 | 40 | 60 | 0 | 0.75 |
| 17 | 15 | 85 | 0 | 0.75 |
| 18 | 0 | 100 | 0 | 0.75 |
| 23 | 0 | 100 | 0 | 0.75 |
| 24 | 0 | 0 | 100 | 0.75 |
| 28 | 0 | 0 | 100 | 0.75 |
| 29 | 0 | 100 | 0 | 0.75 |
| 34 | 0 | 100 | 0 | 0.75 |
| 35 | 70 | 30 | 0 | 0.75 |

Buffer A is 25 mM Tris, 1 mM EDTA, pH 8.0
Buffer B is 25 mM Tris, 1 mM EDTA, 1M NaCl, pH 8.0
Buffer C is 40 mm phosphoric acid The single-stranded DNA was 5'-phosphorylated in preparation for mutagenesis. Twenty-four µL 10* kinase buffer (United States Biochemical, Cleveland, Ohio), 10.4 µL 10 mM adenosine-5'-triphosphate (Boehringer Mannheim, Indianapolis, Ind.), and 2 µL polynucleotide kinase (30 units/µL, United States Biochemical, Cleveland, Ohio) was added to each sample, and the tubes were incubated at 37° C. for 1 hr. The reactions were stopped by incubating the tubes at 70° C. for 10 min. The DNA was purified with one extraction of Tris equilibrated phenol (pH>8.0, United States Biochemical, Cleveland, Ohio):chloroform:isoamyl alcohol (50:49:1) and one extraction with chloroform:isoamyl alcohol (49:1). After the extractions, the DNA was ethanol precipitated and pelleted as described above. The DNA pellets were dried, then dissolved in 50 µL sterile water. The concentration was determined by measuring the absorbance of an aliquot of the DNA at 260 nm using 33 µg/ml for an absorbance of 1.0. Samples were stored at −20° C.

Preparation of Uracil Templates Used in Generation of Spleen Antibody Phage Libraries One ml of E. coli CJ236 (BioRAD, Hercules, Calif.) overnight culture was added to 50 ml 2*YT in a 250 ml baffled shake flask. The culture was grown at 37° C. to OD600=0.6, inoculated with 10 µl of a ¹⁄₁₀₀ dilution of BS45 vector phage stock (described in U.S. patent application Ser. No. 08/835, 159, filed Apr. 4, 1997) and growth continued for 6 hr. Approximately 40 ml of the culture was centrifuged at 12 krpm for 15 minutes at 4° C. The supernatant (30 ml) was transferred to a fresh centrifuge tube and incubated at room temperature for 15 minutes after the addition of 15 µl of 10 mg/ml RNaseA (Boehringer Mannheim, Indianapolis, Ind.). The phage were precipitated by the addition of 7.5 ml of 20% polyethylene glycol 8000 (Fisher Scientific, Pittsburgh, Pa.)/ 3.5M ammonium acetate (Sigma Chemical Co., St. Louis, Mo.) and incubation on ice for 30 min. The sample was centrifuged at 12 krpm for 15 min at 2-8° C. The supernatant was carefully discarded, and the tube briefly spun to remove all traces of supernatant. The pellet was resuspended in 400 µl of high salt buffer (300 mM NaCl, 100 mM Tris pH 8.0, 1 mM EDTA), and transferred to a 1.5 ml tube.

The phage stock was extracted repeatedly with an equal volume of equilibrated phenol:chloroform:isoamyl alcohol (50:49:1) until no trace of a white interface was visible, and then extracted with an equal volume of chloroform:isoamyl alcohol (49:1). The DNA was precipitated with 2.5 volumes of ethanol and ⅕ volume 7.5 M ammonium acetate and incubated 30 min at −20° C. The DNA was centrifuged at 14 krpm for 10 min at 4° C., the pellet washed once with cold 70% ethanol, and dried in vacuo. The uracil template DNA was dissolved in 30 µl sterile water and the concentration determined by A260 using an absorbance of 1.0 for a concentration of 40 µg/ml. The template was diluted to 250 ng/µL with sterile water, aliquoted, and stored at −20° C.

Mutagenesis of Uracil Template with ss-DNA and Electroporation into E. coli to Generate Antibody Phage Libraries Antibody phage display libraries were generated by simultaneously introducing single-stranded heavy and light chain genes onto a phage display vector uracil template. A typical mutagenesis was performed on a 2 µg scale by mixing the following in a 0.2 ml PCR reaction tube: 8 µl of (250 ng/µL) uracil template, 8 µL of 10* annealing buffer (200 mM Tris pH 7.0, 20 mM MgCl2, 500 mM NaCl), 3.33 µl of kinased single-stranded heavy chain insert (100 ng/µL), 3.1 µl of kinased single-stranded light chain insert (100 ng/µL), and sterile water to 80 µl. DNA was annealed in a GeneAmp® 9600 thermal cycler using the following thermal profile: 20 sec at 94° C., 85° C. for 60 sec, 85° C. to 55° C. ramp over 30 min, hold at 55° C. for 15 min. The DNA was transferred to ice after the program finished. The extension/ligation was carried out by adding 8 µl of 10* synthesis buffer (5 mM each dNTP, 10 mM ATP, 100 mM Tris pH 7.4, 50 mM MgCl2, 20 mM DTT), 8 µL T4 DNA ligase (1 U/µL, Boehringer Mannheim, Indianapolis, Ind.), 8 µL diluted T7 DNA polymerase (1 U/µL, New England BioLabs, Beverly, Mass.) and incubating at 37° C. for 30 min. The reaction was stopped with 300 µL of mutagenesis stop buffer (10 mM Tris pH 8.0, 10 mM EDTA). The mutagenesis DNA was extracted once with equilibrated phenol (pH>8):chloroform:isoamyl alcohol (50:49:1), once with chloroform:isoamyl alcohol (49:1), and the DNA was ethanol precipitated at −20° C. for at least 30 min. The DNA was pelleted and the supernatant carefully removed as described above. The sample was briefly spun again and all traces of ethanol removed with a pipetman. The pellet was dried in vacuo. The DNA was resuspended in 4 µL of sterile water.

One microliter of mutagenesis DNA (500 ng) was transferred into 40 µl electrocompetent E. coli DH12S (Gibco/BRL, Gaithersburg, Md.) using electroporation. The transformed cells were mixed with approximately 1.0 ml of overnight XL-1 cells which were diluted with 2*YT broth to 60% the original volume. This mixture was then transferred to a 15-ml sterile culture tube and 9 ml of top agar added for plating on a 150-mm LB agar plate. Plates were incubated for 4 hrs at 37° C. and then transferred to 20° C. overnight. First round antibody phage were made by eluting phage off these plates in 10 ml of 2*YT, spinning out debris, and taking the supernatant. These samples are the antibody phage display libraries used for selecting antibodies against Cadherin-17. Efficiency of the electroporations was measured by plating 10 µl of a $10^{-4}$ dilution of suspended cells on LB agar plates, follow by overnight incubation of plates at 37° C. The efficiency was calculated by multiplying the number of plaques on the $10^{-4}$ dilution plate by 106. Library electroporation efficiencies are typically greater than $1*10^7$ phage under these conditions.

Transformation of E. coli by Electroporation

Electrocompetent E. coli cells were thawed on ice. DNA was mixed with 40 L of these cells by gently pipetting the cells up and down 2-3 times, being careful not to introduce an air bubble. The cells were transferred to a Gene Pulser cuvette (0.2 cm gap, BioRAD, Hercules, Calif.) that had been cooled on ice, again being careful not to introduce an air bubble in the transfer. The cuvette was placed in the E. coli Pulser (BioRAD, Hercules, Calif.) and electroporated with the voltage set at 1.88 kV according to the manufacturer's recommendation. The transformed sample was immediately resuspended in 1 ml of 2*YT broth or 1 ml of a mixture of 400 µl 2*YT/600 µl overnight XL-1 cells and processed as procedures dictated.

Plating M13 Phage or Cells Transformed with Antibody Phage-Display Vector Mutagenesis Reaction Phage samples were added to 200 µL of an overnight culture of E. coli XL1-Blue when plating on 100 mm LB agar plates or to 600 µL of overnight cells when plating on 150 mm plates in sterile 15 ml culture tubes. After adding LB top agar (3 ml for 100 mm plates or 9 ml for 150 mm plates, top agar stored at 55° C. (see, Appendix A1, Sambrook et al., supra.), the mixture was evenly distributed on an LB agar plate that had been pre-warmed (37° C.-55° C.) to remove any excess moisture on the agar surface. The plates were cooled at room temperature until the top agar solidified. The plates were inverted and incubated at 37° C. as indicated.

Preparation of Biotinylated Cadherin-17 and Biotinylated Antibodies

Concentrated recombinant Cadherin-17 antigen (full length extracellular domain) was extensively dialyzed into BBS (20 mM borate, 150 mM NaCl, 0.1% NaN3, pH 8.0). After dialysis, 1 mg of Cadherin-17 (1 mg/ml in BBS) was reacted with a 15 fold molar excess of biotin-XX-NHS ester (Molecular Probes, Eugene, Oreg., stock solution at 40 mM in DMSO). The reaction was incubated at room temperature for 90 min and then quenched with taurine (Sigma Chemical Co., St. Louis, Mo.) at a final concentration of 20 mM. The biotinylated reaction mixture was then dialyzed against BBS at 2-8° C. After dialysis, biotinylated Cadherin-17 was diluted in panning buffer (40 mM Tris, 150 mM NaCl, 20 mg/ml BSA, 0.1% Tween 20, pH 7.5), aliquoted, and stored at −80° C. until needed.

Antibodies were reacted with 3-(N-maleimidylpropionyl) biocytin (Molecular Probes, Eugene, Oreg.) using a free cysteine located at the carboxy terminus of the heavy chain. Antibodies were reduced by adding DTT to a final concentration of 1 mM for 30 min at room temperature. Reduced antibody was passed through a Sephadex® G50 desalting column equilibrated in 50 mM potassium phosphate, 10 mM boric acid, 150 mM NaCl, pH 7.0. 3-(N-maleimidylpropionyl)-biocytin was added to a final concentration of 1 mM and the reaction allowed to proceed at room temperature for 60 min. Samples were then dialyzed extensively against BBS and stored at 2-8° C.

Preparation of Avidin Magnetic Latex

The magnetic latex (Estapor, 10% solids, Bangs Laboratories, Fishers, Ind.) was thoroughly resuspended and 2 ml aliquoted into a 15 ml conical tube. The magnetic latex was suspended in 12 ml distilled water and separated from the solution for 10 min using a magnet (PerSeptive Biosystems®, Framingham, Mass.). While maintaining the separation of the magnetic latex with the magnet, the liquid was carefully removed using a 10 ml sterile pipette. This washing process was repeated an additional three times. After the final wash, the latex was resuspended in 2 ml of distilled water. In a separate 50 ml conical tube, 10 mg of avidin-HS (NeutrAvidin®, Pierce, Rockford, Ill.) was dissolved in 18 ml of 40 mM Tris, 0.15 M sodium chloride, pH 7.5 (TBS). While vortexing, the 2 ml of washed magnetic latex was added to the diluted avidin-HS and the mixture mixed an additional 30 seconds. This mixture was incubated at 45° C. for 2 hr, shaking every 30 minutes. The avidin magnetic latex was separated from the solution using a magnet and washed three times with 20 ml BBS as described above. After the final wash, the latex was resuspended in 10 ml BBS and stored at 4° C.

Immediately prior to use, the avidin magnetic latex was equilibrated in panning buffer (40 mM Tris, 150 mM NaCl, 20 mg/ml BSA, 0.1% Tween 20, pH 7.5). The avidin magnetic latex needed for a panning experiment (200 µl/sample) was added to a sterile 15 ml centrifuge tube and brought to 10 ml with panning buffer. The tube was placed on the magnet for 10 min to separate the latex. The solution was carefully removed with a 10 ml sterile pipette as described above. The magnetic latex was resuspended in 10 ml of panning buffer to begin the second wash. The magnetic latex was washed a total of 3 times with panning buffer. After the final wash, the latex was resuspended in panning buffer to the starting volume.

Example 2

Selection of Recombinant Polyclonal Antibodies to Cadherin-17 Antigen

Binding reagents that specifically bind to Cadherin-17 were selected from the phage display libraries created from hyperimmunized mice as described in Example 1.

Panning

First round antibody phage were prepared as described in Example 1 using BS45 uracil template. Electroporations of mutagenesis DNA were performed yielding phage samples derived from different immunized mice. To create more diversity in the recombinant polyclonal library, each phage sample was panned separately.

Before the first round of functional panning with biotinylated Cadherin-17 antigen, antibody phage libraries were selected for phage displaying both heavy and light chains on their surface by panning with 7F11-magnetic latex (as described in Examples 21 and 22 of U.S. patent application Ser. No. 08/835,159, filed Apr. 4, 1997). Functional panning of these enriched libraries was performed in principle as described in Example 16 of U.S. patent application Ser. No. 08/835,159. Specifically, 10 µL of $1*10^{-6}$ M biotinylated Cadherin-17 antigen was added to the phage samples (approximately $1*10^{-8}$ M Cadherin-17 final concentration), and the mixture allowed to come to equilibrium overnight at 2-8° C.

After reaching equilibrium, samples were panned with avidin magnetic latex to capture antibody phage bound to Cadherin-17. Equilibrated avidin magnetic latex (Example 1), 200 µL latex per sample, was incubated with the phage for 10 min at room temperature. After 10 min, approximately 9 ml of panning buffer was added to each phage sample, and the magnetic latex separated from the solution using a magnet. After a ten minute separation, unbound phage was carefully removed using a 10 ml sterile pipette. The magnetic latex was then resuspended in 10 ml of panning buffer to begin the second wash. The latex was washed a total of three times as described above. For each wash, the tubes were in contact with the magnet for 10 min to separate unbound phage from the magnetic latex. After the third wash, the magnetic latex was resuspended in 1 ml of panning buffer and transferred to a 1.5 mL tube. The entire volume of magnetic latex for each sample was then collected and resuspended in 200 µl 2*YT and plated on 150 mm LB plates as described in Example 1 to amplify bound phage. Plates were incubated at 37° C. for 4 hr, then overnight at 20° C.

The 150 mm plates used to amplify bound phage were used to generate the next round of antibody phage. After the overnight incubation, second round antibody phage were eluted from the 150 mm plates by pipetting 10 mL of 2*YT media onto the lawn and gently shaking the plate at room temperature for 20 min. The phage samples were then transferred to 15 ml disposable sterile centrifuge tubes with a plug seal cap, and the debris from the LB plate pelleted by centrifuging the tubes for 15 min at 3500 rpm. The supernatant containing the second round antibody phage was then transferred to a new tube.

A second round of functional panning was set up by diluting 100 µL of each phage stock into 900 µL of panning buffer in 15 ml disposable sterile centrifuge tubes. Biotinylated Cadherin-17 antigen was then added to each sample as described for the first round of panning, and the phage samples incubated for 1 hr at room temperature. The phage samples were then panned with avidin magnetic latex as described above. The progress of panning was monitored at this point by plating aliquots of each latex sample on 100 mm LB agar plates to determine the percentage of kappa positives. The majority of latex from each panning (99%) was plated on 150 mm LB agar plates to amplify the phage bound to the latex. The 100 mm LB agar plates were incubated at 37° C. for 6-7 hr, after which the plates were transferred to room temperature and nitrocellulose filters (pore size 0.45 mm, BA85 Protran, Schleicher and Schuell, Keene, N.H.) were overlaid onto the plaques.

Plates with nitrocellulose filters were incubated overnight at room temperature and then developed with a goat anti-mouse kappa alkaline phosphatase conjugate to determine the percentage of kappa positives as described below. Phage samples with lower percentages (<70%) of kappa positives in the population were subjected to a round of panning with 7F11-magnetic latex before performing a third functional round of panning overnight at 2-8° C. using biotinylated Cadherin-17 antigen at approximately $2*10^{-9}$ M. This round of panning was also monitored for kappa positives. Individual phage samples that had kappa positive percentages greater than 80% were pooled and subjected to a final round of panning overnight at 2-8° C. at $5*10^{-9}$ M Cadherin-17. Antibody genes contained within the eluted phage from this fourth round of functional panning were subcloned into the expression vector, pBRncoH3.

The subcloning process was done generally as described in Example 18 of U.S. patent application Ser. No. 08/835,159. After subcloning, the expression vector was electroporated into DH10B cells and the mixture grown overnight in 2*YT containing 1% glycerol and 10 µg/ml tetracycline. After a second round of growth and selection in tetracycline, aliquots of cells were frozen at −80° C. as the source for Cadherin-17 polyclonal antibody production. Monoclonal antibodies were selected from these polyclonal mixtures by plating a sample of the mixture on LB agar plates containing 10 µg/ml tetracycline and screening for antibodies that recognized Cadherin-17.

Expression and Purification of Recombinant Antibodies Against Cadherin-17

A shake flask inoculum was generated overnight from a −70° C. cell bank in an Innova® 4330 incubator shaker (New Brunswick Scientific, Edison, N.J.) set at 37° C., 300 rpm. The inoculum was used to seed a 20 L fermentor (Applikon, Foster City, Calif.) containing defined culture medium (Pack et al. (1993) Bio/Technology 11: 1271-1277) supplemented with 3 g/L L-leucine, 3 g/L L-isoleucine, 12 g/L casein digest (Difco, Detroit, Mich.), 12.5 g/L glycerol and 10 µg/ml tetracycline. The temperature, pH and dissolved oxygen in the fermentor were controlled at 26° C., 6.0-6.8 and 25% saturation, respectively. Foam was controlled by addition of polypropylene glycol (Dow, Midland, Mich.). Glycerol was added to the fermentor in a fed-batch mode. Fab expression was induced by addition of L(+)-arabinose (Sigma, St. Louis, Mo.) to 2 g/L during the late logarithmic growth phase. Cell density was measured by optical density at 600 nm in an UV-1201 spectrophotometer (Shimadzu, Columbia, Md.). Following run termination and adjustment of pH to 6.0, the culture was passed twice through an M-210B-EH Microfluidizer (Microfluidics, Newton, Mass.) at 17,000 psi. The high pressure homogenization of the cells released the Fab into the culture supernatant.

The first step in purification was expanded bed immobilized metal affinity chromatography (EB-IMAC). Streamline® chelating resin (Pharmacia, Piscataway, N.J.) was charged with 0.1 M NiCl2 and was then expanded and equilibrated in 50 mM acetate, 200 mM NaCl, 10 mM imidazole, 0.01% NaN3, pH 6.0 buffer flowing in the upward direction. A stock solution was used to bring the culture homogenate to 10 mM imidazole, following which it was diluted two-fold or higher in equilibration buffer to reduce the wet solids content to less than 5% by weight. It was then loaded onto the Streamline® column flowing in the upward direction at a superficial velocity of 300 cm/hr. The cell debris passed through unhindered, but the Fab was captured by means of the high affinity interaction between nickel and the hexahistidine tag on the Fab heavy chain. After washing, the expanded bed was converted to a packed bed and the Fab was eluted with 20 mM borate, 150 mM NaCl, 200 mM imidazole, 0.01% NaN3, pH 8.0 buffer flowing in the downward direction.

The second step in the purification used ion-exchange chromatography (IEC). Q Sepharose® FastFlow resin (Pharmacia, Piscataway, N.J.) was equilibrated in 20 mM borate, 37.5 mM NaCl, 0.01% NaN3, pH 8.0. The Fab elution pool from the EB-IMAC step was diluted four-fold in 20 mM borate, 0.01% NaN3, pH 8.0 and loaded onto the IEC column. After washing, the Fab was eluted with a 37.5-200 mM NaCl salt gradient. The elution fractions were evaluated for purity using an Xcell II™ SDS-PAGE system (Novex®, San Diego, Calif.) prior to pooling. Finally, the Fab pool was concentrated and diafiltered into 20 mM borate, 150 mM NaCl, 0.01% NaN3, pH 8.0 buffer for storage. This was achieved in a Sartocon Slice™ system fitted with a 10,000 MWCO cassette (Sartorius, Bohemia, N.Y.). The final purification yields were typically 50%. The concentration of the purified Fab was measured by UV absorbance at 280 nm, assuming an absorbance of 1.6 for a 1 mg/ml solution.

Example 3

Selection of Antibodies to Cadherin-17 Antigen From Tumor Membrane Preparations

Antibodies selected in Example 2 were further screened against tumor membrane preparations to isolate antibodies that preferentially bind to Cadherin-17 on cancer cells and not to normal intestinal epithelia.

Biotinylated plasma membrane preparations from paired colorectal cancer and normal adjacent tissue samples were used to pan phage samples with avidin magnetic latex to capture antibody phage bound to Cadherin-17 as described in Example 2. Antibodies were selected from these polyclonal mixtures by screening for antibodies that preferentially bind to Cadherin-17 on the colorectal cancer cells and not to the normal intestinal epithelia. These antibodies were then isolated as described in Example 4 and analyzed for binding to Cadherin-17.

Example 4

Selection of Monoclonal Antibodies to Cadherin-17 from the Recombinant Polyclonal Antibody Mixtures Monoclonal antibodies against Cadherin-17 were isolated from clones containing the recombinant polyclonal mixtures (Example 3) by plating a diluted sample of the mixture on LB agar plates containing 10 µg/ml tetracycline. Individual colonies were then tested for the ability to produce antibody that recognized recombinant Cadherin-17 using surface plasmon resonance (BIACORE®) (BIACORE®, Uppsala, Sweden). Small scale production of these monoclonal antibodies was accomplished using a Ni-chelate batch-binding method (see below). Antibodies isolated from this method were diluted 1:3 in HBS-EP (0.01 M HEPES, pH 7.4, 0.15 M NaCl, 3 mM EDTA, 0.005% polysorbate 20 (v/v)), captured with a goat anti-mouse kappa antibody (Southern Biotechnology Associates, Inc, Birmingham, Ala.) coupled to a BIACORE® CM5 sensor chip, and tested for the ability to bind recombinant Cadherin-17.

Minipreparation of Monoclonal Antibodies by Ni-Chelate Batch-Binding Method

Individual colonies were isolated from the recombinant polyclonal mixtures (Example 3) and used to inoculate 3 ml cultures of 2*YT medium containing 1% glycerol supplemented with 10 µg/ml tetracycline. These cultures were grown in an Innova 4330 incubator shaker (New Brunswick Scientific, Edison, N.J.) set at 37° C., 300 rpm. The next morning 0.5 ml of each culture was used to inoculate shake flasks containing 50 ml of defined medium, (Pack et al. (1993) Bio/Technology 11: 1271-1277) supplemented with 3 g/L L-leucine, 3 g/L L-isoleucine, 12 g/L casein digest (Difco, Detroit, Mich.), 12.5 g/L glycerol and 10 µg/ml tetracycline. These cultures were shaken at 300 rpm, 37° C. until an optical density of 4 was reached at 600 nm. Fab expression was then induced by adding L(+)-arabinose (Sigma, St. Louis, Mo.) to 2 g/L and shifting the temperature to 23° C. with overnight shaking. The next day the following was added to the 50 ml cultures: 0.55 ml of 1 M imidazole, 5 ml B-PER (Pierce, Rockford, Ill.) and 2 ml Ni-chelating resin (Chelating Sepharose® FastFlow resin Pharmacia, Piscataway, N.J.). The mixture was shaken at 300 rpm, 23° C. for 1 hour after which time shaking was stopped and the resin allowed to settle to the bottom of the flasks for 15 minutes.

The supernatant was then poured off and the resin resuspended in 40 ml of BBS (20 mM borate, 150 mM NaCl, 0.1% NaN3, pH 8.0) containing 10 mM imidazole. This suspension was transferred to a 50 ml conical tube and the resin washed a total of 3 times with BBS containing 10 mM imidazole. Washing was accomplished by low speed centrifugation (1100 rpm for 1 minute), removal of supernatant and, resuspension of the resin in BBS containing 10 mM imidazole. After the supernatant of the final wash was poured off, 0.5 ml of 1 M imidazole was added to each tube, vortex briefly, and transferred to a sterile microcentrifuge tube. The samples were then centrifuged at 14 krpm for 1 minutes and the supernatant transferred to a new microcentrifuge tube. Antibodies contained in the supernatant were then analyzed for binding to Cadherin-17 using a BIACORE® (BIACORE®, Uppsala, Sweden).

Example 5

Specificity of Monoclonal Antibodies to Cadherin-17 Determined by Flow Cytometry Analysis The specificity of antibodies against Cadherin-17 selected in Example 4 was tested by flow cytometry. To test the ability of the antibodies to bind to cell surface Cadherin-17 protein, the antibodies were incubated with Cadherin-17-expressing cells: LoVo and LS174T, human colorectal cancer lines. Cells were washed and resuspended in PBS. Four microliters of the suspensions were applied to wells of an eight well microscope slide and allowed to air dry. The slides were lightly heated to fix the smears to the slide and covered with 0.1 mg/ml of antibody diluted in PBS containing 1% BSA. The smears were incubated with antibody for 1 h at 37° C. in a moist chamber. After washing the slides three times by soaking in PBS for 5 min each, the smears were covered with fluorescein isothiocyanate-conjugated rabbit anti-mouse IgG (H&L) F(ab')2 (Zymed® Laboratories, Inc., South San Francisco, Calif.) diluted 1:80 in PBS, 1% BSA, 0.05% Evans Blue (Sigma). The slides were incubated for 1 h at 37° C. in a moist chamber then washed as described above. After a final wash in deionized water, the slides were allowed to air dry in the dark. Coverslips were mounted using a 90% glycerol mounting medium containing 10 mg/ml p-phenylenediamine, pH 8.0.

The results of the flow cytometry analysis demonstrated that 14 monoclonal antibodies designated PTA001_A1, PTA001_A2, PTA001_A3, PTA001_A4, PTA001_A5, PTA001_A6, PTA001_A7, PTA001_A8, PTA001_A9, PTA001_A10, PTA001_A11, PTA001_A12, PTA001_A13 and PTA001_A14 bind effectively to cell-surface human Cadherin-17.

Example 6

Structural Characterization of Monoclonal Antibodies to Cadherin-17

The cDNA sequences encoding the heavy and light chain variable regions of the PTA001_A1, PTA001_A2, PTA001_A3, PTA001_A4, PTA001_A5, PTA001_A6, PTA001_A7, PTA001_A8, PTA001_A9, PTA001_A10, PTA001_A11, PTA001_A12, PTA001_A13 and PTA001_A14 monoclonal antibodies were obtained using standard PCR techniques and were sequenced using standard DNA sequencing techniques.

The antibody sequences may be mutagenized to revert back to germline residues at one or more residues.

The nucleotide and amino acid sequences of the heavy chain variable region of PTA001_A1 are shown in FIG. 1 and in SEQ ID NO:59 and 35, respectively.

The nucleotide and amino acid sequences of the light chain variable region of PTA001_A1 are shown in FIG. 13 and in SEQ ID NO:71 and 47, respectively.

Comparison of the PTA001_A1 heavy chain immunoglobulin sequence to the known murine germline immunoglobulin heavy chain sequences demonstrated that the PTA001_A1 heavy chain utilizes a $V_H$ segment from murine germline $V_H$ 7-39. Further analysis of the PTA001_A1 $V_H$ sequence using the Kabat system of CDR region determination led to the delineation of the heavy chain CDR1, CDR2 and CDR3 regions as shown in FIG. 1, and in SEQ ID NOs:1, 5 and 14, respectively. The alignment of the PTA001_A1 CDR1 $V_H$ sequence to the germline $V_H$ 7-39 sequence is shown in FIG. 25.

Comparison of the PTA001_A1 light chain immunoglobulin sequence to the known murine germline immunoglobulin light chain sequences demonstrated that the PTA001_A1 light chain utilizes a $V_K$ segment from murine germline $V_K$ 1-110. Further analysis of the PTA001_A1 $V_K$ sequence using the Kabat system of CDR region determination led to the delineation of the light chain CDR1, CDR2 and CDR3 regions as shown in FIG. 13 and in SEQ ID NOs:22, 28 and 32, respectively. The alignments of the PTA001_A1 CDR1 and CDR3 $V_K$ sequences to the germline $V_K$ 1-110 sequence are shown in FIGS. 27 and 29 respectively.

The nucleotide and amino acid sequences of the heavy chain variable region of PTA001_A2 are shown in FIG. 2 and in SEQ ID NO:60 and 36, respectively.

The nucleotide and amino acid sequences of the light chain variable region of PTA001_A2 are shown in FIG. 14 and in SEQ ID NO:72 and 48, respectively.

Comparison of the PTA001_A2 heavy chain immunoglobulin sequence to the known murine germline immunoglobulin heavy chain sequences demonstrated that the PTA001_A2 heavy chain utilizes a $V_H$ segment from murine germline $V_H$ region VH105 and $V_H$ II gene H17. Further analysis of the PTA001_A2 $V_H$ sequence using the Kabat system of CDR region determination led to the delineation of the heavy chain CDR1, CDR2 and CDR3 regions as shown in FIG. 2 and in SEQ ID NOs:2, 6 and 15, respectively. The alignment of the PTA001_A2 CDR1 $V_H$ sequence to the germline $V_H$ II gene H17 sequence is shown in FIG. 25 and the alignment of the PTA001_A2 CDR2 $V_H$ sequence to the germline $V_H$ II region VH105 is shown in FIG. 26.

Comparison of the PTA001_A2 light chain immunoglobulin sequence to the known murine germline immunoglobulin light chain sequences demonstrated that the PTA001_A2 light chain utilizes a $V_K$ segment from murine germline $V_K$ 24-140. Further analysis of the PTA001_A2 $V_K$ sequence using the Kabat system of CDR region determination led to the delineation of the light chain CDR1, CDR2 and CDR3 regions as shown in FIG. 14, and in SEQ ID NOs:23, 29 and 33, respectively. The alignments of the PTA001_A2 CDR1, CDR2 and CDR3 $V_K$ sequences to the germline $V_K$ 24-140 sequence are shown in FIGS. 27, 28 and 29 respectively.

The nucleotide and amino acid sequences of the heavy chain variable region of PTA001_A3 are shown in FIG. 3 and in SEQ ID NO:61 and 37, respectively.

The nucleotide and amino acid sequences of the light chain variable region of PTA001_A3 are shown in FIG. 14 and in SEQ ID NO:72 and 48, respectively.

Comparison of the PTA001_A3 heavy chain immunoglobulin sequence to the known murine germline immunoglobulin heavy chain sequences demonstrated that the PTA001_A3 heavy chain utilizes a $V_H$ segment from murine germline $V_H$ II region VH105 and $V_H$ II gene H17. Further analysis of the PTA001_A3 $V_H$ sequence using the Kabat system of CDR region determination led to the delineation of the heavy chain CDR1, CDR2 and CDR3 regions as shown in FIG. 3, and in SEQ ID NOs: 3, 7 and 16, respectively. The alignment of the PTA001_A3 CDR1 $V_H$ sequence to the germline $V_H$ II gene H17 sequence is shown in FIG. 25 and the alignment of the PTA001_A3 CDR2 $V_H$ sequence to the germline $V_H$ II region VH105 is shown in FIG. 26.

Comparison of the PTA001_A3 light chain immunoglobulin sequence to the known murine germline immunoglobulin light chain sequences demonstrated that the PTA001_A3 light chain utilizes a $V_K$ segment from murine germline $V_K$ 24-140. Further analysis of the PTA001_A3 $V_K$ sequence using the Kabat system of CDR region determination led to the delineation of the light chain CDR1, CDR2 and CDR3 regions as shown in FIG. 14 and in SEQ ID NOs:23, 29, and 33, respectively. The alignments of the PTA001_A3 CDR1, CDR2 and CDR3 $V_K$ sequences to the germline $V_K$ 24-140 sequence are shown in FIGS. 27, 28 and 29 respectively.

The nucleotide and amino acid sequences of the heavy chain variable region of PTA001_A4 are shown in FIG. 4 and in SEQ ID NO:62 and 38, respectively.

The nucleotide and amino acid sequences of the light chain variable region of PTA001_A4 are shown in FIG. 15 and in SEQ ID NO:73 and 49, respectively.

Comparison of the PTA001_A4 heavy chain immunoglobulin sequence to the known murine germline immunoglobulin heavy chain sequences demonstrated that the PTA001_A4 heavy chain utilizes a $V_H$ segment from murine germline $V_H$ II region VH105 and $V_H$ II gene H17. Further analysis of the PTA001_A4 $V_H$ sequence using the Kabat system of CDR region determination led to the delineation of the heavy chain CDR1, CDR2 and CDR3 regions as shown in FIG. 4 and in SEQ ID NOs: 4, 8 and 17, respectively. The alignment of the PTA001_A4 CDR1 $V_H$ sequence to the germline $V_H$ II gene H17 sequence is shown in FIG. 25 and the alignment of the PTA001_A4 CDR2 $V_H$ sequence to the germline $V_H$ II region VH105 is shown in FIG. 26.

Comparison of the PTA001_A4 light chain immunoglobulin sequence to the known murine germline immunoglobulin light chain sequences demonstrated that the PTA001_A4 light chain utilizes a $V_K$ segment from murine germline $V_K$ 8-30. Further analysis of the PTA001_A4 $V_K$ sequence using the Kabat system of CDR region determination led to the delineation of the light chain CDR1, CDR2 and CDR3 regions as shown in FIG. 15 and in SEQ ID NOs:24, 30, and 34, respectively. The alignments of the PTA001_A4 CDR1, CDR2 and CDR3 $V_K$ sequences to the germline $V_K$ 8-30 sequence are shown in FIGS. 27, 28 and 29 respectively.

The nucleotide and amino acid sequences of the heavy chain variable region of PTA001_A5 are shown in FIG. 5 and in SEQ ID NO:63 and 39, respectively.

The nucleotide and amino acid sequences of the light chain variable region of PTA001_A5 are shown in FIG. 16 and in SEQ ID NO:74 and 50, respectively.

Comparison of the PTA001_A5 heavy chain immunoglobulin sequence to the known murine germline immunoglobulin heavy chain sequences demonstrated that the PTA001_A5 heavy chain utilizes a $V_H$ segment from murine germline $V_H$ II region VH105 and $V_H$ II gene H17. Further analysis of the PTA001_A5 $V_H$ sequence using the Kabat system of CDR region determination led to the delineation of the heavy chain CDR1, CDR2 and CDR3 regions as shown in FIG. 5, and in SEQ ID NOs: 3, 7 and 18, respectively. The alignment of the PTA001_A5 CDR1 $V_H$ sequence to the germline $V_H$ II gene H17 sequence is shown in FIG. 25 and the alignment of the PTA001_A5 CDR2 $V_H$ sequence to the germline $V_H$ II region VH105 is shown in FIG. 26.

Comparison of the PTA001_A5 light chain immunoglobulin sequence to the known murine germline immunoglobulin light chain sequences demonstrated that the PTA001_A5 light chain utilizes a $V_K$ segment from murine germline $V_K$ 24-140. Further analysis of the PTA001_A5 $V_K$ sequence using the Kabat system of CDR region determination led to the delineation of the light chain CDR1, CDR2 and CDR3 regions as shown in FIG. 16, and in SEQ ID NOs:25, 31, and 33, respectively. The alignments of the PTA001_A5 CDR1, CDR2 and CDR3 $V_K$ sequences to the germline $V_K$ 24-140 sequence are shown in FIGS. 27, 28 and 29 respectively.

The nucleotide and amino acid sequences of the heavy chain variable region of PTA001_A6 are shown in FIG. 6 and in SEQ ID NO:64 and 40, respectively.

The nucleotide and amino acid sequences of the light chain variable region of PTA001_A6 are shown in FIG. 17 and in SEQ ID NO:75 and 51, respectively.

Comparison of the PTA001_A6 heavy chain immunoglobulin sequence to the known murine germline immunoglobulin heavy chain sequences demonstrated that the PTA001_A6 heavy chain utilizes a $V_H$ segment from murine germline $V_H$ II region VH105 and $V_H$ II gene H17. Further analysis of the PTA001_A6 $V_H$ sequence using the Kabat system of CDR region determination led to the delineation of the heavy chain CDR1, CDR2 and CDR3 regions as shown in FIG. 6 and in SEQ ID NOs: 3, 7 and 16, respectively. The alignment of the PTA001_A6 CDR1 $V_H$ sequence to the germline $V_H$ II gene H17 sequence is shown in FIG. 25 and the alignment of the PTA001_A6 CDR2 $V_H$ sequence to the germline $V_H$ II region VH105 is shown in FIG. 26.

Comparison of the PTA001_A6 light chain immunoglobulin sequence to the known murine germline immunoglobulin light chain sequences demonstrated that the PTA001_A6 light chain utilizes a $V_K$ segment from murine germline $V_K$ 24-140. Further analysis of the PTA001_A6 $V_K$ sequence using the Kabat system of CDR region determination led to the delineation of the light chain CDR1, CDR2 and CDR3 regions as shown in FIG. 17 and in SEQ ID NOs:23, 29, and 33, respectively. The alignments of the PTA001_A6 CDR1, CDR2 and CDR3 $V_K$ sequences to the germline $V_K$ 24-140 sequence are shown in FIGS. 27, 28 and 29 respectively.

The nucleotide and amino acid sequences of the heavy chain variable region of PTA001_A7 are shown in FIG. 7 and in SEQ ID NO:65 and 41, respectively.

The nucleotide and amino acid sequences of the light chain variable region of PTA001_A7 are shown in FIG. 18 and in SEQ ID NO:76 and 52, respectively.

Comparison of the PTA001_A7 heavy chain immunoglobulin sequence to the known murine germline immunoglobulin heavy chain sequences demonstrated that the PTA001_A7 heavy chain utilizes a $V_H$ segment from murine germline $V_H$ II region VH105 and $V_H$ II gene H17. Further analysis of the PTA001_A7 $V_H$ sequence using the Kabat system of CDR region determination led to the delineation of the heavy chain CDR1, CDR2 and CDR3 regions as shown in FIG. 7 and in SEQ ID NOs: 3, 9 and 19, respectively. The alignment of the PTA001_A7 CDR1 $V_H$ sequence to the germline $V_H$ II gene H17 sequence is shown in FIG. 25 and the alignment of the PTA001_A7 CDR2 $V_H$ sequence to the germline $V_H$ II region VH105 is shown in FIG. 26.

Comparison of the PTA001_A7 light chain immunoglobulin sequence to the known murine germline immunoglobulin light chain sequences demonstrated that the PTA001_A7 light chain utilizes a $V_K$ segment from murine germline $V_K$ 24-140. Further analysis of the PTA001_A7 $V_K$ sequence using the Kabat system of CDR region determination led to the delineation of the light chain CDR1, CDR2 and CDR3 regions as shown in FIG. 18 and in SEQ ID NOs:26, 29, and 33, respectively. The alignments of the PTA001_A7 CDR1, CDR2 and CDR3 $V_K$ sequences to the germline $V_K$ 24-140 sequence are shown in FIGS. 27, 28 and 29 respectively.

The nucleotide and amino acid sequences of the heavy chain variable region of PTA001_A8 are shown in FIG. 8 and in SEQ ID NO:66 and 42, respectively.

The nucleotide and amino acid sequences of the light chain variable region of PTA001_A8 are shown in FIG. 19 and in SEQ ID NO:77 and 53, respectively.

Comparison of the PTA001_A8 heavy chain immunoglobulin sequence to the known murine germline immunoglobulin heavy chain sequences demonstrated that the PTA001_A8 heavy chain utilizes a $V_H$ segment from murine germline $V_H$ II region VH105 and $V_H$ II gene H17. Further analysis of the PTA001_A8 $V_H$ sequence using the Kabat system of CDR region determination led to the delineation of the heavy chain CDR1, CDR2 and CDR3 regions as shown in FIG. 8 and in SEQ ID NOs: 3, 7 and 16, respectively. The alignment of the PTA001_A8 CDR1 $V_H$ sequence to the germline $V_H$ II gene H17 sequence is shown in FIG. 25 and the alignment of the PTA001_A8 CDR2 $V_H$ sequence to the germline $V_H$ II region VH105 is shown in FIG. 26.

Comparison of the PTA001_A8 light chain immunoglobulin sequence to the known murine germline immunoglobulin light chain sequences demonstrated that the PTA001_A8 light chain utilizes a $V_K$ segment from murine germline $V_K$ 24-140. Further analysis of the PTA001_A8 $V_K$ sequence using the Kabat system of CDR region determination led to the delineation of the light chain CDR1, CDR2 and CDR3 regions as shown in FIG. 19 and in SEQ ID NOs:25, 31, and 33, respectively. The alignments of the PTA001_A8 CDR1, CDR2 and CDR3 $V_k$ sequences to the germline $V_K$ 24-140 sequence are shown in FIGS. 27, 28 and 29 respectively.

The nucleotide and amino acid sequences of the heavy chain variable region of PTA001_A9 are shown in FIG. 6 and in SEQ ID NO:64 and 40, respectively.

The nucleotide and amino acid sequences of the light chain variable region of PTA001_A9 are shown in FIG. 20 and in SEQ ID NO:78 and 54, respectively.

Comparison of the PTA001_A9 heavy chain immunoglobulin sequence to the known murine germline immunoglobulin heavy chain sequences demonstrated that the PTA001_A9 heavy chain utilizes a $V_H$ segment from murine germline $V_H$ II region VH105 and $V_H$ II gene H17. Further analysis of the PTA001_A9 $V_H$ sequence using the Kabat system of CDR region determination led to the delineation of the heavy chain CDR1, CDR2 and CDR3 regions as shown in FIG. 6 and in SEQ ID NOs: 3, 7 and 16, respectively. The alignment of the PTA001_A9 CDR1 $V_H$ sequence to the germline $V_H$ II gene H17 sequence is shown in FIG. 25 and the alignment of the PTA001_A9 CDR2 $V_H$ sequence to the germline $V_H$ II region VH105 is shown in FIG. 26.

Comparison of the PTA001_A9 light chain immunoglobulin sequence to the known murine germline immunoglobulin light chain sequences demonstrated that the PTA001_A9 light chain utilizes a $V_K$ segment from murine germline $V_K$ 24-140. Further analysis of the PTA001_A9 $V_K$ sequence using the Kabat system of CDR region determination led to the delineation of the light chain CDR1, CDR2 and CDR3 regions as shown in FIG. 20 and in SEQ ID NOs:23, 29, and 33, respectively. The alignments of the PTA001_A9 CDR1, CDR2 and CDR3 $V_K$ sequences to the germline $V_K$ 24-140 sequence are shown in FIGS. 27, 28 and 29 respectively.

The nucleotide and amino acid sequences of the heavy chain variable region of PTA001_A10 are shown in FIG. 6 and in SEQ ID NO:64 and 40, respectively.

The nucleotide and amino acid sequences of the light chain variable region of PTA001_A10 are shown in FIG. 21 and in SEQ ID NO:79 and 55, respectively.

Comparison of the PTA001_A10 heavy chain immunoglobulin sequence to the known murine germline immunoglobulin heavy chain sequences demonstrated that the PTA001_A10 heavy chain utilizes a $V_H$ segment from murine germline $V_H$ II region VH105 and $V_H$ II gene H17. Further analysis of the PTA001_A10 $V_H$ sequence using the Kabat system of CDR region determination led to the delineation of the heavy chain CDR1, CDR2 and CDR3 regions as shown in FIG. 6 and in SEQ ID NOs: 3, 7 and 16, respectively. The alignment of the PTA001_A10 CDR1 $V_H$ sequence to the germline $V_H$ II gene H17 sequence is shown in FIG. 25 and the alignment of the PTA001_A10 CDR2 $V_H$ sequence to the germline $V_H$ II region VH105 is shown in FIG. 26.

Comparison of the PTA001_A10 light chain immunoglobulin sequence to the known murine germline immunoglobulin light chain sequences demonstrated that the PTA001_A10 light chain utilizes a $V_K$ segment from murine germline $V_K$ 24-140. Further analysis of the PTA001_A10 $V_K$ sequence using the Kabat system of CDR region determination led to the delineation of the light chain CDR1, CDR2 and CDR3 regions as shown in FIG. 21 and in SEQ ID NOs:25, 29, and 33, respectively. The alignments of the PTA001_A10 CDR1, CDR2 and CDR3 $V_K$ sequences to the germline $V_K$ 24-140 sequence are shown in FIGS. 27, 28 and 29 respectively.

The nucleotide and amino acid sequences of the heavy chain variable region of PTA001_A11 are shown in FIG. 9 and in SEQ ID NO:67 and 43, respectively.

The nucleotide and amino acid sequences of the light chain variable region of PTA001_A11 are shown in FIG. 22 and in SEQ ID NO:80 and 56, respectively.

Comparison of the PTA001_A11 heavy chain immunoglobulin sequence to the known murine germline immunoglobulin heavy chain sequences demonstrated that the PTA001_A11 heavy chain utilizes a $V_H$ segment from murine germline $V_H$ II region VH105 and $V_H$ II gene H17. Further analysis of the PTA001_A11 $V_H$ sequence using the Kabat system of CDR region determination led to the delineation of the heavy chain CDR1, CDR2 and CDR3 regions as shown in FIG. 9 and in SEQ ID NOs: 3, 10 and 20, respectively. The alignment of the PTA001_A11 CDR1 $V_H$ sequence to the germline $V_H$ II gene H17 sequence is shown in FIG. 25 and the alignment of the PTA001_A11 CDR2 $V_H$ sequence to the germline $V_H$ II region VH105 is shown in FIG. 26.

Comparison of the PTA001_A11 light chain immunoglobulin sequence to the known murine germline immunoglobulin light chain sequences demonstrated that the PTA001_A11 light chain utilizes a $V_K$ segment from murine germline $V_K$ 24-140. Further analysis of the PTA001_A11 $V_K$ sequence using the Kabat system of CDR region determination led to the delineation of the light chain CDR1, CDR2 and CDR3 regions as shown in FIG. 22 and in SEQ ID NOs:27, 29, and 33, respectively. The alignments of the PTA001_A11 CDR1, CDR2 and CDR3 $V_K$ sequences to the germline $V_K$ 24-140 sequence are shown in FIGS. 27, 28 and 29 respectively.

The nucleotide and amino acid sequences of the heavy chain variable region of PTA001_A12 are shown in FIG. 10 and in SEQ ID NO:68 and 44, respectively.

The nucleotide and amino acid sequences of the light chain variable region of PTA001_A12 are shown in FIG. 21 and in SEQ ID NO:81 and 55, respectively.

Comparison of the PTA001_A12 heavy chain immunoglobulin sequence to the known murine germline immunoglobulin heavy chain sequences demonstrated that the PTA001_A12 heavy chain utilizes a $V_H$ segment from murine germline $V_H$ II region VH105 and $V_H$ II gene H17. Further analysis of the PTA001_A12 $V_H$ sequence using the Kabat system of CDR region determination led to the delineation of the heavy chain CDR1, CDR2 and CDR3 regions as shown in FIG. 10 and in SEQ ID NOs: 3, 11 and 21, respectively. The alignment of the PTA001_A12 CDR1 $V_H$ sequence to the germline $V_H$ II gene H17 sequence is shown in FIG. 25 and the alignment of the PTA001_A12 CDR2 $V_H$ sequence to the germline $V_H$ II region VH105 is shown in FIG. 26.

Comparison of the PTA001_A12 light chain immunoglobulin sequence to the known murine germline immunoglobulin light chain sequences demonstrated that the PTA001_A12 light chain utilizes a $V_K$ segment from murine germline $V_K$ 24-140. Further analysis of the PTA001_A12 $V_K$ sequence using the Kabat system of CDR region determination led to the delineation of the light chain CDR1, CDR2 and CDR3 regions as shown in FIG. 21 and in SEQ ID NOs:25, 29, and 33, respectively. The alignments of the PTA001_A12 CDR1, CDR2 and CDR3 $V_K$ sequences to the germline $V_K$ 24-140 sequence are shown in FIGS. 27, 28 and 29 respectively.

The nucleotide and amino acid sequences of the heavy chain variable region of PTA001_A13 are shown in FIG. 11 and in SEQ ID NO:69 and 45, respectively.

The nucleotide and amino acid sequences of the light chain variable region of PTA001_A13 are shown in FIG. 23 and in SEQ ID NO:82 and 57, respectively.

Comparison of the PTA001_A13 heavy chain immunoglobulin sequence to the known murine germline immunoglobulin heavy chain sequences demonstrated that the PTA001_A13 heavy chain utilizes a $V_H$ segment from murine germline $V_H$ II region VH105 and $V_H$ II gene H17. Further analysis of the PTA001_A13 $V_H$ sequence using the Kabat system of CDR region determination led to the delineation of the heavy chain CDR1, CDR2 and CDR3 regions as shown in FIG. 11 and in SEQ ID NOs: 3, 12 and 18, respectively. The alignment of the PTA001_A13 CDR1 $V_H$ sequence to the germline $V_H$ II gene H17 sequence is shown in FIG. 25 and the alignment of the PTA001_A13 CDR2 $V_H$ sequence to the germline $V_H$ II region VH105 is shown in FIG. 26.

Comparison of the PTA001_A13 light chain immunoglobulin sequence to the known murine germline immunoglobulin light chain sequences demonstrated that the PTA001_A13 light chain utilizes a $V_K$ segment from murine germline $V_K$ 24-140. Further analysis of the PTA001_A13 $V_K$ sequence using the Kabat system of CDR region determination led to the delineation of the light chain CDR1, CDR2 and CDR3 regions as shown in FIG. 23 and in SEQ ID NOs:25, 31, and 33, respectively. The alignments of the PTA001_A13 CDR1, CDR2 and CDR3 $V_K$ sequences to the germline $V_K$ 24-140 sequence are shown in FIGS. 27, 28 and 29 respectively.

The nucleotide and amino acid sequences of the heavy chain variable region of PTA001_A14 are shown in FIG. 12 and in SEQ ID NO:70 and 46, respectively.

The nucleotide and amino acid sequences of the light chain variable region of PTA001_A14 are shown in FIG. 24 and in SEQ ID NO:83 and 58, respectively.

Comparison of the PTA001_A14 heavy chain immunoglobulin sequence to the known murine germline immunoglobulin heavy chain sequences demonstrated that the PTA001_A14 heavy chain utilizes a $V_H$ segment from murine germline $V_H$ II region VH105 and $V_H$ II gene H17. Further analysis of the PTA001_A14 $V_H$ sequence using the Kabat system of CDR region determination led to the delineation of the heavy chain CDR1, CDR2 and CDR3 regions as shown in FIG. 12 and in SEQ ID NOs: 2, 13 and 15, respectively. The alignment of the PTA001_A14 CDR1 $V_H$ sequence to the germline $V_H$ II gene H17 sequence is shown in FIG. 25 and the alignment of the PTA001_A14 CDR2 $V_H$ sequence to the germline $V_H$ II region VH105 is shown in FIG. 26.

Comparison of the PTA001_A14 light chain immunoglobulin sequence to the known murine germline immunoglobulin light chain sequences demonstrated that the PTA001_A14 light chain utilizes a $V_K$ segment from murine germline $V_K$ 24-140. Further analysis of the PTA001_A14 $V_K$ sequence using the Kabat system of CDR region determination led to the delineation of the light chain CDR1, CDR2 and CDR3 regions as shown in FIG. 24 and in SEQ ID NOs:23, 29, and 33, respectively. The alignments of the PTA001_A14 CDR1, CDR2 and CDR3 $V_K$ sequences to the germline $V_K$ 24-140 sequence are shown in FIGS. 27, 28 and 29 respectively.

Example 7

Immunohistochemistry on FFPE Sections Using Anti-Cadherin-17 Antibodies

Immunohistochemistry was performed on FFPE sections of colorectal tumor and normal adjacent tissue using the anti-Cadherin-17 antibodies PTA001_A3, PTA001_A4, PTA001_A6, PTA001_A8 and PTA001_A9.

EX-De-Wax was from BioGenex®, CA, USA. Tissue sections and arrays were from Biomax®, MD, USA.

Slides were heated for 2 h at 60° C. in 50 ml Falcons in a water bath with no buffer. Each Falcon had one slide or two slides back-to back with long gel loading tip between them to prevent slides from sticking to each other. Slides were deparaffinised in EZ-DeWax for 5 min in black slide rack, then rinsed well with the same DeWax solution using 1 ml pipette, then washed with water from the wash bottle. Slides were placed in a coplin jar filled with water until the pressure cooker was ready; the water was changed a couple of times.

Water was exchanged for antigen retrieval solution=1× citrate buffer, pH 6 (DAKO). Antigen was retrieved by the pressure cooker method. The slides in the plastic coplin jar in antigen retrieval solution were placed into a pressure cooker which was then heated up to position 6 (the highest setting). 15-20 min into the incubation, the temperature was reduced to position 3 and left at that (when the temperature inside the pressure cooker was 117° C.) for another 20-25 minutes. Then the hob was switched off and the cooker was placed onto the cold hob and the pressure was released by carefully moving the handle into the position between "open" and "closed". The whole system was left to release the pressure and to cool down for another 20 minutes. The lid was opened and samples taken out to rest on the bench. The slides were washed 1×5 min with PBS-3T (0.5 L PBS+3 drops of Tween-20) and placed in PBS.

After antigen retrieval, slides were mounted in the Shandon Coverplate system. Trapping of air bubbles between the slide and plastic coverplate was prevented by placing the coverplate into the coplin jar filled with PBS and gently sliding the slide with tissue sections into the coverplate. The slide was pulled out of the coplin jar while holding it tightly together with the coverplate. The assembled slide was placed into the rack, letting PBS trapped in the funnel and between the slide and coverplate to run through. Slides were washed with 2×2 ml (or 4×1 ml) PBS-3T, 1×2 ml PBS, waiting until all PBS had gone through the slide and virtually no PBS was left in the funnel.

Endogenous peroxide blockade was performed using 1-4 drops of peroxide solution per slide; the incubation time was 5 minutes. The slides were rinsed with water and then once with 2 ml PBS-3T and once with 2 ml PBS; it was important to wait until virtually no liquid was left in the funnel before adding a new portion of wash buffer.

The primary antibody was diluted with an Antibody diluent reagent (DAKO). Optimal dilution was determined to be 1:400. Up to 200 µl of diluted primary antibody was applied to each slide and incubated for 45 minutes at room temperature. Slides were washed with 2×2 ml (or 4×1 ml) PBS-3T and then 1×2 ml PBS.

The goat anti-mouse kappa HRP secondary (1 mg/ml, cat.1050-05, Southern Biotech) was applied 2×2 drops per slide and incubated for 35 min at room temperature. The slides were washed as above.

The DAB substrate was made up in dilution buffer; 2 ml containing 2 drops of substrate was enough for 10 slides. The DAB reagent was applied to the slides by applying a few drops at a time and left for 10 min. The slides were washed 1×2 ml (or 2×1 ml) with PBS-3T and 1×2 ml (or 2×1 ml) with PBS.

Hematoxylin (DAKO) was applied; 1 ml was enough for 10 slides and slides were incubated for 1 min at room temperature. The funnels of the Shandon Coverplate system were filled with 2 ml of water and let to run through. When slides were clear of the excess of hematoxylin, the system was disassembled, tissue sections and/or arrays were washed with water from the wash bottle and placed into black slide rack. Tissues were dehydrated by incubating in EZ-DeWax for 5 min and then in 95% ethanol for 2-5 min.

Slides were left to dry on the bench at room temperature and then mounted in mounting media and covered with coverslip.

Immunohistochemical analysis on antibodies PTA001_A3, PTA001_A4, PTA001_A6, PTA001_A8 and PTA001_A9 revealed specific membrane staining of tumor cells in colorectal cancer and no appreciable staining of normal adjacent tissue in all cases. Antibody PTA001_A4, in particular, showed clear specific membrane staining of tumor cells.

Example 8

Immunohistochemistry on Frozen Sections Using Anti-Cadherin-17 Antibodies

Immunohistochemistry was performed on frozen paired tumor and normal adjacent tissues using the anti-Cadherin-17 antibodies PTA001_A4, PTA001_A6, PTA001_A8 and PTA001_A9.

Tissue sections were from BioChain® Institute Inc., CA, USA.

Frozen sections were washed with PBS twice for 3 minutes each and were then placed in PBS.

Endogenous peroxide blockade was performed using Peroxidase Blocker (S2001, DAKO). 1-4 drops of peroxidase blocker was added to each slide and incubated for 5 minutes. The slides were rinsed three times with 3 ml PBS.

The primary antibody was diluted with an Antibody diluent reagent (DAKO). 150 µl of diluted primary antibody was applied to each slide and incubated for 45 minutes at room temperature. Slides were washed with twice for 3 minutes with PBS-3T (500 ml PBS+3 drops of Tween-20) and then once for 3 minutes with PBS.

The goat anti-mouse kappa HRP secondary was applied at 1:1000 (1 mg/ml, cat.1050-05, Southern Biotech) and incubated for 35 min at room temperature. The slides were washed as above.

The DAB substrate was made up in dilution buffer; 2 ml containing 2 drops of substrate was enough for 10 slides. The DAB reagent was applied to the slides by applying a few drops at a time and incubated for 10 min. The slides were washed once for 3 minutes with PBS-3T and twice for 3 minutes with water.

Hematoxylin (DAKO) was applied; 1 ml was enough for 10 slides and slides were incubated for 1 min at room temperature.

Slides were left to dry on the bench at room temperature and then mounted in water-based mounting media from Vector and covered with coverslip.

Immunohistochemical analysis on antibodies PTA001_A4, PTA001_A6, PTA001_A8 and PTA001_A9 on three colorectal cancer samples along with the paired normal adjacent tissue samples revealed strong specific membrane staining of tumor cells in colorectal cancer and some weak staining of normal adjacent tissue. Antibody PTA001_A4, in particular, showed clear specific membrane staining of tumor cells.

Example 9

Western Blotting Using Anti-Cadherin-17 Antibodies

Western blotting was performed using anti-Cadherin-17 antibodies PTA001_A3, PTA001_A4, PTA001_A6, PTA001_A8 and PTA001_A9 to detect Cadherin-17 in a panel of genetically characterized colorectal cancer cell lines representing combinations of three critical mutation phenotypes (p53, APC and RER+/−).

Snap frozen cell pellets were lysed in modified RIPA buffer (50 mM Tris-HCl, pH 7.4, 1% NP-40, 0.25% Na-deoxycholate, 150 mM NaCl, 1 mM EDTA) containing protease inhibitors (Roche) and cleared by spinning down at 18,000 g for 15 min at 4 C. The 4×LDS sample loading buffer (Invitrogen® Inc.) was added to the cleared lysate to a final concentration of 1×; sample was heated for 10 min at 70° C. and kept at −80° C. afterwards. Before loading on a gel samples were re-heated.

Proteins from 10 µg (PC/JW) and 20 µg (other cell lines) of lysate per lane were separated by mini-gel electrophoresis on NuPAGE® Novex® precast mini-gel (Invitrogen, UK). Gels were blotted onto nitrocellulose membrane with iBlot® Dry Blotting System (Invitrogen, UK).

Membrane was incubated with animal-free blocker (Vector) and probed with anti-Cadherin-17 antibody in animal-free blocker at 1:500 dilution, at 4 C, for 14-18 h, rotating. The secondary was anti-mouse DyLight® 488 conjugate (Pierce).

A clear signal was detected at a size corresponding to the Cadherin-17 protein (92 kDa) in 11 of the 14 chosen colorectal cell lines for all 5 Cadherin-17 antibodies (PTA001_A3, PTA001_A4, PTA001_A6, PTA001_A8 and PTA001_A9). FIG. 25 shows the Western blotting analysis of Cadherin-17 for antibody PTA001_A4. Cell lines were carefully selected for different genetic backgrounds relevant to the initiation and progression of CRC (RER+=replication error positive tumor phenotype; RER−=replication error deficient tumor phenotype; p53 wild type or mutant and APC wild type or mutant genotype). Table 2 below shows the phenotype of the colorectal tumor derived cell lines.

TABLE 2

Phenotype of colorectal tumor derived cell lines

| Cell line | Characteristics |
|---|---|
| LS411 | Colorectal carcinoma, Tumor stage: Dukes' type B; Tumorigenic in nude mice. |
| LoVo | Colorectal adenocarcinoma, Dukes' type C, grade IV derived from metastatic site; Tumorigenic in nude mice. |
| Vaco 5 | Colorectal carcinoma. |
| DLD-1 | Colorectal adenocarcinoma, Dukes' type C; Tumorigenic in nude mice. |
| LS 174T | Colorectal carcinoma, Dukes' type B, Tumorigenic in nude mice. |
| HCT 116 | Colorectal carcinoma, Tumorigenic in nude mice. |
| PC/JW | Adenocarcinoma. Tumorigenic in ethylic nude mice. |
| C99 | Colorectal adenocarcinoma. |
| C84 | Colorectal adenocarcinoma. |
| HT29 | Colorectal adenocarcinoma, Tumorigenic in nude mice. |
| LS513 | Colorectal carcinoma, Dukes' type C; Tumorigenic in nude mice. |
| NCI-H716 | Colorectal adenocarcinoma; Tumorigenic in nude mice. |
| Caco2 | Colorectal adenocarcinoma |
| Colo205 | Colorectal adenocarcinoma |

Example 10

Internalization of Anti-Cadherin-17 Antibodies

PTA001_A4 was shown to be internalized by LoVo cells upon binding to the cells using a Immunofluorescence microscopy assay. The Immunofluorescence microscopy assay showed internalization of the anti-Cadherin-17 monoclonal antibodies through binding of an anti-human IgG secondary antibody conjugated to Fluorescein isothiocyanate (GamK-FITC). First, PTA001_A4 were bound to the surface of the LoVo cells. Then, the secondary antibody conjugated to Fluorescein isothiocyanate were bound to the primary antibodies. Next, the PTA001_A4/secondary antibody FITC conjugate complex was internalized by the cells.

The Immunofluorescence microscopy assay was conducted as follows. LoVo cell were incubated at 37° C. for 12 hours for cells to adhere to each other. PTA001_A4 and secondary antibody conjugated to Fluorescein isothiocyanate were serially diluted, washed with FACS buffer (PBS, 2% FBS) and then added to the culture media. The media was then washed again with FACS buffer (PBS, 2% FBS) and incubated at 37%, after which 200 ul 2% PFA was added. Coverslips were mounted using a 9 ul aqeous mountaing media and the cells were then visualized at regular time intervals using Leica fluorescent microscope. FIG. 32A and FIG. 32B shows surface binding of PTA001_A4/secondary antibody FITC conjugate complex to LoVo cells after 60 minutes of incubation and internalization of PTA001_A4/secondary antibody FITC conjugate complex after 120 minutes.

The monoclonal antibody, PTA001_A4, was shown to be internalized by LS147T and LoVo cells upon binding to the cells using a MabZap assay. The MabZAP assay showed internalization of the anti-CDH17 monoclonal antibodies through binding of an anti-human IgG secondary antibody conjugated to the toxin saporin. (Advanced Targeting System, San Diego, Calif., IT-22-100). First, PTA001_A4 was bound to the surface of the LS147T and LoVo cells. Then, the MabZAP antibodies were bound to the primary antibodies. Next, the MabZAP complex was internalized by the cells. The entrance of Saporin into the cells resulted in protein synthesis inhibition and eventual cell death.

Figure 35A:
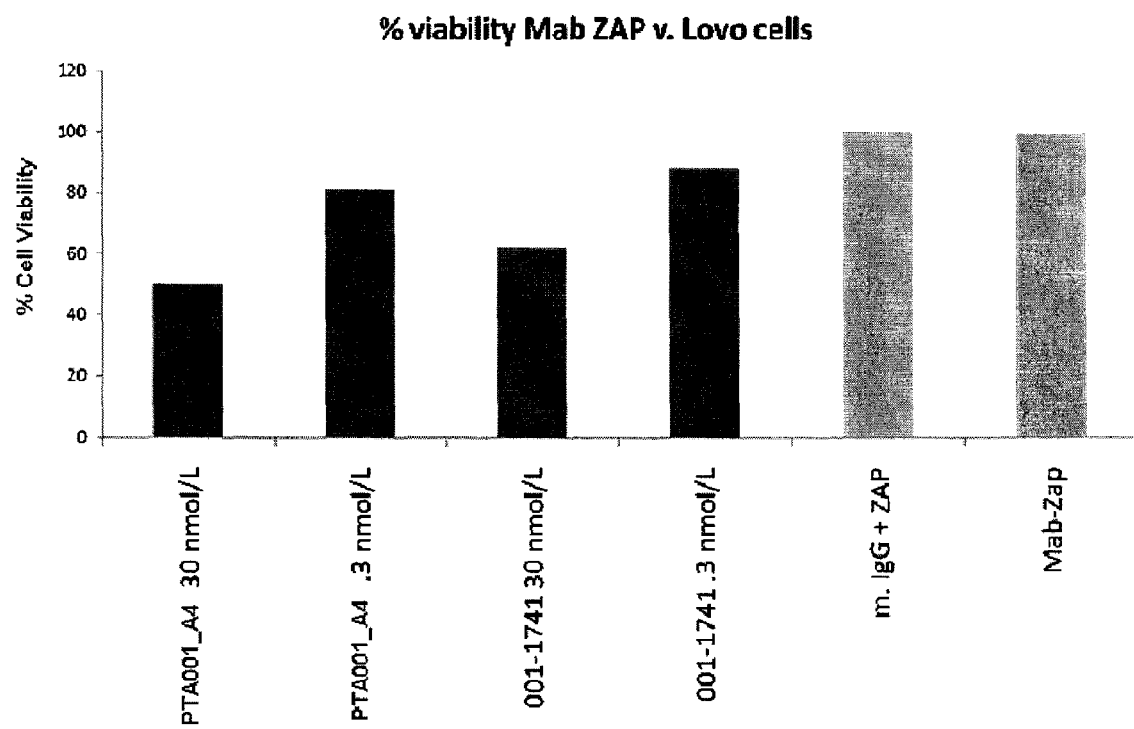
FIG. 35A shows results of internalisation of PTA001_A4 by MabZAP assay in LoVo colon cancer cells.
Figure 35B:
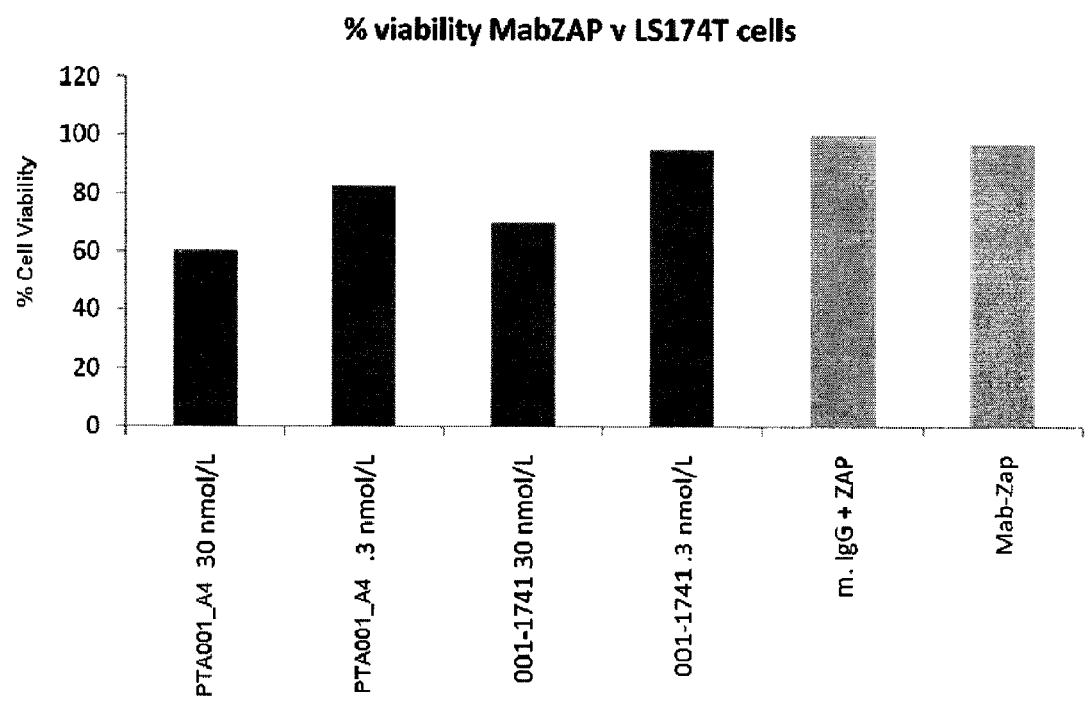
FIG. 35B shows results of internalisation of PTA001_A4 by MabZAP assay in LS174T colon cancer cells.

The MabZAP assay was conducted as follows. Each of the cells was seeded at a density of $5 \times 10^3$ cells per well. The anti-CDH17 monoclonal antibodies or an isotype control human IgG were serially diluted then added to the cells. The MabZAP was then added at a concentration of 50 µg/ml and the plates allowed to incubate for 48 and 72 hours. Cell viability in the plates was detected by CellTiter-Glo® Luminescent Cell Viability Assay kit (Promega, G7571) and the plates were read at 490 nM by a Luminomitor (Tuner BioSystems, Sunnyvale, Calif.). The data was analyzed by Prism (Graphpad). Cell death was proportional to the concentration of PTA001_A4 and monoclonal antibody. FIGS. 35A and 35B show that the anti-CDH17 monoclonal antibodies were efficiently internalized by LS174T and LoVo cells respectively as compared to the anti-human IgG isotype control antibody.

SEQUENCE LISTING

| SEQ ID NO | SEQUENCE DESCRIPTION | SEQUENCE |
|---|---|---|
| 1 | VH CDR1 amino acid PTA001_A1 | GFTFSNYGMS |
| 2 | VH CDR1 amino acid PTA001_A2, PTA001_A14 | GYTFSDHAIH |
| 3 | VH CDR1 amino acid PTA001_A3, PTA001_A5, PTA001_A6, PTA001_A7, PTA001_A8, PTA001_A9, PTA001_A10, PTA001_A11, PTA001_A12, PTA001_A13 | GYTFTDHAIH |
| 4 | VH CDR1 amino acid PTA001_A4 | GYTLTDHTIH |
| 5 | VH CDR2 amino acid PTA001_A1 | AINRDGGTTYYTDNVKG |
| 6 | VH CDR2 amino acid PTA001_A2 | YIYPRHGTTNYNENFKG |
| 7 | VH CDR2 amino acid PTA001_A3, PTA001_A5, | YIYPEHGTIKYNEKFKG |

SEQUENCE LISTING

| SEQ ID NO | SEQUENCE DESCRIPTION | SEQUENCE |
|---|---|---|
| | PTA001_A6, PTA001_A8, PTA001_A9, PTA001_A10 | |
| 8 | VH CDR2 amino acid PTA001_A4 | YIYPRDGITGYNEKFKG |
| 9 | VH CDR2 amino acid PTA001_A7 | YIYPRDGFTKYNEKFKG |
| 10 | VH CDR2 amino acid PTA001_A11 | YIYPEHGSITYNEKFKG |
| 11 | VH CDR2 amino acid PTA001_A12 | YIYPRDDFAKVNEKFKG |
| 12 | VH CDR2 amino acid PTA001_A13 | YIYPEHGTITYNEKFKG |
| 13 | VH CDR2 amino acid PTA001_A14 | YIFPRDAFSLNNEKFKG |
| 14 | VH CDR3 amino acid PTA001_A1 | FLLWDGWYFDV |
| 15 | VH CDR3 amino acid PTA001_A2, PTA001_A14 | RNYFYVMDY |
| 16 | VH CDR3 amino acid PTA001_A3, PTA001_A6, PTA001_A8, PTA001_A9, PTA001_A10 | TNYFYVMEY |
| 17 | VH CDR3 amino acid PTA001_A4 | GYSYRNYAYYYDY |
| 18 | VH CDR3 amino acid PTA001_A5, PTA001_A13 | RNYLYIMDY |
| 19 | VH CDR3 amino acid PTA001_A7 | TNYFYTMDY |
| 20 | VH CDR3 amino acid PTA001_A11 | RNYLYVMDY |
| 21 | VH CDR3 amino acid PTA001_A12 | TNYLYIMDY |
| 22 | VK CDR1 amino acid PTA001_A1 | RSSQSLLHSNGNTYLH |
| 23 | VK CDR1 amino acid PTA001_A2, PTA001_A3, PTA001_A6, PTA001_A9, PTA001_A14 | TSSKSLLRSNGNTYLY |
| 24 | VK CDR1 amino acid PTA001_A4 | KSSQSLLHSSNQKNYLA |
| 25 | VK CDR1 amino acid PTA001_A5, PTA001_A8, PTA001_A10, PTA001_A12, PTA001_A13 | RSSKSLLRSNGNTYLY |
| 26 | VK CDR1 amino acid PTA001_A7 | RSSKSLLRTNGNTYLH |
| 27 | VK CDR1 amino acid PTA001_A11 | RSTKSLLRSNGNTYLY |
| 28 | VK CDR2 amino acid PTA001_A1 | KVSNRFS |
| 29 | VK CDR2 amino acid PTA001_A2, PTA001_A3, | RMSNLAS |

| SEQ ID NO | SEQUENCE DESCRIPTION | SEQUENCE |
|---|---|---|
|  | PTA001_A6, PTA001_A7, PTA001_A9, PTA001_A10, PTA001_A11, PTA001_A12, PTA001_A14 |  |
| 30 | VK CDR2 amino acid PTA001_A4 | WASTRES |
| 31 | VK CDR2 amino acid PTA001_A5, PTA001_A8, PTA001_A13 | RLSNLAS |
| 32 | VK CDR3 amino acid PTA001_A1 | SQSTHVLT |
| 33 | VK CDR3 amino acid PTA001_A2, PTA001_A3, PTA001_A5, PTA001_A6, PTA001_A7, PTA001_A8, PTA001_A9, PTA001_A10, PTA001_A11, PTA001_A12, PTA001_A13, PTA001_A14 | MQHLEYPFT |
| 34 | VK CDR3 amino acid PTA001_A4 | QQYYSYPWT |
| 35 | VH amino acid PTA001_A1 | LGKPWRYPRFVHGENKVKQSTIALALLPLLFTPVAKAEVQLLETGGGVVKPG GSLKLSCAASGFTFSNYGMSWVRQTPEKRLEWVAAINRDGGTTYYTDNVKG RETISRDNAKNSLYLQMSSLRSEDTALYYCARQFLLWDGWYFDVWGAGTTV TVSSAKTTPPSVYPLAPGSAAQTNSMVTLGCLVKGYFPEPVTVTWNSGSLSSG VHTFPAVLQSDLYTLSSSVTVPSSTWPSETVTCNVAHPASSTKVDKKIVPRDC |
| 36 | VH amino acid PTA001_A2 | LGKPWRYPRFVHGENKVKQSTIALALLPLLFTPVAKAQVQLQQSDAELVKPG ASVKISCKVSGYTFSDHAIHWMSQRPGQGLKWIGYIYPRHGTTNYNENFKGK ATLTADTSSSTAYMQLNSLTSEDSAVYFCARMRNYFYVMDYWGQGTSVTVS SAKTTPPSVYPLAPGSAAQTNSMVTLGCLVKGYFPEPVTVTWNSGSLSSGVH TFPAVLQSDLYTLSSSVTVPSSTWPSETVTCNVAHPASSTKVDKKIVPRDC |
| 37 | VH amino acid PTA001_A3 | LGKPWRYPRFVHGENKVKQSTIALALLPLLFTPVAKAQVLLQQSDAELVKPG ASVKISCKASGYTFTDHAIHWVKQRPEQGLEWIGYIYPEHGTIKYNEKFKGKA TLTADKSSSTAYMQLNSLTSEDSAVYFCSRLTNYFYVMEYWGQGTSVTVSSA KTTPPSVYPLAPGSAAQTNSMVTLGCLVKGYFPEPVTVTWNSGSLSSGVHTFP AVLQSDLYTLSSSVTVPSSTWPSETVTCNVAHPASSTKVDKKIVPRDC |
| 38 | VH amino acid PTA001_A4 (with leader sequence) | LGKPWRYPRFVHGENKVKQSTIALALLPLLFTPVAKAEVQLQQSVAELVKPG ASVKMSCKVSGYTLTDHTIHWMKQRPEQGLEWIGYIYPRDGITGYNEKFKGK ATLTADTSSSTAYMQLNSLTSEDSAVYFCARWGYSYRNYAYYYDYWGQGT TLTVSSAKTTPPSVYPLAPGSAAQTNSMVTLGCLVKGYFPEPVTVTWNSGSLS SGVHTFPAVLQSDLYTLSSSVTVPSSTWPSETVTCNVAHPASSTKVDKKIVPR DC |
| 39 | VH amino acid PTA001_A5 (with leader sequence) | LGKPWRYPRFVHGENKVKQSTIALALLPLLFTPVAKAQVQLQQSDADLVKPG ASVKISCKASGYTFTDHAIHWVKQRPEQGLEWIGYIYPEHGTIKYNEKFKGKA TLTADKSSSTAYMQLNSLTSEDSAVYFCARLRNYLYIMDYWGQGTSVTVSSA KTTPPSVYPLAPGSAAQTNSMVTLGCLVKGYFPEPVTVTWNSGSLSSGVHTFP AVLQSDLYTLSSSVTVPSSTWPSETVTCNVAHPASSTKVDKKIVPRDC |
| 40 | VH amino acid PTA001_A6, PTA001_A9, PTA001_A10 | LGKPWRYPRFVHGENKVKQSTIALALLPLLFTPVAKAQVQLQQSDAELVKPG ASVKISCKASGYTFTDHAIHWVKQRPEQGLEWIGYIYPEHGTIKYNEKFKGKA TLTADKSSSTAYMQLNSLTSEDSAVYFCSRLTNYFYVMEYWGQGTSVTVSSA KTTPPSVYPLAPGSAAQTNSMVTLGCLVKGYFPEPVTVTWNSGSLSSGVHTFP AVLQSDLYTLSSSVTVPSSTWPSETVTCNVAHPASSTKVDKKIVPRDC |
| 41 | VH amino acid PTA001_A7 | LGKPWRYPRFVHGENKVKQSTIALALLPLLFTPVAKAQVQLQQSDAELVKPG ASVKISCKVSGYTFTDHAIHWMKQRPEQGLEWIGYIYPRDGFTKYNEKFKGK ATLTADTSSSTAYMQLNSLTSEDSTVYFCARMTNYFYTMDYWGQGTSVTVS SAKTTPPSVYPLAPGSAAQTNSMVTLGCLVKGYFPEPVTVTWNSGSLSSGVH TFPAVLQSDLYTLSSSVTVPSSTWPSETVTCNVAHPASSTKVDKKIVPRDC |
| 42 | VH amino acid PTA001_A8 | LGKPWRYPRFVHGENKVKQSTIALALLPLLFTPVAKAQVQLQQSDADLVKPG ASVKISCKASGYTFTDHAIHWVKQRPEQGLEWIGYIYPEHGTIKYNEKFKGKA TLTADKSSSTAYMQLNSLTSEDSAVYFCSRLTNYFYVMEYWGQGTSVTVSSA KTTPPSVYPLAPGSAAQTNSMVTLGCLVKGYFPEPVTVTWNSGSLSSGVHTFP AVLQSDLYTLSSSVTVPSSTWPSETVTCNVAHPASSTKVDKKIVPRDC |

| SEQ ID NO | SEQUENCE DESCRIPTION | SEQUENCE |
|---|---|---|
| 43 | VH amino acid PTA001_A11 | LGKPWRYPRFVHGENKVKQSTIALALLPLLFTPVAKAQVQLQQSDAELVKPG ASVKISCKASGYTFTDHAIHWVKQRPEQGLEWIGYIYPEHGSITYNEKFKGKA TLTADKSSSTVYMHLNSLTSEDSAVYFCARLRNYLYVMDYWGQGTSVTVSS AKTTPPSVYPLAPGSAAQTNSMVTLGCLVKGYFPEPVTVTWNSGSLSSGVHT FPAVLQSDLYTLSSSVTVPSSTWPSETVTCNVAHPASSTKVDKKIVPRDC |
| 44 | VH amino acid PTA001_A12 | LGKPWRYPRFVHGENKVKQSTIALALLPLLFTPVAKAQVQLQQSEAELVKPG ASVKLSCKASGYTFTDHAIHWMKQRPEQGLEWIGYIYPRDDFAKVNEKFKG KATLTADTSSSTAYMQLNSLTSEDSAVYFCARMTNYLYIMDYWGQGTSVTV SSAKTTPPSVYPLAPGSAAQTNSMVTLGCLVKGYFPEPVTVTWNSGSLSSGV HTFPAVLQSDLYTLSSSVTVPSSTWPSETVTCNVAHPASSTKVDKKIVPRDC |
| 45 | VH amino acid PTA001_A13 | LGKPWRYPRFVHGENKVKQSTIALALLPLLFTPVAKAQVQLQQSDAELVKPG ASVKISCKASGYTFTDHAIHWVKQRPEQGLEWIGYIYPEHGTITYNEKFKGKA TLTADKSSSTVYMHLNSLTSEDSAVYFCARLRNYLYIMDYWGQGTSVTVSSA KTTPPSVYPLAPGSAAQTNSMVTLGCLVKGYFPEPVTVTWNSGSLSSGVHTFP AVLQSDLYTLSSSVTVPSSTWPSETVTCNVAHPASSTKVDKKIVPRDC |
| 46 | VH amino acid PTA001_A14 | LGKPWRYPRFVHGENKVKQSTIALALLPLLFTPVAKAQVQLQQSDAALVKPG ASVKISCKVSGYTFSDHAIHWMKQRPEQGLEWIGYIFPRDAFSLNNEKFKGK ATLSADTSSSTAYMELTSLTFEDSAVYFCARMRNYFYVMDYWGQGTSVTVS SAKTTPPSVYTLAPGSAAQTNSMVTLGCLVKGYFPEPVTVTWNSGSLSSGVH TFPAVLQSDLYTLSSSVTVPSSTWPSETVTCNVAHPASSTKVDKKIVPRDC |
| 47 | VK amino acid PTA001_A1 | RILPDAFYRNSLLFLHTRFFGWSETMKYLLPTAAAGLLLLAAQPAMADVVLT QTPLSLPVTLGDQASISCRSSQSLLHSNGNTYLHWYLLKPGQSPKLLIYKVSN RFSGVPDRFSGSGSGTDFTLKITRVEAEDLGVYFCSQSTHVLTFGAGTKLELK RADAAPTVSIFPPSSEQLTSGGASVVCFLNNFYPKDINVKWKIDGSERQNGVL NSWTDQDSKDSTYSMSSTLTLTKDEYERHNSYTCEATHKTSTSPIVKSFNRNE SYPYDVPDYAS |
| 48 | VK amino acid PTA001_A2, PTA001_A3 | RILPDAFYRNSLLFLHTRFFGWSETMKYLLPTAAAGLLLLAAQPAMADIVMT QAAPSVPVTPGESVSISCTSSKSLLRSNGNTYLYWFLQRPGQSPQLLIYRMSNL ASGVPDRFSGSGSGTAFTLRISRVEAEDVGVYYCMQHLEYPFTFGSGTKLEIK RADAAPTVSIFPPSSEQLTSGGASVVCFLNNFYPKDINVKWKIDGSERQNGVL NSWTDQDSKDSTYSMSSTLTLTKDEYERHNSYTCEATHKTSTSPIVKSFNRNE SYPYDVPDYAS |
| 49 | VK amino acid PTA001_A4 | RILPDAFYRNSLLFLHTRFFGWSETMKYLLPTAAAGLLLLAAQPAMADIVMS QSPSSLAVSVGEKVTMSCKSSQSLLHSSNQKNYLAWYQQKPGQSPKVLIYWA STRESGVPDRFTGSGSGTDFTLTITSVKSEDLAVYYCQQYYSYPWTFGGGTRL EIKRADAAPTVSIFPPSSEQLTSGGASVVCFLNNFYPKDINVKWKIDGSERQNG VLNSWTDQDSKDSTYSMSSTLTLTKDEYERHNSYTCEATHKTSTSPIVKSFNR NESYPYDVPDYAS |
| 50 | VK amino acid PTA001_A5 | RILPDAFYRNSLLFLHTRFFGWSETMKYLLPTAAAGLLLLAAQPAMADIVMT QAAPSVPVTPGESVSISCRSSKSLLRSNGNTYLYWFLQRPGQSPQLLIYRLSNL ASGVPDRFSGSGSGTAFTLRISRVEAEDVGVYYCMQHLEYPFTFGSGTKLEIK RADAAPTVSIFPPSSEQLTSGGASVVCFLNNFYPKDINVKWKIDGSERQNGVL NSWTDQDSKDSTYSMSSTLTLTKDEYERHNSYTCEATHKTSTSPIVKSFNRNE SYPYDVPDYAS |
| 51 | VK amino acid PTA001_A6 | RILPDAFYRNSLLFLHTRFFGWSETIKYLLPTAAAGLLLLAAQPAMADIVMTQ AAPSVPVTPGESVSISCTSSKSLLRSNGNTYLYWFLQRPGQSPQLLIYRMSNLA SGVPDRFSGSGSGTAFTLRISRVEAEDVGVYYCMQHLEYPFTFGSGTKLEIKR ADAAPTVSILPPSSEQLTSGGASVVCFLNNFYPKDINVKWKIDGSERQNGVLN SWTDQDSKDSTYSMSSTLTLTKDEYERHNSYTCEATHKTSTSPIVKSFNRNES YPYDVPDYAS |
| 52 | VK amino acid PTA001_A7 | RILPDAFYRNSLLFLHTRFFGWSETMKYLLPTAAAGLLLLAAQPAMADIVMT QAAPSVPVTPGESVSISCRSSKSLLRTNGNTYLHWFLQRPGQSPQLLIYRMSNL ASGVPDRFSGSGSGTVFTLRISRVEAEDVGVYYCMQHLEYPFTFGSGTKLEIK RADAAPTVSIFPPSSEQLTSGGASVVCFLNNFYPKDINVKWKIDGSERQNGVL NSWTDQDSKDSTYSMSSTLTLTKDEYERHNSYTCEATHKTSTSPIVKSFNRNE SYPYDVPDYAS |
| 53 | VK amino acid PTA001_A8 | RILPYAFYRNSLLFLHTRFFGWSETMKYLLPTAAAGLLLLAAQPAMADIVMT QAAPSVPVTPGESVSISCRSSKSLLRSNGNTYLYWFLQRPGQSPQLLIYRLSNL ASGVPDRFSGSGSGTAFTLRISRVEAEDVGVYYCMQHLEYPFTFGSGTKLEIK RADAAPTVSIFPPSSEQLTSGGASVVCFLNNFYPKDINVKWKIDGSERQNGVL NSWTDQDSKDSTYSMSSTLTLTKDEYERHNSYTCEATHKTSTSPIVKSFNRNE SYPYDVPDYAS |

SEQUENCE LISTING

| SEQ ID NO | SEQUENCE DESCRIPTION | SEQUENCE |
|---|---|---|
| 54 | VK amino acid PTA001_A9 | RILPDAFYRNSLLFLHTRFFGWSETMKYLLPTAAAGLLLLAAQPAMADIVMT<br>QAAPSVPVTPGESVSISCTSSKSLLRSNGNTYLYWFLQRPGQSPQLLIYRMSNL<br>ASGVPDRFSGSGSGTAFTLRISRVEAEDVGVYYCMQHLEYPFTFGSGTKLEIK<br>RADAAPTVSISPPSSEQLTSGGASVVCFLNNFYPKDINVKWKIDGSERQNGVL<br>NSWTDQDSKDSTYSMSSTLTLTKDEYERHNSYTCEATHKTSTSPIVKSFNRNE<br>SYPYDVPDYAS |
| 55 | VK amino acid PTA001_A10, PTA001_A12 | RILPDAFYRNSLLFLHTRFFGWSETMKYLLPTAAAGLLLLAAQPAMADIVMT<br>QAAPSVPVTPGESVSISCRSSKSLLRSNGNTYLYWFLQRPGQSPQLLIYRMSNL<br>ASGVPDRFSGSGSGTAFTLRISRVEAEDVGVYYCMQHLEYPFTFGGGTKLEIK<br>RADAAPTVSIFPPSSEQLTSGGASVVCFLNNFYPKDINVKWKIDGSERQNGVL<br>NSWTDQDSKDSTYSMSSTLTLTKDEYERHNSYTCEATHKTSTSPIVKSFNRNE<br>SYPYDVPDYAS |
| 56 | VK amino acid PTA001_A11 | RILPDAFYRNSLLFLHTRFFGWSETMKYLLPTAAAGLLLLAAQPAMADIVMT<br>QAAPSVPVTPGESVSISCRSTKSLLRSNGNTYLYWFLQRPGQSPQLLIYRMSNL<br>ASGVPDRFSGSGSGTAFTLRISRVEAEDVGVYYCMQHLEYPFTFGGGTKLEIK<br>RADAAPTVSIFPPSSEQLTSGGASVVCFLNNFYPKDINVKWKIDGSERQNGVL<br>NSWTDQDSKDSTYSMSSTLTLTKDEYERHNSYTCEATHKTSTSPIVKSFNRNE<br>SYPYDVPDYAS |
| 57 | VK amino acid PTA001_A13 | RILPDAFYRNSLLFLHTRFFGWSETMKYLLPTAAAGLLLLAAQPAMADIVMT<br>QAAPSVPVTPGESVSISCRSSKSLLRSNGNTYLYWFLQRPGQSPQLLIYRLSNL<br>ASGVPDRFSGSGSGTAFTLRISRVEAEDVGVYYCMQHLEYPFTFGSGTKLEIK<br>RADAAPTVSIFPQYSEQLTTGGASVVCFLNNFYPKDINVKWKIDGSERQNGVL<br>NSWTDQDSKDSTYSMSSTLTLTKDEYERHNSYTCEATHKTSTSPIVKSFNRNE<br>SYPYDVPDYAS |
| 58 | VK amino acid PTA001_A14 | RILPDAFYRNSLLFLHTRFFGWSETMKYLLPTAAAGLLLLAAQPAMADIVMT<br>QAAPSVPVTPGESVSISCTSSKSLLRSNGNTYLYWFLQRPGQSPQLLIYRMSNL<br>ASGVPDRFSGSGSGTAFTLRISRVEAEDVGVYYCMQHLEYPFTFGSGTNLEIK<br>RADAAPTVSIFTTSREQLTSGGASVVCFLNNFYPKDINVK |
| 59 | VH n.t. PTA001_A1 | TGACTGGGAAAACCCTGGCGTTACCCACGCTTTGTACATGGAGAAAATAA<br>AGTGAAACAAAGCACTATTGCACTGGCACTCTTACCGCTCTTATTTACCCC<br>TGTGGCAAAAGCCGAAGTGCAGCTGTTGGAGACTGGGGGAGGCGTAGTG<br>AAGCCCGGAGGGTCCCTTAAACTCTCCTGTGCAGCCTCTGGATTCACTTTC<br>AGTAACTATGGCATGTCTTGGGTTCGCCAGACTCCGGAGAAGAGGCTGGA<br>GTGGGTCGCAGCCATTAATCGTGATGGTGGTACCACCTACTATACAGACA<br>ATGTGAAGGGCCGATTCACCATCTCCAGAGACAATGCCAAGAACAGCCTG<br>TACCTGCAAATGAGCAGTCTGAGGTCTGAGGACACAGCCTTGTATTACTG<br>TGCAAGACAGTTCCTTCTCTGGGACGGCTGGTACTTCGATGTCTGGGGCGC<br>AGGGACCACGGTCACCGTCTCCTCAGCCAAAACGACACCCCCATCTGTCT<br>ATCCACTGGCCCCTGGATCTGCTGCCCAAACTAACTCCATGGTGACCCTGG<br>GATGCCTGGTCAAGGGCTATTTCCCTGAGCCAGTGACAGTGACCTGGAAC<br>TCTGGATCCCTGTCCAGCGGTGTGCACACCTTCCCAGCTGTCCTGCAGTCT<br>GACCTCTACACTCTGAGCAGCTCAGTGACTGTCCCCTCCAGCACCTGGCCC<br>AGCGAGACCGTCACCTGCAACGTTGCCCACCCGGCCAGCAGCACCAAGGT<br>GGACAAGAAAATTGTGCCCAGGGATTGT |
| 60 | VH n.t. PTA001_A2 | TGACTGGGAAAACCCTGGCGTTACCCACGCTTTGTACATGGAGAAAATAA<br>AGTGAAACAAAGCACTATTGCACTGGCACTCTTACCGCTCTTATTTACCCC<br>TGTGGCAAAAGCCCAGGTTCAGCTGCAACAGTCTGACGCTGAGTTGGTGA<br>AACCTGGAGCTTCAGTGAAGATATCCTGCAAGGTTTCTGGCTACACCTTCA<br>GTGACCATGCTATTCACTGGATGAGTCAGAGACCTGGACAGGGCCTGAAA<br>TGGATTGGATATATTTATCCTAGACATGGGACTACTAACTACAATGAGAA<br>CTTCAAGGGCAAGGCCACACTGACTGCAGACACATCCTCCAGCACAGCCT<br>ACATGCAGCTCAACAGCCTGACATCTGAAGATTCTGCCGTCTATTTCTGTG<br>CAAGAAATGAGAAACTACTTCTATGTTATGGACTACTGGGGTCAAGGAACC<br>TCAGTCACCGTCTCCTCAGCCAAAACGACACCCCCATCTGTCTATCCACTG<br>GCCCCTGGATCTGCTGCCCAAACTAACTCCATGGTGACCCTGGGATGCCTG<br>GTCAAGGGCTATTTCCCTGAGCCAGTGACAGTGACCTGGAACTCTGGATC<br>CCTGTCCAGCGGTGTGCACACCTTCCCAGCTGTCCTGCAGTCTGACCTCTA<br>CACTCTGAGCAGCTCAGTGACTGTCCCCTCCAGCACCTGGCCCAGCGAGA<br>CCGTCACCTGCAACGTTGCCCACCCGGCCAGCAGCACCAAGGTGGACAAG<br>AAAATTGTGCCCAGGGATTGT |
| 61 | VH n.t. PTA001_A3 | TGACTGGGAAAACCCTGGCGTTACCCACGCTTTGTACATGGAGAAAATAA<br>AGTGAAACAAAGCACTATTGCACTGGCACTCTTACCGCTCTTATTTACCCC<br>TGTGGCAAAAGCCCAGGTTCTGCTGCAACAGTCTGACGCTGAGTTGGTGA<br>AACCTGGGGCTTCAGTGAAGATATCCTGCAAGGCTTCTGGCTACACCTTCA<br>CTGACCATGCTATTCACTGGGTGAAGCAGAGGCCTGAACAGGGCCTGGAA<br>TGGATTGGATATATTTATCCTGAACATGGAACTATTAAGTATAATGAGAA<br>GTTCAAGGGCAAGGCCACATTGACTGCAGATAAATCCTCCAGCACTGCCT<br>ATATGCAGCTCAACAGCCTGACATCTGAGGATTCAGCAGTGTATTTCTGTT |

| SEQ ID NO | SEQUENCE DESCRIPTION | SEQUENCE |
|---|---|---|
| | | CAAGACTCACTAACTACTTCTATGTTATGGAGTATTGGGGTCAAGGAACCT CAGTCACCGTCTCCTCAGCCAAAACGACACCCCCATCTGTCTATCCACTGG CCCCTGGATCTGCTGCCCAAACTAACTCCATGGTGACCCTGGGATGCCTGG TCAAGGGCTATTTCCCTGAGCCAGTGACAGTGACCTGGAACTCTGGATCC CTGTCCAGCGGTGTGCACACCTTCCCAGCTGTCCTGCAGTCTGACCTCTAC ACTCTGAGCAGCTCAGTGACTGTCCCCTCCAGCACCTGGCCCAGCGAGAC CGTCACCTGCAACGTTGCCCACCCGGCCAGCAGCACCAAGGTGGACAAGA AAATTGTGCCCAGGGATTGT |
| 62 | VH n.t. PTA001_A4 | TGACTGGGAAAACCCTGGCGTTACCCACGCTTTGTACATGGAGAAAATAA AGTGAAACAAAGCACTATTGCACTGGCACTCTTACCGCTCTTATTTACCCC TGTGGCAAAAGCCGAGGTTCAGCTGCAGCAGTCTGTCGCTGAGTTGGTGA AACCTGGAGCTTCAGTGAAGATGTCATGCAAGGTTTCTGGCTACACCCTC ACTGACCATACTATTCACTGGATGAAGCAGAGGCCTGAACAGGGCCTGGA ATGGATTGGATATATTTACCCTAGAGATGGAATAACTGGGTACAATGAGA AGTTCAAGGGCAAGGCCACACTGACTGCAGACACTTCTTCCAGCACAGCC TACATGCAGCTCAACAGCCTGACATCTGAGGATTCTGCAGTCTATTTCTGT GCCAGATGGGCTATAGTTACAGGAATTACGCGTACTACTATGACTACTG GGGCCAAGGCACCACTCTCACAGTCTCCTCAGCCAAAACGACACCCCCAT CTGTCTATCCACTGGCCCCTGGATCTGCTGCCCAAACTAACTCCATGGTGA CCCTGGGATGCCTGGTCAAGGGCTATTTCCCTGAGCCAGTGACAGTGACC TGGAACTCTGGATCCCTGTCCAGCGGTGTGCACACCTTCCCAGCTGTCCTG CAGTCTGACCTCTACACTCTGAGCAGCTCAGTGACTGTCCCCTCCAGCACC TGGCCCAGCGAGACCGTCACCTGCAACGTTGCCCACCCGGCCAGCAGCAC CAAGGTGGACAAGAAAATTGTGCCCAGGGATTGT |
| 63 | VH n.t. PTA001_A5 | TGACTGGGAAAACCCTGGCGTTACCCACGCTTTGTACATGGAGAAAATAA AGTGAAACAAAGCACTATTGCACTGGCACTCTTACCGCTCTTATTTACCCC TGTGGCAAAAGCCCAGGTTCAGCTGCAACAGTCTGACGCTGACTTGGTGA AACCTGGGGCTTCAGTGAAGATATCCTGCAAGGCTTCTGGCTACACCTTCA CTGACCATGCTATTCACTGGGTGAAACAGAGGCCTGAACAGGGCCTGGAA TGGATTGGATATATTTATCCTGAACATGGAACTATTAAGTATAATGAGAA GTTCAAGGGCAAGGCCACATTGACTGCAGATAAATCCTCCAGCACTGCCT ATATGCAGCTCAACAGCCTGACATCTGAGGATTCAGCAGTGTATTTCTGTG CAAGACTCAGGAACTATTTGTATATTATGGACTACTGGGGTCAAGGAACC TCAGTCACCGTCTCCTCAGCCAAAACGACACCCCCATCTGTCTATCCACTG GCCCCTGGATCTGCTGCCCAAACTAACTCCATGGTGACCCTGGGATGCCTG GTCAAGGGCTATTTCCCTGAGCCAGTGACAGTGACCTGGAACTCTGGATC CCTGTCCAGCGGTGTGCACACCTTCCCAGCTGTCCTGCAGTCTGACCTCTA CACTCTGAGCAGCTCAGTGACTGTCCCCTCCAGCACCTGGCCCAGCGAGA CCGTCACCTGCAACGTTGCCCACCCGGCCAGCAGCACCAAGGTGGACAAG AAAATTGTGCCCAGGGATTGT |
| 64 | VH n.t. PTA001_A6, PTA001_A9, PTA001_A10 | TGACTGGGAAAACCCTGGCGTTACCCACGCTTTGTACATGGAGAAAATAA AGTGAAACAAAGCACTATTGCACTGGCACTCTTACCGCTCTTATTTACCCC TGTGGCAAAAGCCCAGGTTCAGCTGCAACAGTCTGACGCTGAGTTGGTGA AACCTGGGGCTTCAGTGAAGATATCCTGCAAGGCTTCTGGCTACACCTTCA CTGACCATGCTATTCACTGGGTGAAGCAGAGGCCTGAACAGGGCCTGGAA TGGATTGGATATATTTATCCTGAACATGGAACTATTAAGTATAATGAGAA GTTCAAGGGCAAGGCCACATTGACTGCAGATAAATCCTCCAGCACTGCCT ATATGCAGCTCAACAGCCTGACATCTGAGGATTCAGCAGTGTATTTCTGTT CAAGACTCACTAACTACTTCTATGTTATGGAGTATTGGGGTCAAGGAACCT CAGTCACCGTCTCCTCAGCCAAAACGACACCCCCATCTGTCTATCCACTGG CCCCTGGATCTGCTGCCCAAACTAACTCCATGGTGACCCTGGGATGCCTGG TCAAGGGCTATTTCCCTGAGCCAGTGACAGTGACCTGGAACTCTGGATCC CTGTCCAGCGGTGTGCACACCTTCCCAGCTGTCCTGCAGTCTGACCTCTAC ACTCTGAGCAGCTCAGTGACTGTCCCCTCCAGCACCTGGCCCAGCGAGAC CGTCACCTGCAACGTTGCCCACCCGGCCAGCAGCACCAAGGTGGACAAGA AAATTGTGCCCAGGGATTGT |
| 65 | VH n.t. PTA001_A7 | TGACTGGGAAAACCCTGGCGTTACCCACGCTTTGTACATGGAGAAAATAA AGTGAAACAAAGCACTATTGCACTGGCACTCTTACCGCTCTTATTTACCCC TGTGGCAAAAGCCCAGGTTCAGCTGCAACAGTCTGACGCTGAGTTGGTGA AACCTGGAGCCTCAGTGAAGATATCCTGCAAGGTTTCTGGCTACACCTTCA CTGACCATGCTATTCACTGGATGAAACAGAGGCCTGAACAGGGCCTGGAA TGGATTGGATATATTTATCCTAGAGATGGTTTTACTAAGTACAATGAGAAG TTCAAGGGCAAGGCCACACTGACTGCAGACACATCCTCCAGCACAGCCTA CATGCAGCTCAACAGCCTGACATCTGAGGATTCTACAGTCTATTTCTGTGC AAGAATGACTAACTACTTCTATACTATGGACTACTGGGGTCAAGGAACCT CAGTCACCGTCTCCTCAGCCAAAACGACACCCCCATCTGTCTATCCACTGG CCCCTGGATCTGCTGCCCAAACTAACTCCATGGTGACCCTGGGATGCCTGG TCAAGGGCTATTTCCCTGAGCCAGTGACAGTGACCTGGAACTCTGGATCC CTGTCCAGCGGTGTGCACACCTTCCCAGCTGTCCTGCAGTCTGACCTCTAC ACTCTGAGCAGCTCAGTGACTGTCCCCTCCAGCACCTGGCCCAGCGAGAC |

SEQUENCE LISTING

| SEQ ID NO | SEQUENCE DESCRIPTION | SEQUENCE |
|---|---|---|
| | | CGTCACCTGCAACGTTGCCCACCCGGCCAGCAGCACCAAGGTGGACAAGA<br>AAATTGTGCCCAGGGATTGT |
| 66 | VH n.t. PTA001_A8 | TGACTGGGAAAACCCTGGCGTTACCCACGCTTTGTACATGGAGAAAATAA<br>AGTGAAACAAAGCACTATTGCACTGGCACTCTTACCGCTCTTATTTACCCC<br>TGTGGCAAAAGCCCAGGTTCAGCTGCAACAGTCTGACGCTGACTTGGTGA<br>AACCTGGGGCTTCAGTGAAGATATCCTGCAAGGCTTCTGGCTACACCTTCA<br>CTGACCATGCTATTCACTGGGTGAAACAGAGGCCTGAACAGGGCCTGGAA<br>TGGATTGGATATATTTATCCTGAACATGGAACTATTAAGTATAATGAGAA<br>GTTCAAGGGCAAGGCCACATTGACTGCAGATAAATCCTCCAGCACTGCCT<br>ATATGCAGCTCAACAGCCTGACATCTGAGGATTCAGCAGTGTATTTCTGTT<br>CAAGACTCACTAACTACTTCTATGTTATGGAGTATTGGGGTCAAGGAACCT<br>CAGTCACCGTCTCCTCAGCCAAAACGACACCCCCATCTGTCTATCCACTGG<br>CCCCTGGATCTGCTGCCCAAACTAACTCCATGGTGACCCTGGGATGCCTGG<br>TCAAGGGCTATTTCCCTGAGCCAGTGACAGTGACCTGGAACTCTGGATCC<br>CTGTCCAGCGGTGTGCACACCTTCCCAGCTGTCCTGCAGTCTGACCTCTAC<br>ACTCTGAGCAGCTCAGTGACTGTCCCCTCCAGCACCTGGCCCAGCGAGAC<br>CGTCACCTGCAACGTTGCCCACCCGGCCAGCAGCACCAAGGTGGACAAGA<br>AAATTGTGCCCAGGGATTGT |
| 67 | VH n.t. PTA001_A11 | TGACTGGGAAAACCCTGGCGTTACCCACGCTTTGTACATGGAGAAAATAA<br>AGTGAAACAAAGCACTATTGCACTGGCACTCTTACCGCTCTTATTTACCCC<br>TGTGGCAAAAGCCCAGGTTCAGCTGCAACAGTCTGACGCTGAGTTGGTGA<br>AACCTGGGGCTTCAGTGAAGATATCCTGCAAGGCTTCTGGCTACACCTTCA<br>CTGACCATGCTATTCACTGGGTGAAGCAGAGGCCTGAACAGGGCCTGGAA<br>TGGATTGGATATATTTATCCTGAACATGGTAGTATTACGTATAATGAGAAG<br>TTCAAGGGCAAGGCCACATTGACTGCAGATAAATCCTCCAGTACTGTCTA<br>TATGCACCTCAATAGCCTGACATCTGAGGATTCAGCAGTGTATTTCTGTGC<br>AAGACTCAGGAACTACTTGTATGTTATGGACTACTGGGGTCAAGGAACCT<br>CAGTCACCGTCTCCTCAGCCAAAACGACACCCCCATCTGTCTATCCACTGG<br>CCCCTGGATCTGCTGCCCAAACTAACTCCATGGTGACCCTGGGATGCCTGG<br>TCAAGGGCTATTTCCCTGAGCCAGTGACAGTGACCTGGAACTCTGGATCC<br>CTGTCCAGCGGTGTGCACACCTTCCCAGCTGTCCTGCAGTCTGACCTCTAC<br>ACTCTGAGCAGCTCAGTGACTGTCCCCTCCAGCACCTGGCCCAGCGAGAC<br>CGTCACCTGCAACGTTGCCCACCCGGCCAGCAGCACCAAGGTGGACAAGA<br>AAATTGTGCCCAGGGATTGT |
| 68 | VH n.t. PTA001_A12 | TGACTGGGAAAACCCTGGCGTTACCCACGCTTTGTACATGGAGAAAATAA<br>AGTGAAACAAAGCACTATTGCACTGGCACTCTTACCGCTCTTATTTACCCC<br>TGTGGCAAAAGCCCAGGTTCAGCTGCAACAGTCTGAGGCTGAGCTTGTGA<br>AGCCTGGGGCTTCAGTGAAGCTGTCCTGCAAGGCTTCTGGCTACACCTTCA<br>CTGACCATGCTATTCACTGGATGAAACAGAGGCCTGAACAGGGCCTGGAA<br>TGGATTGGATATATCTACCCCAGAGATGATTTTGCTAAGGTGAATGAGAA<br>GTTCAAGGGCAAGGCCACACTGACAGCAGACACATCCTCAGCACAGCCT<br>ACATGCAGCTCAACAGCCTGACATCTGAGGATTCTGCAGTCTATTTCTGTG<br>CAAGAATGACTAACTACCTCTATATTATGGACTACTGGGGTCAAGGAACC<br>TCAGTCACCGTCTCCTCAGCCAAAACGACACCCCCATCTGTCTATCCACTG<br>GCCCCTGGATCTGCTGCCCAAACTAACTCCATGGTGACCCTGGGATGCCTG<br>GTCAAGGGCTATTTCCCTGAGCCAGTGACAGTGACCTGGAACTCTGGATC<br>CCTGTCCAGCGGTGTGCACACCTTCCCAGCTGTCCTGCAGTCTGACCTCTA<br>CACTCTGAGCAGCTCAGTGACTGTCCCCTCCAGCACCTGGCCCAGCGAGA<br>CCGTCACCTGCAACGTTGCCCACCCGGCCAGCAGCACCAAGGTGGACAAG<br>AAAATTGTGCCCAGGGATTGT |
| 69 | VH n.t. PTA001_A13 | TGACTGGGAAAACCCTGGCGTTACCCACGCTTTGTACATGGAGAAAATAA<br>AGTGAAACAAAGCACTATTGCACTGGCACTCTTACCGCTCTTATTTACCCC<br>TGTGGCAAAAGCCCAGGTTCAGCTGCAACAGTCTGACGCTGAGTTGGTGA<br>AACCTGGGGCTTCAGTGAAGATATCCTGCAAGGCTTCTGGCTACACCTTCA<br>CTGACCATGCTATTCACTGGGTGAAGCAGAGGCCTGAACAGGGCCTGGAA<br>TGGATTGGATATATTTATCCTGAACATGGTACTATTACGTATAATGAGAAG<br>TTCAAGGGCAAGGCCACATTGACTGCAGATAAATCCTCCAGTACTGTCTA<br>TATGCACCTCAATAGCCTGACATCTGAGGATTCAGCAGTGTATTTCTGTGC<br>AAGACTCAGGAACTATTTGTATATTATGGACTACTGGGGTCAAGGAACCT<br>CAGTCACCGTCTCCTCAGCCAAAACGACACCCCCATCTGTCTATCCACTGG<br>CCCCGGATCTGCTGCCCAAACTAACTCCATGGTGACCCTGGGATGCCTG<br>GTCAAGGGCTATTTCCCTGAGCCAGTGACAGTGACCTGGAACTCTGGATC<br>CCTGTCCAGCGGTGTGCACACCTTCCCAGCTGTCCTGCAGTCTGACCTCTA<br>CACTCTGAGCAGCTCAGTGACTGTCCCCTCCAGCACCTGGCCCAGCGAGA<br>CCGTCACCTGCAACGTTGCCCACCCGGCCAGCAGCACCAAGGTGGACAAG<br>AAAATTGTGCCCAGGGATTGT |
| 70 | VH n.t. PTA001_A14 | TGACTGGGAAAACCCTGGCGTTACCCACGCTTTGTACATGGAGAAAATAA<br>AGTGAAACAAAGCACTATTGCACTGGCACTCTTACCGCTCTTATTTACCCC<br>TGTGGCAAAAGCCCAGGTTCAGCTGCAACAGTCTGACGCCGCGTTGGTGA |

SEQUENCE LISTING

| SEQ ID NO | SEQUENCE DESCRIPTION | SEQUENCE |
|---|---|---|
| | | AACCTGGAGCTTCAGTGAAGATATCGTGCAAGGTTTCTGGCTACACCTTCA<br>GTGACCATGCTATTCACTGGATGAAGCAGAGGCCTGAACAGGGCCTGGAA<br>TGGATTGGATATATTTTTCCTAGAGATGCTTTTAGTTTGAACAATGAGAAG<br>TTCAAGGGCAAGGCCACACTGAGTGCAGACACATCCTCCAGCACAGCCTA<br>CATGGAGCTCACCAGCCTGACATTTGAGGATTCTGCAGTCTATTTCTGTGC<br>AAGAATGAGAAACTACTTCTATGTTATGGACTACTGGGGTCAAGGAACCT<br>CAGTCACCGTCTCCTCAGCCAAAACGACACCCCCATCTGTCTATACACTGG<br>CCCCTGGATCTGCTGCCCAAACTAACTCCATGGTGACCCTGGGATGCCTGG<br>TCAAGGGCTATTTCCCTGAGCCAGTGACAGTGACCTGGAACTCTGGATCC<br>CTGTCCAGCGGTGTGCACACCTTCCCAGCTGTCCTGCAGTCTGACCTCTAC<br>ACTCTGAGCAGCTCAGTGACTGTCCCCTCCAGCACCTGGCCCAGCGAGAC<br>CGTCACCTGCAACGTTGCCCACCCGGCCAGCAGCACCAAGGTGGACAAGA<br>AAATTGTGCCCAGGGATTGT |
| 71 | VK n.t. PTA001_A1 | TAAGATTAGCGGATCCTACCTGACGCTTTTTATCGCAACTCTCTACTGTTT<br>CTCCATACCCGTTTTTTTGGATGGAGTGAAACGATGAAATACCTATTGCCT<br>ACGGCAGCCGCTGGATTGTTATTACTCGCTGCCCAACCAGCCATGGCCGA<br>TGTTGTGCTGACCCAGACTCCACTCTCCCTGCCTGTCACTCTTGGAGATCA<br>AGCCTCCATCTCTTGCAGATCTAGTCAGAGCCTTTTACACAGTAATGGAAA<br>CACCTATTTACATTGGTACCTGCTGAAGCAGGCCAGTCTCCAAAGCTCCT<br>GATCTACAAAGTTTCCAACCGATTTTCTGGGGTCCCAGACAGGTTCAGTGG<br>CAGTGGATCAGGGACAGATTTCACACTCAAGATCACCAGAGTGGAGGCTG<br>AGGATCTGGGAGTTTATTTCTGCTCTCAAAGTACACATGTGCTCACGTTCG<br>GTGCTGGGACCAAGCTGGAGCTGAAACGGGCTGATGCTGCACCAACTGTA<br>TCCATCTTCCCACCATCCAGTGAGCAGTTAACATCTGGAGGTGCCTCAGTC<br>GTGTGCTTCTTGAACAACTTCTACCCCAAAGACATCAATGTCAAGTGGAA<br>GATTGATGGCAGTAACGACAAAATGGCGTCCTGAACAGTTGGACTGATC<br>AGGACAGCAAAGACAGCACCTACAGCATGAGCAGCACCCTCACGTTGACC<br>AAGGACGAGTATGAACGACATAACAGCTATACCTGTGAGGCCACTCACAA<br>GACATCAACTTCACCCATTGTCAAGAGCTTCAACAGGAATGAGTCTTATCC<br>ATATGATGTGCCAGATTATGCGAGCTAA |
| 72 | VK n.t. PTA001_A2, PTA001_A3 | TAAGATTAGCGGATCCTACCTGACGCTTTTTATCGCAACTCTCTACTGTTT<br>CTCCATACCCGTTTTTTTGGATGGAGTGAAACGATGAAATACCTATTGCCT<br>ACGGCAGCCGCTGGATTGTTATTACTCGCTGCCCAACCAGCCATGGCCGA<br>TATTGTGATGACCCAGGCTGCACCCTCTGTACCTGTCACTCCTGGAGAGTC<br>AGTATCCATCTCCTGCACGTCTAGTAAGAGTCTCCTGCGTAGTAATGGCAA<br>CACTTACTTGTATTGGTTCCTGCAGAGGCCAGGCCAGTCTCCTCAGCTCCT<br>GATATATCGGATGTCCAACCTTGCCTCGGGAGTCCCAGACAGGTTCAGTG<br>GCAGTGGGTCAGGAACTGCTTTCACACTGAGAATCAGTAGAGTGGAGGCT<br>GAGGATGTGGGTGTTTATTACTGTATGCAACATCTAGAATATCCTTTCACG<br>TTCGGCTCGGGGACAAAGTTGGAAATAAAACGGGCTGATGCTGCACCAAC<br>TGTATCCATCTTCCCACCATCCAGTGAGCAGTTAACATCTGGAGGTGCCTC<br>AGTCGTGTGCTTCTTGAACAACTTCTACCCCAAAGACATCAATGTCAAGTG<br>GAAGATTGATGGCAGTAACGACAAAATGGCGTCCTGAACAGTTGGACTG<br>ATCAGGACAGCAAAGACAGCACCTACAGCATGAGCAGCACCCTCACGTTG<br>ACCAAGGACGAGTATGAACGACATAACAGCTATACCTGTGAGGCCACTCA<br>CAAGACATCAACTTCACCCATTGTCAAGAGCTTCAACAGGAATGAGTCTT<br>ATCCATATGATGTGCCAGATTATGCGAGCTAA |
| 73 | VK n.t. PTA001_A4 | TAAGATTAGCGGATCCTACCTGACGCTTTTTATCGCAACTCTCTACTGTTT<br>CTCCATACCCGTTTTTTTGGATGGAGTGAAACGATGAAATACCTATTGCCT<br>ACGGCAGCCGCTGGATTGTTATTACTCGCTGCCCAACCAGCCATGGCCGA<br>CATCGTTATGTCTCAGTCTCCATCCTCCCTAGCTGTGTCAGTTGGAGAGAA<br>GGTTACTATGAGCTGCAAGTCCAGCCAGAGCCTTTTACATAGTAGCAATC<br>AAAAGAACTACTTGGCCTGGTACCAGCAGAAACCAGGGCAGTCTCCTAAA<br>GTGCTGATTTACTGGGCATCCACTAGAGAATCTGGGGTCCCTGATCGCTTC<br>ACAGGCAGTGGATCTGGGACAGATTTCACTCTCACCATCACCAGTGTGAA<br>GTCTGAAGACCTGGCAGTTTATTACTGTCAGCAATATTATAGCTATCCGTG<br>GACGTTCGGTGGCGGCACCAGGCTGGAAATCAAACGGGCTGATGCTGCAC<br>CAACTGTATCCATCTTCCCACCATCCAGTGAGCAGTTAACATCTGGAGGTG<br>CCTCAGTCGTGTGCTTCTTGAACAACTTCTACCCCAAAGACATCAATGTCA<br>AGTGGAAGATTGATGGCAGTAACGACAAAATGGCGTCCTGAACAGTTGG<br>ACTGATCAGGACAGCAAAGACAGCACCTACAGCATGAGCAGCACCCTCAC<br>GTTGACCAAGGACGAGTATGAACGACATAACAGCTATACCTGTGAGGCCA<br>CTCACAAGACATCAACTTCACCCATTGTCAAGAGCTTCAACAGGAATGAG<br>TCTTATCCATATGATGTGCCAGATTATGCGAGCTAA |
| 74 | VK n.t. PTA001_A5 | TAAGATTAGCGGATCCTACCTGACGCTTTTTATCGCAACTCTCTACTGTTT<br>CTCCATACCCGTTTTTTTGGATGGAGTGAAACGATGAAATACCTATTGCCT<br>ACGGCAGCCGCTGGATTGTTATTACTCGCTGCCCAACCAGCCATGGCCGA<br>TATTGTGATGACCCAGGCTGCACCCTCTGTACCTGTCACTCCTGGAGAGTC<br>AGTATCCATCTCCTGCAGGTCTAGTAAGAGTCTCCTGCGCAGTAATGGCA<br>ACACTTACTTGTATTGGTTCCTGCAGAGGCCAGGCCAGTCTCCTCAGCTCC |

SEQUENCE LISTING

| SEQ ID NO | SEQUENCE DESCRIPTION | SEQUENCE |
|---|---|---|
| | | TGATATATCGGCTGTCCAACCTTGCCTCAGGAGTCCCAGACAGGTTCAGTG<br>GCAGTGGGTCTGGAACTGCTTTCACACTGAGAATCAGTAGAGTGGAGGCT<br>GAGGATGTGGGTGTTTATTACTGTATGCAACATCTAGAATATCCTTTCACA<br>TTCGGCTCGGGGACAAAGTTGGAAATAAAACGGGCTGATGCTGCACCAAC<br>TGTATCCATCTTCCCACCATCCAGTGAGCAGTTAACATCTGGAGGTGCCTC<br>AGTCGTGTGCTTCTTGAACAACTTCTACCCCAAAGACATCAATGTCAAGTG<br>GAAGATTGATGGCAGTGAACGACAAAATGGCGTCCTGAACAGTTGGACTG<br>ATCAGGACAGCAAAGACAGCACCTACAGCATGAGCAGCACCCTCACGTTG<br>ACCAAGGACGAGTATGAACGACATAACAGCTATACCTGTGAGGCCACTCA<br>CAAGACATCAACTTCACCCATTGTCAAGAGCTTCAACAGGAATGAGTCTT<br>ATCCATATGATGTGCCAGATTATGCGAGCTAA |
| 75 | VK n.t. PTA001_A6 | TAAGATTAGCGGATCCTACCTGACGCTTTTTATCGCAACTCTCTACTGTTT<br>CTCCATACCCGTTTTTTTGGATGGAGTGAAACGATAAAATACCTATTGCCT<br>ACGGCAGCCGCTGGATTGTTATTACTCGCTGCCCAACCAGCCATGGCCGA<br>TATTGTGATGACCCAGGCTGCACCCTCTGTACCTGTCACTCCTGGAGAGTC<br>AGTATCCATCTCCTGCACGTCTAGTAAGAGTCTCCTGCGTAGTAATGGCAA<br>CACTTACTTGTATTGGTTCCTGCAGAGGCCAGGCCAGTCTCCTCAGCTCCT<br>GATATATCGGATGTCCAACCTTGCCTCGGGAGTCCCAGACAGGTTCAGTG<br>GCAGTGGGTCAGGAACTGCTTTCACACTGAGAATCAGTAGAGTGGAGGCT<br>GAGGATGTGGGTGTTTATTACTGTATGCAACATCTAGAATATCCTTTCACG<br>TTCGGCTCGGGGACAAAGTTGGAAATAAAACGGGCTGATGCTGCACCAAC<br>TGTATCCATCCTCCCACCATCCAGTGAGCAGTTAACATCTGGAGGTGCCTC<br>AGTCGTGTGCTTCTTGAACAACTTCTACCCCAAAGACATCAATGTCAAGTG<br>GAAGATTGATGGCAGTGAACGACAAAATGGCGTCCTGAACAGTTGGACTG<br>ATCAGGACAGCAAAGACAGCACCTACAGCATGAGCAGCACCCTCACGTTG<br>ACCAAGGACGAGTATGAACGACATAACAGCTATACCTGTGAGGCCACTCA<br>CAAGACATCAACTTCACCCATTGTCAAGAGCTTCAACAGGAATGAGTCTT<br>ATCCATATGATGTGCCAGATTATGCGAGCTAA |
| 76 | VK n.t. PTA001_A7 | TAAGATTAGCGGATCCTACCTGACGCTTTTTATCGCAACTCTCTACTGTTT<br>CTCCATACCCGTTTTTTTGGATGGAGTGAAACGATGAAATACCTATTGCCT<br>ACGGCAGCCGCTGGATTGTTATTACTCGCTGCCCAACCAGCCATGGCCGA<br>TATTGTGATGACCCAGGCTGCACCCTCTGTACCTGTCACTCCTGGAGAGTC<br>AGTTTCCATCTCCTGCAGGTCTTCTAAGAGTCTCCTGCGTACTAATGGCAA<br>CACTTACTTGCATTGGTTCCTGCAGAGGCCAGGCCAGTCTCCTCAGCTCCT<br>GATATATCGGATGTCCAACCTTGCCTCAGGAGTCCCAGACAGGTTCAGTG<br>GCAGTGGGTCAGGAACTGTTTTCACACTGAGAATCAGTAGAGTGGAGGCT<br>GAGGATGTGGGTGTTTATTACTGTATGCAACATCTAGAATATCCATTCACG<br>TTCGGCTCGGGGACAAAGTTGGAAATAAAAGGGCTGATGCTGCACCAAC<br>TGTATCCATCTTCCCACCATCCAGTGAGCAGTTAACATCTGGAGGTGCCTC<br>AGTCGTGTGCTTCTTGAACAACTTCTACCCCAAAGACATCAATGTCAAGTG<br>GAAGATTGATGGCAGTGAACGACAAAATGGCGTCCTGAACAGTTGGACTG<br>ATCAGGACAGCAAAGACAGCACCTACAGCATGAGCAGCACCCTCACGTTG<br>ACCAAGGACGAGTATGAACGACATAACAGCTATACCTGTGAGGCCACTCA<br>CAAGACATCAACTTCACCCATTGTCAAGAGCTTCAACAGGAATGAGTCTT<br>ATCCATATGATGTGCCAGATTATGCGAGCTAA |
| 77 | VK n.t. PTA001_A8 | TAAGATTAGCGGATCCTACCTTACGCTTTTTATCGCAACTCTCTACTGTTTC<br>TCCATACCCGTTTTTTTGGATGGAGTGAAACGATGAAATACCTATTGCCTA<br>CGGCAGCCGCTGGATTGTTATTACTCGCTGCCCAACCAGCCATGGCCGAT<br>ATTGTGATGACCCAGGCTGCACCCTCTGTACCTGTCACTCCTGGAGAATCA<br>GTATCCATCTCCTGCAGGTCTAGTAAGAGTCTCCTGCGTAGTAATGGCAAC<br>ACTTACTTGTATTGGTTCCTGCAGAGGCCAGGCCAGTCTCCTCAGCTCCTG<br>ATATATCGGCTGTCTAACCTTGCCTCAGGAGTCCCAGACAGGTTCAGTGGC<br>AGTGGGTCAGGAACTGCTTTCACACTGAGAATCAGTAGAGTGGAGGCTGA<br>GGATGTGGGTGTTTATTACTGTATGCAACATCTAGAATATCCTTTCACATT<br>CGGCTCGGGGACAAAGTTGGAAATAAAACGGGCTGATGCTGCACCAACTG<br>TATCCATCTTCCCACCATCCAGTGAGCAGTTAACATCTGGAGGTGCCTCAG<br>TCGTGTGCTTCTTGAACAACTTCTACCCCAAAGACATCAATGTCAAGTGGA<br>AGATTGATGGCAGTGAACGACAAAATGGCGTCCTGAACAGTTGGACTGAT<br>CAGGACAGCAAAGACAGCACCTACAGCATGAGCAGCACCCTCACGTTGAC<br>CAAGGACGAGTATGAACGACATAACAGCTATACCTGTGAGGCCACTCACA<br>AGACATCAACTTCACCCATTGTCAAGAGCTTCAACAGGAATGAGTCTTAT<br>CCATATGATGTGCCAGATTATGCGAGCTAA |
| 78 | VK n.t. PTA001_A9 | TAAGATTAGCGGATCCTACCTGACGCTTTTTATCGCAACTCTCTACTGTTT<br>CTCCATACCCGTTTTTTTGGATGGAGTGAAACGATGAAATACCTATTGCCT<br>ACGGCAGCCGCTGGATTGTTATTACTCGCTGCCCAACCAGCCATGGCCGA<br>TATTGTGATGACCCAGGCTGCACCCTCTGTACCTGTCACTCCTGGAGAGTC<br>AGTATCCATCTCCTGCACGTCTAGTAAGAGTCTCCTGCGTAGTAATGGCAA<br>CACTTACTTGTATTGGTTCCTGCAGAGGCCAGGCCAGTCTCCTCAGCTCCT<br>GATATATCGGATGTCCAACCTTGCCTCGGGAGTCCCAGACAGGTTCAGTG<br>GCAGTGGGTCAGGAACTGCTTTCACACTGAGAATCAGTAGAGTGGAGGCT |

| SEQ ID NO | SEQUENCE DESCRIPTION | SEQUENCE |
|---|---|---|
| | | GAGGATGTGGGTGTTTATTACTGTATGCAACATCTAGAATATCCTTTCACG<br>TTCGGCTCGGGGACAAAGTTGGAAATAAAACGGGCTGATGCTGCACCAAC<br>TGTATCCATCTCCCCACCATCCAGTGAGCAGTTAACATCTGGAGGTGCCTC<br>AGTCGTGTGCTTCTTGAACAACTTCTACCCCAAAGACATCAATGTCAAGTG<br>GAAGATTGATGGCAGTGAACGACAAAATGGCGTCCTGAACAGTTGGACTG<br>ATCAGGACAGCAAAGACAGCACCTACAGCATGAGCAGCACCCTCACGTTG<br>ACCAAGGACGAGTATGAACGACATAACAGCTATACCTGTGAGGCCACTCA<br>CAAGACATCAACTTCACCCATTGTCAAGAGCTTCAACAGGAATGAGTCTT<br>ATCCATATGATGTGCCAGATTATGCGAGCTAA |
| 79 | VK n.t. PTA001_A10 | TAAGATTAGCGGATCCTACCTGACGCTTTTTATCGCAACTCTCTACTGTTT<br>CTCCATACCCGTTTTTTTGGATGGAGTGAAACGATGAAATACCTATTGCCT<br>ACGGCAGCCGCTGGATTGTTATTACTCGCTGCCCAACCAGCCATGGCCGA<br>TATTGTGATGACCCAGGCTGCACCCTCTGTACCTGTCACTCCTGGAGAGTC<br>AGTATCCATCTCCTGCAGGTCCAGTAAGAGTCTCCTGCGTAGTAATGGCA<br>ACACTTACTTGTATTGGTTCCTGCAGAGGCCAGGCCAGTCTCCTCAGCTCC<br>TCATATATCGGATGTCCAACCTTGCCTCAGGAGTCCCAGACAGGTTCAGTG<br>GCAGTGGGTCAGGAACTGCCTTCACACTGAGAATCAGTAGAGTGGAGGCT<br>GAGGATGTGGGTGTTTATTACTGTATGCAACATCTAGAATATCCTTTCACG<br>TTCGGAGGGGGGACCAAGCTGGAAATAAAACGGGCTGATGCTGCACCAA<br>CTGTATCCATCTTCCCACCATCCAGTGAGCAGTTAACATCTGGAGGTGCCT<br>CAGTCGTGTGCTTCTTGAACAACTTCTACCCCAAAGACATCAATGTCAAGT<br>GGAAGATTGATGGCAGTGAACGACAAAATGGCGTCCTGAACAGTTGGACT<br>GATCAGGACAGCAAAGACAGCACCTACAGCATGAGCAGCACCCTCACGTT<br>GACCAAGGACGAGTATGAACGACATAACAGCTATACCTGTGAGGCCACTC<br>ACAAGACATCAACTTCACCCATTGTCAAGAGCTTCAACAGGAATGAGTCT<br>TATCCATATGATGTGCCAGATTATGCGAGCTAA |
| 80 | VK n.t. PTA001_A11 | TAAGATTAGCGGATCCTACCTGACGCTTTTTATCGCAACTCTCTTCTGTTTC<br>TCCATACCCGTTTTTTTGGATGGAGTGAAACGATGAAATACCTATTGCCTA<br>CGGCAGCCGCTGGATTGTTATTACTCGCTGCCCAACCAGCCATGGCCGAT<br>ATTGTGATGACCCAGGCTGCACCCTCTGTATCTGTCACTCCTGGAGAGTCA<br>GTATCCATCTCCTGCAGGTCTACTAAGAGTCTCCTGCGTAGTAATGGCAAC<br>ACTTACTTGTATTGGTTCCTCCAGAGGCCAGGCCAGTCTCCTCAGCTCCTG<br>ATATATCGGATGTCCAACCTTGCCTCAGGAGTCCCAGACAGGTTCAGTGG<br>CAGTGGGTCAGGAACTGCTTTCACACTGAGAATCAGTAGAGTGGAGGCTG<br>AGGATGTGGGTGTTTATTACTGTATGCAACATCTAGAATATCCTTTCACGT<br>TCGGAGGGGGGACCAAGCTGGAAATAAAACGGGCTGATGCTGCACCAAC<br>TGTATCCATCTTCCCACCATCCAGTGAGCAGTTAACATCTGGAGGTGCCTC<br>AGTCGTGTGCTTCTTGAACAACTTCTACCCCAAAGACATCAATGTCAAGTG<br>GAAGATTGATGGCAGTGAACGACAAAATGGCGTCCTGAACAGTTGGACTG<br>ATCAGGACAGCAAAGACAGCACCTACAGCATGAGCAGCACCCTCACGTTG<br>ACCAAGGACGAGTATGAACGACATAACAGCTATACCTGTGAGGCCACTCA<br>CAAGACATCAACTTCACCCATTGTCAAGAGCTTCAACAGGAATGAGTCTT<br>ATCCATATGATGTGCCAGATTATGCGAGCTAA |
| 81 | VK n.t. PTA001_A12 | TAAGATTAGCGGATCCTACCTGACGCTTTTTATCGCAACTCTCTACTGTTT<br>CTCCATACCCGTTTTTTTGGATGGAGTGAAACGATGAAATACCTATTGCCT<br>ACGGCAGCCGCTGGATTGTTATTACTCGCTGCCCAACCAGCCATGGCCGA<br>TATTGTGATGACCCAGGCTGCACCCTCTGTACCTGTCACTCCTGGAGAGTC<br>AGTATCCATCTCCTGCAGGTCTAGTAAGAGTCTCCTACGTAGTAATGGCAA<br>CACTTACTTGTATTGGTTCCTGCAGAGGCCAGGCCAGTCTCCTCAGCTCCT<br>GATATATCGGATGTCCAACCTTGCCTCAGGAGTCCCAGACAGGTTCAGTG<br>GCAGTGGGTCAGGAACTGCCTTCACACTGAGAATCAGTAGAGTGGAGGCT<br>GAGGATGTGGGTGTTTATTACTGTATGCAACATCTAGAATATCCTTTCACG<br>TTCGGAGGGGGGACCAAGCTGGAAATAAAACGGGCTGATGCTGCACCAA<br>CTGTATCCATCTTCCCACCATCCAGTGAGCAGTTAACATCTGGAGGTGCCT<br>CAGTCGTGTGCTTCTTGAACAACTTCTACCCCAAAGACATCAATGTCAAGT<br>GGAAGATTGATGGCAGTGAACGACAAAATGGCGTCCTGAACAGTTGGACT<br>GATCAGGACAGCAAAGACAGCACCTACAGCATGAGCAGCACCCTCACGTT<br>GACCAAGGACGAGTATGAACGACATAACAGCTATACCTGTGAGGCCACTC<br>ACAAGACATCAACTTCACCCATTGTCAAGAGCTTCAACAGGAATGAGTCT<br>TATCCATATGATGTGCCAGATTATGCGAGCTAA |
| 82 | VK n.t. PTA001_A13 | TAAGATTAGCGGATCCTACCTGACGCTTTTTATCGCAACTCTCTACTGTTT<br>CTCCATACCCGTTTTTTTGGATGGAGTGAAACGATGAAATACCTATTGCCT<br>ACGGCAGCCGCTGGATTGTTATTACTCGCTGCCCAACCAGCCATGGCCGA<br>TATTGTGATGACCCAGGCTGCACCCTCTGTACCTGTCACTCCTGGAGAGTC<br>AGTATCCATCTCCTGCAGGTCTAGTAAGAGTCTCCTGCGCAGTAATGGCA<br>ACACTTACTTGTATTGGTTCCTGCAGAGGCCAGGCCAGTCTCCTCAGCTCC<br>TGATATATCGGCTGTCCAACCTTGCCTCAGGAGTCCCAGACAGGTTCAGTG<br>GCAGTGGGTCAGGAACTGCTTTCACACTGAGAATCAGTAGAGTGGAGGCT<br>GAGGATGTGGGTGTTTATTACTGTATGCAACATCTAGAATATCCTTTCACA<br>TTCGGCTCGGGGACAAAGTTGGAAATAAAACGGGCTGATGCTGCACCAAC |

| SEQ ID NO | SEQUENCE DESCRIPTION | SEQUENCE |
|---|---|---|
| | | TGTATCCATCTTCCCACAATACAGTGAGCAGTTAACAACTGGAGGTGCCTC AGTCGTGTGCTTCTTGAACAACTTCTACCCCAAAGACATCAATGTCAAGTG GAAGATTGATGGCAGTGAACGACAAAATGGCGTCCTGAACAGTTGGACTG ATCAGGACAGCAAAGACAGCACCTACAGCATGAGCAGCACCCTCACGTTG ACCAAGGACGAGTATGAACGACATAACAGCTATACCTGTGAGGCCACTCA CAAGACATCAACTTCACCCATTGTCAAGAGCTTCAACAGGAATGAGTCTT ATCCATATGATGTGCCAGATTATGCGAGCTAA |
| 83 | VK n.t. PTA001_A14 | CGGATCCTACCTGACGCTTTTTATCGCAACTCTCTACTGTTTCTCCATACCC GTTTTTTTGGATGGAGTGAAACGATGAAATACCTATTGCCTACGGCAGCC GCTGGATTGTTATTACTCGCTGCCCAACCAGCCATGGCCGATATTGTGATG ACCCAGGCTGCACCCTCTGTACCTGTCACTCCTGGAGAGTCAGTATCCATC TCCTGCACGTCTAGTAAGAGTCTCCTGCGTAGTAATGGCAACACTTACTTG TATTGGTTCCTGCAGAGGCCAGGCCAGTCTCCTCAGCTCCTGATATATCGG ATGTCCAACCTTGCCTCGGGAGTCCCAGACAGGTTCAGTGGCAGTGGGTC AGGAACTGCTTTCACACTGAGAATCAGTAGAGTGGAGGCTGAGGATGTGG GTGTTTATTACTGTATGCAACATCTAGAATATCCTTTCACGTTCGGCTCGG GGACAAATTTGGAAATAAAACGGGCTGATGCTGCACCAACTGTATCCATC TTCACAACATCCAGAGAGCAGTTAACATCTGGAGGTGCCTCAGTCGTGTG CTTCTTGAACAACTTCTACCCCAAAGACATCAATGTCAAG |
| 84 | VH CDR1 n.t. PTA001_A1 | GGATTCACTTTCAGTAACTATGGCATGTCT |
| 85 | VH CDR1 n.t. PTA001_A2, PTA001_A14 | GGCTACACCTTCAGTGACCATGCTATTCAC |
| 86 | VH CDR1 n.t. PTA001_A3, PTA001_A5, PTA001_A6, PTA001_A7, PTA001_A8, PTA001_A9, PTA001_A10, PTA001_A11, PTA001_A12, PTA001_A13 | GGCTACACCTTCACTGACCATGCTATTCAC |
| 87 | VH CDR1 n.t. PTA001_A4 | GGCTACACCCTCACTGACCATACTATTCAC |
| 88 | VH CDR2 n.t. PTA001_A1 | GCCATTAATCGTGATGGTGGTACCACCTACTATACAGACAATGTGAAGGGC |
| 89 | VH CDR2 n.t. PTA001_A2 | TATATTTATCCTAGACATGGGACTACTAACTACAATGAGAACTTCAAGGGC |
| 90 | VH CDR2 n.t. PTA001_A3, PTA001_A5, PTA001_A6, PTA001_A8, PTA001_A9, PTA001_A10 | TATATTTATCCTGAACATGGAACTATTAAGTATAATGAGAAGTTCAAGGGC |
| 91 | VH CDR2 n.t. PTA001_A4 | TATATTTACCCTAGAGATGGAATAACTGGGTACAATGAGAAGTTCAAGGGC |
| 92 | VH CDR2 n.t. PTA001_A7 | TATATTTATCCTAGAGATGGTTTTACTAAGTACAATGAGAAGTTCAAGGGC |
| 93 | VH CDR2 n.t. PTA001_A11 | TATATTTATCCTGAACATGGTAGTATTACGTATAATGAGAAGTTCAAGGGC |
| 94 | VH CDR2 n.t. PTA001_A12 | TATATCTACCCCAGAGATGATTTTGCTAAGGTGAATGAGAAGTTCAAGGGC |
| 95 | VH CDR2 n.t. PTA001_A13 | TATATTTATCCTGAACATGGTACTATTACGTATAATGAGAAGTTCAAGGGC |
| 96 | VH CDR2 n.t. PTA001_A14 | TATATTTTTCCTAGAGATGCTTTTAGTTTGAACAATGAGAAGTTCAAGGGC |
| 97 | VH CDR3 n.t. PTA001_A1 | TTCCTTCTCTGGGACGGCTGGTACTTCGATGTC |
| 98 | VH CDR3 n.t. PTA001_A2, PTA001_A14 | AGAAACTACTTCTATGTTATGGACTAC |
| 99 | VH CDR3 n.t. PTA001_A3, PTA001_A6, PTA001_A8, PTA001_A9, PTA001_A10 | ACTAACTACTTCTATGTTATGGAGTAT |
| 100 | VH CDR3 n.t. PTA001_A4 | GGCTATAGTTACAGGAATTACGCGTACTACTATGACTAC |
| 101 | VH CDR3 n.t. PTA001_A5, PTA001_A13 | AGGAACTATTTGTATATTATGGACTAC |
| 102 | VH CDR3 n.t. PTA001_A7 | ACTAACTACTTCTATACATGGACTAC |
| 103 | VH CDR3 n.t. PTA001_A11 | AGGAACTACTTGTATGTTATGGACTAC |

| SEQ ID NO | SEQUENCE DESCRIPTION | SEQUENCE |
|---|---|---|
| 104 | VH CDR3 n.t. PTA001_A12 | ACTAACTACCTCTATATTATGGACTAC |
| 105 | VK CDR1 n.t. PTA001_A1 | AGATCTAGTCAGAGCCTTTTACACAGTAATGGAAACACCTATTTACAT |
| 106 | VK CDR1 n.t. PTA001_A2, PTA001_A3, PTA001_A6, PTA001_A9, PTA001_A14 | ACGTCTAGTAAGAGTCTCCTGCGTAGTAATGGCAACACTTACTTGTAT |
| 107 | VK CDR1 n.t. PTA001_A4 | AAGTCCAGCCAGAGCCTTTTACATAGTAGCAATCAAAAGAACTACTTGGCC |
| 108 | VK CDR1 n.t. PTA001_A5, PTA001_A13 | AGGTCTAGTAAGAGTCTCCTGCGCAGTAATGGCAACACTTACTTGTAT |
| 109 | VK CDR1 n.t. PTA001_A7 | AGGTCTTCTAAGAGTCTCCTGCGTACTAATGGCAACACTTACTTGCAT |
| 110 | VK CDR1 n.t. PTA001_A8 | AGGTCTAGTAAGAGTCTCCTGCGTAGTAATGGCAACACTTACTTGTAT |
| 111 | VK CDR1 n.t. PTA001_A10 | AGGTCCAGTAAGAGTCTCCTGCGTAGTAATGGCAACACTTACTTGTAT |
| 112 | VK CDR1 n.t. PTA001_A11 | AGGTCTACTAAGAGTCTCCTGCGTAGTAATGGCAACACTTACTTGTAT |
| 113 | VK CDR1 n.t. PTA001_A12 | AGGTCTAGTAAGAGTCTCCTACGTAGTAATGGCAACACTTACTTGTAT |
| 114 | VK CDR2 n.t. PTA001_A1 | AAAGTTTCCAACCGATTTTCT |
| 115 | VK CDR2 n.t. PTA001_A2, PTA001_A3, PTA001_A6, PTA001_A9, PTA001_A14 | CGGATGTCCAACCTTGCCTCG |
| 116 | VK CDR2 n.t. PTA001_A4 | TGGGCATCCACTAGAGAATCT |
| 117 | VK CDR2 n.t. PTA001_A5, PTA001_A13 | CGGCTGTCCAACCTTGCCTCA |
| 118 | VK CDR2 n.t. PTA001_A7, PTA001_A10, PTA001_A11, PTA001_A12 | CGGATGTCCAACCTTGCCTCA |
| 119 | VK CDR2 n.t. PTA001_A8 | CGGCTGTCTAACCTTGCCTCA |
| 120 | VK CDR3 n.t. PTA001_A1 | TCTCAAAGTACACATGTGCTCACG |
| 121 | VK CDR3 n.t. PTA001_A2, PTA001_A3, PTA001_A6, PTA001_A9, PTA001_A10, PTA001_A11, PTA001_A12, PTA001_A14 | ATGCAACATCTAGAATATCCTTTCACG |
| 122 | VK CDR3 n.t. PTA001_A4 | CAGCAATATTATAGCTATCCGTGGACG |
| 123 | VK CDR3 n.t. PTA001_A5, PTA001_A8, PTA001_A13 | ATGCAACATCTAGAATATCCTTTCACA |
| 124 | VK CDR3 n.t. PTA001_A7 | ATGCAACATCTAGAATATCCATTCACG |
| 125 | VH7-39 (Genbank AJ851868.3) n.t. 240-269 | GGATTCACTTTCAGTAGCTATGGCATGTCT |
| 126 | VHII gene H17 (GenBank X02466.1) n.t. 67-96 | GGCTACACCTTCACTGACCATACTATTCAC |
| 127 | VHII region VH105 (Genbank J00507) n.t. 1096-1146 | TATATTTATCCTAGAGATGGTAGTACTAAGTACAATGAGAAGTTCAAGGGC |
| 128 | VK1-110 (GenBank AY591695.1) n.t. 1738-1785 | AGATCTAGTCAGAGCCTTGTACACAGTAATGGAAACACCTATTTACAT |
| 129 | VK1-110 (GenBank AY591695.1) n.t. 1948-1971 | TCTCAAAGTACACATGTTCCTCCC |
| 130 | VK8-30 (GenBank AJ235948.1) n.t. 510-560 | AAGTCCAGTCAGAGCCTTTTATATAGTAGCAATCAAAAGAACTACTTGGCC |
| 131 | VK8-30 (GenBank | TGGGCATCCACTAGGGAATCT |

| SEQ ID NO | SEQUENCE DESCRIPTION | SEQUENCE |
|---|---|---|
| | AJ235948.1) n.t. 606-626 | |
| 132 | VK8-30 (GenBank AJ235948.1) n.t. 723-749 | CAGCAATATTATAGCTATCCTCCCACA |
| 133 | VK24-140 (GenBank AY591710.1) n.t. 1807-1854 | AGGTCTAGTAAGAGTCTCCTGCATAGTAATGGCAACACTTACTTGTAT |
| 134 | VK24-140 (GenBank AY591710.1) n.t. 1900-1920 | CGGATGTCCAACCTTGCCTCA |
| 135 | VK24-140 (GenBank AY591710.1) n.t. 2017-2043 | ATGCAACATCTAGAATATCCTTTCACA |
| 136 | Cadherin-17 ECD domains 1-2 | QEGKFSGPLKPMTFSIYEGQEPSQIIFQFKANPPAVTFELTGETDNIFVIEREGLL YYNRALDRETRSTHNLQVAALDANGIIVEGPVPITIKVKDINDNRPTFLQSKYE GSVRQNSRPGKPFLYVNATDLDDPATPNGQLYYQIVIQLPMINNVMYFQINN KTGAISLTREGSQELNPAKNPSYNLVISVKDMGGQSENSFSDTTSVDIIVTENI WKAPKP |
| 137 | Cadherin-17 ECD | QEGKFSGPLKPMTFSIYEGQEPSQIIFQFKANPPAVTFELTGETDNIFVIEREGLL YYNRALDRETRSTHNLQVAALDANGIIVEGPVPITIKVKDINDNRPTFLQSKYE GSVRQNSRPGKPFLYVNATDLDDPATPNGQLYYQIVIQLPMINNVMYFQINN KTGAISLTREGSQELNPAKNPSYNLVISVKDMGGQSENSFSDTTSVDIIVTENI WKAPKPVEMVENSTDPHPIKITQVRWNDPGAQYSLVDKEKLPRFPPFSIDQEG DIYVTQPLDREEKDAYVFYAVAKDEYGKPLSYPLEIHVKVKDINDNPPTCPSP VTVFEVQENERLGNSIGTLTAHDRDEENTANSFLNYRIVEQTPKLPMDGLFLI QTYAGMLQLAKQSLKKQDTPQYNLTIEVSDKDFKTLCFVQINVIDINDQIPIFE KSDYGNLTLAEDTNIGSTILTIQATDADEPFTGSSKILYHIIKGDSEGRLGVDTD PHTNTGYVIIKKPLDFETAAVSNIVFKAENPEPLVFGVKYNASSFAKFTLIVTD VNEAPQFSQHVFQAKVSEDVAIGTKVGNVTAKDPEGLDISYSLRGDTRGWLK IDHVTGEIFSVAPLDREAGSPYRVQVVATEVGGSSLSSVSEFHLILMDVNDNPP RLAKDYTGLFFCHPLSAPGSLIFEATDDDQHLFRGPHFTFSLGSGSLQNDWEV SKINGTHARLSTRHTDFEEREYVVLIRINDGGRPPLEGIVSLPVTFCSCVEGSCF RPAGHQTGIPTVGM |
| 138 | Mature VH amino acid PTA001_A4 (without leader sequence) | EVQLQQSVAELVKPGASVKMSCKVSGYTLTDHTIHWMKQRPEQGLEWIGYI YPRDGITGYNEKFKGKATLTADTSSSTAYMQLNSLTSEDSAVYFCARWGYSY RNYAYYYDYWGQGTTLTVSS |
| 139 | Mature VK amino acid PTA001_A4 (without leader sequence) | DIVMSQSPSSLAVSVGEKVTMSCKSSQSLLHSSNQKNYLAWYQQKPGQSPKVLIY WASTR ESGVPDRFTGSGSGTDFTLTITSVKSEDLAVYYCQQYYSYPWTFGGGTRLEIKRA |

What is claimed is:

1. An isolated anti-Cadherin-17 antibody comprising:
   a. a heavy chain variable region comprising
      i. a CDR1 of SEQ ID NO:4
      ii. a CDR2 of SEQ ID NO:8 and
      iii. a CDR3 of SEQ ID NO:17; and
   b. a light chain variable region comprising
      i. a CDR1 of SEQ ID NO:24
      ii. a CDR2 of SEQ ID NO:30 and
      iii. a CDR3 of SEQ ID NO:34.

2. The antibody of claim 1, wherein said antibody is a full-length antibody of an IgG1, IgG2, IgG3, or IgG4 isotype.

3. The antibody of claim 1, wherein said antibody is selected from the group consisting of: a whole antibody, a monoclonal antibody, an antibody fragment, a humanized antibody, a single chain antibody, a defucosylated antibody, an antibody mimetic and a bispecific antibody.

4. An isolated nucleic acid molecule encoding the heavy or light chain of the antibody of claim 1.

5. An expression vector comprising the nucleic acid molecule of claim 4.

6. A host cell comprising the expression vector of claim 5.

7. A method for preparing an anti-Cadherin-17 antibody, said method comprising the steps of:
   obtaining a host cell that contains one or more nucleic acid molecules encoding the antibody of claim 1;
   growing the host cell in a host cell culture; providing host cell culture conditions wherein the one or more nucleic acid molecules are expressed; and recovering the antibody from the host cell or from the host cell culture.

8. An isolated anti-Cadherin-17 antibody comprising a heavy chain variable region comprising the mature portion of SEQ ID NO:38 and a light chain variable region comprising the mature portion of SEQ ID NO:49.

9. An isolated anti-Cadherin-17 antibody according to claim 1 comprising a heavy chain variable region comprising SEQ ID NO: 138, or an amino acid sequence at least 95% identical thereto, and a light chain variable region comprising SEQ ID NO: 139, or an amino acid sequence at least 95% identical thereto.

10. The isolated anti-Cadherin-17 antibody of claim 8, wherein the antibody comprises a heavy chain variable region comprising SEQ ID NO: 138 and a light chain variable region comprising SEQ ID NO: 139.

11. An immunoconjugate comprising an antibody according to any one of claims 1 and 8-10 conjugated to a therapeutic agent.

12. The immunoconjugate of claim 11 wherein the therapeutic agent is a cytotoxin.

13. A composition comprising the isolated antibody of any one of claims 1 and 8-10 and a pharmaceutically acceptable carrier.

14. A method for treating cancer associated with target cancer cells expressing Cadherin-17, said method comprising the step of administering to a subject the immunoconjugate of claim 11, in an amount effective to treat the cancer.

15. The method of claim 14, wherein said cancer is a human cancer.

16. The method of claim 15, wherein said human cancer is colorectal cancer.

17. The method of claim 15, wherein said human cancer is gastric cancer or pancreatic cancer.

* * * * *

SEQUENCE LISTING

<160> NUMBER OF SEQ ID NOS: 139

<210> SEQ ID NO 1
<211> LENGTH: 10
<212> TYPE: PRT
<213> ORGANISM: Homo sapiens

<400> SEQUENCE: 1

Gly Phe Thr Phe Ser Asn Tyr Gly Met Ser
1               5                   10

<210> SEQ ID NO 2
<211> LENGTH: 10
<212> TYPE: PRT
<213> ORGANISM: Homo sapiens

<400> SEQUENCE: 2

Gly Tyr Thr Phe Ser Asp His Ala Ile His
1               5                   10

<210> SEQ ID NO 3
<211> LENGTH: 10
<212> TYPE: PRT
<213> ORGANISM: Homo sapiens

<400> SEQUENCE: 3

Gly Tyr Thr Phe Thr Asp His Ala Ile His
1               5                   10

<210> SEQ ID NO 4
<211> LENGTH: 10
<212> TYPE: PRT
<213> ORGANISM: Homo sapiens

<400> SEQUENCE: 4

Gly Tyr Thr Leu Thr Asp His Thr Ile His
1               5                   10

<210> SEQ ID NO 5
<211> LENGTH: 17
<212> TYPE: PRT
<213> ORGANISM: Homo sapiens

<400> SEQUENCE: 5

Ala Ile Asn Arg Asp Gly Gly Thr Thr Tyr Tyr Thr Asp Asn Val Lys
1               5                   10                  15

Gly

<210> SEQ ID NO 6
<211> LENGTH: 17
<212> TYPE: PRT
<213> ORGANISM: Homo sapiens

<400> SEQUENCE: 6

Tyr Ile Tyr Pro Arg His Gly Thr Thr Asn Tyr Asn Glu Asn Phe Lys
1               5                   10                  15

Gly

<210> SEQ ID NO 7
<211> LENGTH: 17
<212> TYPE: PRT
<213> ORGANISM: Homo sapiens

<400> SEQUENCE: 7

Tyr Ile Tyr Pro Glu His Gly Thr Ile Lys Tyr Asn Glu Lys Phe Lys
1               5                   10                  15

Gly

<210> SEQ ID NO 8
<211> LENGTH: 17
<212> TYPE: PRT
<213> ORGANISM: Homo sapiens

<400> SEQUENCE: 8

Tyr Ile Tyr Pro Arg Asp Gly Ile Thr Gly Tyr Asn Glu Lys Phe Lys
1               5                   10                  15

Gly

<210> SEQ ID NO 9
<211> LENGTH: 17
<212> TYPE: PRT
<213> ORGANISM: Homo sapiens

-continued

<400> SEQUENCE: 9

Tyr Ile Tyr Pro Arg Asp Gly Phe Thr Lys Tyr Asn Glu Lys Phe Lys
1               5                   10                  15

Gly

<210> SEQ ID NO 10
<211> LENGTH: 17
<212> TYPE: PRT
<213> ORGANISM: Homo sapiens

<400> SEQUENCE: 10

Tyr Ile Tyr Pro Glu His Gly Ser Ile Thr Tyr Asn Glu Lys Phe Lys
1               5                   10                  15

Gly

<210> SEQ ID NO 11
<211> LENGTH: 17
<212> TYPE: PRT
<213> ORGANISM: Homo sapiens

<400> SEQUENCE: 11

Tyr Ile Tyr Pro Arg Asp Asp Phe Ala Lys Val Asn Glu Lys Phe Lys
1               5                   10                  15

Gly

<210> SEQ ID NO 12
<211> LENGTH: 17
<212> TYPE: PRT
<213> ORGANISM: Homo sapiens

<400> SEQUENCE: 12

Tyr Ile Tyr Pro Glu His Gly Thr Ile Thr Tyr Asn Glu Lys Phe Lys
1               5                   10                  15

Gly

<210> SEQ ID NO 13
<211> LENGTH: 17
<212> TYPE: PRT
<213> ORGANISM: Homo sapiens

<400> SEQUENCE: 13

Tyr Ile Phe Pro Arg Asp Ala Phe Ser Leu Asn Asn Glu Lys Phe Lys
1               5                   10                  15

Gly

<210> SEQ ID NO 14
<211> LENGTH: 11
<212> TYPE: PRT
<213> ORGANISM: Homo sapiens

<400> SEQUENCE: 14

Phe Leu Leu Trp Asp Gly Trp Tyr Phe Asp Val
1               5                   10

<210> SEQ ID NO 15
<211> LENGTH: 9
<212> TYPE: PRT
<213> ORGANISM: Homo sapiens

<400> SEQUENCE: 15

Arg Asn Tyr Phe Tyr Val Met Asp Tyr

<210> SEQ ID NO 16
<211> LENGTH: 9
<212> TYPE: PRT
<213> ORGANISM: Homo sapiens

<400> SEQUENCE: 16

Thr Asn Tyr Phe Tyr Val Met Glu Tyr
1               5

<210> SEQ ID NO 17
<211> LENGTH: 13
<212> TYPE: PRT
<213> ORGANISM: Homo sapiens

<400> SEQUENCE: 17

Gly Tyr Ser Tyr Arg Asn Tyr Ala Tyr Tyr Tyr Asp Tyr
1               5                   10

<210> SEQ ID NO 18
<211> LENGTH: 9
<212> TYPE: PRT
<213> ORGANISM: Homo sapiens

<400> SEQUENCE: 18

Arg Asn Tyr Leu Tyr Ile Met Asp Tyr
1               5

<210> SEQ ID NO 19
<211> LENGTH: 9
<212> TYPE: PRT
<213> ORGANISM: Homo sapiens

<400> SEQUENCE: 19

Thr Asn Tyr Phe Tyr Thr Met Asp Tyr
1               5

<210> SEQ ID NO 20
<211> LENGTH: 9
<212> TYPE: PRT
<213> ORGANISM: Homo sapiens

<400> SEQUENCE: 20

Arg Asn Tyr Leu Tyr Val Met Asp Tyr
1               5

<210> SEQ ID NO 21
<211> LENGTH: 9
<212> TYPE: PRT
<213> ORGANISM: Homo sapiens

<400> SEQUENCE: 21

Thr Asn Tyr Leu Tyr Ile Met Asp Tyr
1               5

<210> SEQ ID NO 22
<211> LENGTH: 16
<212> TYPE: PRT
<213> ORGANISM: Homo sapiens

<400> SEQUENCE: 22

Arg Ser Ser Gln Ser Leu Leu His Ser Asn Gly Asn Thr Tyr Leu His
1               5                   10                  15

<210> SEQ ID NO 23
<211> LENGTH: 16
<212> TYPE: PRT
<213> ORGANISM: Homo sapiens

<400> SEQUENCE: 23

Thr Ser Ser Lys Ser Leu Leu Arg Ser Asn Gly Asn Thr Tyr Leu Tyr
1               5                   10                  15

<210> SEQ ID NO 24
<211> LENGTH: 17
<212> TYPE: PRT
<213> ORGANISM: Homo sapiens

<400> SEQUENCE: 24

Lys Ser Ser Gln Ser Leu Leu His Ser Ser Asn Gln Lys Asn Tyr Leu
1               5                   10                  15

Ala

<210> SEQ ID NO 25
<211> LENGTH: 16
<212> TYPE: PRT
<213> ORGANISM: Homo sapiens

<400> SEQUENCE: 25

Arg Ser Ser Lys Ser Leu Leu Arg Ser Asn Gly Asn Thr Tyr Leu Tyr
1               5                   10                  15

<210> SEQ ID NO 26
<211> LENGTH: 16
<212> TYPE: PRT
<213> ORGANISM: Homo sapiens

<400> SEQUENCE: 26

Arg Ser Ser Lys Ser Leu Leu Arg Thr Asn Gly Asn Thr Tyr Leu His
1               5                   10                  15

<210> SEQ ID NO 27
<211> LENGTH: 16
<212> TYPE: PRT
<213> ORGANISM: Homo sapiens

<400> SEQUENCE: 27

Arg Ser Thr Lys Ser Leu Leu Arg Ser Asn Gly Asn Thr Tyr Leu Tyr
1               5                   10                  15

<210> SEQ ID NO 28
<211> LENGTH: 7
<212> TYPE: PRT
<213> ORGANISM: Homo sapiens

<400> SEQUENCE: 28

Lys Val Ser Asn Arg Phe Ser
1               5

<210> SEQ ID NO 29
<211> LENGTH: 7
<212> TYPE: PRT
<213> ORGANISM: Homo sapiens

<400> SEQUENCE: 29

Arg Met Ser Asn Leu Ala Ser
1               5

```
<210> SEQ ID NO 30
<211> LENGTH: 7
<212> TYPE: PRT
<213> ORGANISM: Homo sapiens

<400> SEQUENCE: 30

Trp Ala Ser Thr Arg Glu Ser
1               5

<210> SEQ ID NO 31
<211> LENGTH: 7
<212> TYPE: PRT
<213> ORGANISM: Homo sapiens

<400> SEQUENCE: 31

Arg Leu Ser Asn Leu Ala Ser
1               5

<210> SEQ ID NO 32
<211> LENGTH: 8
<212> TYPE: PRT
<213> ORGANISM: Homo sapiens

<400> SEQUENCE: 32

Ser Gln Ser Thr His Val Leu Thr
1               5

<210> SEQ ID NO 33
<211> LENGTH: 9
<212> TYPE: PRT
<213> ORGANISM: Homo sapiens

<400> SEQUENCE: 33

Met Gln His Leu Glu Tyr Pro Phe Thr
1               5

<210> SEQ ID NO 34
<211> LENGTH: 9
<212> TYPE: PRT
<213> ORGANISM: Homo sapiens

<400> SEQUENCE: 34

Gln Gln Tyr Tyr Ser Tyr Pro Trp Thr
1               5

<210> SEQ ID NO 35
<211> LENGTH: 260
<212> TYPE: PRT
<213> ORGANISM: Homo sapiens

<400> SEQUENCE: 35

Leu Gly Lys Pro Trp Arg Tyr Pro Arg Phe Val His Gly Glu Asn Lys
1               5                   10                  15

Val Lys Gln Ser Thr Ile Ala Leu Ala Leu Pro Leu Leu Phe Thr
            20                  25                  30

Pro Val Ala Lys Ala Glu Val Gln Leu Leu Glu Thr Gly Gly Gly Val
        35                  40                  45

Val Lys Pro Gly Gly Ser Leu Lys Leu Ser Cys Ala Ala Ser Gly Phe
    50                  55                  60

Thr Phe Ser Asn Tyr Gly Met Ser Trp Val Arg Gln Thr Pro Glu Lys
65                  70                  75                  80

Arg Leu Glu Trp Val Ala Ala Ile Asn Arg Asp Gly Gly Thr Thr Tyr
```

```
                        85                  90                  95
Tyr Thr Asp Asn Val Lys Gly Arg Phe Thr Ile Ser Arg Asp Asn Ala
                100                 105                 110
Lys Asn Ser Leu Tyr Leu Gln Met Ser Ser Leu Arg Ser Glu Asp Thr
            115                 120                 125
Ala Leu Tyr Tyr Cys Ala Arg Gln Phe Leu Leu Trp Asp Gly Trp Tyr
        130                 135                 140
Phe Asp Val Trp Gly Ala Gly Thr Thr Val Thr Val Ser Ser Ala Lys
145                 150                 155                 160
Thr Thr Pro Pro Ser Val Tyr Pro Leu Ala Pro Gly Ser Ala Ala Gln
                165                 170                 175
Thr Asn Ser Met Val Thr Leu Gly Cys Leu Val Lys Gly Tyr Phe Pro
            180                 185                 190
Glu Pro Val Thr Val Thr Trp Asn Ser Gly Ser Leu Ser Ser Gly Val
        195                 200                 205
His Thr Phe Pro Ala Val Leu Gln Ser Asp Leu Tyr Thr Leu Ser Ser
    210                 215                 220
Ser Val Thr Val Pro Ser Ser Thr Trp Pro Ser Glu Thr Val Thr Cys
225                 230                 235                 240
Asn Val Ala His Pro Ala Ser Ser Thr Lys Val Asp Lys Lys Ile Val
                245                 250                 255
Pro Arg Asp Cys
        260

<210> SEQ ID NO 36
<211> LENGTH: 258
<212> TYPE: PRT
<213> ORGANISM: Homo sapiens

<400> SEQUENCE: 36

Leu Gly Lys Pro Trp Arg Tyr Pro Arg Phe Val His Gly Glu Asn Lys
1               5                   10                  15
Val Lys Gln Ser Thr Ile Ala Leu Ala Leu Leu Pro Leu Leu Phe Thr
            20                  25                  30
Pro Val Ala Lys Ala Gln Val Gln Leu Gln Gln Ser Asp Ala Glu Leu
        35                  40                  45
Val Lys Pro Gly Ala Ser Val Lys Ile Ser Cys Lys Val Ser Gly Tyr
    50                  55                  60
Thr Phe Ser Asp His Ala Ile His Trp Met Ser Gln Arg Pro Gly Gln
65                  70                  75                  80
Gly Leu Lys Trp Ile Gly Tyr Ile Tyr Pro Arg His Gly Thr Thr Asn
                85                  90                  95
Tyr Asn Glu Asn Phe Lys Gly Lys Ala Thr Leu Thr Ala Asp Thr Ser
                100                 105                 110
Ser Ser Thr Ala Tyr Met Gln Leu Asn Ser Leu Thr Ser Glu Asp Ser
            115                 120                 125
Ala Val Tyr Phe Cys Ala Arg Met Arg Asn Tyr Phe Tyr Val Met Asp
        130                 135                 140
Tyr Trp Gly Gln Gly Thr Ser Val Thr Val Ser Ser Ala Lys Thr Thr
145                 150                 155                 160
Pro Pro Ser Val Tyr Pro Leu Ala Pro Gly Ser Ala Ala Gln Thr Asn
                165                 170                 175
Ser Met Val Thr Leu Gly Cys Leu Val Lys Gly Tyr Phe Pro Glu Pro
            180                 185                 190
```

```
Val Thr Val Thr Trp Asn Ser Gly Ser Leu Ser Ser Gly Val His Thr
            195                 200                 205

Phe Pro Ala Val Leu Gln Ser Asp Leu Tyr Thr Leu Ser Ser Ser Val
        210                 215                 220

Thr Val Pro Ser Ser Thr Trp Pro Ser Glu Thr Val Thr Cys Asn Val
225                 230                 235                 240

Ala His Pro Ala Ser Ser Thr Lys Val Asp Lys Lys Ile Val Pro Arg
                245                 250                 255

Asp Cys

<210> SEQ ID NO 37
<211> LENGTH: 258
<212> TYPE: PRT
<213> ORGANISM: Homo sapiens

<400> SEQUENCE: 37

Leu Gly Lys Pro Trp Arg Tyr Pro Arg Phe Val His Gly Glu Asn Lys
1               5                   10                  15

Val Lys Gln Ser Thr Ile Ala Leu Ala Leu Pro Leu Leu Phe Thr
            20                  25                  30

Pro Val Ala Lys Ala Gln Val Leu Leu Gln Gln Ser Asp Ala Glu Leu
        35                  40                  45

Val Lys Pro Gly Ala Ser Val Lys Ile Ser Cys Lys Ala Ser Gly Tyr
    50                  55                  60

Thr Phe Thr Asp His Ala Ile His Trp Val Lys Gln Arg Pro Glu Gln
65              70                  75                  80

Gly Leu Glu Trp Ile Gly Tyr Ile Tyr Pro Glu His Gly Thr Ile Lys
                85                  90                  95

Tyr Asn Glu Lys Phe Lys Gly Lys Ala Thr Leu Thr Ala Asp Lys Ser
            100                 105                 110

Ser Ser Thr Ala Tyr Met Gln Leu Asn Ser Leu Thr Ser Glu Asp Ser
        115                 120                 125

Ala Val Tyr Phe Cys Ser Arg Leu Thr Asn Tyr Phe Tyr Val Met Glu
    130                 135                 140

Tyr Trp Gly Gln Gly Thr Ser Val Thr Val Ser Ser Ala Lys Thr Thr
145                 150                 155                 160

Pro Pro Ser Val Tyr Pro Leu Ala Pro Gly Ser Ala Ala Gln Thr Asn
                165                 170                 175

Ser Met Val Thr Leu Gly Cys Leu Val Lys Gly Tyr Phe Pro Glu Pro
            180                 185                 190

Val Thr Val Thr Trp Asn Ser Gly Ser Leu Ser Ser Gly Val His Thr
        195                 200                 205

Phe Pro Ala Val Leu Gln Ser Asp Leu Tyr Thr Leu Ser Ser Ser Val
    210                 215                 220

Thr Val Pro Ser Ser Thr Trp Pro Ser Glu Thr Val Thr Cys Asn Val
225                 230                 235                 240

Ala His Pro Ala Ser Ser Thr Lys Val Asp Lys Lys Ile Val Pro Arg
                245                 250                 255

Asp Cys

<210> SEQ ID NO 38
<211> LENGTH: 262
<212> TYPE: PRT
<213> ORGANISM: Homo sapiens

<400> SEQUENCE: 38
```

```
Leu Gly Lys Pro Trp Arg Tyr Pro Arg Phe Val His Gly Glu Asn Lys
1               5                   10                  15

Val Lys Gln Ser Thr Ile Ala Leu Ala Leu Leu Pro Leu Leu Phe Thr
            20                  25                  30

Pro Val Ala Lys Ala Glu Val Gln Leu Gln Gln Ser Val Ala Glu Leu
                35                  40                  45

Val Lys Pro Gly Ala Ser Val Lys Met Ser Cys Lys Val Ser Gly Tyr
50                  55                  60

Thr Leu Thr Asp His Thr Ile His Trp Met Lys Gln Arg Pro Glu Gln
65                  70                  75                  80

Gly Leu Glu Trp Ile Gly Tyr Ile Tyr Pro Arg Asp Gly Ile Thr Gly
                85                  90                  95

Tyr Asn Glu Lys Phe Lys Gly Lys Ala Thr Leu Thr Ala Asp Thr Ser
                100                 105                 110

Ser Ser Thr Ala Tyr Met Gln Leu Asn Ser Leu Thr Ser Glu Asp Ser
            115                 120                 125

Ala Val Tyr Phe Cys Ala Arg Trp Gly Tyr Ser Tyr Arg Asn Tyr Ala
        130                 135                 140

Tyr Tyr Tyr Asp Tyr Trp Gly Gln Gly Thr Thr Leu Thr Val Ser Ser
145                 150                 155                 160

Ala Lys Thr Thr Pro Pro Ser Val Tyr Pro Leu Ala Pro Gly Ser Ala
                165                 170                 175

Ala Gln Thr Asn Ser Met Val Thr Leu Gly Cys Leu Val Lys Gly Tyr
                180                 185                 190

Phe Pro Glu Pro Val Thr Val Thr Trp Asn Ser Gly Ser Leu Ser Ser
            195                 200                 205

Gly Val His Thr Phe Pro Ala Val Leu Gln Ser Asp Leu Tyr Thr Leu
        210                 215                 220

Ser Ser Ser Val Thr Val Pro Ser Ser Thr Trp Pro Ser Glu Thr Val
225                 230                 235                 240

Thr Cys Asn Val Ala His Pro Ala Ser Ser Thr Lys Val Asp Lys Lys
                245                 250                 255

Ile Val Pro Arg Asp Cys
            260

<210> SEQ ID NO 39
<211> LENGTH: 258
<212> TYPE: PRT
<213> ORGANISM: Homo sapiens

<400> SEQUENCE: 39

Leu Gly Lys Pro Trp Arg Tyr Pro Arg Phe Val His Gly Glu Asn Lys
1               5                   10                  15

Val Lys Gln Ser Thr Ile Ala Leu Ala Leu Leu Pro Leu Leu Phe Thr
            20                  25                  30

Pro Val Ala Lys Ala Gln Val Gln Leu Gln Gln Ser Asp Ala Asp Leu
                35                  40                  45

Val Lys Pro Gly Ala Ser Val Lys Ile Ser Cys Lys Ala Ser Gly Tyr
50                  55                  60

Thr Phe Thr Asp His Ala Ile His Trp Val Lys Gln Arg Pro Glu Gln
65                  70                  75                  80

Gly Leu Glu Trp Ile Gly Tyr Ile Tyr Pro Glu His Gly Thr Ile Lys
                85                  90                  95

Tyr Asn Glu Lys Phe Lys Gly Lys Ala Thr Leu Thr Ala Asp Lys Ser
```

```
            100                 105                 110
Ser Ser Thr Ala Tyr Met Gln Leu Asn Ser Leu Thr Ser Glu Asp Ser
        115                 120                 125

Ala Val Tyr Phe Cys Ala Arg Leu Arg Asn Tyr Leu Tyr Ile Met Asp
        130                 135                 140

Tyr Trp Gly Gln Gly Thr Ser Val Thr Val Ser Ser Ala Lys Thr Thr
145                 150                 155                 160

Pro Pro Ser Val Tyr Pro Leu Ala Pro Gly Ser Ala Ala Gln Thr Asn
                165                 170                 175

Ser Met Val Thr Leu Gly Cys Leu Val Lys Gly Tyr Phe Pro Glu Pro
                180                 185                 190

Val Thr Val Thr Trp Asn Ser Gly Ser Leu Ser Ser Gly Val His Thr
                195                 200                 205

Phe Pro Ala Val Leu Gln Ser Asp Leu Tyr Thr Leu Ser Ser Ser Val
        210                 215                 220

Thr Val Pro Ser Ser Thr Trp Pro Ser Glu Thr Val Thr Cys Asn Val
225                 230                 235                 240

Ala His Pro Ala Ser Ser Thr Lys Val Asp Lys Lys Ile Val Pro Arg
                245                 250                 255

Asp Cys

<210> SEQ ID NO 40
<211> LENGTH: 258
<212> TYPE: PRT
<213> ORGANISM: Homo sapiens

<400> SEQUENCE: 40

Leu Gly Lys Pro Trp Arg Tyr Pro Arg Phe Val His Gly Glu Asn Lys
1               5                   10                  15

Val Lys Gln Ser Thr Ile Ala Leu Ala Leu Pro Leu Leu Phe Thr
            20                  25                  30

Pro Val Ala Lys Ala Gln Val Gln Leu Gln Gln Ser Asp Ala Glu Leu
        35                  40                  45

Val Lys Pro Gly Ala Ser Val Lys Ile Ser Cys Lys Ala Ser Gly Tyr
    50                  55                  60

Thr Phe Thr Asp His Ala Ile His Trp Val Lys Gln Arg Pro Glu Gln
65                  70                  75                  80

Gly Leu Glu Trp Ile Gly Tyr Ile Tyr Pro Glu His Gly Thr Ile Lys
                85                  90                  95

Tyr Asn Glu Lys Phe Lys Gly Lys Ala Thr Leu Thr Ala Asp Lys Ser
            100                 105                 110

Ser Ser Thr Ala Tyr Met Gln Leu Asn Ser Leu Thr Ser Glu Asp Ser
        115                 120                 125

Ala Val Tyr Phe Cys Ser Arg Leu Thr Asn Tyr Phe Tyr Val Met Glu
        130                 135                 140

Tyr Trp Gly Gln Gly Thr Ser Val Thr Val Ser Ser Ala Lys Thr Thr
145                 150                 155                 160

Pro Pro Ser Val Tyr Pro Leu Ala Pro Gly Ser Ala Ala Gln Thr Asn
                165                 170                 175

Ser Met Val Thr Leu Gly Cys Leu Val Lys Gly Tyr Phe Pro Glu Pro
                180                 185                 190

Val Thr Val Thr Trp Asn Ser Gly Ser Leu Ser Ser Gly Val His Thr
                195                 200                 205

Phe Pro Ala Val Leu Gln Ser Asp Leu Tyr Thr Leu Ser Ser Ser Val
```

Thr Val Pro Ser Ser Thr Trp Pro Ser Glu Thr Val Thr Cys Asn Val
225                 230                 235                 240

Ala His Pro Ala Ser Ser Thr Lys Val Asp Lys Lys Ile Val Pro Arg
                245                 250                 255

Asp Cys

<210> SEQ ID NO 41
<211> LENGTH: 258
<212> TYPE: PRT
<213> ORGANISM: Homo sapiens

<400> SEQUENCE: 41

Leu Gly Lys Pro Trp Arg Tyr Pro Arg Phe Val His Gly Glu Asn Lys
1               5                   10                  15

Val Lys Gln Ser Thr Ile Ala Leu Ala Leu Pro Leu Leu Phe Thr
                20                  25                  30

Pro Val Ala Lys Ala Gln Val Gln Leu Gln Gln Ser Asp Ala Glu Leu
            35                  40                  45

Val Lys Pro Gly Ala Ser Val Lys Ile Ser Cys Lys Val Ser Gly Tyr
    50                  55                  60

Thr Phe Thr Asp His Ala Ile His Trp Met Lys Gln Arg Pro Glu Gln
65                  70                  75                  80

Gly Leu Glu Trp Ile Gly Tyr Ile Tyr Pro Arg Asp Gly Phe Thr Lys
                85                  90                  95

Tyr Asn Glu Lys Phe Lys Gly Lys Ala Thr Leu Thr Ala Asp Thr Ser
            100                 105                 110

Ser Ser Thr Ala Tyr Met Gln Leu Asn Ser Leu Thr Ser Glu Asp Ser
        115                 120                 125

Thr Val Tyr Phe Cys Ala Arg Met Thr Asn Tyr Phe Tyr Thr Met Asp
130                 135                 140

Tyr Trp Gly Gln Gly Thr Ser Val Thr Val Ser Ser Ala Lys Thr Thr
145                 150                 155                 160

Pro Pro Ser Val Tyr Pro Leu Ala Pro Gly Ser Ala Ala Gln Thr Asn
                165                 170                 175

Ser Met Val Thr Leu Gly Cys Leu Val Lys Gly Tyr Phe Pro Glu Pro
            180                 185                 190

Val Thr Val Thr Trp Asn Ser Gly Ser Leu Ser Ser Gly Val His Thr
        195                 200                 205

Phe Pro Ala Val Leu Gln Ser Asp Leu Tyr Thr Leu Ser Ser Ser Val
210                 215                 220

Thr Val Pro Ser Ser Thr Trp Pro Ser Glu Thr Val Thr Cys Asn Val
225                 230                 235                 240

Ala His Pro Ala Ser Ser Thr Lys Val Asp Lys Lys Ile Val Pro Arg
                245                 250                 255

Asp Cys

<210> SEQ ID NO 42
<211> LENGTH: 258
<212> TYPE: PRT
<213> ORGANISM: Homo sapiens

<400> SEQUENCE: 42

Leu Gly Lys Pro Trp Arg Tyr Pro Arg Phe Val His Gly Glu Asn Lys
1               5                   10                  15

Val Lys Gln Ser Thr Ile Ala Leu Ala Leu Pro Leu Leu Phe Thr
            20                  25                  30

Pro Val Ala Lys Ala Gln Val Gln Leu Gln Gln Ser Asp Ala Asp Leu
        35                  40                  45

Val Lys Pro Gly Ala Ser Val Lys Ile Ser Cys Lys Ala Ser Gly Tyr
 50                  55                  60

Thr Phe Thr Asp His Ala Ile His Trp Val Lys Gln Arg Pro Glu Gln
 65                  70                  75                  80

Gly Leu Glu Trp Ile Gly Tyr Ile Tyr Pro Glu His Gly Thr Ile Lys
                85                  90                  95

Tyr Asn Glu Lys Phe Lys Gly Lys Ala Thr Leu Thr Ala Asp Lys Ser
            100                 105                 110

Ser Ser Thr Ala Tyr Met Gln Leu Asn Ser Leu Thr Ser Glu Asp Ser
        115                 120                 125

Ala Val Tyr Phe Cys Ser Arg Leu Thr Asn Tyr Phe Tyr Val Met Glu
    130                 135                 140

Tyr Trp Gly Gln Gly Thr Ser Val Thr Val Ser Ser Ala Lys Thr Thr
145                 150                 155                 160

Pro Pro Ser Val Tyr Pro Leu Ala Pro Gly Ser Ala Ala Gln Thr Asn
                165                 170                 175

Ser Met Val Thr Leu Gly Cys Leu Val Lys Gly Tyr Phe Pro Glu Pro
            180                 185                 190

Val Thr Val Thr Trp Asn Ser Gly Ser Leu Ser Ser Gly Val His Thr
        195                 200                 205

Phe Pro Ala Val Leu Gln Ser Asp Leu Tyr Thr Leu Ser Ser Ser Val
    210                 215                 220

Thr Val Pro Ser Ser Thr Trp Pro Ser Glu Thr Val Thr Cys Asn Val
225                 230                 235                 240

Ala His Pro Ala Ser Ser Thr Lys Val Asp Lys Lys Ile Val Pro Arg
                245                 250                 255

Asp Cys

<210> SEQ ID NO 43
<211> LENGTH: 258
<212> TYPE: PRT
<213> ORGANISM: Homo sapiens

<400> SEQUENCE: 43

Leu Gly Lys Pro Trp Arg Tyr Pro Arg Phe Val His Gly Glu Asn Lys
1               5                   10                  15

Val Lys Gln Ser Thr Ile Ala Leu Ala Leu Pro Leu Leu Phe Thr
            20                  25                  30

Pro Val Ala Lys Ala Gln Val Gln Leu Gln Gln Ser Asp Ala Glu Leu
        35                  40                  45

Val Lys Pro Gly Ala Ser Val Lys Ile Ser Cys Lys Ala Ser Gly Tyr
 50                  55                  60

Thr Phe Thr Asp His Ala Ile His Trp Val Lys Gln Arg Pro Glu Gln
 65                  70                  75                  80

Gly Leu Glu Trp Ile Gly Tyr Ile Tyr Pro Glu His Gly Ser Ile Thr
                85                  90                  95

Tyr Asn Glu Lys Phe Lys Gly Lys Ala Thr Leu Thr Ala Asp Lys Ser
            100                 105                 110

Ser Ser Thr Val Tyr Met His Leu Asn Ser Leu Thr Ser Glu Asp Ser
        115                 120                 125

```
Ala Val Tyr Phe Cys Ala Arg Leu Arg Asn Tyr Leu Tyr Val Met Asp
            130                 135                 140

Tyr Trp Gly Gln Gly Thr Ser Val Thr Val Ser Ser Ala Lys Thr Thr
145                 150                 155                 160

Pro Pro Ser Val Tyr Pro Leu Ala Pro Gly Ser Ala Ala Gln Thr Asn
                165                 170                 175

Ser Met Val Thr Leu Gly Cys Leu Val Lys Gly Tyr Phe Pro Glu Pro
            180                 185                 190

Val Thr Val Thr Trp Asn Ser Gly Ser Leu Ser Ser Gly Val His Thr
        195                 200                 205

Phe Pro Ala Val Leu Gln Ser Asp Leu Tyr Thr Leu Ser Ser Ser Val
    210                 215                 220

Thr Val Pro Ser Ser Thr Trp Pro Ser Glu Thr Val Thr Cys Asn Val
225                 230                 235                 240

Ala His Pro Ala Ser Ser Thr Lys Val Asp Lys Lys Ile Val Pro Arg
                245                 250                 255

Asp Cys

<210> SEQ ID NO 44
<211> LENGTH: 258
<212> TYPE: PRT
<213> ORGANISM: Homo sapiens

<400> SEQUENCE: 44

Leu Gly Lys Pro Trp Arg Tyr Pro Arg Phe His Gly Glu Asn Lys
1               5                   10                  15

Val Lys Gln Ser Thr Ile Ala Leu Ala Leu Leu Pro Leu Leu Phe Thr
            20                  25                  30

Pro Val Ala Lys Ala Gln Val Gln Leu Gln Gln Ser Glu Ala Glu Leu
        35                  40                  45

Val Lys Pro Gly Ala Ser Val Lys Leu Ser Cys Lys Ala Ser Gly Tyr
    50                  55                  60

Thr Phe Thr Asp His Ala Ile His Trp Met Lys Gln Arg Pro Glu Gln
65                  70                  75                  80

Gly Leu Glu Trp Ile Gly Tyr Ile Tyr Pro Arg Asp Asp Phe Ala Lys
                85                  90                  95

Val Asn Glu Lys Phe Lys Gly Lys Ala Thr Leu Thr Ala Asp Thr Ser
            100                 105                 110

Ser Ser Thr Ala Tyr Met Gln Leu Asn Ser Leu Thr Ser Glu Asp Ser
        115                 120                 125

Ala Val Tyr Phe Cys Ala Arg Met Thr Asn Tyr Leu Tyr Ile Met Asp
    130                 135                 140

Tyr Trp Gly Gln Gly Thr Ser Val Thr Val Ser Ser Ala Lys Thr Thr
145                 150                 155                 160

Pro Pro Ser Val Tyr Pro Leu Ala Pro Gly Ser Ala Ala Gln Thr Asn
                165                 170                 175

Ser Met Val Thr Leu Gly Cys Leu Val Lys Gly Tyr Phe Pro Glu Pro
            180                 185                 190

Val Thr Val Thr Trp Asn Ser Gly Ser Leu Ser Ser Gly Val His Thr
        195                 200                 205

Phe Pro Ala Val Leu Gln Ser Asp Leu Tyr Thr Leu Ser Ser Ser Val
    210                 215                 220

Thr Val Pro Ser Ser Thr Trp Pro Ser Glu Thr Val Thr Cys Asn Val
225                 230                 235                 240
```

Ala His Pro Ala Ser Ser Thr Lys Val Asp Lys Lys Ile Val Pro Arg
            245                 250                 255

Asp Cys

<210> SEQ ID NO 45
<211> LENGTH: 258
<212> TYPE: PRT
<213> ORGANISM: Homo sapiens

<400> SEQUENCE: 45

Leu Gly Lys Pro Trp Arg Tyr Pro Arg Phe Val His Gly Glu Asn Lys
1               5                   10                  15

Val Lys Gln Ser Thr Ile Ala Leu Ala Leu Leu Pro Leu Leu Phe Thr
            20                  25                  30

Pro Val Ala Lys Ala Gln Val Gln Leu Gln Gln Ser Asp Ala Glu Leu
        35                  40                  45

Val Lys Pro Gly Ala Ser Val Lys Ile Ser Cys Lys Ala Ser Gly Tyr
    50                  55                  60

Thr Phe Thr Asp His Ala Ile His Trp Val Lys Gln Arg Pro Glu Gln
65                  70                  75                  80

Gly Leu Glu Trp Ile Gly Tyr Ile Tyr Pro Glu His Gly Thr Ile Thr
                85                  90                  95

Tyr Asn Glu Lys Phe Lys Gly Lys Ala Thr Leu Thr Ala Asp Lys Ser
            100                 105                 110

Ser Ser Thr Val Tyr Met His Leu Asn Ser Leu Thr Ser Glu Asp Ser
        115                 120                 125

Ala Val Tyr Phe Cys Ala Arg Leu Arg Asn Tyr Leu Tyr Ile Met Asp
    130                 135                 140

Tyr Trp Gly Gln Gly Thr Ser Val Thr Val Ser Ser Ala Lys Thr Thr
145                 150                 155                 160

Pro Pro Ser Val Tyr Pro Leu Ala Pro Gly Ser Ala Ala Gln Thr Asn
                165                 170                 175

Ser Met Val Thr Leu Gly Cys Leu Val Lys Gly Tyr Phe Pro Glu Pro
            180                 185                 190

Val Thr Val Thr Trp Asn Ser Gly Ser Leu Ser Ser Gly Val His Thr
        195                 200                 205

Phe Pro Ala Val Leu Gln Ser Asp Leu Tyr Thr Leu Ser Ser Ser Val
    210                 215                 220

Thr Val Pro Ser Ser Thr Trp Pro Ser Glu Thr Val Thr Cys Asn Val
225                 230                 235                 240

Ala His Pro Ala Ser Ser Thr Lys Val Asp Lys Lys Ile Val Pro Arg
            245                 250                 255

Asp Cys

<210> SEQ ID NO 46
<211> LENGTH: 258
<212> TYPE: PRT
<213> ORGANISM: Homo sapiens

<400> SEQUENCE: 46

Leu Gly Lys Pro Trp Arg Tyr Pro Arg Phe Val His Gly Glu Asn Lys
1               5                   10                  15

Val Lys Gln Ser Thr Ile Ala Leu Ala Leu Leu Pro Leu Leu Phe Thr
            20                  25                  30

Pro Val Ala Lys Ala Gln Val Gln Leu Gln Gln Ser Asp Ala Ala Leu
        35                  40                  45

-continued

```
Val Lys Pro Gly Ala Ser Val Lys Ile Ser Cys Lys Val Ser Gly Tyr
         50                  55                  60

Thr Phe Ser Asp His Ala Ile His Trp Met Lys Gln Arg Pro Glu Gln
 65                  70                  75                  80

Gly Leu Glu Trp Ile Gly Tyr Ile Phe Pro Arg Asp Ala Phe Ser Leu
                 85                  90                  95

Asn Asn Glu Lys Phe Lys Gly Lys Ala Thr Leu Ser Ala Asp Thr Ser
            100                 105                 110

Ser Ser Thr Ala Tyr Met Glu Leu Thr Ser Leu Thr Phe Glu Asp Ser
        115                 120                 125

Ala Val Tyr Phe Cys Ala Arg Met Arg Asn Tyr Phe Tyr Val Met Asp
    130                 135                 140

Tyr Trp Gly Gln Gly Thr Ser Val Thr Val Ser Ser Ala Lys Thr Thr
145                 150                 155                 160

Pro Pro Ser Val Tyr Thr Leu Ala Pro Gly Ser Ala Ala Gln Thr Asn
                165                 170                 175

Ser Met Val Thr Leu Gly Cys Leu Val Lys Gly Tyr Phe Pro Glu Pro
            180                 185                 190

Val Thr Val Thr Trp Asn Ser Gly Ser Leu Ser Ser Gly Val His Thr
        195                 200                 205

Phe Pro Ala Val Leu Gln Ser Asp Leu Tyr Thr Leu Ser Ser Ser Val
    210                 215                 220

Thr Val Pro Ser Ser Thr Trp Pro Ser Glu Thr Val Thr Cys Asn Val
225                 230                 235                 240

Ala His Pro Ala Ser Ser Thr Lys Val Asp Lys Lys Ile Val Pro Arg
                245                 250                 255

Asp Cys

<210> SEQ ID NO 47
<211> LENGTH: 275
<212> TYPE: PRT
<213> ORGANISM: Homo sapiens

<400> SEQUENCE: 47

Arg Ile Leu Pro Asp Ala Phe Tyr Arg Asn Ser Leu Leu Phe Leu His
 1               5                  10                  15

Thr Arg Phe Phe Gly Trp Ser Glu Thr Met Lys Tyr Leu Leu Pro Thr
             20                  25                  30

Ala Ala Ala Gly Leu Leu Leu Leu Ala Ala Gln Pro Ala Met Ala Asp
         35                  40                  45

Val Val Leu Thr Gln Thr Pro Leu Ser Leu Pro Val Thr Leu Gly Asp
 50                  55                  60

Gln Ala Ser Ile Ser Cys Arg Ser Ser Gln Ser Leu Leu His Ser Asn
 65                  70                  75                  80

Gly Asn Thr Tyr Leu His Trp Tyr Leu Leu Lys Pro Gly Gln Ser Pro
                 85                  90                  95

Lys Leu Leu Ile Tyr Lys Val Ser Asn Arg Phe Ser Gly Val Pro Asp
            100                 105                 110

Arg Phe Ser Gly Ser Gly Ser Gly Thr Asp Phe Thr Leu Lys Ile Thr
        115                 120                 125

Arg Val Glu Ala Glu Asp Leu Gly Val Tyr Phe Cys Ser Gln Ser Thr
    130                 135                 140

His Val Leu Thr Phe Gly Ala Gly Thr Lys Leu Glu Leu Lys Arg Ala
145                 150                 155                 160
```

```
Asp Ala Ala Pro Thr Val Ser Ile Phe Pro Ser Ser Glu Gln Leu
                165                 170                 175

Thr Ser Gly Gly Ala Ser Val Val Cys Phe Leu Asn Asn Phe Tyr Pro
            180                 185                 190

Lys Asp Ile Asn Val Lys Trp Lys Ile Asp Gly Ser Glu Arg Gln Asn
            195                 200                 205

Gly Val Leu Asn Ser Trp Thr Asp Gln Asp Ser Lys Asp Ser Thr Tyr
210                 215                 220

Ser Met Ser Ser Thr Leu Thr Leu Thr Lys Asp Glu Tyr Glu Arg His
225                 230                 235                 240

Asn Ser Tyr Thr Cys Glu Ala Thr His Lys Thr Ser Thr Ser Pro Ile
            245                 250                 255

Val Lys Ser Phe Asn Arg Asn Glu Ser Tyr Pro Tyr Asp Val Pro Asp
            260                 265                 270

Tyr Ala Ser
        275

<210> SEQ ID NO 48
<211> LENGTH: 276
<212> TYPE: PRT
<213> ORGANISM: Homo sapiens

<400> SEQUENCE: 48

Arg Ile Leu Pro Asp Ala Phe Tyr Arg Asn Ser Leu Leu Phe Leu His
1               5                   10                  15

Thr Arg Phe Phe Gly Trp Ser Glu Thr Met Lys Tyr Leu Leu Pro Thr
            20                  25                  30

Ala Ala Ala Gly Leu Leu Leu Leu Ala Ala Gln Pro Ala Met Ala Asp
            35                  40                  45

Ile Val Met Thr Gln Ala Ala Pro Ser Val Pro Val Thr Pro Gly Glu
50                  55                  60

Ser Val Ser Ile Ser Cys Thr Ser Lys Ser Leu Leu Arg Ser Asn
65                  70                  75                  80

Gly Asn Thr Tyr Leu Tyr Trp Phe Leu Gln Arg Pro Gly Gln Ser Pro
            85                  90                  95

Gln Leu Leu Ile Tyr Arg Met Ser Asn Leu Ala Ser Gly Val Pro Asp
            100                 105                 110

Arg Phe Ser Gly Ser Gly Ser Gly Thr Ala Phe Thr Leu Arg Ile Ser
            115                 120                 125

Arg Val Glu Ala Glu Asp Val Gly Val Tyr Tyr Cys Met Gln His Leu
            130                 135                 140

Glu Tyr Pro Phe Thr Phe Gly Ser Gly Thr Lys Leu Glu Ile Lys Arg
145                 150                 155                 160

Ala Asp Ala Ala Pro Thr Val Ser Ile Phe Pro Pro Ser Ser Glu Gln
                165                 170                 175

Leu Thr Ser Gly Gly Ala Ser Val Val Cys Phe Leu Asn Asn Phe Tyr
            180                 185                 190

Pro Lys Asp Ile Asn Val Lys Trp Lys Ile Asp Gly Ser Glu Arg Gln
            195                 200                 205

Asn Gly Val Leu Asn Ser Trp Thr Asp Gln Asp Ser Lys Asp Ser Thr
            210                 215                 220

Tyr Ser Met Ser Ser Thr Leu Thr Leu Thr Lys Asp Glu Tyr Glu Arg
225                 230                 235                 240

His Asn Ser Tyr Thr Cys Glu Ala Thr His Lys Thr Ser Thr Ser Pro
```

```
                        245                 250                 255
Ile Val Lys Ser Phe Asn Arg Asn Glu Ser Tyr Pro Tyr Asp Val Pro
                260                 265                 270

Asp Tyr Ala Ser
            275

<210> SEQ ID NO 49
<211> LENGTH: 277
<212> TYPE: PRT
<213> ORGANISM: Homo sapiens

<400> SEQUENCE: 49

Arg Ile Leu Pro Asp Ala Phe Tyr Arg Asn Ser Leu Leu Phe Leu His
1               5                   10                  15

Thr Arg Phe Phe Gly Trp Ser Glu Thr Met Lys Tyr Leu Leu Pro Thr
                20                  25                  30

Ala Ala Ala Gly Leu Leu Leu Ala Ala Gln Pro Ala Met Ala Asp
            35                  40                  45

Ile Val Met Ser Gln Ser Pro Ser Ser Leu Ala Val Ser Val Gly Glu
50                  55                  60

Lys Val Thr Met Ser Cys Lys Ser Ser Gln Ser Leu Leu His Ser Ser
65                  70                  75                  80

Asn Gln Lys Asn Tyr Leu Ala Trp Tyr Gln Gln Lys Pro Gly Gln Ser
                85                  90                  95

Pro Lys Val Leu Ile Tyr Trp Ala Ser Thr Arg Glu Ser Gly Val Pro
            100                 105                 110

Asp Arg Phe Thr Gly Ser Gly Ser Gly Thr Asp Phe Thr Leu Thr Ile
        115                 120                 125

Thr Ser Val Lys Ser Glu Asp Leu Ala Val Tyr Tyr Cys Gln Gln Tyr
    130                 135                 140

Tyr Ser Tyr Pro Trp Thr Phe Gly Gly Gly Thr Arg Leu Glu Ile Lys
145                 150                 155                 160

Arg Ala Asp Ala Ala Pro Thr Val Ser Ile Phe Pro Pro Ser Ser Glu
                165                 170                 175

Gln Leu Thr Ser Gly Gly Ala Ser Val Val Cys Phe Leu Asn Asn Phe
            180                 185                 190

Tyr Pro Lys Asp Ile Asn Val Lys Trp Lys Ile Asp Gly Ser Glu Arg
        195                 200                 205

Gln Asn Gly Val Leu Asn Ser Trp Thr Asp Gln Asp Ser Lys Asp Ser
    210                 215                 220

Thr Tyr Ser Met Ser Ser Thr Leu Thr Leu Thr Lys Asp Glu Tyr Glu
225                 230                 235                 240

Arg His Asn Ser Tyr Thr Cys Glu Ala Thr His Lys Thr Ser Thr Ser
                245                 250                 255

Pro Ile Val Lys Ser Phe Asn Arg Asn Glu Ser Tyr Pro Tyr Asp Val
            260                 265                 270

Pro Asp Tyr Ala Ser
        275

<210> SEQ ID NO 50
<211> LENGTH: 276
<212> TYPE: PRT
<213> ORGANISM: Homo sapiens

<400> SEQUENCE: 50

Arg Ile Leu Pro Asp Ala Phe Tyr Arg Asn Ser Leu Leu Phe Leu His
```

```
            1               5                  10                 15
Thr Arg Phe Phe Gly Trp Ser Glu Thr Met Lys Tyr Leu Leu Pro Thr
            20                 25                 30

Ala Ala Ala Gly Leu Leu Leu Ala Ala Gln Pro Ala Met Ala Asp
            35                 40                 45

Ile Val Met Thr Gln Ala Ala Pro Ser Val Pro Val Thr Pro Gly Glu
 50                    55                 60

Ser Val Ser Ile Ser Cys Arg Ser Ser Lys Ser Leu Leu Arg Ser Asn
 65                    70                 75                 80

Gly Asn Thr Tyr Leu Tyr Trp Phe Leu Gln Arg Pro Gly Gln Ser Pro
                85                 90                 95

Gln Leu Leu Ile Tyr Arg Leu Ser Asn Leu Ala Ser Gly Val Pro Asp
                100                105                110

Arg Phe Ser Gly Ser Gly Ser Gly Thr Ala Phe Thr Leu Arg Ile Ser
                115                120                125

Arg Val Glu Ala Glu Asp Val Gly Val Tyr Tyr Cys Met Gln His Leu
                130                135                140

Glu Tyr Pro Phe Thr Phe Gly Ser Gly Thr Lys Leu Glu Ile Lys Arg
145                 150                155                160

Ala Asp Ala Ala Pro Thr Val Ser Ile Phe Pro Pro Ser Ser Glu Gln
                165                170                175

Leu Thr Ser Gly Gly Ala Ser Val Val Cys Phe Leu Asn Asn Phe Tyr
                180                185                190

Pro Lys Asp Ile Asn Val Lys Trp Lys Ile Asp Gly Ser Glu Arg Gln
                195                200                205

Asn Gly Val Leu Asn Ser Trp Thr Asp Gln Asp Ser Lys Asp Ser Thr
                210                215                220

Tyr Ser Met Ser Ser Thr Leu Thr Leu Thr Lys Asp Glu Tyr Glu Arg
225                 230                235                240

His Asn Ser Tyr Thr Cys Glu Ala Thr His Lys Thr Ser Thr Ser Pro
                245                250                255

Ile Val Lys Ser Phe Asn Arg Asn Glu Ser Tyr Pro Tyr Asp Val Pro
                260                265                270

Asp Tyr Ala Ser
                275

<210> SEQ ID NO 51
<211> LENGTH: 276
<212> TYPE: PRT
<213> ORGANISM: Homo sapiens

<400> SEQUENCE: 51

Arg Ile Leu Pro Asp Ala Phe Tyr Arg Asn Ser Leu Leu Phe Leu His
 1                  5                  10                 15

Thr Arg Phe Phe Gly Trp Ser Glu Thr Ile Lys Tyr Leu Leu Pro Thr
                20                 25                 30

Ala Ala Ala Gly Leu Leu Leu Ala Ala Gln Pro Ala Met Ala Asp
                35                 40                 45

Ile Val Met Thr Gln Ala Ala Pro Ser Val Pro Val Thr Pro Gly Glu
 50                    55                 60

Ser Val Ser Ile Ser Cys Thr Ser Ser Lys Ser Leu Leu Arg Ser Asn
 65                    70                 75                 80

Gly Asn Thr Tyr Leu Tyr Trp Phe Leu Gln Arg Pro Gly Gln Ser Pro
                85                 90                 95
```

```
Gln Leu Leu Ile Tyr Arg Met Ser Asn Leu Ala Ser Gly Val Pro Asp
            100                 105                 110

Arg Phe Ser Gly Ser Gly Ser Gly Thr Ala Phe Thr Leu Arg Ile Ser
        115                 120                 125

Arg Val Glu Ala Glu Asp Val Gly Val Tyr Tyr Cys Met Gln His Leu
    130                 135                 140

Glu Tyr Pro Phe Thr Phe Gly Ser Gly Thr Lys Leu Glu Ile Lys Arg
145                 150                 155                 160

Ala Asp Ala Ala Pro Thr Val Ser Ile Leu Pro Pro Ser Ser Glu Gln
                165                 170                 175

Leu Thr Ser Gly Gly Ala Ser Val Val Cys Phe Leu Asn Asn Phe Tyr
            180                 185                 190

Pro Lys Asp Ile Asn Val Lys Trp Lys Ile Asp Gly Ser Glu Arg Gln
        195                 200                 205

Asn Gly Val Leu Asn Ser Trp Thr Asp Gln Asp Ser Lys Asp Ser Thr
    210                 215                 220

Tyr Ser Met Ser Ser Thr Leu Thr Leu Thr Lys Asp Glu Tyr Glu Arg
225                 230                 235                 240

His Asn Ser Tyr Thr Cys Glu Ala Thr His Lys Thr Ser Thr Ser Pro
                245                 250                 255

Ile Val Lys Ser Phe Asn Arg Asn Glu Ser Tyr Pro Tyr Asp Val Pro
            260                 265                 270

Asp Tyr Ala Ser
            275

<210> SEQ ID NO 52
<211> LENGTH: 276
<212> TYPE: PRT
<213> ORGANISM: Homo sapiens

<400> SEQUENCE: 52

Arg Ile Leu Pro Asp Ala Phe Tyr Arg Asn Ser Leu Leu Phe Leu His
1               5                   10                  15

Thr Arg Phe Phe Gly Trp Ser Glu Thr Met Lys Tyr Leu Leu Pro Thr
            20                  25                  30

Ala Ala Ala Gly Leu Leu Leu Ala Ala Gln Pro Ala Met Ala Asp
        35                  40                  45

Ile Val Met Thr Gln Ala Ala Pro Ser Val Pro Val Thr Pro Gly Glu
    50                  55                  60

Ser Val Ser Ile Ser Cys Arg Ser Ser Lys Ser Leu Leu Arg Thr Asn
65                  70                  75                  80

Gly Asn Thr Tyr Leu His Trp Phe Leu Gln Arg Pro Gly Gln Ser Pro
                85                  90                  95

Gln Leu Leu Ile Tyr Arg Met Ser Asn Leu Ala Ser Gly Val Pro Asp
            100                 105                 110

Arg Phe Ser Gly Ser Gly Ser Gly Thr Val Phe Thr Leu Arg Ile Ser
        115                 120                 125

Arg Val Glu Ala Glu Asp Val Gly Val Tyr Tyr Cys Met Gln His Leu
    130                 135                 140

Glu Tyr Pro Phe Thr Phe Gly Ser Gly Thr Lys Leu Glu Ile Lys Arg
145                 150                 155                 160

Ala Asp Ala Ala Pro Thr Val Ser Ile Phe Pro Pro Ser Ser Glu Gln
                165                 170                 175

Leu Thr Ser Gly Gly Ala Ser Val Val Cys Phe Leu Asn Asn Phe Tyr
            180                 185                 190
```

```
Pro Lys Asp Ile Asn Val Lys Trp Lys Ile Asp Gly Ser Glu Arg Gln
        195                 200                 205

Asn Gly Val Leu Asn Ser Trp Thr Asp Gln Asp Ser Lys Asp Ser Thr
210                 215                 220

Tyr Ser Met Ser Ser Thr Leu Thr Leu Thr Lys Asp Glu Tyr Glu Arg
225                 230                 235                 240

His Asn Ser Tyr Thr Cys Glu Ala Thr His Lys Thr Ser Thr Ser Pro
                245                 250                 255

Ile Val Lys Ser Phe Asn Arg Asn Glu Ser Tyr Pro Tyr Asp Val Pro
        260                 265                 270

Asp Tyr Ala Ser
        275

<210> SEQ ID NO 53
<211> LENGTH: 276
<212> TYPE: PRT
<213> ORGANISM: Homo sapiens

<400> SEQUENCE: 53

Arg Ile Leu Pro Tyr Ala Phe Tyr Arg Asn Ser Leu Leu Phe Leu His
1               5                   10                  15

Thr Arg Phe Phe Gly Trp Ser Glu Thr Met Lys Tyr Leu Leu Pro Thr
            20                  25                  30

Ala Ala Ala Gly Leu Leu Leu Ala Ala Gln Pro Ala Met Ala Asp
        35                  40                  45

Ile Val Met Thr Gln Ala Ala Pro Ser Val Pro Val Thr Pro Gly Glu
50                  55                  60

Ser Val Ser Ile Ser Cys Arg Ser Ser Lys Ser Leu Leu Arg Ser Asn
65                  70                  75                  80

Gly Asn Thr Tyr Leu Tyr Trp Phe Leu Gln Arg Pro Gly Gln Ser Pro
                85                  90                  95

Gln Leu Leu Ile Tyr Arg Leu Ser Asn Leu Ala Ser Gly Val Pro Asp
            100                 105                 110

Arg Phe Ser Gly Ser Gly Ser Gly Thr Ala Phe Thr Leu Arg Ile Ser
        115                 120                 125

Arg Val Glu Ala Glu Asp Val Gly Val Tyr Tyr Cys Met Gln His Leu
130                 135                 140

Glu Tyr Pro Phe Thr Phe Gly Ser Gly Thr Lys Leu Glu Ile Lys Arg
145                 150                 155                 160

Ala Asp Ala Ala Pro Thr Val Ser Ile Phe Pro Pro Ser Ser Glu Gln
                165                 170                 175

Leu Thr Ser Gly Gly Ala Ser Val Val Cys Phe Leu Asn Asn Phe Tyr
            180                 185                 190

Pro Lys Asp Ile Asn Val Lys Trp Lys Ile Asp Gly Ser Glu Arg Gln
        195                 200                 205

Asn Gly Val Leu Asn Ser Trp Thr Asp Gln Asp Ser Lys Asp Ser Thr
210                 215                 220

Tyr Ser Met Ser Ser Thr Leu Thr Leu Thr Lys Asp Glu Tyr Glu Arg
225                 230                 235                 240

His Asn Ser Tyr Thr Cys Glu Ala Thr His Lys Thr Ser Thr Ser Pro
                245                 250                 255

Ile Val Lys Ser Phe Asn Arg Asn Glu Ser Tyr Pro Tyr Asp Val Pro
        260                 265                 270

Asp Tyr Ala Ser
```

```
<210> SEQ ID NO 54
<211> LENGTH: 276
<212> TYPE: PRT
<213> ORGANISM: Homo sapiens

<400> SEQUENCE: 54

Arg Ile Leu Pro Asp Ala Phe Tyr Arg Asn Ser Leu Leu Phe Leu His
1               5                   10                  15

Thr Arg Phe Phe Gly Trp Ser Glu Thr Met Lys Tyr Leu Leu Pro Thr
            20                  25                  30

Ala Ala Ala Gly Leu Leu Leu Ala Ala Gln Pro Ala Met Ala Asp
        35                  40                  45

Ile Val Met Thr Gln Ala Ala Pro Ser Val Pro Val Thr Pro Gly Glu
    50                  55                  60

Ser Val Ser Ile Ser Cys Thr Ser Ser Lys Ser Leu Leu Arg Ser Asn
65                  70                  75                  80

Gly Asn Thr Tyr Leu Tyr Trp Phe Leu Gln Arg Pro Gly Gln Ser Pro
                85                  90                  95

Gln Leu Leu Ile Tyr Arg Met Ser Asn Leu Ala Ser Gly Val Pro Asp
            100                 105                 110

Arg Phe Ser Gly Ser Gly Ser Gly Thr Ala Phe Thr Leu Arg Ile Ser
        115                 120                 125

Arg Val Glu Ala Glu Asp Val Gly Val Tyr Tyr Cys Met Gln His Leu
130                 135                 140

Glu Tyr Pro Phe Thr Phe Gly Ser Gly Thr Lys Leu Glu Ile Lys Arg
145                 150                 155                 160

Ala Asp Ala Ala Pro Thr Val Ser Ile Ser Pro Pro Ser Ser Glu Gln
                165                 170                 175

Leu Thr Ser Gly Gly Ala Ser Val Val Cys Phe Leu Asn Asn Phe Tyr
            180                 185                 190

Pro Lys Asp Ile Asn Val Lys Trp Lys Ile Asp Gly Ser Glu Arg Gln
        195                 200                 205

Asn Gly Val Leu Asn Ser Trp Thr Asp Gln Asp Ser Lys Asp Ser Thr
210                 215                 220

Tyr Ser Met Ser Ser Thr Leu Thr Leu Thr Lys Asp Glu Tyr Glu Arg
225                 230                 235                 240

His Asn Ser Tyr Thr Cys Glu Ala Thr His Lys Thr Ser Thr Ser Pro
                245                 250                 255

Ile Val Lys Ser Phe Asn Arg Asn Glu Ser Tyr Pro Tyr Asp Val Pro
            260                 265                 270

Asp Tyr Ala Ser
        275

<210> SEQ ID NO 55
<211> LENGTH: 276
<212> TYPE: PRT
<213> ORGANISM: Homo sapiens

<400> SEQUENCE: 55

Arg Ile Leu Pro Asp Ala Phe Tyr Arg Asn Ser Leu Leu Phe Leu His
1               5                   10                  15

Thr Arg Phe Phe Gly Trp Ser Glu Thr Met Lys Tyr Leu Leu Pro Thr
            20                  25                  30

Ala Ala Ala Gly Leu Leu Leu Ala Ala Gln Pro Ala Met Ala Asp
```

```
                35                  40                  45
Ile Val Met Thr Gln Ala Ala Pro Ser Val Pro Val Thr Pro Gly Glu
 50                  55                  60
Ser Val Ser Ile Ser Cys Arg Ser Ser Lys Ser Leu Leu Arg Ser Asn
65                  70                  75                  80
Gly Asn Thr Tyr Leu Tyr Trp Phe Leu Gln Arg Pro Gly Gln Ser Pro
                85                  90                  95
Gln Leu Leu Ile Tyr Arg Met Ser Asn Leu Ala Ser Gly Val Pro Asp
            100                 105                 110
Arg Phe Ser Gly Ser Gly Ser Gly Thr Ala Phe Thr Leu Arg Ile Ser
        115                 120                 125
Arg Val Glu Ala Glu Asp Val Gly Val Tyr Tyr Cys Met Gln His Leu
    130                 135                 140
Glu Tyr Pro Phe Thr Phe Gly Gly Gly Thr Lys Leu Glu Ile Lys Arg
145                 150                 155                 160
Ala Asp Ala Ala Pro Thr Val Ser Ile Phe Pro Pro Ser Ser Glu Gln
                165                 170                 175
Leu Thr Ser Gly Gly Ala Ser Val Val Cys Phe Leu Asn Asn Phe Tyr
            180                 185                 190
Pro Lys Asp Ile Asn Val Lys Trp Lys Ile Asp Gly Ser Glu Arg Gln
        195                 200                 205
Asn Gly Val Leu Asn Ser Trp Thr Asp Gln Asp Ser Lys Asp Ser Thr
    210                 215                 220
Tyr Ser Met Ser Ser Thr Leu Thr Leu Thr Lys Asp Glu Tyr Glu Arg
225                 230                 235                 240
His Asn Ser Tyr Thr Cys Glu Ala Thr His Lys Thr Ser Thr Ser Pro
                245                 250                 255
Ile Val Lys Ser Phe Asn Arg Asn Glu Ser Tyr Pro Tyr Asp Val Pro
            260                 265                 270
Asp Tyr Ala Ser
        275

<210> SEQ ID NO 56
<211> LENGTH: 276
<212> TYPE: PRT
<213> ORGANISM: Homo sapiens

<400> SEQUENCE: 56

Arg Ile Leu Pro Asp Ala Phe Tyr Arg Asn Ser Leu Phe Leu His
1               5                  10                  15
Thr Arg Phe Phe Gly Trp Ser Glu Thr Met Lys Tyr Leu Leu Pro Thr
                20                  25                  30
Ala Ala Ala Gly Leu Leu Leu Leu Ala Ala Gln Pro Ala Met Ala Asp
            35                  40                  45
Ile Val Met Thr Gln Ala Ala Pro Ser Val Ser Val Thr Pro Gly Glu
 50                  55                  60
Ser Val Ser Ile Ser Cys Arg Ser Thr Lys Ser Leu Leu Arg Ser Asn
65                  70                  75                  80
Gly Asn Thr Tyr Leu Tyr Trp Phe Leu Gln Arg Pro Gly Gln Ser Pro
                85                  90                  95
Gln Leu Leu Ile Tyr Arg Met Ser Asn Leu Ala Ser Gly Val Pro Asp
            100                 105                 110
Arg Phe Ser Gly Ser Gly Ser Gly Thr Ala Phe Thr Leu Arg Ile Ser
        115                 120                 125
```

```
Arg Val Glu Ala Glu Asp Val Gly Val Tyr Tyr Cys Met Gln His Leu
130                 135                 140

Glu Tyr Pro Phe Thr Phe Gly Gly Gly Thr Lys Leu Glu Ile Lys Arg
145                 150                 155                 160

Ala Asp Ala Ala Pro Thr Val Ser Ile Phe Pro Pro Ser Ser Glu Gln
            165                 170                 175

Leu Thr Ser Gly Gly Ala Ser Val Val Cys Phe Leu Asn Asn Phe Tyr
        180                 185                 190

Pro Lys Asp Ile Asn Val Lys Trp Lys Ile Asp Gly Ser Glu Arg Gln
            195                 200                 205

Asn Gly Val Leu Asn Ser Trp Thr Asp Gln Asp Ser Lys Asp Ser Thr
210                 215                 220

Tyr Ser Met Ser Ser Thr Leu Thr Leu Thr Lys Asp Glu Tyr Glu Arg
225                 230                 235                 240

His Asn Ser Tyr Thr Cys Glu Ala Thr His Lys Thr Ser Thr Ser Pro
            245                 250                 255

Ile Val Lys Ser Phe Asn Arg Asn Glu Ser Tyr Pro Tyr Asp Val Pro
            260                 265                 270

Asp Tyr Ala Ser
        275

<210> SEQ ID NO 57
<211> LENGTH: 276
<212> TYPE: PRT
<213> ORGANISM: Homo sapiens

<400> SEQUENCE: 57

Arg Ile Leu Pro Asp Ala Phe Tyr Arg Asn Ser Leu Leu Phe Leu His
1               5                   10                  15

Thr Arg Phe Phe Gly Trp Ser Glu Thr Met Lys Tyr Leu Leu Pro Thr
            20                  25                  30

Ala Ala Ala Gly Leu Leu Leu Ala Ala Gln Pro Ala Met Ala Asp
            35                  40                  45

Ile Val Met Thr Gln Ala Ala Pro Ser Val Pro Val Thr Pro Gly Glu
50                  55                  60

Ser Val Ser Ile Ser Cys Arg Ser Ser Lys Ser Leu Leu Arg Ser Asn
65                  70                  75                  80

Gly Asn Thr Tyr Leu Tyr Trp Phe Leu Gln Arg Pro Gly Gln Ser Pro
            85                  90                  95

Gln Leu Leu Ile Tyr Arg Leu Ser Asn Leu Ala Ser Gly Val Pro Asp
            100                 105                 110

Arg Phe Ser Gly Ser Gly Ser Gly Thr Ala Phe Thr Leu Arg Ile Ser
            115                 120                 125

Arg Val Glu Ala Glu Asp Val Gly Val Tyr Tyr Cys Met Gln His Leu
130                 135                 140

Glu Tyr Pro Phe Thr Phe Gly Ser Gly Thr Lys Leu Glu Ile Lys Arg
145                 150                 155                 160

Ala Asp Ala Ala Pro Thr Val Ser Ile Phe Pro Gln Tyr Ser Glu Gln
            165                 170                 175

Leu Thr Thr Gly Gly Ala Ser Val Val Cys Phe Leu Asn Asn Phe Tyr
        180                 185                 190

Pro Lys Asp Ile Asn Val Lys Trp Lys Ile Asp Gly Ser Glu Arg Gln
            195                 200                 205

Asn Gly Val Leu Asn Ser Trp Thr Asp Gln Asp Ser Lys Asp Ser Thr
210                 215                 220
```

Tyr Ser Met Ser Ser Thr Leu Thr Leu Thr Lys Asp Glu Tyr Glu Arg
225                 230                 235                 240

His Asn Ser Tyr Thr Cys Glu Ala Thr His Lys Thr Ser Thr Ser Pro
            245                 250                 255

Ile Val Lys Ser Phe Asn Arg Asn Glu Ser Tyr Pro Tyr Asp Val Pro
        260                 265                 270

Asp Tyr Ala Ser
        275

<210> SEQ ID NO 58
<211> LENGTH: 199
<212> TYPE: PRT
<213> ORGANISM: Homo sapiens

<400> SEQUENCE: 58

Arg Ile Leu Pro Asp Ala Phe Tyr Arg Asn Ser Leu Leu Phe Leu His
1               5                   10                  15

Thr Arg Phe Phe Gly Trp Ser Glu Thr Met Lys Tyr Leu Leu Pro Thr
            20                  25                  30

Ala Ala Ala Gly Leu Leu Leu Ala Ala Gln Pro Ala Met Ala Asp
        35                  40                  45

Ile Val Met Thr Gln Ala Ala Pro Ser Val Pro Val Thr Pro Gly Glu
    50                  55                  60

Ser Val Ser Ile Ser Cys Thr Ser Ser Lys Ser Leu Leu Arg Ser Asn
65                  70                  75                  80

Gly Asn Thr Tyr Leu Tyr Trp Phe Leu Gln Arg Pro Gly Gln Ser Pro
                85                  90                  95

Gln Leu Leu Ile Tyr Arg Met Ser Asn Leu Ala Ser Gly Val Pro Asp
            100                 105                 110

Arg Phe Ser Gly Ser Gly Ser Gly Thr Ala Phe Thr Leu Arg Ile Ser
        115                 120                 125

Arg Val Glu Ala Glu Asp Val Gly Val Tyr Tyr Cys Met Gln His Leu
    130                 135                 140

Glu Tyr Pro Phe Thr Phe Gly Ser Gly Thr Asn Leu Glu Ile Lys Arg
145                 150                 155                 160

Ala Asp Ala Ala Pro Thr Val Ser Ile Phe Thr Thr Ser Arg Glu Gln
                165                 170                 175

Leu Thr Ser Gly Gly Ala Ser Val Val Cys Phe Leu Asn Asn Phe Tyr
            180                 185                 190

Pro Lys Asp Ile Asn Val Lys
        195

<210> SEQ ID NO 59
<211> LENGTH: 783
<212> TYPE: DNA
<213> ORGANISM: Homo sapiens

<400> SEQUENCE: 59
tgactgggaa aaccctggcg ttacccacgc tttgtacatg agaaaataa agtgaaacaa      60 agcactattg cactggcact cttaccgctc ttatttaccc ctgtggcaaa agccgaagtg     120
cagctgttgg agactggggg aggcgtagtg aagcccggag ggtcccttaa actctcctgt    180
gcagcctctg gattcacttt cagtaactat ggcatgtctt gggttcgcca gactccggag    240
aagaggctgg agtgggtcgc agccattaat cgtgatggtg gtaccaccta ctatacagac    300
aatgtgaagg gccgattcac catctcccaga gacaatgcca agaacagcct gtacctgcaa    360

```
atgagcagtc tgaggtctga ggacacagcc ttgtattact gtgcaagaca gttccttctc    420
tgggacggct ggtacttcga tgtctggggc cagggacca cggtcaccgt ctcctcagcc     480
aaaacgacac cccatctgt ctatccactg gcccctggat ctgctgccca aactaactcc     540
atggtgaccc tgggatgcct ggtcaagggc tatttccctg agccagtgac agtgacctgg    600
aactctggat ccctgtccag cggtgtgcac accttcccag ctgtcctgca gtctgacctc    660
tacactctga gcagctcagt gactgtcccc tccagcacct ggcccagcga gaccgtcacc    720
tgcaacgttg cccacccggc cagcagcacc aaggtggaca gaaaattgt gcccagggat    780 tgt                                                                  783

<210> SEQ ID NO 60
<211> LENGTH: 777
<212> TYPE: DNA
<213> ORGANISM: Homo sapiens

<400> SEQUENCE: 60
tgactgggaa aaccctggcg ttacccacgc tttgtacatg gagaaaataa agtgaaacaa    60
agcactattg cactggcact cttaccgctc ttatttaccc ctgtggcaaa gcccaggtt    120 cagctgcaac agtctgacgc tgagttggtg aaacctggag cttcagtgaa gatatcctgc    180
aaggtttctg gctacacctt cagtgaccat gctattcact ggatgagtca gagacctgga    240
cagggcctga atggattgg atatatttat cctagacatg gactactaa ctacaatgag     300 aacttcaagg gcaaggccac actgactgca gacacatcct ccagcacagc ctacatgcag    360
ctcaacagcc tgacatctga agattctgcc gtctatttct gtgcaagaat gagaaactac    420
ttctatgtta tggactactg gggtcaagga acctcagtca ccgtctcctc agccaaaacg    480 acaccccat ctgtctatcc actggcccct ggatctgctg cccaaactaa ctccatggtg     540
accctgggat gcctggtcaa gggctatttc cctgagccag tgacagtgac ctggaactct    600
ggatccctgt ccagcggtgt gcacaccttc ccagctgtcc tgcagtctga cctctacact    660
ctgagcagct cagtgactgt cccctccagc acctggccca gcgagaccgt cacctgcaac    720
gttgcccacc cggccagcag caccaaggtg gacaagaaaa ttgtgcccag ggattgt       777

<210> SEQ ID NO 61
<211> LENGTH: 777
<212> TYPE: DNA
<213> ORGANISM: Homo sapiens

<400> SEQUENCE: 61
tgactgggaa aaccctggcg ttacccacgc tttgtacatg gagaaaataa agtgaaacaa    60
agcactattg cactggcact cttaccgctc ttatttaccc ctgtggcaaa gcccaggtt    120 ctgctgcaac agtctgacgc tgagttggtg aaacctgggg cttcagtgaa gatatcctgc    180
aaggcttctg gctacacctt cactgaccat gctattcact gggtgaagca gaggcctgaa    240
cagggcctgg aatggattgg atatatttat cctgaacatg gaactattaa gtataatgag    300
aagttcaagg gcaaggccac attgactgca gataaatcct ccagcactgc ctatatgcag    360
ctcaacagcc tgacatctga ggattcagca gtgtatttct gttcaagact cactaactac    420
ttctatgtta tggagtattg gggtcaagga acctcagtca ccgtctcctc agccaaaacg    480 acaccccat ctgtctatcc actggcccct ggatctgctg cccaaactaa ctccatggtg     540
accctgggat gcctggtcaa gggctatttc cctgagccag tgacagtgac ctggaactct    600
```

```
ggatccctgt ccagcggtgt gcacaccttc ccagctgtcc tgcagtctga cctctacact    660
ctgagcagct cagtgactgt cccctccagc acctggccca gcgagaccgt cacctgcaac    720
gttgcccacc cggccagcag caccaaggtg acaagaaaa ttgtgcccag ggattgt        777

<210> SEQ ID NO 62
<211> LENGTH: 789
<212> TYPE: DNA
<213> ORGANISM: Homo sapiens

<400> SEQUENCE: 62
tgactgggaa aaccctggcg ttacccacgc tttgtacatg gagaaaataa agtgaaacaa     60
agcactattg cactggcact cttaccgctc ttatttaccc ctgtggcaaa agccgaggtt    120
cagctgcagc agtctgtcgc tgagttggtg aaacctggag cttcagtgaa gatgtcatgc    180
aaggtttctg gctacacct cactgaccat actattcact ggatgaagca gaggcctgaa    240
cagggcctgg aatggattgg atatatttac cctagagatg gaataactgg gtacaatgag    300
aagttcaagg gcaaggccac actgactgca gacacttctt ccagcacagc ctacatgcag    360
ctcaacagcc tgacatctga ggattctgca gtctatttct gtgccagatg gggctatagt    420
tacaggaatt acgcgtacta ctatgactac tggggccaag gcaccactct cacagtctcc    480
tcagccaaaa cgacaccccc atctgtctat ccactggccc ctggatctgc tgcccaaact    540
aactccatgg tgaccctggg atgcctggtc aagggctatt ccctgagcc agtgacagtg    600 acctggaact ctggatccct gtccagcggt gtgcacacct cccagctgt cctgcagtct    660 gacctctaca ctctgagcag ctcagtgact gtcccctcca gcacctggcc cagcgagacc    720
gtcacctgca acgttgccca cccggccagc agcaccaagg tggacaagaa aattgtgccc    780
agggattgt                                                            789

<210> SEQ ID NO 63
<211> LENGTH: 777
<212> TYPE: DNA
<213> ORGANISM: Homo sapiens

<400> SEQUENCE: 63
tgactgggaa aaccctggcg ttacccacgc tttgtacatg gagaaaataa agtgaaacaa     60
agcactattg cactggcact cttaccgctc ttatttaccc ctgtggcaaa agcccaggtt    120
cagctgcaac agtctgacgc tgacttggtg aaacctgggg cttcagtgaa gatatcctgc    180
aaggcttctg gctacacctt cactgaccat gctattcact gggtgaaaca gaggcctgaa    240
cagggcctgg aatggattgg atatatttat cctgaacatg gaactattaa gtataatgag    300
aagttcaagg gcaaggccac attgactgca gataaatcct ccagcactgc ctatatgcag    360
ctcaacagcc tgacatctga ggattcagca gtgtatttct gtgcaagact caggaactat    420
ttgtatatta tggactactg gggtcaagga acctcagtca ccgtctcctc agccaaaacg    480 acaccccat ctgtctatcc actggcccct ggatctgctg cccaaactaa ctccatggtg    540
accctgggat gcctggtcaa gggctatttc cctgagccag tgacagtgac ctggaactct    600
ggatccctgt ccagcggtgt gcacaccttc ccagctgtcc tgcagtctga cctctacact    660
ctgagcagct cagtgactgt cccctccagc acctggccca gcgagaccgt cacctgcaac    720
gttgcccacc cggccagcag caccaaggtg acaagaaaa ttgtgcccag ggattgt        777

<210> SEQ ID NO 64
<211> LENGTH: 777
```

```
<212> TYPE: DNA
<213> ORGANISM: Homo sapiens

<400> SEQUENCE: 64
tgactgggaa aaccctggcg ttacccacgc tttgtacatg gagaaaataa agtgaaacaa      60
agcactattg cactggcact cttaccgctc ttatttaccc ctgtggcaaa agcccaggtt     120
cagctgcaac agtctgacgc tgagttggtg aaacctgggg cttcagtgaa gatatcctgc     180
aaggcttctg gctacacctt cactgaccat gctattcact gggtgaagca gaggcctgaa     240
cagggcctgg aatggattgg atatatttat cctgaacatg gaactattaa gtataatgag     300
aagttcaagg gcaaggccac attgactgca gataaatcct ccagcactgc ctatatgcag     360
ctcaacagcc tgacatctga ggattcagca gtgtatttct gttcaagact cactaactac     420
ttctatgtta tggagtattg gggtcaagga acctcagtca ccgtctcctc agccaaaacg     480
acacccccat ctgtctatcc actggcccct ggatctgctg cccaaactaa ctccatggtg     540
accctgggat gcctggtcaa gggctatttc cctgagccag tgacagtgac ctggaactct     600
ggatccctgt ccagcggtgt gcacaccttc ccagctgtcc tgcagtctga cctctacact     660
ctgagcagct cagtgactgt cccctccagc acctggccca gcgagaccgt cacctgcaac     720
gttgcccacc cggccagcag caccaaggtg acaagaaaa ttgtgcccag ggattgt         777

<210> SEQ ID NO 65
<211> LENGTH: 777
<212> TYPE: DNA
<213> ORGANISM: Homo sapiens

<400> SEQUENCE: 65
tgactgggaa aaccctggcg ttacccacgc tttgtacatg gagaaaataa agtgaaacaa      60
agcactattg cactggcact cttaccgctc ttatttaccc ctgtggcaaa agcccaggtt     120
cagctgcaac agtctgacgc tgagttggtg aaacctggag cctcagtgaa gatatcctgc     180
aaggtttctg gctacacctt cactgaccat gctattcact ggatgaaaca gaggcctgaa     240
cagggcctgg aatggattgg atatatttat cctagagatg gttttactaa gtacaatgag     300
aagttcaagg gcaaggccac actgactgca gacacatcct ccagcacagc ctacatgcag     360
ctcaacagcc tgacatctga ggattctaca gtctatttct gtgcaagaat gactaactac     420
ttctatacta tggactactg gggtcaagga acctcagtca ccgtctcctc agccaaaacg     480
acacccccat ctgtctatcc actggcccct ggatctgctg cccaaactaa ctccatggtg     540
accctgggat gcctggtcaa gggctatttc cctgagccag tgacagtgac ctggaactct     600
ggatccctgt ccagcggtgt gcacaccttc ccagctgtcc tgcagtctga cctctacact     660
ctgagcagct cagtgactgt cccctccagc acctggccca gcgagaccgt cacctgcaac     720
gttgcccacc cggccagcag caccaaggtg acaagaaaa ttgtgcccag ggattgt         777

<210> SEQ ID NO 66
<211> LENGTH: 777
<212> TYPE: DNA
<213> ORGANISM: Homo sapiens

<400> SEQUENCE: 66
tgactgggaa aaccctggcg ttacccacgc tttgtacatg gagaaaataa agtgaaacaa      60
agcactattg cactggcact cttaccgctc ttatttaccc ctgtggcaaa agcccaggtt     120
cagctgcaac agtctgacgc tgacttggtg aaacctgggg cttcagtgaa gatatcctgc     180
```

```
aaggcttctg gctacacctt cactgaccat gctattcact gggtgaaaca gaggcctgaa      240
cagggcctgg aatggattgg atatatttat cctgaacatg gaactattaa gtataatgag      300
aagttcaagg gcaaggccac attgactgca gataaatcct ccagcactgc ctatatgcag      360
ctcaacagcc tgacatctga ggattcagca gtgtatttct gttcaagact cactaactac      420
ttctatgtta tggagtattg gggtcaagga acctcagtca ccgtctcctc agccaaaacg      480 acaccccat ctgtctatcc actggcccct ggatctgctg cccaaactaa ctccatggtg       540
accctgggat gcctggtcaa gggctatttc cctgagccag tgacagtgac ctggaactct      600
ggatccctgt ccagcggtgt gcacaccttc cagctgtcc tgcagtctga cctctacact       660
ctgagcagct cagtgactgt cccctccagc acctggccca gcgagaccgt cacctgcaac      720
gttgcccacc cggccagcag caccaaggtg gacaagaaaa ttgtgcccag ggattgt        777
```

<210> SEQ ID NO 67
<211> LENGTH: 777
<212> TYPE: DNA
<213> ORGANISM: Homo sapiens

<400> SEQUENCE: 67

```
tgactgggaa aaccctggcg ttacccacgc tttgtacatg gagaaaataa agtgaaacaa       60
agcactattg cactggcact cttaccgctc ttatttaccc ctgtggcaaa gcccaggtt      120 cagctgcaac agtctgacgc tgagttggtg aaacctgggg cttcagtgaa gatatcctgc      180
aaggcttctg gctacacctt cactgaccat gctattcact gggtgaagca gaggcctgaa      240
cagggcctgg aatggattgg atatatttat cctgaacatg gtagtattac gtataatgag      300
aagttcaagg gcaaggccac attgactgca gataaatcct ccagtactgt ctatatgcac      360
ctcaatagcc tgacatctga ggattcagca gtgtatttct gtgcaagact caggaactac      420
ttgtatgtta tggactactg gggtcaagga acctcagtca ccgtctcctc agccaaaacg      480 acaccccat ctgtctatcc actggcccct ggatctgctg cccaaactaa ctccatggtg       540
accctgggat gcctggtcaa gggctatttc cctgagccag tgacagtgac ctggaactct      600
ggatccctgt ccagcggtgt gcacaccttc cagctgtcc tgcagtctga cctctacact       660
ctgagcagct cagtgactgt cccctccagc acctggccca gcgagaccgt cacctgcaac      720
gttgcccacc cggccagcag caccaaggtg gacaagaaaa ttgtgcccag ggattgt        777
```

<210> SEQ ID NO 68
<211> LENGTH: 777
<212> TYPE: DNA
<213> ORGANISM: Homo sapiens

<400> SEQUENCE: 68

```
tgactgggaa aaccctggcg ttacccacgc tttgtacatg gagaaaataa agtgaaacaa       60
agcactattg cactggcact cttaccgctc ttatttaccc ctgtggcaaa gcccaggtt      120 cagctgcaac agtctgaggc tgagcttgtg aagcctgggg cttcagtgaa gctgtcctgc      180
aaggcttctg gctacacctt cactgaccat gctattcact ggatgaaaca gaggcctgaa      240
cagggcctgg aatggattgg atatatctac cccagagatg attttgctaa ggtgaatgag      300
aagttcaagg gcaaggccac actgacagca gacacatcct ccagcacagc ctacatgcag      360
ctcaacagcc tgacatctga ggattctgca gtctatttct gtgcaagaat gactaactac      420
ctctatatta tggactactg gggtcaagga acctcagtca ccgtctcctc agccaaaacg      480 acaccccat ctgtctatcc actggcccct ggatctgctg cccaaactaa ctccatggtg       540
```

```
accctgggat gcctggtcaa gggctatttc cctgagccag tgacagtgac ctggaactct    600
ggatccctgt ccagcggtgt gcacaccttc ccagctgtcc tgcagtctga cctctacact    660
ctgagcagct cagtgactgt cccctccagc acctggccca gcgagaccgt cacctgcaac    720
gttgcccacc cggccagcag caccaaggtg gacaagaaaa ttgtgcccag ggattgt       777
```

<210> SEQ ID NO 69
<211> LENGTH: 777
<212> TYPE: DNA
<213> ORGANISM: Homo sapiens

<400> SEQUENCE: 69

```
tgactgggaa aaccctggcg ttacccacgc tttgtacatg agaaaataa agtgaaacaa     60 agcactattg cactggcact cttaccgctc ttatttaccc ctgtggcaaa agcccaggtt    120
cagctgcaac agtctgacgc tgagttggtg aaacctgggg cttcagtgaa gatatcctgc    180
aaggcttctg gctacacctt cactgaccat gctattcact gggtgaagca gaggcctgaa    240
cagggcctgg aatggattgg atatatttat cctgaacatg gtactattac gtataatgag    300
aagttcaagg gcaaggccac attgactgca gataaatcct ccagtactgt ctatatgcac    360
ctcaatagcc tgacatctga ggattcagca gtgtatttct gtgcaagact caggaactat    420
ttgtatatta tggactactg gggtcaagga acctcagtca ccgtctcctc agccaaaacg    480 acaccccat ctgtctatcc actggccccc ggatctgctg cccaaactaa ctccatggtg     540
accctgggat gcctggtcaa gggctatttc cctgagccag tgacagtgac ctggaactct    600
ggatccctgt ccagcggtgt gcacaccttc ccagctgtcc tgcagtctga cctctacact    660
ctgagcagct cagtgactgt cccctccagc acctggccca gcgagaccgt cacctgcaac    720
gttgcccacc cggccagcag caccaaggtg gacaagaaaa ttgtgcccag ggattgt       777
```

<210> SEQ ID NO 70
<211> LENGTH: 777
<212> TYPE: DNA
<213> ORGANISM: Homo sapiens

<400> SEQUENCE: 70

```
tgactgggaa aaccctggcg ttacccacgc tttgtacatg agaaaataa agtgaaacaa     60 agcactattg cactggcact cttaccgctc ttatttaccc ctgtggcaaa agcccaggtt    120
cagctgcaac agtctgacgc cgcgttggtg aaacctggag cttcagtgaa gatatcgtgc    180
aaggtttctg gctacacctt cagtgaccat gctattcact ggatgaagca gaggcctgaa    240
cagggcctgg aatggattgg atatatttt cctagagatg cttttagttt gaacaatgag     300
aagttcaagg gcaaggccac actgagtgca gacacatcct ccagcacagc ctacatggag    360
ctcaccagcc tgacatttga ggattctgca gtctatttct gtgcaagaat gagaaactac    420
ttctatgtta tggactactg gggtcaagga acctcagtca ccgtctcctc agccaaaacg    480 acaccccat ctgtctatac actggcccct ggatctgctg cccaaactaa ctccatggtg     540
accctgggat gcctggtcaa gggctatttc cctgagccag tgacagtgac ctggaactct    600
ggatccctgt ccagcggtgt gcacaccttc ccagctgtcc tgcagtctga cctctacact    660
ctgagcagct cagtgactgt cccctccagc acctggccca gcgagaccgt cacctgcaac    720
gttgcccacc cggccagcag caccaaggtg gacaagaaaa ttgtgcccag ggattgt       777
```

<210> SEQ ID NO 71

<211> LENGTH: 837
<212> TYPE: DNA
<213> ORGANISM: Homo sapiens

<400> SEQUENCE: 71

```
taagattagc ggatcctacc tgacgctttt tatcgcaact ctctactgtt tctccatacc    60
cgttttttg  gatggagtga aacgatgaaa tacctattgc ctacggcagc cgctggattg    120
ttattactcg ctgcccaacc agccatggcc gatgttgtgc tgacccagac tccactctcc    180
ctgcctgtca ctcttggaga tcaagcctcc atctcttgca gatctagtca gagccttta    240
cacagtaatg aaacaccta  tttacattgg tacctgctga agccaggcca gtctccaaag   300
ctcctgatct acaaagtttc caaccgattt tctggggtcc cagacaggtt cagtggcagt   360
ggatcaggga cagatttcac actcaagatc accagagtgg aggctgagga tctgggagtt   420
tatttctgct ctcaaagtac acatgtgctc acgttcggtg ctgggaccaa gctggagctg   480
aaacgggctg atgctgcacc aactgtatcc atcttcccac catccagtga gcagttaaca   540
tctggaggtg cctcagtcgt gtgcttcttg aacaacttct accccaaaga catcaatgtc   600
aagtggaaga ttgatggcag tgaacgacaa atggcgtcc  tgaacagttg gactgatcag   660
gacagcaaag acagcaccta cagcatgagc agcaccctca cgttgaccaa ggacgagtat   720
gaacgacata acagctatac ctgtgaggcc actcacaaga catcaacttc acccattgtc   780
aagagcttca caggaatga  gtcttatcca tatgatgtgc agattatgc  gagctaa      837
```

<210> SEQ ID NO 72
<211> LENGTH: 840
<212> TYPE: DNA
<213> ORGANISM: Homo sapiens

<400> SEQUENCE: 72

```
taagattagc ggatcctacc tgacgctttt tatcgcaact ctctactgtt tctccatacc    60
cgttttttg  gatggagtga aacgatgaaa tacctattgc ctacggcagc cgctggattg    120
ttattactcg ctgcccaacc agccatggcc gatattgtga tgacccaggc tgcaccctct   180
gtacctgtca ctcctggaga gtcagtatcc atctcctgca gtctagtaa  gagtctcctg   240
cgtagtaatg gcaacactta cttgtattgg ttcctgcaga ggccaggcca gtctcctcag   300
ctcctgatat atcggatgtc caaccttgcc tcgggagtcc cagacaggtt cagtggcagt   360
gggtcaggaa ctgctttcac actgagaatc agtagagtgg aggctgagga tgtgggtgtt   420
tattactgta tgcaacatct agaatatcct ttcacgttcg gctcgggac  aaagttggaa   480
ataaaacggg ctgatgctgc accaactgta tccatcttcc caccatccag tgagcagtta   540
acatctggag gtgcctcagt cgtgtgcttc ttgaacaact tctacccaa  agacatcaat   600
gtcaagtgga agattgatgg cagtgaacga caaaatggcg tcctgaacag ttggactgat   660
caggacagca agacagcac  ctacagcatg agcagcaccc tcacgttgac caaggacgag   720
tatgaacgac ataacagcta cctgtgagg  ccactcaca  agacatcaac ttcacccatt   780
gtcaagagct tcaacaggaa tgagtcttat ccatatgatg tgccagatta tgcgagctaa   840
```

<210> SEQ ID NO 73
<211> LENGTH: 843
<212> TYPE: DNA
<213> ORGANISM: Homo sapiens

<400> SEQUENCE: 73

```
taagattagc ggatcctacc tgacgctttt tatcgcaact ctctactgtt tctccatacc    60
```

```
cgttttttg  gatggagtga  aacgatgaaa  tacctattgc  ctacggcagc  cgctggattg      120
ttattactcg  ctgcccaacc  agccatggcc  gacatcgtta  tgtctcagtc  tccatcctcc     180
ctagctgtgt  cagttggaga  gaaggttact  atgagctgca  agtccagcca  gagcctttta     240
catagtagca  atcaaaagaa  ctacttggcc  tggtaccagc  agaaaccagg  gcagtctcct     300
aaagtgctga  tttactgggc  atccactaga  gaatctgggg  tccctgatcg  cttcacaggc     360
agtggatctg  ggacagattt  cactctcacc  atcaccagtg  tgaagtctga  agacctggca     420
gtttattact  gtcagcaata  ttatagctat  ccgtggacgt  tcggtggcgg  caccaggctg     480
gaaatcaaac  gggctgatgc  tgcaccaact  gtatccatct  tcccaccatc  cagtgagcag     540
ttaacatctg  gaggtgcctc  agtcgtgtgc  ttcttgaaca  acttctaccc  caaagacatc     600
aatgtcaagt  ggaagattga  tggcagtgaa  cgacaaaatg  gcgtcctgaa  cagttggact     660
gatcaggaca  gcaaagacag  cacctacagc  atgagcagca  ccctcacgtt  gaccaaggac     720
gagtatgaac  gacataacag  ctatacctgt  gaggccactc  acaagacatc  aacttcaccc     780
attgtcaaga  gcttcaacag  gaatgagtct  tatccatatg  atgtgccaga  ttatgcgagc     840
taa                                                                      843

<210> SEQ ID NO 74
<211> LENGTH: 840
<212> TYPE: DNA
<213> ORGANISM: Homo sapiens

<400> SEQUENCE: 74
taagattagc  ggatcctacc  tgacgctttt  tatcgcaact  ctctactgtt  tctccatacc      60 cgttttttg  gatggagtga  aacgatgaaa  tacctattgc  ctacggcagc  cgctggattg      120
ttattactcg  ctgcccaacc  agccatggcc  gatattgtga  tgacccaggc  tgcaccctct     180
gtacctgtca  ctcctggaga  gtcagtatcc  atctcctgca  ggtctagtaa  gagtctcctg     240
cgcagtaatg  gcaacactta  cttgtattgg  ttcctgcaga  ggccaggcca  gtctcctcag     300
ctcctgatat  atcggctgtc  caaccttgcc  tcaggagtcc  cagacaggtt  cagtggcagt     360
gggtctggaa  ctgctttcac  actgagaatc  agtagagtgg  aggctgagga  tgtgggtgtt     420
tattactgta  tgcaacatct  agaatatcct  ttcacattcg  gctcggggac  aaagttggaa     480
ataaaacggg  ctgatgctgc  accaactgta  tccatcttcc  caccatccag  tgagcagtta     540
acatctggag  gtgcctcagt  cgtgtgcttc  ttgaacaact  tctaccccaa  agacatcaat     600
gtcaagtgga  agattgatgg  cagtgaacga  caaaatggcg  tcctgaacag  ttggactgat     660
caggacagca  agacagcac  ctacagcatg  agcagcaccc  tcacgttgac  caaggacgag     720
tatgaacgac  ataacagcta  tacctgtgag  gccactcaca  agacatcaac  ttcacccatt     780
gtcaagagct  tcaacaggaa  tgagtcttat  ccatatgatg  tgccagatta  tgcgagctaa     840

<210> SEQ ID NO 75
<211> LENGTH: 840
<212> TYPE: DNA
<213> ORGANISM: Homo sapiens

<400> SEQUENCE: 75
taagattagc  ggatcctacc  tgacgctttt  tatcgcaact  ctctactgtt  tctccatacc      60 cgttttttg  gatggagtga  aacgataaaa  tacctattgc  ctacggcagc  cgctggattg      120
ttattactcg  ctgcccaacc  agccatggcc  gatattgtga  tgacccaggc  tgcaccctct     180
```

```
gtacctgtca ctcctggaga gtcagtatcc atctcctgca cgtctagtaa gagtctcctg    240
cgtagtaatg caacactta cttgtattgg ttcctgcaga ggccaggcca gtctcctcag    300
ctcctgatat atcggatgtc caaccttgcc tcgggagtcc agacaggtt cagtggcagt    360 gggtcaggaa ctgctttcac actgagaatc agtagagtgg aggctgagga tgtgggtgtt    420
tattactgta tgcaacatct agaatatcct ttcacgttcg gctcggggac aaagttggaa    480
ataaaacggg ctgatgctgc accaactgta tccatcctcc caccatccag tgagcagtta    540
acatctggag gtgcctcagt cgtgtgcttc ttgaacaact ctaccccaa agacatcaat    600 gtcaagtgga agattgatgg cagtgaacga caaaatggcg tcctgaacag ttggactgat    660
caggacagca aagacagcac ctacagcatg agcagcaccc tcacgttgac caaggacgag    720
tatgaacgac ataacagcta tacctgtgag gccactcaca agacatcaac ttcacccatt    780
gtcaagagct tcaacaggaa tgagtcttat ccatatgatg tgccagatta tgcgagctaa    840

<210> SEQ ID NO 76
<211> LENGTH: 840
<212> TYPE: DNA
<213> ORGANISM: Homo sapiens

<400> SEQUENCE: 76
taagattagc ggatcctacc tgacgctttt tatcgcaact ctctactgtt tctccatacc     60 cgttttttg gatggagtga aacgatgaaa tacctattgc ctacggcagc cgctggattg    120
ttattactcg ctgcccaacc agccatggcc gatattgtga tgacccaggc tgcaccctct    180
gtacctgtca ctcctggaga gtcagtttcc atctcctgca ggtcttctaa gagtctcctg    240
cgtactaatg caacactta cttgcattgg ttcctgcaga ggccaggcca gtctcctcag    300
ctcctgatat atcggatgtc caaccttgcc tcaggagtcc agacaggtt cagtggcagt    360 gggtcaggaa ctgttttcac actgagaatc agtagagtgg aggctgagga tgtgggtgtt    420
tattactgta tgcaacatct agaatatcca ttcacgttcg gctcggggac aaagttggaa    480
ataaaagggg ctgatgctgc accaactgta tccatcttcc caccatccag tgagcagtta    540
acatctggag gtgcctcagt cgtgtgcttc ttgaacaact ctaccccaa agacatcaat    600 gtcaagtgga agattgatgg cagtgaacga caaaatggcg tcctgaacag ttggactgat    660
caggacagca aagacagcac ctacagcatg agcagcaccc tcacgttgac caaggacgag    720
tatgaacgac ataacagcta tacctgtgag gccactcaca agacatcaac ttcacccatt    780
gtcaagagct tcaacaggaa tgagtcttat ccatatgatg tgccagatta tgcgagctaa    840

<210> SEQ ID NO 77
<211> LENGTH: 840
<212> TYPE: DNA
<213> ORGANISM: Homo sapiens

<400> SEQUENCE: 77
taagattagc ggatcctacc ttacgctttt tatcgcaact ctctactgtt tctccatacc     60 cgttttttg gatggagtga aacgatgaaa tacctattgc ctacggcagc cgctggattg    120
ttattactcg ctgcccaacc agccatggcc gatattgtga tgacccaggc tgcaccctct    180
gtacctgtca ctcctggaga atcagtatcc atctcctgca ggtctagtaa gagtctcctg    240
cgtagtaatg caacactta cttgtattgg ttcctgcaga ggccaggcca gtctcctcag    300
ctcctgatat atcggctgtc taaccttgcc tcaggagtcc agacaggtt cagtggcagt    360 gggtcaggaa ctgctttcac actgagaatc agtagagtgg aggctgagga tgtgggtgtt    420
```

```
tattactgta tgcaacatct agaatatcct ttcacattcg gctcggggac aaagttggaa    480
ataaaacggg ctgatgctgc accaactgta tccatcttcc caccatccag tgagcagtta    540
acatctggag gtgcctcagt cgtgtgcttc ttgaacaact tctaccccaa agacatcaat    600
gtcaagtgga gagattgatgg cagtgaacga caaaatggcg tcctgaacag ttggactgat    660
caggacagca agacagcac ctacagcatg agcagcaccc tcacgttgac caaggacgag    720
tatgaacgac ataacagcta tacctgtgag gccactcaca agacatcaac ttcacccatt    780
gtcaagagct tcaacaggaa tgagtcttat ccatatgatg tgccagatta tgcgagctaa    840
```

<210> SEQ ID NO 78
<211> LENGTH: 840
<212> TYPE: DNA
<213> ORGANISM: Homo sapiens

<400> SEQUENCE: 78

```
taagattagc ggatcctacc tgacgctttt tatcgcaact ctctactgtt tctccatacc     60 cgttttttg gatggagtga aacgatgaaa taccttattgc ctacggcagc cgctggattg    120
ttattactcg ctgcccaacc agccatggcc gatattgtga tgacccaggc tgcaccctct    180
gtacctgtca ctcctggaga gtcagtatcc atctcctgca cgtctagtaa gagtctcctg    240
cgtagtaatg caacactta cttgtattgg ttcctgcaga ggccaggcca gtctcctcag    300
ctcctgatat atcggatgtc caaccttgcc tcgggagtcc cagacaggtt cagtggcagt    360
gggtcaggaa ctgctttcac actgagaatc agtagagtgg aggctgagga tgtgggtgtt    420
tattactgta tgcaacatct agaatatcct ttcacgttcg gctcggggac aaagttggaa    480
ataaaacggg ctgatgctgc accaactgta tccatctccc caccatccag tgagcagtta    540
acatctggag gtgcctcagt cgtgtgcttc ttgaacaact tctaccccaa agacatcaat    600
gtcaagtgga gagattgatgg cagtgaacga caaaatggcg tcctgaacag ttggactgat    660
caggacagca agacagcac ctacagcatg agcagcaccc tcacgttgac caaggacgag    720
tatgaacgac ataacagcta tacctgtgag gccactcaca agacatcaac ttcacccatt    780
gtcaagagct tcaacaggaa tgagtcttat ccatatgatg tgccagatta tgcgagctaa    840
```

<210> SEQ ID NO 79
<211> LENGTH: 840
<212> TYPE: DNA
<213> ORGANISM: Homo sapiens

<400> SEQUENCE: 79

```
taagattagc ggatcctacc tgacgctttt tatcgcaact ctctactgtt tctccatacc     60 cgttttttg gatggagtga aacgatgaaa taccttattgc ctacggcagc cgctggattg    120
ttattactcg ctgcccaacc agccatggcc gatattgtga tgacccaggc tgcaccctct    180
gtacctgtca ctcctggaga gtcagtatcc atctcctgca ggtccagtaa gagtctcctg    240
cgtagtaatg caacactta cttgtattgg ttcctgcaga ggccaggcca gtctcctcag    300
ctcctcatat atcggatgtc caaccttgcc tcaggagtcc cagacaggtt cagtggcagt    360
gggtcaggaa ctgccttcac actgagaatc agtagagtgg aggctgagga tgtgggtgtt    420
tattactgta tgcaacatct agaatatcct ttcacgttcg gagggggac caagctggaa    480 ataaaacggg ctgatgctgc accaactgta tccatcttcc caccatccag tgagcagtta    540
acatctggag gtgcctcagt cgtgtgcttc ttgaacaact tctaccccaa agacatcaat    600
```

```
gtcaagtgga agattgatgg cagtgaacga caaaatggcg tcctgaacag ttggactgat    660
caggacagca agacagcac ctacagcatg agcagcaccc tcacgttgac caaggacgag     720
tatgaacgac ataacagcta tacctgtgag gccactcaca agacatcaac ttcacccatt    780
gtcaagagct tcaacaggaa tgagtcttat ccatatgatg tgccagatta tgcgagctaa    840
```

<210> SEQ ID NO 80
<211> LENGTH: 840
<212> TYPE: DNA
<213> ORGANISM: Homo sapiens

<400> SEQUENCE: 80

```
taagattagc ggatcctacc tgacgctttt tatcgcaact ctcttctgtt tctccatacc     60 cgttttttg gatggagtga aacgatgaaa tacctattgc ctacggcagc cgctggattg     120
ttattactcg ctgcccaacc agccatggcc gatattgtga tgacccaggc tgcaccctct    180
gtatctgtca ctcctggaga gtcagtatcc atctcctgca ggtctactaa gagtctcctg    240
cgtagtaatg gcaacactta cttgtattgg ttcctccaga ggccaggcca gtctcctcag    300
ctcctgatat atcggatgtc aaccttgcc tcaggagtcc cagacaggtt cagtggcagt     360
gggtcaggaa ctgctttcac actgagaatc agtagagtgg aggctgagga tgtgggtgtt    420
tattactgta tgcaacatct agaatatcct ttcacgttcg gagggggac caagctggaa     480 ataaaacggg ctgatgctgc accaactgta tccatcttcc caccatccag tgagcagtta    540
acatctggag gtgcctcagt cgtgtgcttc ttgaacaact ctaccccaa agacatcaat     600 gtcaagtgga agattgatgg cagtgaacga caaaatggcg tcctgaacag ttggactgat    660
caggacagca agacagcac ctacagcatg agcagcaccc tcacgttgac caaggacgag     720
tatgaacgac ataacagcta tacctgtgag gccactcaca agacatcaac ttcacccatt    780
gtcaagagct tcaacaggaa tgagtcttat ccatatgatg tgccagatta tgcgagctaa    840
```

<210> SEQ ID NO 81
<211> LENGTH: 840
<212> TYPE: DNA
<213> ORGANISM: Homo sapiens

<400> SEQUENCE: 81

```
taagattagc ggatcctacc tgacgctttt tatcgcaact ctctactgtt tctccatacc     60 cgttttttg gatggagtga aacgatgaaa tacctattgc ctacggcagc cgctggattg     120
ttattactcg ctgcccaacc agccatggcc gatattgtga tgacccaggc tgcaccctct    180
gtacctgtca ctcctggaga gtcagtatcc atctcctgca ggtctagtaa gagtctccta    240
cgtagtaatg gcaacactta cttgtattgg ttcctgcaga ggccaggcca gtctcctcag    300
ctcctgatat atcggatgtc aaccttgcc tcaggagtcc cagacaggtt cagtggcagt     360
gggtcaggaa ctgccttcac actgagaatc agtagagtgg aggctgagga tgtgggtgtt    420
tattactgta tgcaacatct agaatatcct ttcacgttcg gagggggac caagctggaa     480 ataaaacggg ctgatgctgc accaactgta tccatcttcc caccatccag tgagcagtta    540
acatctggag gtgcctcagt cgtgtgcttc ttgaacaact ctaccccaa agacatcaat     600 gtcaagtgga agattgatgg cagtgaacga caaaatggcg tcctgaacag ttggactgat    660
caggacagca agacagcac ctacagcatg agcagcaccc tcacgttgac caaggacgag     720
tatgaacgac ataacagcta tacctgtgag gccactcaca agacatcaac ttcacccatt    780
gtcaagagct tcaacaggaa tgagtcttat ccatatgatg tgccagatta tgcgagctaa    840
```

<210> SEQ ID NO 82
<211> LENGTH: 840
<212> TYPE: DNA
<213> ORGANISM: Homo sapiens

<400> SEQUENCE: 82

```
taagattagc ggatcctacc tgacgctttt tatcgcaact ctctactgtt tctccatacc    60
cgttttttg  gatggagtga aacgatgaaa tacctattgc ctacggcagc cgctggattg   120
ttattactcg  ctgcccaacc agccatggcc gatattgtga tgacccaggc tgcaccctct   180
gtacctgtca ctcctggaga gtcagtatcc atctcctgca ggtctagtaa gagtctcctg   240
cgcagtaatg gcaacactta cttgtattgg ttcctgcaga ggccaggcca gtctcctcag   300
ctcctgatat atcggctgtc caaccttgcc tcaggagtcc cagacaggtt cagtggcagt   360
gggtcaggaa ctgctttcac actgagaatc agtagagtgg aggctgagga tgtgggtgtt   420
tattactgta tgcaacatct agaatatcct ttcacattcg gctcgggac  aaagttggaa   480
ataaaacggg ctgatgctgc accaactgta tccatcttcc cacaatacag tgagcagtta   540
acaactggag gtgcctcagt cgtgtgcttc ttgaacaact tctacccaa  agacatcaat   600
gtcaagtgga agattgatgg cagtgaacga caaaatggcg tcctgaacag ttggactgat   660
caggacagca agacagcac  ctacagcatg agcagcaccc tcacgttgac caaggacgag   720
tatgaacgac ataacagcta tacctgtgag gccactcaca agacatcaac ttcacccatt   780
gtcaagagct caacaggaa  tgagtcttat ccatatgatg tgccagatta tgcgagctaa   840
```

<210> SEQ ID NO 83
<211> LENGTH: 597
<212> TYPE: DNA
<213> ORGANISM: Homo sapiens

<400> SEQUENCE: 83

```
cggatcctac ctgacgcttt ttatcgcaac tctctactgt ttctccatac ccgttttttt    60
ggatggagtg aaacgatgaa atacctattg cctacggcag ccgctggatt gttattactc   120
gctgcccaac cagccatggc cgatattgtg atgacccagg ctgcaccctc tgtacctgtc   180
actcctggag agtcagtatc catctcctgc acgtctagta agagtctcct gcgtagtaat   240
ggcaacactt acttgtattg gttcctgcag aggccaggcc agtctcctca gctcctgata   300
tatcggatgt ccaaccttgc ctcgggagtc ccagacaggt tcagtggcag tgggtcagga   360
actgctttca cactgagaat cagtagagtg gaggctgagg atgtgggtgt ttattactgt   420
atgcaacatc tagaatatcc tttcacgttc ggctcgggga caaatttgga aataaaacgg   480
gctgatgctg caccaactgt atccatcttc acaacatcca gagagcagtt aacatctgga   540
ggtgcctcag tcgtgtgctt cttgaacaac ttctacccca agacatcaa  tgtcaag     597
```

<210> SEQ ID NO 84
<211> LENGTH: 30
<212> TYPE: DNA
<213> ORGANISM: Homo sapiens

<400> SEQUENCE: 84

```
ggattcactt tcagtaacta tggcatgtct                                     30
```

<210> SEQ ID NO 85
<211> LENGTH: 30
<212> TYPE: DNA

<213> ORGANISM: Homo sapiens

<400> SEQUENCE: 85
ggctacacct tcagtgacca tgctattcac                                30

<210> SEQ ID NO 86
<211> LENGTH: 30
<212> TYPE: DNA
<213> ORGANISM: Homo sapiens

<400> SEQUENCE: 86
ggctacacct tcactgacca tgctattcac                                30

<210> SEQ ID NO 87
<211> LENGTH: 30
<212> TYPE: DNA
<213> ORGANISM: Homo sapiens

<400> SEQUENCE: 87
ggctacaccc tcactgacca tactattcac                                30

<210> SEQ ID NO 88
<211> LENGTH: 51
<212> TYPE: DNA
<213> ORGANISM: Homo sapiens

<400> SEQUENCE: 88
gccattaatc gtgatggtgg taccacctac tatacagaca atgtgaaggg c         51

<210> SEQ ID NO 89
<211> LENGTH: 51
<212> TYPE: DNA
<213> ORGANISM: Homo sapiens

<400> SEQUENCE: 89
tatatttatc ctagacatgg gactactaac tacaatgaga acttcaaggg c         51

<210> SEQ ID NO 90
<211> LENGTH: 51
<212> TYPE: DNA
<213> ORGANISM: Homo sapiens

<400> SEQUENCE: 90
tatatttatc ctgaacatgg aactattaag tataatgaga agttcaaggg c         51

<210> SEQ ID NO 91
<211> LENGTH: 51
<212> TYPE: DNA
<213> ORGANISM: Homo sapiens

<400> SEQUENCE: 91
tatatttacc ctagagatgg aataactggg tacaatgaga agttcaaggg c         51

<210> SEQ ID NO 92
<211> LENGTH: 51
<212> TYPE: DNA
<213> ORGANISM: Homo sapiens

<400> SEQUENCE: 92
tatatttatc ctagagatgg ttttactaag tacaatgaga agttcaaggg c         51

<210> SEQ ID NO 93
<211> LENGTH: 51

```
<212> TYPE: DNA
<213> ORGANISM: Homo sapiens

<400> SEQUENCE: 93
tatatttatc ctgaacatgg tagtattacg tataatgaga agttcaaggg c          51

<210> SEQ ID NO 94
<211> LENGTH: 51
<212> TYPE: DNA
<213> ORGANISM: Homo sapiens

<400> SEQUENCE: 94
tatatctacc ccagagatga ttttgctaag gtgaatgaga agttcaaggg c          51

<210> SEQ ID NO 95
<211> LENGTH: 51
<212> TYPE: DNA
<213> ORGANISM: Homo sapiens

<400> SEQUENCE: 95
tatatttatc ctgaacatgg tactattacg tataatgaga agttcaaggg c          51

<210> SEQ ID NO 96
<211> LENGTH: 51
<212> TYPE: DNA
<213> ORGANISM: Homo sapiens

<400> SEQUENCE: 96
tatatttttc ctagagatgc ttttagtttg aacaatgaga agttcaaggg c          51

<210> SEQ ID NO 97
<211> LENGTH: 33
<212> TYPE: DNA
<213> ORGANISM: Homo sapiens

<400> SEQUENCE: 97
ttccttctct gggacggctg gtacttcgat gtc                              33

<210> SEQ ID NO 98
<211> LENGTH: 27
<212> TYPE: DNA
<213> ORGANISM: Homo sapiens

<400> SEQUENCE: 98
agaaactact tctatgttat ggactac                                     27

<210> SEQ ID NO 99
<211> LENGTH: 27
<212> TYPE: DNA
<213> ORGANISM: Homo sapiens

<400> SEQUENCE: 99
actaactact tctatgttat ggagtat                                     27

<210> SEQ ID NO 100
<211> LENGTH: 39
<212> TYPE: DNA
<213> ORGANISM: Homo sapiens

<400> SEQUENCE: 100
ggctatagtt acaggaatta cgcgtactac tatgactac                        39

<210> SEQ ID NO 101
```

-continued

```
<211> LENGTH: 27
<212> TYPE: DNA
<213> ORGANISM: Homo sapiens

<400> SEQUENCE: 101
aggaactatt tgtatattat ggactac                                              27

<210> SEQ ID NO 102
<211> LENGTH: 27
<212> TYPE: DNA
<213> ORGANISM: Homo sapiens

<400> SEQUENCE: 102
actaactact tctatactat ggactac                                              27

<210> SEQ ID NO 103
<211> LENGTH: 27
<212> TYPE: DNA
<213> ORGANISM: Homo sapiens

<400> SEQUENCE: 103
aggaactact tgtatgttat ggactac                                              27

<210> SEQ ID NO 104
<211> LENGTH: 27
<212> TYPE: DNA
<213> ORGANISM: Homo sapiens

<400> SEQUENCE: 104
actaactacc tctatattat ggactac                                              27

<210> SEQ ID NO 105
<211> LENGTH: 48
<212> TYPE: DNA
<213> ORGANISM: Homo sapiens

<400> SEQUENCE: 105
agatctagtc agagccttttt acacagtaat ggaaacacct atttacat                       48

<210> SEQ ID NO 106
<211> LENGTH: 48
<212> TYPE: DNA
<213> ORGANISM: Homo sapiens

<400> SEQUENCE: 106
acgtctagta agagtctcct gcgtagtaat ggcaacactt acttgtat                        48

<210> SEQ ID NO 107
<211> LENGTH: 51
<212> TYPE: DNA
<213> ORGANISM: Homo sapiens

<400> SEQUENCE: 107
aagtccagcc agagccttttt acatagtagc aatcaaaaga actacttggc c                   51

<210> SEQ ID NO 108
<211> LENGTH: 48
<212> TYPE: DNA
<213> ORGANISM: Homo sapiens

<400> SEQUENCE: 108
aggtctagta agagtctcct gcgcagtaat ggcaacactt acttgtat                        48
```

```
<210> SEQ ID NO 109
<211> LENGTH: 48
<212> TYPE: DNA
<213> ORGANISM: Homo sapiens

<400> SEQUENCE: 109
aggtcttcta agagtctcct gcgtactaat ggcaacactt acttgcat          48

<210> SEQ ID NO 110
<211> LENGTH: 48
<212> TYPE: DNA
<213> ORGANISM: Homo sapiens

<400> SEQUENCE: 110
aggtctagta agagtctcct gcgtagtaat ggcaacactt acttgtat          48

<210> SEQ ID NO 111
<211> LENGTH: 48
<212> TYPE: DNA
<213> ORGANISM: Homo sapiens

<400> SEQUENCE: 111
aggtccagta agagtctcct gcgtagtaat ggcaacactt acttgtat          48

<210> SEQ ID NO 112
<211> LENGTH: 48
<212> TYPE: DNA
<213> ORGANISM: Homo sapiens

<400> SEQUENCE: 112
aggtctacta agagtctcct gcgtagtaat ggcaacactt acttgtat          48

<210> SEQ ID NO 113
<211> LENGTH: 48
<212> TYPE: DNA
<213> ORGANISM: Homo sapiens

<400> SEQUENCE: 113
aggtctagta agagtctcct acgtagtaat ggcaacactt acttgtat          48

<210> SEQ ID NO 114
<211> LENGTH: 21
<212> TYPE: DNA
<213> ORGANISM: Homo sapiens

<400> SEQUENCE: 114
aaagtttcca accgattttc t                                       21

<210> SEQ ID NO 115
<211> LENGTH: 21
<212> TYPE: DNA
<213> ORGANISM: Homo sapiens

<400> SEQUENCE: 115
cggatgtcca accttgcctc g                                       21

<210> SEQ ID NO 116
<211> LENGTH: 21
<212> TYPE: DNA
<213> ORGANISM: Homo sapiens

<400> SEQUENCE: 116
tgggcatcca ctagagaatc t                                       21
```

```
<210> SEQ ID NO 117
<211> LENGTH: 21
<212> TYPE: DNA
<213> ORGANISM: Homo sapiens

<400> SEQUENCE: 117
cggctgtcca accttgcctc a                                              21

<210> SEQ ID NO 118
<211> LENGTH: 21
<212> TYPE: DNA
<213> ORGANISM: Homo sapiens

<400> SEQUENCE: 118
cggatgtcca accttgcctc a                                              21

<210> SEQ ID NO 119
<211> LENGTH: 21
<212> TYPE: DNA
<213> ORGANISM: Homo sapiens

<400> SEQUENCE: 119
cggctgtcta accttgcctc a                                              21

<210> SEQ ID NO 120
<211> LENGTH: 24
<212> TYPE: DNA
<213> ORGANISM: Homo sapiens

<400> SEQUENCE: 120
tctcaaagta cacatgtgct cacg                                           24

<210> SEQ ID NO 121
<211> LENGTH: 27
<212> TYPE: DNA
<213> ORGANISM: Homo sapiens

<400> SEQUENCE: 121
atgcaacatc tagaatatcc tttcacg                                        27

<210> SEQ ID NO 122
<211> LENGTH: 27
<212> TYPE: DNA
<213> ORGANISM: Homo sapiens

<400> SEQUENCE: 122
cagcaatatt atagctatcc gtggacg                                        27

<210> SEQ ID NO 123
<211> LENGTH: 27
<212> TYPE: DNA
<213> ORGANISM: Homo sapiens

<400> SEQUENCE: 123
atgcaacatc tagaatatcc tttcaca                                        27

<210> SEQ ID NO 124
<211> LENGTH: 27
<212> TYPE: DNA
<213> ORGANISM: Homo sapiens

<400> SEQUENCE: 124
atgcaacatc tagaatatcc attcacg                                        27
```

-continued

```
<210> SEQ ID NO 125
<211> LENGTH: 30
<212> TYPE: DNA
<213> ORGANISM: Homo sapiens

<400> SEQUENCE: 125
ggattcactt tcagtagcta tggcatgtct                                        30

<210> SEQ ID NO 126
<211> LENGTH: 30
<212> TYPE: DNA
<213> ORGANISM: Homo sapiens

<400> SEQUENCE: 126
ggctacacct tcactgacca tactattcac                                        30

<210> SEQ ID NO 127
<211> LENGTH: 51
<212> TYPE: DNA
<213> ORGANISM: Homo sapiens

<400> SEQUENCE: 127
tatatttatc ctagagatgg tagtactaag tacaatgaga agttcaaggg c                51

<210> SEQ ID NO 128
<211> LENGTH: 48
<212> TYPE: DNA
<213> ORGANISM: Homo sapiens

<400> SEQUENCE: 128
agatctagtc agagccttgt acacagtaat ggaaacacct atttacat                   48

<210> SEQ ID NO 129
<211> LENGTH: 24
<212> TYPE: DNA
<213> ORGANISM: Homo sapiens

<400> SEQUENCE: 129
tctcaaagta cacatgttcc tccc                                             24

<210> SEQ ID NO 130
<211> LENGTH: 51
<212> TYPE: DNA
<213> ORGANISM: Homo sapiens

<400> SEQUENCE: 130
aagtccagtc agagcctttt atatagtagc aatcaaaaga actacttggc c                51

<210> SEQ ID NO 131
<211> LENGTH: 21
<212> TYPE: DNA
<213> ORGANISM: Homo sapiens

<400> SEQUENCE: 131
tgggcatcca ctagggaatc t                                                21

<210> SEQ ID NO 132
<211> LENGTH: 27
<212> TYPE: DNA
<213> ORGANISM: Homo sapiens

<400> SEQUENCE: 132
```
cagcaatatt atagctatcc tcccaca    27

<210> SEQ ID NO 133
<211> LENGTH: 48
<212> TYPE: DNA
<213> ORGANISM: Homo sapiens

<400> SEQUENCE: 133
aggtctagta agagtctcct gcatagtaat ggcaacactt acttgtat    48

<210> SEQ ID NO 134
<211> LENGTH: 21
<212> TYPE: DNA
<213> ORGANISM: Homo sapiens

<400> SEQUENCE: 134
cggatgtcca accttgcctc a    21

<210> SEQ ID NO 135
<211> LENGTH: 27
<212> TYPE: DNA
<213> ORGANISM: Homo sapiens

<400> SEQUENCE: 135
atgcaacatc tagaatatcc tttcaca    27

<210> SEQ ID NO 136
<211> LENGTH: 222
<212> TYPE: PRT
<213> ORGANISM: Homo sapiens

<400> SEQUENCE: 136

Gln Glu Gly Lys Phe Ser Gly Pro Leu Lys Pro Met Thr Phe Ser Ile
1               5                   10                  15

Tyr Glu Gly Gln Glu Pro Ser Gln Ile Ile Phe Gln Phe Lys Ala Asn
                20                  25                  30

Pro Pro Ala Val Thr Phe Glu Leu Thr Gly Glu Thr Asp Asn Ile Phe
            35                  40                  45

Val Ile Glu Arg Glu Gly Leu Leu Tyr Tyr Asn Arg Ala Leu Asp Arg
        50                  55                  60

Glu Thr Arg Ser Thr His Asn Leu Gln Val Ala Ala Leu Asp Ala Asn
65                  70                  75                  80

Gly Ile Ile Val Glu Gly Pro Val Pro Ile Thr Ile Lys Val Lys Asp
                85                  90                  95

Ile Asn Asp Asn Arg Pro Thr Phe Leu Gln Ser Lys Tyr Glu Gly Ser
            100                 105                 110

Val Arg Gln Asn Ser Arg Pro Gly Lys Pro Phe Leu Tyr Val Asn Ala
        115                 120                 125

Thr Asp Leu Asp Asp Pro Ala Thr Pro Asn Gly Gln Leu Tyr Tyr Gln
    130                 135                 140

Ile Val Ile Gln Leu Pro Met Ile Asn Asn Val Met Tyr Phe Gln Ile
145                 150                 155                 160

Asn Asn Lys Thr Gly Ala Ile Ser Leu Thr Arg Glu Gly Ser Gln Glu
                165                 170                 175

Leu Asn Pro Ala Lys Asn Pro Ser Tyr Asn Leu Val Ile Ser Val Lys
            180                 185                 190

Asp Met Gly Gly Gln Ser Glu Asn Ser Phe Ser Asp Thr Thr Ser Val
        195                 200                 205

```
Asp Ile Ile Val Thr Glu Asn Ile Trp Lys Ala Pro Lys Pro
    210                 215                 220

<210> SEQ ID NO 137
<211> LENGTH: 765
<212> TYPE: PRT
<213> ORGANISM: Homo sapiens

<400> SEQUENCE: 137

Gln Glu Gly Lys Phe Ser Gly Pro Leu Lys Pro Met Thr Phe Ser Ile
1               5                   10                  15

Tyr Glu Gly Gln Glu Pro Ser Gln Ile Ile Phe Gln Phe Lys Ala Asn
            20                  25                  30

Pro Pro Ala Val Thr Phe Glu Leu Thr Gly Glu Thr Asp Asn Ile Phe
        35                  40                  45

Val Ile Glu Arg Glu Gly Leu Leu Tyr Tyr Asn Arg Ala Leu Asp Arg
    50                  55                  60

Glu Thr Arg Ser Thr His Asn Leu Gln Val Ala Ala Leu Asp Ala Asn
65                  70                  75                  80

Gly Ile Ile Val Glu Gly Pro Val Pro Ile Thr Ile Lys Val Lys Asp
                85                  90                  95

Ile Asn Asp Asn Arg Pro Thr Phe Leu Gln Ser Lys Tyr Glu Gly Ser
            100                 105                 110

Val Arg Gln Asn Ser Arg Pro Gly Lys Pro Phe Leu Tyr Val Asn Ala
        115                 120                 125

Thr Asp Leu Asp Asp Pro Ala Thr Pro Asn Gly Gln Leu Tyr Tyr Gln
    130                 135                 140

Ile Val Ile Gln Leu Pro Met Ile Asn Asn Val Met Tyr Phe Gln Ile
145                 150                 155                 160

Asn Asn Lys Thr Gly Ala Ile Ser Leu Thr Arg Glu Gly Ser Gln Glu
                165                 170                 175

Leu Asn Pro Ala Lys Asn Pro Ser Tyr Asn Leu Val Ile Ser Val Lys
            180                 185                 190

Asp Met Gly Gly Gln Ser Glu Asn Ser Phe Ser Asp Thr Thr Ser Val
        195                 200                 205

Asp Ile Ile Val Thr Glu Asn Ile Trp Lys Ala Pro Lys Pro Val Glu
    210                 215                 220

Met Val Glu Asn Ser Thr Asp Pro His Pro Ile Lys Ile Thr Gln Val
225                 230                 235                 240

Arg Trp Asn Asp Pro Gly Ala Gln Tyr Ser Leu Val Asp Lys Glu Lys
                245                 250                 255

Leu Pro Arg Phe Pro Phe Ser Ile Asp Gln Glu Gly Asp Ile Tyr Val
            260                 265                 270

Thr Gln Pro Leu Asp Arg Glu Glu Lys Asp Ala Tyr Val Phe Tyr Ala
        275                 280                 285

Val Ala Lys Asp Glu Tyr Gly Lys Pro Leu Ser Tyr Pro Leu Glu Ile
    290                 295                 300

His Val Lys Val Lys Asp Ile Asn Asp Asn Pro Pro Thr Cys Pro Ser
305                 310                 315                 320

Pro Val Thr Val Phe Glu Val Gln Glu Asn Glu Arg Leu Gly Asn Ser
                325                 330                 335

Ile Gly Thr Leu Thr Ala His Asp Arg Asp Glu Glu Asn Thr Ala Asn
            340                 345                 350

Ser Phe Leu Asn Tyr Arg Ile Val Glu Gln Thr Pro Lys Leu Pro Met
        355                 360                 365
```

-continued

Asp Gly Leu Phe Leu Ile Gln Thr Tyr Ala Gly Met Leu Gln Leu Ala
        370                 375                 380
Lys Gln Ser Leu Lys Lys Gln Asp Thr Pro Gln Tyr Asn Leu Thr Ile
385                 390                 395                 400
Glu Val Ser Asp Lys Asp Phe Lys Thr Leu Cys Phe Val Gln Ile Asn
                405                 410                 415
Val Ile Asp Ile Asn Asp Gln Ile Pro Ile Phe Glu Lys Ser Asp Tyr
            420                 425                 430
Gly Asn Leu Thr Leu Ala Glu Asp Thr Asn Ile Gly Ser Thr Ile Leu
            435                 440                 445
Thr Ile Gln Ala Thr Asp Ala Asp Glu Pro Phe Thr Gly Ser Ser Lys
        450                 455                 460
Ile Leu Tyr His Ile Ile Lys Gly Asp Ser Glu Gly Arg Leu Gly Val
465                 470                 475                 480
Asp Thr Asp Pro His Thr Asn Thr Gly Tyr Val Ile Ile Lys Lys Pro
                485                 490                 495
Leu Asp Phe Glu Thr Ala Ala Val Ser Asn Ile Val Phe Lys Ala Glu
            500                 505                 510
Asn Pro Glu Pro Leu Val Phe Gly Val Lys Tyr Asn Ala Ser Ser Phe
        515                 520                 525
Ala Lys Phe Thr Leu Ile Val Thr Asp Val Asn Glu Ala Pro Gln Phe
530                 535                 540
Ser Gln His Val Phe Gln Ala Lys Val Ser Glu Asp Val Ala Ile Gly
545                 550                 555                 560
Thr Lys Val Gly Asn Val Thr Ala Lys Asp Pro Glu Gly Leu Asp Ile
                565                 570                 575
Ser Tyr Ser Leu Arg Gly Asp Thr Arg Gly Trp Leu Lys Ile Asp His
            580                 585                 590
Val Thr Gly Glu Ile Phe Ser Val Ala Pro Leu Asp Arg Glu Ala Gly
            595                 600                 605
Ser Pro Tyr Arg Val Gln Val Val Ala Thr Glu Val Gly Gly Ser Ser
        610                 615                 620
Leu Ser Ser Val Ser Glu Phe His Leu Ile Leu Met Asp Val Asn Asp
625                 630                 635                 640
Asn Pro Pro Arg Leu Ala Lys Asp Tyr Thr Gly Leu Phe Phe Cys His
                645                 650                 655
Pro Leu Ser Ala Pro Gly Ser Leu Ile Phe Glu Ala Thr Asp Asp Asp
            660                 665                 670
Gln His Leu Phe Arg Gly Pro His Phe Thr Phe Ser Leu Gly Ser Gly
            675                 680                 685
Ser Leu Gln Asn Asp Trp Glu Val Ser Lys Ile Asn Gly Thr His Ala
        690                 695                 700
Arg Leu Ser Thr Arg His Thr Asp Phe Glu Glu Arg Glu Tyr Val Val
705                 710                 715                 720
Leu Ile Arg Ile Asn Asp Gly Gly Arg Pro Pro Leu Glu Gly Ile Val
                725                 730                 735
Ser Leu Pro Val Thr Phe Cys Ser Cys Val Glu Gly Ser Cys Phe Arg
            740                 745                 750
Pro Ala Gly His Gln Thr Gly Ile Pro Thr Val Gly Met
        755                 760                 765

<210> SEQ ID NO 138
<211> LENGTH: 123

```
<212> TYPE: PRT
<213> ORGANISM: Homo sapiens

<400> SEQUENCE: 138

Glu Val Gln Leu Gln Gln Ser Val Ala Glu Leu Val Lys Pro Gly Ala
1               5                   10                  15

Ser Val Lys Met Ser Cys Lys Val Ser Gly Tyr Thr Leu Thr Asp His
            20                  25                  30

Thr Ile His Trp Met Lys Gln Arg Pro Glu Gln Gly Leu Glu Trp Ile
        35                  40                  45

Gly Tyr Ile Tyr Pro Arg Asp Gly Ile Thr Gly Tyr Asn Glu Lys Phe
    50                  55                  60

Lys Gly Lys Ala Thr Leu Thr Ala Asp Thr Ser Ser Thr Ala Tyr
65                  70                  75                  80

Met Gln Leu Asn Ser Leu Thr Ser Glu Asp Ser Ala Val Tyr Phe Cys
            85                  90                  95

Ala Arg Trp Gly Tyr Ser Tyr Arg Asn Tyr Ala Tyr Tyr Tyr Asp Tyr
            100                 105                 110

Trp Gly Gln Gly Thr Thr Leu Thr Val Ser Ser
            115                 120

<210> SEQ ID NO 139
<211> LENGTH: 115
<212> TYPE: PRT
<213> ORGANISM: Homo sapiens

<400> SEQUENCE: 139

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu His Ser
            20                  25                  30

Ser Asn Gln Lys Asn Tyr Leu Ala Trp Tyr Gln Gln Lys Pro Gly Gln
        35                  40                  45

Ser Pro Lys Val Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Thr Ser Val Lys Ser Glu Asp Leu Ala Val Tyr Tyr Cys Gln Gln
            85                  90                  95

Tyr Tyr Ser Tyr Pro Trp Thr Phe Gly Gly Gly Thr Arg Leu Glu Ile
            100                 105                 110

Lys Arg Ala
        115
```